US009056903B2

(12) United States Patent
Feinstein et al.

(10) Patent No.: US 9,056,903 B2
(45) Date of Patent: Jun. 16, 2015

(54) THERAPEUTIC USES OF INHIBITORS OF RTP801

(75) Inventors: Elena Feinstein, Rehovot (IL); Rami Skaliter, Nes Ziona (IL)

(73) Assignee: Quark Pharmaceuticals, Inc. CA (US)

( * ) Notice: Subject to any disclaimer, the term of this patent is extended or adjusted under 35 U.S.C. 154(b) by 710 days.

(21) Appl. No.: 13/233,907

(22) Filed: Sep. 15, 2011

(65) Prior Publication Data

US 2012/0156208 A1  Jun. 21, 2012

Related U.S. Application Data

(62) Division of application No. 11/655,636, filed on Jan. 18, 2007, now Pat. No. 8,067,570.

(60) Provisional application No. 60/760,586, filed on Jan. 20, 2006, provisional application No. 60/796,901, filed on May 1, 2006, provisional application No. 60/851,000, filed on Oct. 10, 2006.

(51) Int. Cl.
| C12N 15/113 | (2010.01) |
| C07K 16/18 | (2006.01) |
| C07K 14/47 | (2006.01) |
| C07K 16/22 | (2006.01) |
| A61K 39/00 | (2006.01) |

(52) U.S. Cl.
CPC ............ *C07K 16/18* (2013.01); *A61K 2039/505* (2013.01); *C07K 14/4747* (2013.01); *C07K 16/22* (2013.01); *C12N 15/113* (2013.01); *C12N 2310/14* (2013.01); *C12N 2310/321* (2013.01)

(58) Field of Classification Search
None
See application file for complete search history.

(56) References Cited

U.S. PATENT DOCUMENTS

| 5,898,031 A | 4/1999 | Crooke |
| 6,107,094 A | 8/2000 | Crooke |
| 6,372,249 B1 | 4/2002 | Smith et al. |
| 6,455,674 B1 | 9/2002 | Einat et al. |
| 6,506,559 B1 | 1/2003 | Fire et al. |
| 6,555,667 B1 | 4/2003 | Einat et al. |
| 6,673,549 B1 | 1/2004 | Furness et al. |
| 6,740,738 B2 | 5/2004 | Einat et al. |
| 7,056,704 B2 | 6/2006 | Tuschl et al. |
| 7,078,196 B2 | 7/2006 | Tuschl et al. |
| 7,432,249 B2 | 10/2008 | Crooke |
| 7,432,250 B2 | 10/2008 | Crooke |
| 7,452,987 B2 | 11/2008 | Giese et al. |
| 7,459,547 B2 | 12/2008 | Zamore et al. |
| 7,629,321 B2 | 12/2009 | Crooke |
| 2002/0119463 A1 | 8/2002 | Faris |
| 2002/0137077 A1 | 9/2002 | Hopkins et al. |
| 2003/0104973 A1 | 6/2003 | Einat et al. |
| 2003/0108871 A1 | 6/2003 | Kaser |
| 2003/0165864 A1 | 9/2003 | Lasek et al. |
| 2003/0207840 A1 | 11/2003 | Riggins et al. |
| 2005/0080246 A1 | 4/2005 | Allerson |
| 2006/0217329 A1 | 9/2006 | Feinstein |
| 2007/0281326 A1 | 12/2007 | Wechsler |
| 2008/0064650 A1 | 3/2008 | Feinstein |
| 2008/0188647 A1 | 8/2008 | Khvorova |
| 2008/0269156 A1 | 10/2008 | Feinstein et al. |

FOREIGN PATENT DOCUMENTS

| DE | 19816395 | 10/1999 |
| EP | 1009753 B1 | 9/2003 |
| EP | 1 394 274 A2 | 3/2004 |
| JP | 2003-259877 | 9/2003 |
| WO | WO 99/09046 | 2/1999 |
| WO | WO 00/14283 | 3/2000 |
| WO | WO 00/44895 | 8/2000 |
| WO | WO 00/44914 A1 | 8/2000 |
| WO | WO 00/61620 | 10/2000 |
| WO | WO 00/77022 | 12/2000 |
| WO | WO 01/12659 A2 | 2/2001 |
| WO | WO 01/36646 A1 | 5/2001 |
| WO | WO 01/68836 A2 | 9/2001 |
| WO | WO 01/68836 A3 | 9/2001 |
| WO | WO 01/70979 A2 | 9/2001 |
| WO | WO 01/75164 A2 | 10/2001 |
| WO | WO 01/77289 A2 | 10/2001 |
| WO | WO 02/31111 A2 | 4/2002 |
| WO | WO 02/44321 | 6/2002 |
| WO | WO 02/46465 A2 | 6/2002 |
| WO | WO 02/55693 | 7/2002 |
| WO | WO 02/059300 A2 | 8/2002 |
| WO | WO 02/059300 A3 | 8/2002 |
| WO | WO 02/101075 A2 | 12/2002 |
| WO | WO 03/010205 A1 | 2/2003 |
| WO | WO 03/064621 A2 | 8/2003 |
| WO | WO 03/064621 A3 | 8/2003 |
| WO | WO 03/070918 A2 | 8/2003 |

(Continued)

OTHER PUBLICATIONS

Scherer et al., (2003), "Approaches for the Sequence-Specific Knockdown of mRNA." *Nat. Biotechnol.*, 21(12):1457-1465.
Scherer and Rossi, (2004) "Therapeutic Applications of RNA Interferences: Recent Advances in siRNA Design". *Advances in Genetics* 22:1-21.
Shoshani, T., et al., (2002) "Identification of a Novel Hypoxia-Inducible Factor 1-Responsive Gene RTP801, Involved in Apoptosis." *Mol. Cell. Biol.*, 22(7): 2283-2293.
Nuttal, A., (1999) "Sound-Induced Cochlear Ischemia/Hypoxia as a Mechanism of Hearing Loss (Review)." *Noise & Health*, 5: 17-31.
Bliss, M. and Simini, B., (1999) "When Are the Seeds of Postoperative Pressure Sores Sown?" *BMJ*, 319, 863-864.
Arden, G.B., et al., (2005) "Spare the Rod and Spoil the Eye?" *Br. J. Ophthalmol.*, 89: 764-769.
Biju, M.P., et al., (2005) "Protection of HIF-1-deficient primary renal tubular epithelial cells from hypoxia-induced cell death is glucose dependent." *Am. J. Physiol. Renal Physiol.*, 289: F1217-F1226.

(Continued)

*Primary Examiner* — Tracy Vivlemore
(74) *Attorney, Agent, or Firm* — Nutter McClennen & Fish LLP

(57) ABSTRACT

The present invention provides novel molecules, compositions, methods and uses for treating microvascular disorders, eye diseases respiratory conditions and hearing disorders based upon inhibition of the RTP801 gene and/or protein.

19 Claims, 39 Drawing Sheets

(56) References Cited

FOREIGN PATENT DOCUMENTS

| WO | WO 03/074654 A2 | 9/2003 |
| WO | WO 03/101283 | 12/2003 |
| WO | WO 2004/015107 A2 | 2/2004 |
| WO | WO 2004/018999 A2 | 3/2004 |
| WO | WO 2004/030615 A2 | 4/2004 |
| WO | WO 2004/035615 A2 | 4/2004 |
| WO | WO 2004/039956 A2 | 5/2004 |
| WO | WO 2004/045543 A2 | 6/2004 |
| WO | WO 2004/045545 A2 | 6/2004 |
| WO | WO 2004/060270 A2 | 7/2004 |
| WO | WO 2004/076633 A2 | 9/2004 |
| WO | WO 2004/091383 A2 | 10/2004 |
| WO | WO 2004/111191 A2 | 12/2004 |
| WO | WO 2004/111191 A3 | 12/2004 |
| WO | WO 2005/016000 A1 | 2/2005 |
| WO | WO 2005/062937 A2 | 7/2005 |
| WO | WO 2005/062937 A3 | 7/2005 |
| WO | WO 03/062394 A2 | 7/2007 |
| WO | WO 03/062394 A3 | 7/2007 |
| WO | WO 2007/084684 | 7/2007 |
| WO | WO 2007/087451 A2 | 8/2007 |
| WO | WO 2007/087451 A3 | 8/2007 |

OTHER PUBLICATIONS

Czauderna, F., et al., (2003) "Structural Variations and Stabilising Modifications of Synthetic siRNAs in Mammalian Cells." *Nucleic Acids Res.*, 31(11): 2705-2716.

Brafman, A.; Mett, I.; Shafir M.; Gottlieb, H.; Damari, G.; Gozlan-Kelner S.; Vishnevskia-Dai V.; Skaliter R.; Einat P.; Faerman A.; Feinstein E.; Shoshani S. (2004) "Inhibition of Oxygen-Induced Reinopethy in RTP801-Deficient Mice." *Investigative Ophthalmology & Visual Science*, vol. 45, No. 10, pp. 3796-3805.

Schwarzer R.; Tondera D.; Arnold W.; Giese K.; Klippel A.; Kaufmann J. (2005) "REDD1 integrates hypoxia-mediated survival signaling downstream of phosphatidylinositol 3-kinase." *Oncogene* 24: 1138-1149.

Nuttall A.L. (1999) "Sound-Induced Cochlear Ischemia/Hypoxia as a Mechanism of Hearing Loss." *Noise & Health* 5: 17-31.

Holley M.C. (2005) "The auditory system, hearing loss and potential targets for drug development." *Drug Discovery Today*, vol. 10, No. 19, pp. 1269-1282.

Amarzguioui M, Holen T, Babaie E, Prydz H. (2003) "Tolerance for mutations and chemical modifications in a siRNA." *Nucleic Acids Res.* 31(2):589 -95.

Barik, Sailen (2005). "Silence of the Transcripts; RNA Interference in Medicine," *J. Mol. Med.* 83:764-773.

Bartel, David P. et al. (2004). "MicroRNAs: Genomics Biogenesis, Mechanism, and Function," *Cell*, 116:281-297.

Bernstein, Emily et al. (2001). "Role for a Bidentate Ribonuclease in the Initiation Step of RNA Interference," *Nature*, 409:363-366.

Bitko, Vira et al. (2004). "Inhibition of Respiratory Viruses by Nasally Administered siRNA," *Nature Medicine*, 11(1):50-55.

Brafman, A. et al., (2004) "Inhibition of Oxygen-Induced Retinopathy in RTP801 -Deficient Mice," *Investigative Ophthalmology & Visual Science*, 45(10): 3796-3805.

Braasch DA, et al. (2003) "RNA interference in mammalian cells by chemically-modified RNA," *Biochemistry*, 42:7967-7975.

Brugarolas, J. et al., (2004) "Regulation of mTOR Function in Response to Hypoxia by REDD1 and The TSC1/TSC2 Tumor Suppressor Complex," *Genes & Development*, 18: 2893-2904.

Brummelkamp, Thijn R. et al. (2002). "A System for Stable Expression of Short Interfering RNAs in Mammalian Cells," *Science*, 296: 550-553.

Caplen, Natasha J. et al. (2001). "Specific Inhibition of Gene Expression by Small Double-Stranded RNAs in Invertebrate Vertebrate Systems," *PNAS*, 98(17):9742-9747.

Chakraborty, Chiranjib (2007) "Potentiality of Small Interfering RNAs (siRNA) as Recent Therapeutic Targets for Gene-Silencing," *Current Drug Targets*, 8:469-482.

Chalk, Alistair M. et al., (2004). "Improved and Automated Prediction of Effective siRNA," *Biochemical and Biophysical Research Communications*, 319:264-274.

Elbashir, Sayda M. et al. (2000). "RNA Interference is Mediated by 21- and 22-nucleotide RNAs," *Genes & Development*, 15:188-200.

Elbashir, Sayda M. et al. (2001). "Duplexes of 21-nucleotide RNAs mediated RNA interference in cultured mammalian cells," *Nature*, 411:494-498.

Elbashir SM, Martinez J, Patkaniowska A, Lendeckel W, Tuschl T. (2001) "Functional anatomy of siRNAs for mediating efficient RNAi in *Drosophila melanogaster* embryo lysate," *EMBO J.* 20(23):6877-88.

Fire, Andrew et al., (1998). "Potent and Specific Genetic Interference by Double-stranded RNA in *Caenorhabditis elegans*," *Nature*, 391:806-811.

Ellisen, L. et al., (2002) "REDD1, A Developmentally Regulated Transcriptional Target of p63 and p53, Links p63 to Regulation of Reactive Oxygen Species," *Molecular Cell*, 10: 995-1005.

Frolov, A. et al., (2003) "Response Markers and The Molecular Mechanisms of Action of Gleevec in Gastrointestinal Stromal Tumors," *Molecular Cancer Therapeutics*, 2: 699-709.

Kim, J. et al., (2003) "Identification of Amyloid β-peptide Responsive Genes by cDNA Microarray Technology: Involvement RTP801 in Amyloid β-peptide Toxicity," *Experimental and Molecular Medicine*, 35(5): 403-411.

Lal, A. et al., (2001) "Transcriptional Response to Hypoxia in Human Tumors," *Journal of the National Cancer Institute*, 93(17): 1337-1343.

Lee, Youngtae et al., (2003). "The nuclear RNase III Drosha initiates microRNA processing," *Nature*, 425:415-419.

Lee, M. et al., (2004) "Sp1-Dependant Regulation of the RTP801 Promoter and Its Application to Hypoxia-Inducible VEGF Plasmid for Ischemic Disease," *Pharmaceutical Research*, 21(5): 736-741.

Levenkova, Natasha et al., (2004). "Gene specific siRNA selector," *Bioinformatics*, 20(3)430-432.

Lewis MI, et al. (2002) "Apoptosis as a potential mechanism of muscle cachexia in chronic obstructive pulmonary disease." *Am. J. Respir. Crit. Care Med.* 166:434-435.

McManus, Michael T. and Sharp, Phillip A., (2002). "Gene Silencing in Mammals by Small Interfering RNAs," *Genetics*, 3:737-747.

Prakash TP, Allerson CR, Dande P, Vickers TA, Sioufi N, Jarres R, Baker BF, Swayze EE, Griffey RH, Bhat B. (2005) "Positional effect of chemical modifications on short interference RNA activity in mammalian cells," *J Med Chem.* 48(13) :4247-53.

Rangasamy, R. et al., (2004) "Genetic Ablation of Nrf2 Enhances Susceptibility to Cigarette Smoke-Induced Emphysema in Mice," *The Journal of Clinical Investigation*, 114(9) : 1248-1259.

Reich, S. et al., (2003). "Small interfering RNA (siRNA) targeting VEGF effectively inhibits ocular neovascularization in a mouse model," *Molecular Vision*, 9:210-216.

Reiling, J. and Hafen, E., (2004) "The Hypoxia-Induced Paralogs Scylla and Charybdis Inhibit Growth by Down-Regulating S6K Activity Upstream of TSC in *Drosophila*," *Genes & Development*, 18:2879-2892.

Richard, E. et al., (2000) "Nonhypoxic Pathway Mediates the Induction of Hypoxia-Inducible Factor 1α in Vascular Smooth Muscle Cells," *The Journal of Biological Chemistry*, 275(35) :26765 -26771.

Schwarzer, R. et al., (2005) "REDD1 Integrates Hypoxia- Mediated Survival Signaling Downstream of Phosphatidylinositol 3-kinase," *Oncogene*, 24: 1138-1149.

Sioud, Moudly and Leirdal, Marianne, (2004). "Potential Design Rules and Enzymatic Synthesis of siRNAs," *Methods in Molecular Biology*, 252:457-468.

Strausberg, R. et al., (2002) "Generation and Initial Analysis of More Than 15,000 Full-Length Human and Mouse cDNA Sequences," *Proceedings of the National Academy of Sciences of the United States of America*, 99(26): 16899-16903.

Suter M, et al. (2000) "Age-related macular degeneration," *J. Biol. Chem.* 275(50):39625-39630.

Tolentino, Michael J. et al., (2004). "Intravitreal Injection of Vascular Endothelial Growth Factor Small Interfering RNA Inhibits Growth and Leakage in a Nonhuman Primate, Laser-induced Model of

(56) References Cited

OTHER PUBLICATIONS

Choroidal Neovascularization," *Retina, The Journal of Retinal and Vitreous Diseases*, 24(1):132-138.
Tuder R, et al. (2003) "Apoptosis and Emphysema: The Missing Link," *Am. J. Respir. Cell. Mol. Biol.* 28:551-554.
Ui-Tei, Kumiko et al., (2004). "Guidelines for the selection of highly effective siRNA sequences for mammalian and chick RNA interference," *Nucleic Acids Research*, 32(3):936-948.
Vignola A, et al. (1999) "Evaluation of apoptosis of eosinophils, macrophages, and T lymphocytes in mucosal biopsy specimens of patients with asthma and chronic bronchitis," *J. Allergy Clin. Immunol.* 103:563-573.
Wang, J. and Ortiz de Montellano, P., (2003) "The Binding Sites on Human Heme Oxygenase-1 for Cytochrome P450 Reductase and Biliverdin Reductase," *The American Society for Biochemistry and Molecular Biology, Inc.*, p. 1-38.
Non-final Official Action issued on Aug. 22, 2007, in connection with U.S. Appl. No. 11/207,119, filed Aug. 16, 2005.
Non-final Official Action issued on Feb. 26, 2008, in connection with U.S. Appl. No. 11/207,119, filed Aug. 16, 2005.
Patented claims granted in connection with U.S. Appl. No. 11/207,119, filed Aug. 16, 2005, now U.S. Patent No. 7,741,299, issued Jun. 22, 2010.
Non-final Official Action issued on Apr. 19, 2011, in connection with U.S. Appl. No. 12/736,230, filed Oct. 20, 2010.
Non-final Official Action issued on Jul. 30, 2009, in connection with U.S. Appl. No. 12/072,392, filed Feb. 26, 2008.
Patented claims granted in connection with U.S. Appl. No. 12/072,392, filed Feb. 26 2008, now U.S. Patent No. 7,872,119, issued Oct. 30, 2008.
Non-final Official Action issued on Jun. 19, 2009, in connection with U.S. Appl. No. 11/803,130, filed May 11, 2007.
Patented claims granted in connection with U.S. Appl. No. 11/803,130, filed May 11, 2007, now U.S. Patent No. 7,723,052, issued May 25, 2010.
Non-final Official Action issued on Jan. 11, 2011, in connection with U.S. Appl. No. 12/800,738, filed May 21, 2010.
Sep. 30, 2004 Non-Final Office Action issued in connection with U.S. Appl. No. 10/091,333.
Dec. 28, 2004 Non-Final Office Action issued in connection with U.S. Appl. No. 10/091,333.
Jun. 15, 2005 Final Office Action issued in connection with U.S. Appl. No. 10/091,333.
Mar. 8, 2006 Non-Final Office Action issued in connection with U.S. Appl. No. 10/091,333.
Nov. 14, 2006 Final Office Action issued in connection with U.S. Appl. No. 10/091,333.
Jul. 6, 2007 Non-Final Office Action issued in connection with U.S. Appl. No. 10/091,333.
Feb. 13, 2008 Non-Final Office Action issued in connection with U.S. Appl. No. 10/091,333.
May 1, 2008 Non-Final Office Action issued in connection with U.S. Appl. No. 11/655,610.
Oct. 2, 2008 Non-Final Office Action issued in connection with U.S. Appl. No. 11/655,610.
Apr. 17, 2009 Notice of Allowability in connection with U.S. Appl. No. 11/655,610.
International Search Report issued by the International Searching Authority (ISA/US) on Aug. 25, 2008 in connection with International Application No. PCT/US07/11266.
Extended European Search Report issued Dec. 7, 2010 in connection with European Patent Application No. 07718224.4.
Granted claims for United Kingdom Patent No. GB 2450840 B, published Dec. 29, 2010.
Office Action issued by the Canadian Intellectual Property Office on Dec. 9, 2010 in connection with Canadian Patent Application No. 2,577,423.
Office Action issued by the Canadian Intellectual Property Office on Dec. 14, 2010 in connection with Canadian Patent Application No. 2,635,723.
Communication pursuant to Article 94(3) EPC issued by the European Patent Office on Dec. 15, 2010 in connection with European Patent Application No. 05786796.2.
Communication pursuant to Article 94(3) EPC issued by the European Patent Office on Sep. 21, 2009 in connection with European Patent Application No. 05786796.2.
Extended European Search Report issued by the European Patent Office on Apr. 29, 2011 in connection with European Patent Application No. 09722841.5.
Written Opinion issued on May 5, 2010 in connection with Singapore Patent Application No. 200805357-1.
First Examination Report issued by the Indian Patent Office on Jul. 15, 2010 in connection with Indian Patent Application No. 1967/DELNP/2007.
Office Action issued by the Argentinean Patent Office on Feb. 26, 2010 in connection with Argentinean Patent Application No. P20070100243.
Office Action issued by the Ukrainian Patent Office on Mar. 2, 2009 in connection with Ukrainian Patent Application No. 200701610, now Ukrainian Patent No. 92465.
Granted claims for Ukrainian Patent No. 92465, issued Nov. 10, 2010.
Office Action issued by the Patent Office of the Russian Federation on Nov. 27, 2008 in connection with Russian Patent Application No. 2008129801.
Office Action issued by the Patent Office of the Russian Federation on Dec. 2, 2009 in connection with Russian Patent Application No. 2008129801.
Office Action issued by the Patent Office of the Russian Federation on May 5, 2010 in connection with Russian Patent Application No. 2008129801.
Office Action issued by the Patent Office of the Russian Federation on Aug. 31, 2010 in connection with Russian Patent Application No. 2008129801.
First Examiner's Report issued by the Chilean Patent Office on Jun. 19, 2009 in connection with Chilean Patent Application No. 141-07.
Second Examiner's Report issued by the Chilean Patent Office on May 11, 2010 in connection with Chilean Patent Application No. 141-07.
First Examiner's Report issued by the Australian Patent Office on Feb. 25, 2010 in connection with Australian Patent Application No. 2005277508.
First Office Action issued by the State Intellectual Property Office of the Peoples Republic of China on Jun. 2, 2010 in connection with Chinese Patent Application No. 200780002708.9.
Examination Report issued by the Intellectual Property Office of New Zealand on May 7, 2010 in connection with New Zealand Patent Application No. 569552.
Office Action issued by the Intellectual Property Office of the Philippines on Jan. 13, 2011 in connection with Philippines Patent Application No. 1-2007-500391.
Office Action issued by the Uzbekistan Patent Office on Oct. 14, 2009 in connection with Uzbekistan Patent No. IAP 20070060.
Office Action issued by the Uzbekistan Patent Office on Sep. 14, 2010 in connection with Uzbekistan Patent Application No. IAP 20070060.
Decision to Grant a Patent for Invention including granted claims issued in connection with Uzbekistan Patent Application No. IAP 20070060.
Examination Report issued by the Intellectual Property Office of New Zealand on Jan. 15, 2010 in connection with New Zealand Patent Application No. 553162.
Claims granted in connection with New Zealand Patent Application No. 553162, now New Zealand Patent No. 553162, granted Jul. 8, 2010.
Notice of Preliminary Rejection issued by the Korean Patent Office on Oct. 25, 2011 in connection with Korean Patent Application No. 2009-7022383.
Notice of Reasons for Rejection issued by the Japanese Patent Office on Sep. 15, 2009 in connection with Japanese Patent Application No. 2007-527969.
Claims granted in connection with Japanese Patent Application No. 2007-527969, now Japanese Patent No. 4468949.

(56) References Cited

OTHER PUBLICATIONS

Notification of the Second Office Action issued by the Patent Office of the Peoples Republic of China on Feb. 5, 2010 in connection with Chinese Patent Application No. 200580034968.5.
Intelnational Search Report issued by the International Searching Authority (ISA/US) on Jan. 24, 2008 in connection with International Application No. PCT/US07/01468.
Written Opinion of the International Searching Authority (ISA/US) issued on Jan. 24, 2008 in connection with International Application No. PCT/US07/01468.
European Patent No. EP 1009753 B1, granted Apr. 20, 2005.
Japanese Patent Publication No. JP 2003-259877 published Sep. 16, 2003.
Jan. 29, 2009 Official Action in European Patent application No. 05786796.2.
Dec. 3, 2008 Office Action in connection with Eurasian Application No. 200700333/28.
Mar. 2, 2009 Official Action in connection with Ukrainian Patent Application No. 200701610.
Jun. 24, 2008 Official Action in connection with New Zealand Patent Application No. 553162.
Feb. 27, 2009 Search Report in connection with Georgian Patent Application No. 76400.
May 7, 2009 Office Action in connection with Japanese Patent Application No. 2007-527969.
Jan. 8, 2008 Notice of Preliminary Rejection in connection with Korean Patent Application No. 2007-7006061.
Mar. 18, 2009 Notice of Final Rejection in connection with Korean Patent Application No. 2007-7006061.
Mar. 18, 2009 Notice of Dismissal of Amendment in connection with Korean Patent Application No. 2007-7006061.
May 27, 2009 Office Action in connection with Uzbekistani Patent Application No. 2007-0060.
Jul. 9, 2009 (?) Official Action in connection with Ukrainian Patent Application No. 200701610.
Jun. 5, 2009 Office Action in connection with Chinese Patent Application No. 200580034968.5.
Jul. 18, 2011 Notice of Allowance and Fee(s) Due in connection with U.S. Appl. No. 11/655,636.

Figure 1

Human RTP801 polynucleotide (SEQ ID NO:1)

```
TTTGGCCCTC GAGGCCAAGA ATTCGGCACG AGGGGGGGAG GTGCGAGCGT GGACCTGGGA   60
CGGGTCTGGG CGGCTCTCGG TGGTTGGCAC GGGTTCGCAC ACCCATTCAA GCGGCAGGAC  120
GCACTTGTCT TAGCAGTTCT CGCTGACCGC GCTAGCTGCG GCTTCTACGC TCCGGCACTC  180
TGAGTTCATC AGCAAACGCC CTGGCGTCTG TCCTCACCAT GCCTAGCCTT TGGGACCGCT  240
TCTCGTCGTC GTCCACCTCC TCTTCGCCCT CGTCCTTGCC CCGAACTCCC ACCCCAGATC  300
GGCCGCCGCG CTCAGCCTGG GGGTCGGCGA CCCGGGAGGA GGGGTTTGAC CGCTCCACGA  360
GCCTGGAGAG CTCGGACTGC GAGTCCCTGG ACAGCAGCAA CAGTGGCTTC GGGCCGGAGG  420
AAGACACGGC TTACCTGGAT GGGGTGTCGT TGCCCGACTT CGAGCTGCTC AGTGACCCTG  480
AGGATGAACA CTTGTGTGCC AACCTGATGC AGCTGCTGCA GGAGAGCCTG GCCCAGGCGC  540
GGCTGGGCTC TCGACGCCCT GCGCGCCTGC TGATGCCTAG CCAGTTGGTA AGCCAGGTGG  600
GCAAAGAACT ACTGCGCCTG GCCTACAGCG AGCCGTGCGG CCTGCGGGGG GCGCTGCTGG  660
ACGTCTGCGT GGAGCAGGGC AAGAGCTGCC ACAGCGTGGG CCAGCTGGCA CTCGACCCCA  720
GCCTGGTGCC CACCTTCCAG CTGACCCTCG TGCTGCGCCT GGACTCACGA CTCTGGCCCA  780
AGATCCAGGG GCTGTTTAGC TCCGCCAACT CTCCCTTCCT CCCTGGCTTC AGCCAGTCCC  840
TGACGCTGAG CACTGGCTTC CGAGTCATCA AGAAGAAGCT GTACAGCTCG GAACAGCTGC  900
TCATTGAGGA GTGTTGAACT TCAACCTGAG GGGCCGACA GTGCCCTCCA AGACAGAGAC  960
GACTGAACTT TTGGGGTGGA GACTAGAGGC AGGAGCTGAG GGACTGATTC CTGTGGTTGG 1020
AAAACTGAGG CAGCCACCTA AGGTGGAGGT GGGGGAATAG TGTTTCCCAG GAAGCTCATT 1080
GAGTTGTGTG CGGGTGGCTG TGCATTGGGG ACACATACCC CTCAGTACTG TAGCATGAAA 1140
CAAAGGCTTA GGGGCCAACA AGGCTTCCAG CTGGATGTGT GTGTAGCATG TACCTTATTA 1200
TTTTTGTTAC TGACAGTTAA CAGTGGTGTG ACATCCAGAG AGCAGCTGGG CTGCTCCCGC 1260
CCCAGCCCGG CCCAGGGTGA AGGAAGAGGC ACGTGCTCCT CAGAGCAGCC GGAGGGAGGG 1320
GGGAGGTCGG AGGTCGTGGA GGTGGTTTGT GTATCTTACT GGTCTGAAGG GACCAAGTGT 1380
GTTTGTTGTT TGTTTTGTAT CTTGTTTTTC TGATCGGAGC ATCACTACTG ACCTGTTGTA 1440
GGCAGCTATC TTACAGACGC ATGAATGTAA GAGTAGGAAG GGGTGGGTGT CAGGGATCAC 1500
TTGGGATCTT TGACACTTGA AAAATTACAC CTGGCAGCTG CGTTTAAGCC TTCCCCCATC 1560
GTGTACTGCA GAGTTGAGCT GGCAGGGGAG GGGCTGAGAG GGTGGGGGCT GGAACCCCTC 1620
CCCGGGAGGA GTGCCATCTG GGTCTTCCAT CTAGAACTGT TTACATGAAG ATAAGATACT 1680
CACTGTTCAT GAATACACTT GATGTTCAAG TATTAAGACC TATGCAATAT TTTTTACTTT 1740
TCTAATAAAC ATGTTTGTTA AAACAAAAAA AAAAAAAAAA AA 1782
```

Figure 2

Human RTP801 polypeptide (SEQ ID NO:2)

```
MPSLWDRFSS SSTSSSPSSL PRTPTPDRPP RSAWGSATRE EGFDRSTSLE 50
SSDCESLDSS NSGFGPEEDT AYLDGVSLPD PELLSDPEDE HLCANLMQLL 100
QESLAQARLG SRRPARLLMP SQLVSQVGKE LLRLAYSEPC GLRGALLDVC 150
VEQGKSCHSV GQLALDPSLV PTFQLTLVLR LDSRLWPKIQ GLFSSANSPF 200
LPGFSQSLTL STGPRVIKKK LYSSEQLLIE EC   232
```

Figure 4 Part I
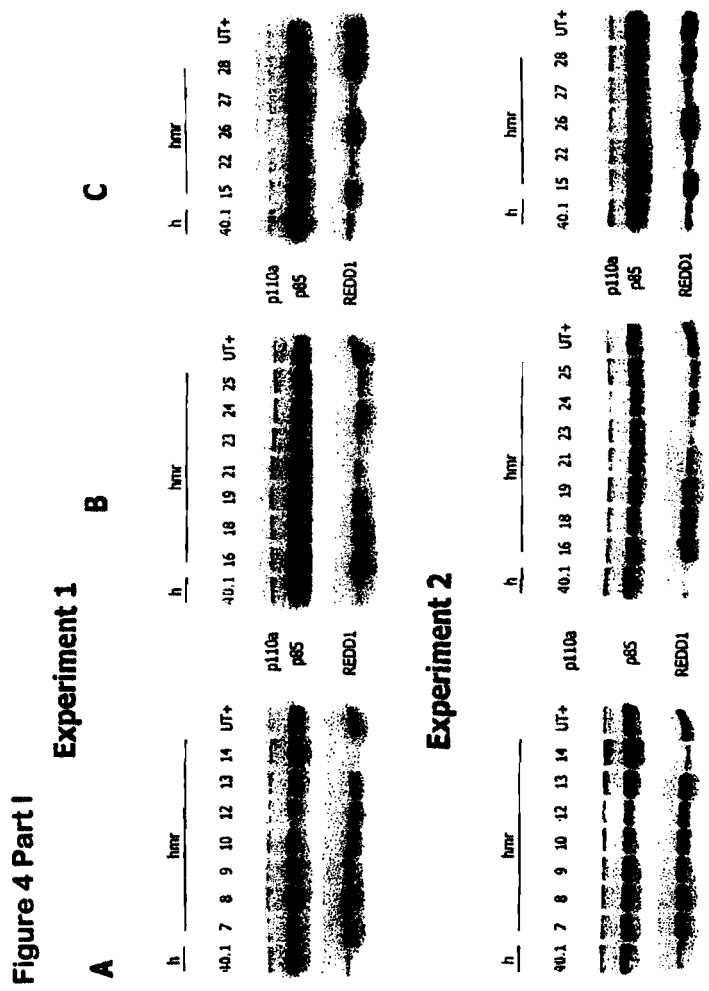

Figure 4 Part II
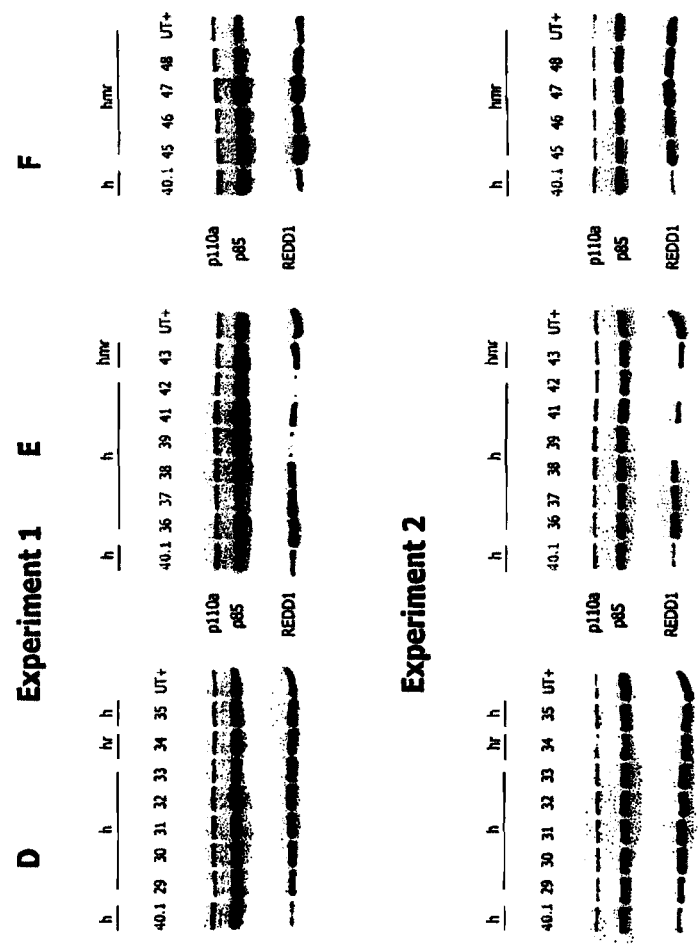

Figure 4 Part III
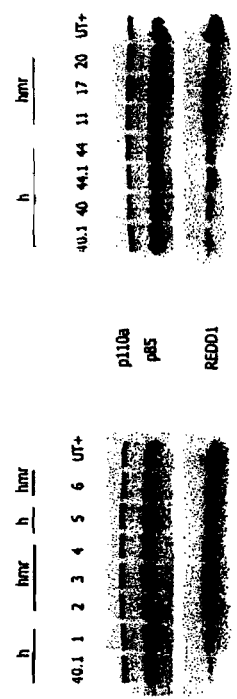
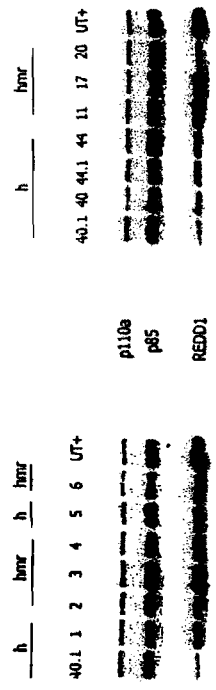

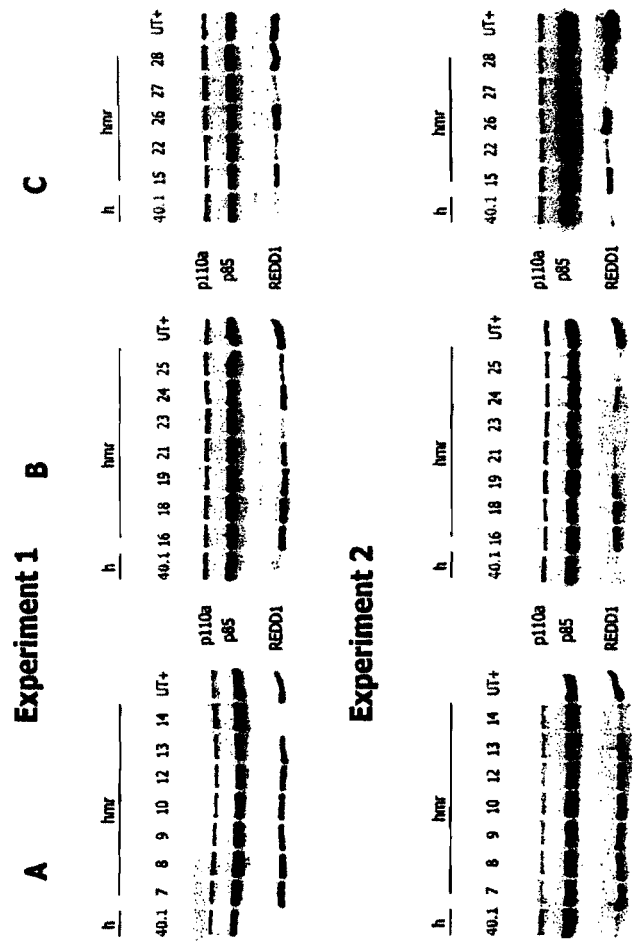
Figure 5 Part I

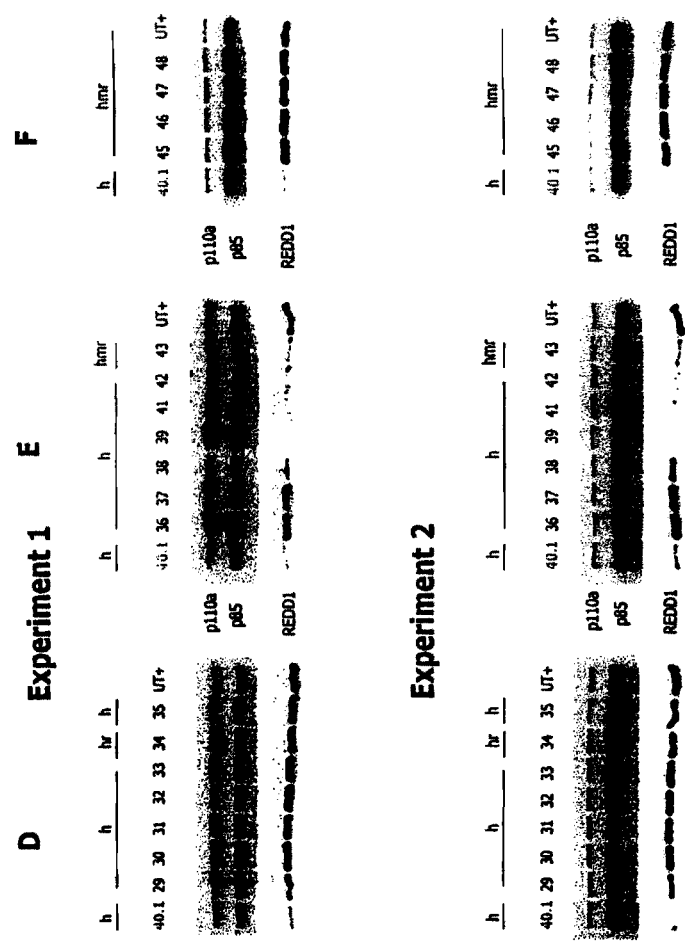
Figure 5 Part II

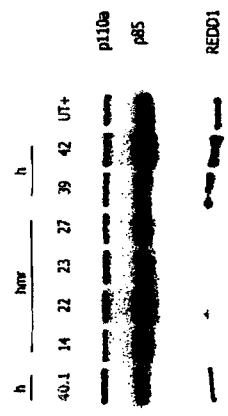
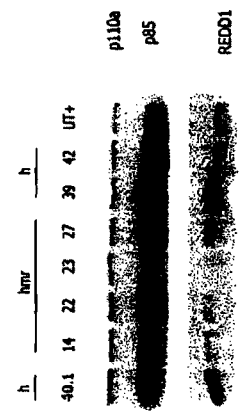
Figure 7

Blood vessel leakage in RTP801 KO mice as compared to control following CNV induction Reduction of CNV volume in response to RTP801 siRNA (REDD14) as compared to controls Reduction of RTP801 expression in the choroids of laser-treated monkeys in response to RTP801 siRNA as compared to a control, measured by Real - Time PCR Figure 11
Reduction of leakage in a non-primate CNV model in response to RTP801 siRNA as compared to a control
a)
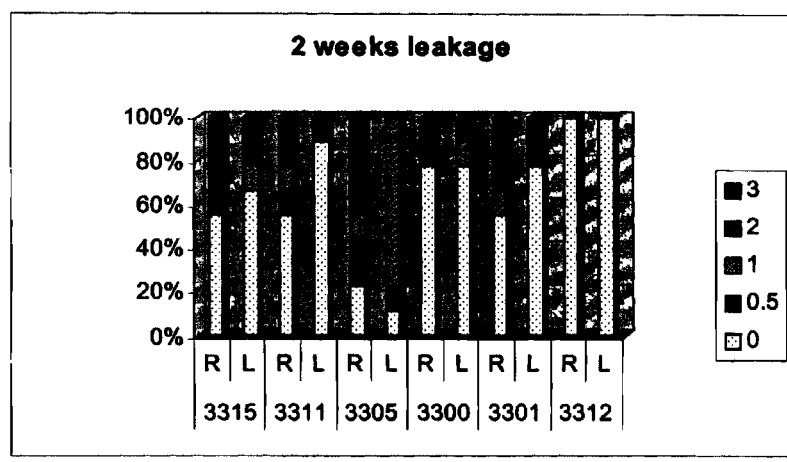
b)
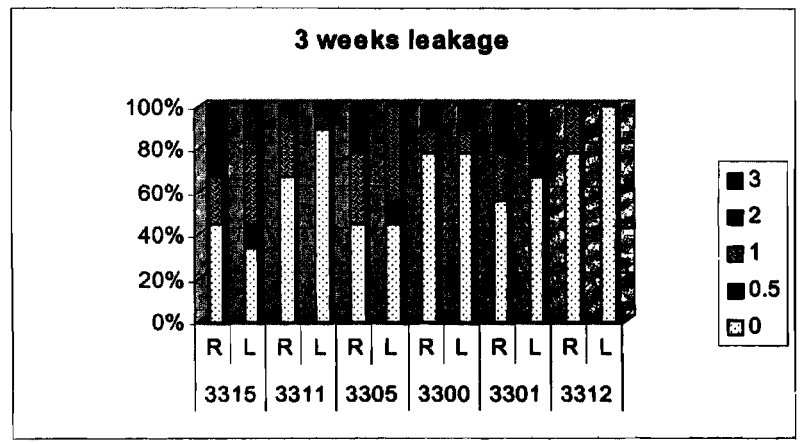

Figure 12
Reduction of neovascularization in a non-primate CNV model in response to RTP801 siRNA as compared to a control
a)
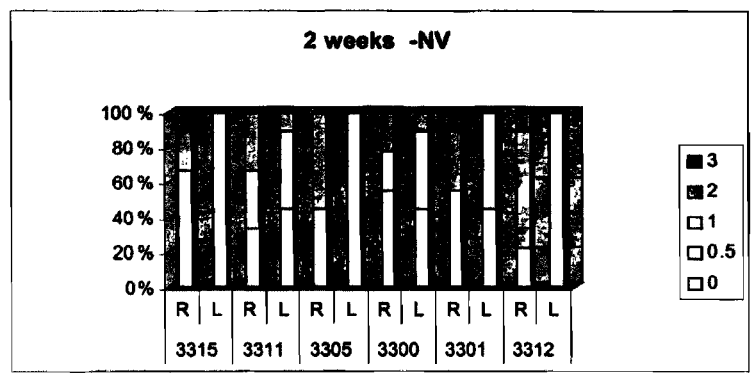
b)
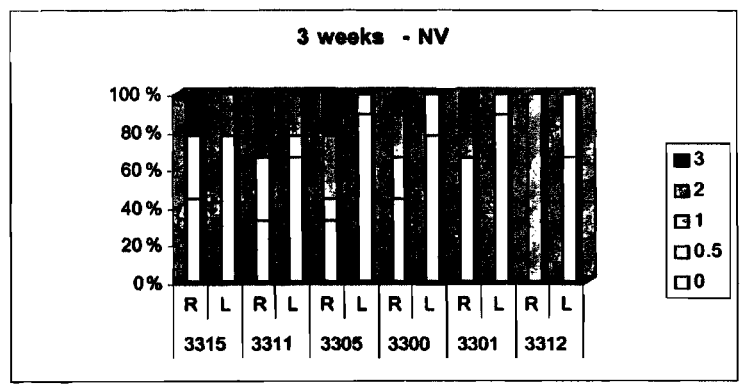

Figure 13
a)
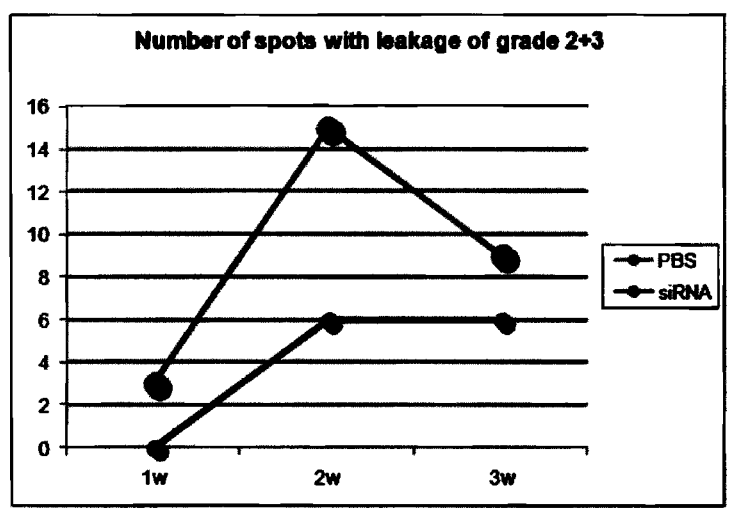
b)
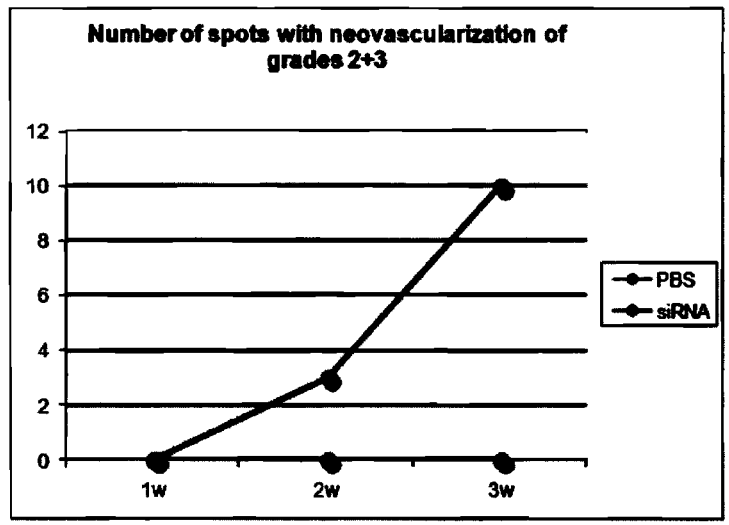

a.

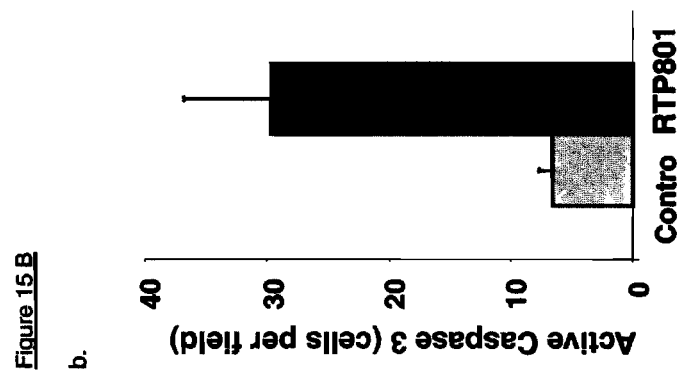
Figure 15 B b.

Figure 26
a)
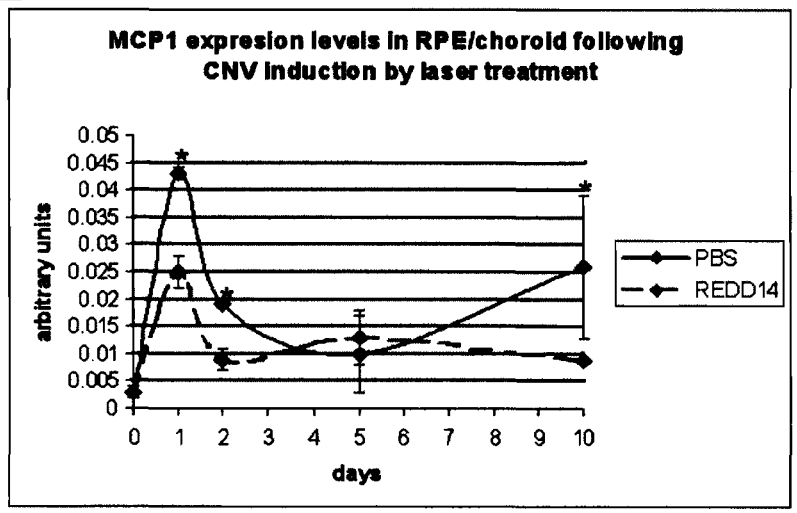
b)
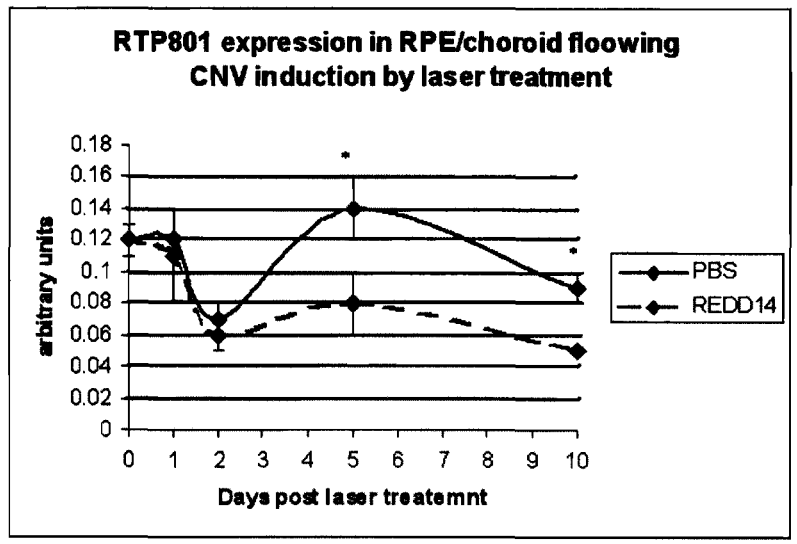

QPCR evaluation of anti RTP801 siRNA activity in HEK293 cells

SEQUENCE LISTING

<160> NUMBER OF SEQ ID NOS: 536

<210> SEQ ID NO 1
<211> LENGTH: 1782
<212> TYPE: DNA
<213> ORGANISM: Homo sapiens

<400> SEQUENCE: 1

```
tttggccctc gaggccaaga attcggcacg aggggggggag gtgcgagcgt ggacctggga      60
cgggtctggg cggctctcgg tggttggcac gggttcgcac acccattcaa gcggcaggac     120
gcacttgtct tagcagttct cgctgaccgc gctagctgcg gcttctacgc tccggcactc     180
tgagttcatc agcaaacgcc ctggcgtctg tcctcaccat gcctagcctt tgggaccgct     240
tctcgtcgtc gtccacctcc tcttcgccct cgtccttgcc ccgaactccc acccagatc      300 ggccgccgcg ctcagcctgg gggtcggcga cccgggagga ggggtttgac cgctccacga     360
gcctggagag ctcggactgc gagtccctgg acagcagcaa cagtggcttc gggccggagg     420
aagacacggc ttacctggat ggggtgtcgt tgcccgactt cgagctgctc agtgaccctg     480
aggatgaaca cttgtgtgcc aacctgatgc agctgctgca ggagagcctg gcccaggcgc     540
ggctgggctc tcgacgccct gcgcgcctgc tgatgcctag ccagttggta agccaggtgg     600
gcaaagaact actgcgcctg gcctacagcg agccgtgcgg cctgcggggg gcgctgctgg     660
```

```
acgtctgcgt ggagcagggc aagagctgcc acagcgtggg ccagctggca ctcgacccca    720
gcctggtgcc caccttccag ctgaccctcg tgctgcgcct ggactcacga ctctggccca    780
agatccaggg gctgtttagc tccgccaact ctcccttcct ccctggcttc agccagtccc    840
tgacgctgag cactggcttc cgagtcatca agaagaagct gtacagctcg aacagctgc     900 tcattgagga gtgttgaact tcaacctgag ggggccgaca gtgccctcca agacagagac    960
gactgaactt ttggggtgga gactagaggc aggagctgag ggactgattc ctgtggttgg   1020
aaaactgagg cagccaccta aggtggaggt gggggaatag tgtttcccag gaagctcatt   1080
gagttgtgtg cgggtggctg tgcattgggg acacataccc ctcagtactg tagcatgaaa   1140
caaaggctta ggggccaaca aggcttccag ctggatgtgt gtgtagcatg taccttatta   1200
tttttgttac tgacagttaa cagtggtgtg acatccagag agcagctggg ctgctcccgc   1260
cccagcccgg cccagggtga aggaagaggc acgtgctcct cagagcagcc ggagggaggg   1320
gggaggtcgg aggtcgtgga ggtggtttgt gtatcttact ggtctgaagg gaccaagtgt   1380
gtttgttgtt tgttttgtat cttgtttttc tgatcggagc atcactactg acctgttgta   1440
ggcagctatc ttacagacgc atgaatgtaa gagtaggaag gggtgggtgt cagggatcac   1500
ttgggatctt tgacacttga aaaattacac ctggcagctg cgtttaagcc ttcccccatc   1560
gtgtactgca gagttgagct ggcagggag gggctgagag ggtgggggct ggaacccctc    1620
cccgggagga gtgccatctg ggtcttccat ctagaactgt ttacatgaag ataagatact   1680
cactgttcat gaatacactt gatgttcaag tattaagacc tatgcaatat tttttacttt   1740
tctaataaac atgtttgtta aaacaaaaaa aaaaaaaaaa aa                      1782
```

<210> SEQ ID NO 2
<211> LENGTH: 232
<212> TYPE: PRT
<213> ORGANISM: Homo sapiens

<400> SEQUENCE: 2

```
Met Pro Ser Leu Trp Asp Arg Phe Ser Ser Ser Thr Ser Ser
1               5                   10                  15

Pro Ser Ser Leu Pro Arg Thr Pro Thr Pro Asp Arg Pro Arg Ser
            20                  25                  30

Ala Trp Gly Ser Ala Thr Arg Glu Gly Phe Asp Arg Ser Thr Ser
        35                  40                      45

Leu Glu Ser Ser Asp Cys Glu Ser Leu Asp Ser Asn Ser Gly Phe
    50                  55                  60

Gly Pro Glu Glu Asp Thr Ala Tyr Leu Asp Gly Val Ser Leu Pro Asp
65                  70                  75                  80

Phe Glu Leu Leu Ser Asp Pro Glu Asp Glu His Leu Cys Ala Asn Leu
                85                  90                  95

Met Gln Leu Leu Gln Glu Ser Leu Ala Gln Ala Arg Leu Gly Ser Arg
            100                 105                 110

Arg Pro Ala Arg Leu Leu Met Pro Ser Gln Leu Val Ser Gln Val Gly
        115                 120                 125

Lys Glu Leu Leu Arg Leu Ala Tyr Ser Glu Pro Cys Gly Leu Arg Gly
    130                 135                 140

Ala Leu Leu Asp Val Cys Val Glu Gln Gly Lys Ser Cys His Ser Val
145                 150                 155                 160

Gly Gln Leu Ala Leu Asp Pro Ser Leu Val Pro Thr Phe Gln Leu Thr
                165                 170                 175
```

```
Leu Val Leu Arg Leu Asp Ser Arg Leu Trp Pro Lys Ile Gln Gly Leu
            180                 185                 190

Phe Ser Ser Ala Asn Ser Pro Phe Leu Pro Gly Phe Ser Gln Ser Leu
            195                 200                 205

Thr Leu Ser Thr Gly Phe Arg Val Ile Lys Lys Lys Leu Tyr Ser Ser
        210                 215                 220

Glu Gln Leu Leu Ile Glu Glu Cys
225                 230

<210> SEQ ID NO 3
<211> LENGTH: 19
<212> TYPE: RNA
<213> ORGANISM: Artificial Sequence
<220> FEATURE:
<223> OTHER INFORMATION: Chemically synthesized

<400> SEQUENCE: 3
gcgcuagcug cggcuucua                                               19

<210> SEQ ID NO 4
<211> LENGTH: 19
<212> TYPE: RNA
<213> ORGANISM: Artificial Sequence
<220> FEATURE:
<223> OTHER INFORMATION: Chemically synthesized

<400> SEQUENCE: 4
cgagccugga gagcucgga                                               19

<210> SEQ ID NO 5
<211> LENGTH: 19
<212> TYPE: RNA
<213> ORGANISM: Artificial Sequence
<220> FEATURE:
<223> OTHER INFORMATION: Chemically synthesized

<400> SEQUENCE: 5
gagucccugg acagcagca                                               19

<210> SEQ ID NO 6
<211> LENGTH: 19
<212> TYPE: RNA
<213> ORGANISM: Artificial Sequence
<220> FEATURE:
<223> OTHER INFORMATION: Chemically synthesized

<400> SEQUENCE: 6
ccaaccugau gcagcugcu                                               19

<210> SEQ ID NO 7
<211> LENGTH: 19
<212> TYPE: RNA
<213> ORGANISM: Artificial Sequence
<220> FEATURE:
<223> OTHER INFORMATION: Chemically synthesized

<400> SEQUENCE: 7
cgugcugcgc cuggacuca                                               19

<210> SEQ ID NO 8
<211> LENGTH: 19
<212> TYPE: RNA
<213> ORGANISM: Artificial Sequence
<220> FEATURE:
```

<223> OTHER INFORMATION: Chemically synthesized

<400> SEQUENCE: 8
ucgcugaccg cgcuagcug                                                    19

<210> SEQ ID NO 9
<211> LENGTH: 19
<212> TYPE: RNA
<213> ORGANISM: Artificial Sequence
<220> FEATURE:
<223> OTHER INFORMATION: Chemically synthesized

<400> SEQUENCE: 9
cugaccgcgc uagcugcgg                                                    19

<210> SEQ ID NO 10
<211> LENGTH: 19
<212> TYPE: RNA
<213> ORGANISM: Artificial Sequence
<220> FEATURE:
<223> OTHER INFORMATION: Chemically synthesized

<400> SEQUENCE: 10
accgcgcuag cugcggcuu                                                    19

<210> SEQ ID NO 11
<211> LENGTH: 19
<212> TYPE: RNA
<213> ORGANISM: Artificial Sequence
<220> FEATURE:
<223> OTHER INFORMATION: Chemically synthesized

<400> SEQUENCE: 11
agccuggaga gcucggacu                                                    19

<210> SEQ ID NO 12
<211> LENGTH: 19
<212> TYPE: RNA
<213> ORGANISM: Artificial Sequence
<220> FEATURE:
<223> OTHER INFORMATION: Chemically synthesized

<400> SEQUENCE: 12
ccuggagagc ucggacugc                                                    19

<210> SEQ ID NO 13
<211> LENGTH: 19
<212> TYPE: RNA
<213> ORGANISM: Artificial Sequence
<220> FEATURE:
<223> OTHER INFORMATION: Chemically synthesized

<400> SEQUENCE: 13
ucccuggaca gcagcaaca                                                    19

<210> SEQ ID NO 14
<211> LENGTH: 19
<212> TYPE: RNA
<213> ORGANISM: Artificial Sequence
<220> FEATURE:
<223> OTHER INFORMATION: Chemically synthesized

<400> SEQUENCE: 14
gacagcagca acaguggcu                                                    19

```
<210> SEQ ID NO 15
<211> LENGTH: 19
<212> TYPE: RNA
<213> ORGANISM: Artificial Sequence
<220> FEATURE:
<223> OTHER INFORMATION: Chemically synthesized

<400> SEQUENCE: 15
acagcagcaa caguggcuu                                                    19

<210> SEQ ID NO 16
<211> LENGTH: 19
<212> TYPE: RNA
<213> ORGANISM: Artificial Sequence
<220> FEATURE:
<223> OTHER INFORMATION: Chemically synthesized

<400> SEQUENCE: 16
gugccaaccu gaugcagcu                                                    19

<210> SEQ ID NO 17
<211> LENGTH: 19
<212> TYPE: RNA
<213> ORGANISM: Artificial Sequence
<220> FEATURE:
<223> OTHER INFORMATION: Chemically synthesized

<400> SEQUENCE: 17
accugaugca gcugcugca                                                    19

<210> SEQ ID NO 18
<211> LENGTH: 19
<212> TYPE: RNA
<213> ORGANISM: Artificial Sequence
<220> FEATURE:
<223> OTHER INFORMATION: Chemically synthesized

<400> SEQUENCE: 18
augcagcugc ugcaggaga                                                    19

<210> SEQ ID NO 19
<211> LENGTH: 19
<212> TYPE: RNA
<213> ORGANISM: Artificial Sequence
<220> FEATURE:
<223> OTHER INFORMATION: Chemically synthesized

<400> SEQUENCE: 19
agccgugcgg ccugcgggg                                                    19

<210> SEQ ID NO 20
<211> LENGTH: 19
<212> TYPE: RNA
<213> ORGANISM: Artificial Sequence
<220> FEATURE:
<223> OTHER INFORMATION: Chemically synthesized

<400> SEQUENCE: 20
cucuggccca agauccagg                                                    19

<210> SEQ ID NO 21
<211> LENGTH: 19
<212> TYPE: RNA
<213> ORGANISM: Artificial Sequence
<220> FEATURE:
<223> OTHER INFORMATION: Chemically synthesized
```

```
<400> SEQUENCE: 21
cagccagucc cugacgcug                                                19

<210> SEQ ID NO 22
<211> LENGTH: 19
<212> TYPE: RNA
<213> ORGANISM: Artificial Sequence
<220> FEATURE:
<223> OTHER INFORMATION: Chemically synthesized

<400> SEQUENCE: 22 cccucagua cuguagcau                                                 19

<210> SEQ ID NO 23
<211> LENGTH: 19
<212> TYPE: RNA
<213> ORGANISM: Artificial Sequence
<220> FEATURE:
<223> OTHER INFORMATION: Chemically synthesized

<400> SEQUENCE: 23
aggcagcuau cuuacagac                                                19

<210> SEQ ID NO 24
<211> LENGTH: 19
<212> TYPE: RNA
<213> ORGANISM: Artificial Sequence
<220> FEATURE:
<223> OTHER INFORMATION: Chemically synthesized

<400> SEQUENCE: 24
cugggucuuc caucuagaa                                                19

<210> SEQ ID NO 25
<211> LENGTH: 19
<212> TYPE: RNA
<213> ORGANISM: Artificial Sequence
<220> FEATURE:
<223> OTHER INFORMATION: Chemically synthesized

<400> SEQUENCE: 25
gaauacacuu gauguucaa                                                19

<210> SEQ ID NO 26
<211> LENGTH: 19
<212> TYPE: RNA
<213> ORGANISM: Artificial Sequence
<220> FEATURE:
<223> OTHER INFORMATION: Chemically synthesized

<400> SEQUENCE: 26
uaagaccuau gcaauauuu                                                19

<210> SEQ ID NO 27
<211> LENGTH: 19
<212> TYPE: RNA
<213> ORGANISM: Artificial Sequence
<220> FEATURE:
<223> OTHER INFORMATION: Chemically synthesized

<400> SEQUENCE: 27
agaccuaugc aauauuuuu                                                19

<210> SEQ ID NO 28
<211> LENGTH: 19
```

```
<212> TYPE: RNA
<213> ORGANISM: Artificial Sequence
<220> FEATURE:
<223> OTHER INFORMATION: Chemically synthesized

<400> SEQUENCE: 28
gcucggacug cgagucccu                                              19

<210> SEQ ID NO 29
<211> LENGTH: 19
<212> TYPE: RNA
<213> ORGANISM: Artificial Sequence
<220> FEATURE:
<223> OTHER INFORMATION: Chemically synthesized

<400> SEQUENCE: 29
uacacuugau guucaagua                                              19

<210> SEQ ID NO 30
<211> LENGTH: 19
<212> TYPE: RNA
<213> ORGANISM: Artificial Sequence
<220> FEATURE:
<223> OTHER INFORMATION: Chemically synthesized

<400> SEQUENCE: 30
uuuucuaaua aacauguuu                                              19

<210> SEQ ID NO 31
<211> LENGTH: 19
<212> TYPE: RNA
<213> ORGANISM: Artificial Sequence
<220> FEATURE:
<223> OTHER INFORMATION: Chemically synthesized

<400> SEQUENCE: 31
cgcacuuguc uuagcaguu                                              19

<210> SEQ ID NO 32
<211> LENGTH: 19
<212> TYPE: RNA
<213> ORGANISM: Artificial Sequence
<220> FEATURE:
<223> OTHER INFORMATION: Chemically synthesized

<400> SEQUENCE: 32
gaccgcuucu cgucgucgu                                              19

<210> SEQ ID NO 33
<211> LENGTH: 19
<212> TYPE: RNA
<213> ORGANISM: Artificial Sequence
<220> FEATURE:
<223> OTHER INFORMATION: Chemically synthesized

<400> SEQUENCE: 33
ccggaggaag acacggcuu                                              19

<210> SEQ ID NO 34
<211> LENGTH: 19
<212> TYPE: RNA
<213> ORGANISM: Artificial Sequence
<220> FEATURE:
<223> OTHER INFORMATION: Chemically synthesized

<400> SEQUENCE: 34
```
gacccugagg augaacacu				19

<210> SEQ ID NO 35
<211> LENGTH: 19
<212> TYPE: RNA
<213> ORGANISM: Artificial Sequence
<220> FEATURE:
<223> OTHER INFORMATION: Chemically synthesized

<400> SEQUENCE: 35
gcugggcucu cgacgcccu				19

<210> SEQ ID NO 36
<211> LENGTH: 19
<212> TYPE: RNA
<213> ORGANISM: Artificial Sequence
<220> FEATURE:
<223> OTHER INFORMATION: Chemically synthesized

<400> SEQUENCE: 36
gcccugcgcg ccugcugau				19

<210> SEQ ID NO 37
<211> LENGTH: 19
<212> TYPE: RNA
<213> ORGANISM: Artificial Sequence
<220> FEATURE:
<223> OTHER INFORMATION: Chemically synthesized

<400> SEQUENCE: 37
gccagguggg caaagaacu				19

<210> SEQ ID NO 38
<211> LENGTH: 19
<212> TYPE: RNA
<213> ORGANISM: Artificial Sequence
<220> FEATURE:
<223> OTHER INFORMATION: Chemically synthesized

<400> SEQUENCE: 38
cuggccuaca gcgagccgu				19

<210> SEQ ID NO 39
<211> LENGTH: 19
<212> TYPE: RNA
<213> ORGANISM: Artificial Sequence
<220> FEATURE:
<223> OTHER INFORMATION: Chemically synthesized

<400> SEQUENCE: 39 gggggggcgcu gcuggacgu				19

<210> SEQ ID NO 40
<211> LENGTH: 19
<212> TYPE: RNA
<213> ORGANISM: Artificial Sequence
<220> FEATURE:
<223> OTHER INFORMATION: Chemically synthesized

<400> SEQUENCE: 40
gcacuggcuu ccgagucau				19

<210> SEQ ID NO 41
<211> LENGTH: 19
<212> TYPE: RNA
<213> ORGANISM: Artificial Sequence

```
<220> FEATURE:
<223> OTHER INFORMATION: Chemically synthesized

<400> SEQUENCE: 41
ccaggaagcu cauugaguu                                          19

<210> SEQ ID NO 42
<211> LENGTH: 19
<212> TYPE: RNA
<213> ORGANISM: Artificial Sequence
<220> FEATURE:
<223> OTHER INFORMATION: Chemically synthesized

<400> SEQUENCE: 42
cguguacugc agaguugag                                          19

<210> SEQ ID NO 43
<211> LENGTH: 19
<212> TYPE: RNA
<213> ORGANISM: Artificial Sequence
<220> FEATURE:
<223> OTHER INFORMATION: Chemically synthesized

<400> SEQUENCE: 43
ggaggugguu uguguaucu                                          19

<210> SEQ ID NO 44
<211> LENGTH: 19
<212> TYPE: RNA
<213> ORGANISM: Artificial Sequence
<220> FEATURE:
<223> OTHER INFORMATION: Chemically synthesized

<400> SEQUENCE: 44
gaccaagugu guuuguugu                                          19

<210> SEQ ID NO 45
<211> LENGTH: 19
<212> TYPE: RNA
<213> ORGANISM: Artificial Sequence
<220> FEATURE:
<223> OTHER INFORMATION: Chemically synthesized

<400> SEQUENCE: 45
gugugccaac cugaugcag                                          19

<210> SEQ ID NO 46
<211> LENGTH: 19
<212> TYPE: RNA
<213> ORGANISM: Artificial Sequence
<220> FEATURE:
<223> OTHER INFORMATION: Chemically synthesized

<400> SEQUENCE: 46
guggagacua gaggcagga                                          19

<210> SEQ ID NO 47
<211> LENGTH: 19
<212> TYPE: RNA
<213> ORGANISM: Artificial Sequence
<220> FEATURE:
<223> OTHER INFORMATION: Chemically synthesized

<400> SEQUENCE: 47
ugccaaccug augcagcug                                          19
```

```
<210> SEQ ID NO 48
<211> LENGTH: 19
<212> TYPE: RNA
<213> ORGANISM: Artificial Sequence
<220> FEATURE:
<223> OTHER INFORMATION: Chemically synthesized

<400> SEQUENCE: 48
caaccugaug cagcugcug                                                  19

<210> SEQ ID NO 49
<211> LENGTH: 19
<212> TYPE: RNA
<213> ORGANISM: Artificial Sequence
<220> FEATURE:
<223> OTHER INFORMATION: Chemically synthesized

<400> SEQUENCE: 49
cugaugcagc ugcugcagg                                                  19

<210> SEQ ID NO 50
<211> LENGTH: 19
<212> TYPE: RNA
<213> ORGANISM: Artificial Sequence
<220> FEATURE:
<223> OTHER INFORMATION: Chemically synthesized

<400> SEQUENCE: 50
gaugcagcug cugcaggag                                                  19

<210> SEQ ID NO 51
<211> LENGTH: 19
<212> TYPE: RNA
<213> ORGANISM: Artificial Sequence
<220> FEATURE:
<223> OTHER INFORMATION: Chemically synthesized

<400> SEQUENCE: 51
caucguguac ugcagaguu                                                  19

<210> SEQ ID NO 52
<211> LENGTH: 19
<212> TYPE: RNA
<213> ORGANISM: Artificial Sequence
<220> FEATURE:
<223> OTHER INFORMATION: Chemically synthesized

<400> SEQUENCE: 52
gguggagacu agaggcagg                                                  19

<210> SEQ ID NO 53
<211> LENGTH: 19
<212> TYPE: RNA
<213> ORGANISM: Artificial Sequence
<220> FEATURE:
<223> OTHER INFORMATION: Chemically synthesized

<400> SEQUENCE: 53
uagaagccgc agcuagcgc                                                  19

<210> SEQ ID NO 54
<211> LENGTH: 19
<212> TYPE: RNA
<213> ORGANISM: Artificial Sequence
<220> FEATURE:
<223> OTHER INFORMATION: Chemically synthesized
```

-continued

<400> SEQUENCE: 54
uccgagcucu ccaggcucg                                               19

<210> SEQ ID NO 55
<211> LENGTH: 19
<212> TYPE: RNA
<213> ORGANISM: Artificial Sequence
<220> FEATURE:
<223> OTHER INFORMATION: Chemically synthesized

<400> SEQUENCE: 55
ugcugcuguc cagggacuc                                               19

<210> SEQ ID NO 56
<211> LENGTH: 19
<212> TYPE: RNA
<213> ORGANISM: Artificial Sequence
<220> FEATURE:
<223> OTHER INFORMATION: Chemically synthesized

<400> SEQUENCE: 56
agcagcugca ucagguugg                                               19

<210> SEQ ID NO 57
<211> LENGTH: 19
<212> TYPE: RNA
<213> ORGANISM: Artificial Sequence
<220> FEATURE:
<223> OTHER INFORMATION: Chemically synthesized

<400> SEQUENCE: 57
ugaguccagg cgcagcacg                                               19

<210> SEQ ID NO 58
<211> LENGTH: 19
<212> TYPE: RNA
<213> ORGANISM: Artificial Sequence
<220> FEATURE:
<223> OTHER INFORMATION: Chemically synthesized

<400> SEQUENCE: 58
cagcuagcgc ggucagcga                                               19

<210> SEQ ID NO 59
<211> LENGTH: 19
<212> TYPE: RNA
<213> ORGANISM: Artificial Sequence
<220> FEATURE:
<223> OTHER INFORMATION: Chemically synthesized

<400> SEQUENCE: 59
ccgcagcuag cgcggucag                                               19

<210> SEQ ID NO 60
<211> LENGTH: 19
<212> TYPE: RNA
<213> ORGANISM: Artificial Sequence
<220> FEATURE:
<223> OTHER INFORMATION: Chemically synthesized

<400> SEQUENCE: 60
aagccgcagc uagcgcggu                                               19

<210> SEQ ID NO 61

```
<211> LENGTH: 19
<212> TYPE: RNA
<213> ORGANISM: Artificial Sequence
<220> FEATURE:
<223> OTHER INFORMATION: Chemically synthesized

<400> SEQUENCE: 61
aguccgagcu cuccaggcu                                                  19

<210> SEQ ID NO 62
<211> LENGTH: 19
<212> TYPE: RNA
<213> ORGANISM: Artificial Sequence
<220> FEATURE:
<223> OTHER INFORMATION: Chemically synthesized

<400> SEQUENCE: 62
gcaguccgag cucuccagg                                                  19

<210> SEQ ID NO 63
<211> LENGTH: 19
<212> TYPE: RNA
<213> ORGANISM: Artificial Sequence
<220> FEATURE:
<223> OTHER INFORMATION: Chemically synthesized

<400> SEQUENCE: 63
uguugcugcu guccaggga                                                  19

<210> SEQ ID NO 64
<211> LENGTH: 19
<212> TYPE: RNA
<213> ORGANISM: Artificial Sequence
<220> FEATURE:
<223> OTHER INFORMATION: Chemically synthesized

<400> SEQUENCE: 64
agccacuguu gcugcuguc                                                  19

<210> SEQ ID NO 65
<211> LENGTH: 19
<212> TYPE: RNA
<213> ORGANISM: Artificial Sequence
<220> FEATURE:
<223> OTHER INFORMATION: Chemically synthesized

<400> SEQUENCE: 65
aagccacugu ugcugcugu                                                  19

<210> SEQ ID NO 66
<211> LENGTH: 19
<212> TYPE: RNA
<213> ORGANISM: Artificial Sequence
<220> FEATURE:
<223> OTHER INFORMATION: Chemically synthesized

<400> SEQUENCE: 66
agcugcauca gguuggcac                                                  19

<210> SEQ ID NO 67
<211> LENGTH: 19
<212> TYPE: RNA
<213> ORGANISM: Artificial Sequence
<220> FEATURE:
<223> OTHER INFORMATION: Chemically synthesized

<400> SEQUENCE: 67
```
ugcagcagcu gcaucaggu					19

<210> SEQ ID NO 68
<211> LENGTH: 19
<212> TYPE: RNA
<213> ORGANISM: Artificial Sequence
<220> FEATURE:
<223> OTHER INFORMATION: Chemically synthesized

<400> SEQUENCE: 68
ucuccugcag cagcugcau					19

<210> SEQ ID NO 69
<211> LENGTH: 19
<212> TYPE: RNA
<213> ORGANISM: Artificial Sequence
<220> FEATURE:
<223> OTHER INFORMATION: Chemically synthesized

<400> SEQUENCE: 69
ccccgcaggc cgcacggcu					19

<210> SEQ ID NO 70
<211> LENGTH: 19
<212> TYPE: RNA
<213> ORGANISM: Artificial Sequence
<220> FEATURE:
<223> OTHER INFORMATION: Chemically synthesized

<400> SEQUENCE: 70
ccuggaucuu gggccagag					19

<210> SEQ ID NO 71
<211> LENGTH: 19
<212> TYPE: RNA
<213> ORGANISM: Artificial Sequence
<220> FEATURE:
<223> OTHER INFORMATION: Chemically synthesized

<400> SEQUENCE: 71
cagcgucagg gacuggcug					19

<210> SEQ ID NO 72
<211> LENGTH: 19
<212> TYPE: RNA
<213> ORGANISM: Artificial Sequence
<220> FEATURE:
<223> OTHER INFORMATION: Chemically synthesized

<400> SEQUENCE: 72
augcuacagu acugagggg					19

<210> SEQ ID NO 73
<211> LENGTH: 19
<212> TYPE: RNA
<213> ORGANISM: Artificial Sequence
<220> FEATURE:
<223> OTHER INFORMATION: Chemically synthesized

<400> SEQUENCE: 73
gucuguaaga uagcugccu					19

<210> SEQ ID NO 74
<211> LENGTH: 19
<212> TYPE: RNA

```
<213> ORGANISM: Artificial Sequence
<220> FEATURE:
<223> OTHER INFORMATION: Chemically synthesized

<400> SEQUENCE: 74
uucuagaugg aagacccag                                                19

<210> SEQ ID NO 75
<211> LENGTH: 19
<212> TYPE: RNA
<213> ORGANISM: Artificial Sequence
<220> FEATURE:
<223> OTHER INFORMATION: Chemically synthesized

<400> SEQUENCE: 75
uugaacauca aguguauuc                                                19

<210> SEQ ID NO 76
<211> LENGTH: 19
<212> TYPE: RNA
<213> ORGANISM: Artificial Sequence
<220> FEATURE:
<223> OTHER INFORMATION: Chemically synthesized

<400> SEQUENCE: 76
aaauauugca uaggucuua                                                19

<210> SEQ ID NO 77
<211> LENGTH: 19
<212> TYPE: RNA
<213> ORGANISM: Artificial Sequence
<220> FEATURE:
<223> OTHER INFORMATION: Chemically synthesized

<400> SEQUENCE: 77
aaaaauauug cauaggucu                                                19

<210> SEQ ID NO 78
<211> LENGTH: 19
<212> TYPE: RNA
<213> ORGANISM: Artificial Sequence
<220> FEATURE:
<223> OTHER INFORMATION: Chemically synthesized

<400> SEQUENCE: 78
agggacucgc aguccgagc                                                19

<210> SEQ ID NO 79
<211> LENGTH: 19
<212> TYPE: RNA
<213> ORGANISM: Artificial Sequence
<220> FEATURE:
<223> OTHER INFORMATION: Chemically synthesized

<400> SEQUENCE: 79
uacuugaaca ucaagugua                                                19

<210> SEQ ID NO 80
<211> LENGTH: 19
<212> TYPE: RNA
<213> ORGANISM: Artificial Sequence
<220> FEATURE:
<223> OTHER INFORMATION: Chemically synthesized

<400> SEQUENCE: 80
aaacauguuu auuagaaaa                                                19
```

```
<210> SEQ ID NO 81
<211> LENGTH: 19
<212> TYPE: RNA
<213> ORGANISM: Artificial Sequence
<220> FEATURE:
<223> OTHER INFORMATION: Chemically synthesized

<400> SEQUENCE: 81
aacugcuaag acaagugcg                                                  19

<210> SEQ ID NO 82
<211> LENGTH: 19
<212> TYPE: RNA
<213> ORGANISM: Artificial Sequence
<220> FEATURE:
<223> OTHER INFORMATION: Chemically synthesized

<400> SEQUENCE: 82
acgacgacga gaagcgguc                                                  19

<210> SEQ ID NO 83
<211> LENGTH: 19
<212> TYPE: RNA
<213> ORGANISM: Artificial Sequence
<220> FEATURE:
<223> OTHER INFORMATION: Chemically synthesized

<400> SEQUENCE: 83
aagccguguc uuccuccgg                                                  19

<210> SEQ ID NO 84
<211> LENGTH: 19
<212> TYPE: RNA
<213> ORGANISM: Artificial Sequence
<220> FEATURE:
<223> OTHER INFORMATION: Chemically synthesized

<400> SEQUENCE: 84
aguguucauc cucaggguc                                                  19

<210> SEQ ID NO 85
<211> LENGTH: 19
<212> TYPE: RNA
<213> ORGANISM: Artificial Sequence
<220> FEATURE:
<223> OTHER INFORMATION: Chemically synthesized

<400> SEQUENCE: 85
agggcgucga gagcccagc                                                  19

<210> SEQ ID NO 86
<211> LENGTH: 19
<212> TYPE: RNA
<213> ORGANISM: Artificial Sequence
<220> FEATURE:
<223> OTHER INFORMATION: Chemically synthesized

<400> SEQUENCE: 86
aucagcaggc gcgcagggc                                                  19

<210> SEQ ID NO 87
<211> LENGTH: 19
<212> TYPE: RNA
<213> ORGANISM: Artificial Sequence
<220> FEATURE:
```

```
<223> OTHER INFORMATION: Chemically synthesized

<400> SEQUENCE: 87
aguucuuugc ccaccuggc                                                    19

<210> SEQ ID NO 88
<211> LENGTH: 19
<212> TYPE: RNA
<213> ORGANISM: Artificial Sequence
<220> FEATURE:
<223> OTHER INFORMATION: Chemically synthesized

<400> SEQUENCE: 88
acggcucgcu guaggccag                                                    19

<210> SEQ ID NO 89
<211> LENGTH: 19
<212> TYPE: RNA
<213> ORGANISM: Artificial Sequence
<220> FEATURE:
<223> OTHER INFORMATION: Chemically synthesized

<400> SEQUENCE: 89
acguccagca gcgcccccc                                                    19

<210> SEQ ID NO 90
<211> LENGTH: 19
<212> TYPE: RNA
<213> ORGANISM: Artificial Sequence
<220> FEATURE:
<223> OTHER INFORMATION: Chemically synthesized

<400> SEQUENCE: 90
augacucgga agccagugc                                                    19

<210> SEQ ID NO 91
<211> LENGTH: 19
<212> TYPE: RNA
<213> ORGANISM: Artificial Sequence
<220> FEATURE:
<223> OTHER INFORMATION: Chemically synthesized

<400> SEQUENCE: 91
aacucaauga gcuuccugg                                                    19

<210> SEQ ID NO 92
<211> LENGTH: 19
<212> TYPE: RNA
<213> ORGANISM: Artificial Sequence
<220> FEATURE:
<223> OTHER INFORMATION: Chemically synthesized

<400> SEQUENCE: 92
cucaacucug caguacacg                                                    19

<210> SEQ ID NO 93
<211> LENGTH: 19
<212> TYPE: RNA
<213> ORGANISM: Artificial Sequence
<220> FEATURE:
<223> OTHER INFORMATION: Chemically synthesized

<400> SEQUENCE: 93
agauacacaa accaccucc                                                    19
```

```
<210> SEQ ID NO 94
<211> LENGTH: 19
<212> TYPE: RNA
<213> ORGANISM: Artificial Sequence
<220> FEATURE:
<223> OTHER INFORMATION: Chemically synthesized

<400> SEQUENCE: 94
acaacaaaca cacuugguc                                                19

<210> SEQ ID NO 95
<211> LENGTH: 19
<212> TYPE: RNA
<213> ORGANISM: Artificial Sequence
<220> FEATURE:
<223> OTHER INFORMATION: Chemically synthesized

<400> SEQUENCE: 95
cugcaucagg uuggcacac                                                19

<210> SEQ ID NO 96
<211> LENGTH: 19
<212> TYPE: RNA
<213> ORGANISM: Artificial Sequence
<220> FEATURE:
<223> OTHER INFORMATION: Chemically synthesized

<400> SEQUENCE: 96
uccugccucu agucuccac                                                19

<210> SEQ ID NO 97
<211> LENGTH: 19
<212> TYPE: RNA
<213> ORGANISM: Artificial Sequence
<220> FEATURE:
<223> OTHER INFORMATION: Chemically synthesized

<400> SEQUENCE: 97
cagcugcauc agguuggca                                                19

<210> SEQ ID NO 98
<211> LENGTH: 19
<212> TYPE: RNA
<213> ORGANISM: Artificial Sequence
<220> FEATURE:
<223> OTHER INFORMATION: Chemically synthesized

<400> SEQUENCE: 98
cagcagcugc aucagguug                                                19

<210> SEQ ID NO 99
<211> LENGTH: 19
<212> TYPE: RNA
<213> ORGANISM: Artificial Sequence
<220> FEATURE:
<223> OTHER INFORMATION: Chemically synthesized

<400> SEQUENCE: 99
ccugcagcag cugcaucag                                                19

<210> SEQ ID NO 100
<211> LENGTH: 19
<212> TYPE: RNA
<213> ORGANISM: Artificial Sequence
<220> FEATURE:
<223> OTHER INFORMATION: Chemically synthesized
```

```
<400> SEQUENCE: 100
cuccugcagc agcugcauc                                          19

<210> SEQ ID NO 101
<211> LENGTH: 19
<212> TYPE: RNA
<213> ORGANISM: Artificial Sequence
<220> FEATURE:
<223> OTHER INFORMATION: Chemically synthesized

<400> SEQUENCE: 101
aacucugcag uacacgaug                                          19

<210> SEQ ID NO 102
<211> LENGTH: 19
<212> TYPE: RNA
<213> ORGANISM: Artificial Sequence
<220> FEATURE:
<223> OTHER INFORMATION: Chemically synthesized

<400> SEQUENCE: 102
ccugccucua gucuccacc                                          19

<210> SEQ ID NO 103
<211> LENGTH: 19
<212> TYPE: RNA
<213> ORGANISM: Artificial Sequence
<220> FEATURE:
<223> OTHER INFORMATION: Chemically synthesized

<400> SEQUENCE: 103
cuagccaguu gguaagcca                                          19

<210> SEQ ID NO 104
<211> LENGTH: 19
<212> TYPE: RNA
<213> ORGANISM: Artificial Sequence
<220> FEATURE:
<223> OTHER INFORMATION: Chemically synthesized

<400> SEQUENCE: 104
ugauuccagu gguuggaaa                                          19

<210> SEQ ID NO 105
<211> LENGTH: 19
<212> TYPE: RNA
<213> ORGANISM: Artificial Sequence
<220> FEATURE:
<223> OTHER INFORMATION: Chemically synthesized

<400> SEQUENCE: 105
ccagugguug gaaaacuga                                          19

<210> SEQ ID NO 106
<211> LENGTH: 19
<212> TYPE: RNA
<213> ORGANISM: Artificial Sequence
<220> FEATURE:
<223> OTHER INFORMATION: Chemically synthesized

<400> SEQUENCE: 106
gcuuccgagu caucaagaa                                          19

<210> SEQ ID NO 107
<211> LENGTH: 19
```

```
<212> TYPE: RNA
<213> ORGANISM: Artificial Sequence
<220> FEATURE:
<223> OTHER INFORMATION: Chemically synthesized

<400> SEQUENCE: 107
ggaagcucau ugaguugug                                                     19

<210> SEQ ID NO 108
<211> LENGTH: 19
<212> TYPE: RNA
<213> ORGANISM: Artificial Sequence
<220> FEATURE:
<223> OTHER INFORMATION: Chemically synthesized

<400> SEQUENCE: 108
ccaucugggu cuuccaucu                                                     19

<210> SEQ ID NO 109
<211> LENGTH: 19
<212> TYPE: RNA
<213> ORGANISM: Artificial Sequence
<220> FEATURE:
<223> OTHER INFORMATION: Chemically synthesized

<400> SEQUENCE: 109
ggaugugugu guagcaugu                                                     19

<210> SEQ ID NO 110
<211> LENGTH: 19
<212> TYPE: RNA
<213> ORGANISM: Artificial Sequence
<220> FEATURE:
<223> OTHER INFORMATION: Chemically synthesized

<400> SEQUENCE: 110
acacauaccc cucaguacu                                                     19

<210> SEQ ID NO 111
<211> LENGTH: 19
<212> TYPE: RNA
<213> ORGANISM: Artificial Sequence
<220> FEATURE:
<223> OTHER INFORMATION: Chemically synthesized

<400> SEQUENCE: 111
acauaccccu caguacugu                                                     19

<210> SEQ ID NO 112
<211> LENGTH: 19
<212> TYPE: RNA
<213> ORGANISM: Artificial Sequence
<220> FEATURE:
<223> OTHER INFORMATION: Chemically synthesized

<400> SEQUENCE: 112
cacuguucau gaauacacu                                                     19

<210> SEQ ID NO 113
<211> LENGTH: 19
<212> TYPE: RNA
<213> ORGANISM: Artificial Sequence
<220> FEATURE:
<223> OTHER INFORMATION: Chemically synthesized

<400> SEQUENCE: 113
```

```
ccagcuggau gugugugua                                                19
```

<210> SEQ ID NO 114
<211> LENGTH: 19
<212> TYPE: RNA
<213> ORGANISM: Artificial Sequence
<220> FEATURE:
<223> OTHER INFORMATION: Chemically synthesized

<400> SEQUENCE: 114

```
cggaacagcu gcucauuga                                                19
```

<210> SEQ ID NO 115
<211> LENGTH: 19
<212> TYPE: RNA
<213> ORGANISM: Artificial Sequence
<220> FEATURE:
<223> OTHER INFORMATION: Chemically synthesized

<400> SEQUENCE: 115

```
gaagcucauu gaguugugu                                                19
```

<210> SEQ ID NO 116
<211> LENGTH: 19
<212> TYPE: RNA
<213> ORGANISM: Artificial Sequence
<220> FEATURE:
<223> OTHER INFORMATION: Chemically synthesized

<400> SEQUENCE: 116

```
ggacacauac cccucagua                                                19
```

<210> SEQ ID NO 117
<211> LENGTH: 19
<212> TYPE: RNA
<213> ORGANISM: Artificial Sequence
<220> FEATURE:
<223> OTHER INFORMATION: Chemically synthesized

<400> SEQUENCE: 117

```
ggaucuuuga cacuugaaa                                                19
```

<210> SEQ ID NO 118
<211> LENGTH: 19
<212> TYPE: RNA
<213> ORGANISM: Artificial Sequence
<220> FEATURE:
<223> OTHER INFORMATION: Chemically synthesized

<400> SEQUENCE: 118

```
guagcaugua ccuuauuau                                                19
```

<210> SEQ ID NO 119
<211> LENGTH: 19
<212> TYPE: RNA
<213> ORGANISM: Artificial Sequence
<220> FEATURE:
<223> OTHER INFORMATION: Chemically synthesized

<400> SEQUENCE: 119

```
ucaguacugu agcauggaa                                                19
```

<210> SEQ ID NO 120
<211> LENGTH: 19
<212> TYPE: RNA
<213> ORGANISM: Artificial Sequence

```
<220> FEATURE:
<223> OTHER INFORMATION: Chemically synthesized

<400> SEQUENCE: 120
uguguagcau guaccuuau                                              19

<210> SEQ ID NO 121
<211> LENGTH: 19
<212> TYPE: RNA
<213> ORGANISM: Artificial Sequence
<220> FEATURE:
<223> OTHER INFORMATION: Chemically synthesized

<400> SEQUENCE: 121
cuggaugugu guguagcau                                              19

<210> SEQ ID NO 122
<211> LENGTH: 19
<212> TYPE: RNA
<213> ORGANISM: Artificial Sequence
<220> FEATURE:
<223> OTHER INFORMATION: Chemically synthesized

<400> SEQUENCE: 122
acacuugaug uucaaguau                                              19

<210> SEQ ID NO 123
<211> LENGTH: 19
<212> TYPE: RNA
<213> ORGANISM: Artificial Sequence
<220> FEATURE:
<223> OTHER INFORMATION: Chemically synthesized

<400> SEQUENCE: 123
gcaugaaugu aagaguagg                                              19

<210> SEQ ID NO 124
<211> LENGTH: 19
<212> TYPE: RNA
<213> ORGANISM: Artificial Sequence
<220> FEATURE:
<223> OTHER INFORMATION: Chemically synthesized

<400> SEQUENCE: 124
agcagcaaca guggcuucg                                              19

<210> SEQ ID NO 125
<211> LENGTH: 19
<212> TYPE: RNA
<213> ORGANISM: Artificial Sequence
<220> FEATURE:
<223> OTHER INFORMATION: Chemically synthesized

<400> SEQUENCE: 125
augaauguaa gaguaggaa                                              19

<210> SEQ ID NO 126
<211> LENGTH: 19
<212> TYPE: RNA
<213> ORGANISM: Artificial Sequence
<220> FEATURE:
<223> OTHER INFORMATION: Chemically synthesized

<400> SEQUENCE: 126
cagcagcaac aguggcuuc                                              19
```

```
<210> SEQ ID NO 127
<211> LENGTH: 19
<212> TYPE: RNA
<213> ORGANISM: Artificial Sequence
<220> FEATURE:
<223> OTHER INFORMATION: Chemically synthesized

<400> SEQUENCE: 127
caugaaugua agaguagga                                                19

<210> SEQ ID NO 128
<211> LENGTH: 19
<212> TYPE: RNA
<213> ORGANISM: Artificial Sequence
<220> FEATURE:
<223> OTHER INFORMATION: Chemically synthesized

<400> SEQUENCE: 128
gauguucaag uauuaagac                                                19

<210> SEQ ID NO 129
<211> LENGTH: 19
<212> TYPE: RNA
<213> ORGANISM: Artificial Sequence
<220> FEATURE:
<223> OTHER INFORMATION: Chemically synthesized

<400> SEQUENCE: 129
ugaugcagcu gcugcagga                                                19

<210> SEQ ID NO 130
<211> LENGTH: 19
<212> TYPE: RNA
<213> ORGANISM: Artificial Sequence
<220> FEATURE:
<223> OTHER INFORMATION: Chemically synthesized

<400> SEQUENCE: 130
gaauacacuu gauguucaa                                                19

<210> SEQ ID NO 131
<211> LENGTH: 19
<212> TYPE: RNA
<213> ORGANISM: Artificial Sequence
<220> FEATURE:
<223> OTHER INFORMATION: Chemically synthesized

<400> SEQUENCE: 131
ugaauacacu ugauguuca                                                19

<210> SEQ ID NO 132
<211> LENGTH: 19
<212> TYPE: RNA
<213> ORGANISM: Artificial Sequence
<220> FEATURE:
<223> OTHER INFORMATION: Chemically synthesized

<400> SEQUENCE: 132
auacacuuga uguucaagu                                                19

<210> SEQ ID NO 133
<211> LENGTH: 19
<212> TYPE: RNA
<213> ORGANISM: Artificial Sequence
<220> FEATURE:
<223> OTHER INFORMATION: Chemically synthesized
```

```
<400> SEQUENCE: 133
caugaauaca cuugauguu                                                    19

<210> SEQ ID NO 134
<211> LENGTH: 19
<212> TYPE: RNA
<213> ORGANISM: Artificial Sequence
<220> FEATURE:
<223> OTHER INFORMATION: Chemically synthesized

<400> SEQUENCE: 134
cuggacagca gcaacagug                                                    19

<210> SEQ ID NO 135
<211> LENGTH: 19
<212> TYPE: RNA
<213> ORGANISM: Artificial Sequence
<220> FEATURE:
<223> OTHER INFORMATION: Chemically synthesized

<400> SEQUENCE: 135
guucaugaau acacuugau                                                    19

<210> SEQ ID NO 136
<211> LENGTH: 19
<212> TYPE: RNA
<213> ORGANISM: Artificial Sequence
<220> FEATURE:
<223> OTHER INFORMATION: Chemically synthesized

<400> SEQUENCE: 136
ucaugaauac acuugaugu                                                    19

<210> SEQ ID NO 137
<211> LENGTH: 19
<212> TYPE: RNA
<213> ORGANISM: Artificial Sequence
<220> FEATURE:
<223> OTHER INFORMATION: Chemically synthesized

<400> SEQUENCE: 137
uggacagcag caacagugg                                                    19

<210> SEQ ID NO 138
<211> LENGTH: 19
<212> TYPE: RNA
<213> ORGANISM: Artificial Sequence
<220> FEATURE:
<223> OTHER INFORMATION: Chemically synthesized

<400> SEQUENCE: 138
ugugugccaa ccugaugca                                                    19

<210> SEQ ID NO 139
<211> LENGTH: 19
<212> TYPE: RNA
<213> ORGANISM: Artificial Sequence
<220> FEATURE:
<223> OTHER INFORMATION: Chemically synthesized

<400> SEQUENCE: 139
uucaugaaua cacuugaug                                                    19

<210> SEQ ID NO 140
```

```
<210> SEQ ID NO 140
<211> LENGTH: 19
<212> TYPE: RNA
<213> ORGANISM: Artificial Sequence
<220> FEATURE:
<223> OTHER INFORMATION: Chemically synthesized

<400> SEQUENCE: 140
aaccugaugc agcugcugc                                               19

<210> SEQ ID NO 141
<211> LENGTH: 19
<212> TYPE: RNA
<213> ORGANISM: Artificial Sequence
<220> FEATURE:
<223> OTHER INFORMATION: Chemically synthesized

<400> SEQUENCE: 141
agucccugga cagcagcaa                                               19

<210> SEQ ID NO 142
<211> LENGTH: 19
<212> TYPE: RNA
<213> ORGANISM: Artificial Sequence
<220> FEATURE:
<223> OTHER INFORMATION: Chemically synthesized

<400> SEQUENCE: 142
cccucaguac uguagcaug                                               19

<210> SEQ ID NO 143
<211> LENGTH: 19
<212> TYPE: RNA
<213> ORGANISM: Artificial Sequence
<220> FEATURE:
<223> OTHER INFORMATION: Chemically synthesized

<400> SEQUENCE: 143
ccuggacagc agcaacagu                                               19

<210> SEQ ID NO 144
<211> LENGTH: 19
<212> TYPE: RNA
<213> ORGANISM: Artificial Sequence
<220> FEATURE:
<223> OTHER INFORMATION: Chemically synthesized

<400> SEQUENCE: 144
ugugccaacc ugaugcagc                                               19

<210> SEQ ID NO 145
<211> LENGTH: 19
<212> TYPE: RNA
<213> ORGANISM: Artificial Sequence
<220> FEATURE:
<223> OTHER INFORMATION: Chemically synthesized

<400> SEQUENCE: 145
aauacacuug auguucaag                                               19

<210> SEQ ID NO 146
<211> LENGTH: 19
<212> TYPE: RNA
<213> ORGANISM: Artificial Sequence
<220> FEATURE:
<223> OTHER INFORMATION: Chemically synthesized

<400> SEQUENCE: 146
```
augaauacac uugauguuc                                              19

<210> SEQ ID NO 147
<211> LENGTH: 19
<212> TYPE: RNA
<213> ORGANISM: Artificial Sequence
<220> FEATURE:
<223> OTHER INFORMATION: Chemically synthesized

<400> SEQUENCE: 147
ugaugcagcu gcugcagga                                              19

<210> SEQ ID NO 148
<211> LENGTH: 19
<212> TYPE: RNA
<213> ORGANISM: Artificial Sequence
<220> FEATURE:
<223> OTHER INFORMATION: Chemically synthesized

<400> SEQUENCE: 148
agaacuguuu acaugaaga                                              19

<210> SEQ ID NO 149
<211> LENGTH: 19
<212> TYPE: RNA
<213> ORGANISM: Artificial Sequence
<220> FEATURE:
<223> OTHER INFORMATION: Chemically synthesized

<400> SEQUENCE: 149
aucuagaacu guuuacaug                                              19

<210> SEQ ID NO 150
<211> LENGTH: 19
<212> TYPE: RNA
<213> ORGANISM: Artificial Sequence
<220> FEATURE:
<223> OTHER INFORMATION: Chemically synthesized

<400> SEQUENCE: 150
ccaugccuag ccuuuggga                                              19

<210> SEQ ID NO 151
<211> LENGTH: 19
<212> TYPE: RNA
<213> ORGANISM: Artificial Sequence
<220> FEATURE:
<223> OTHER INFORMATION: Chemically synthesized

<400> SEQUENCE: 151
cuagaacugu uuacaugaa                                              19

<210> SEQ ID NO 152
<211> LENGTH: 19
<212> TYPE: RNA
<213> ORGANISM: Artificial Sequence
<220> FEATURE:
<223> OTHER INFORMATION: Chemically synthesized

<400> SEQUENCE: 152
gaacuguuua caugaagau                                              19

<210> SEQ ID NO 153
<211> LENGTH: 19
<212> TYPE: RNA

```
<213> ORGANISM: Artificial Sequence
<220> FEATURE:
<223> OTHER INFORMATION: Chemically synthesized

<400> SEQUENCE: 153
ggucuuccau cuagaacug                                                19

<210> SEQ ID NO 154
<211> LENGTH: 19
<212> TYPE: RNA
<213> ORGANISM: Artificial Sequence
<220> FEATURE:
<223> OTHER INFORMATION: Chemically synthesized

<400> SEQUENCE: 154
ccaucuagaa cuguuuaca                                                19

<210> SEQ ID NO 155
<211> LENGTH: 19
<212> TYPE: RNA
<213> ORGANISM: Artificial Sequence
<220> FEATURE:
<223> OTHER INFORMATION: Chemically synthesized

<400> SEQUENCE: 155
cuuccaucua gaacuguuu                                                19

<210> SEQ ID NO 156
<211> LENGTH: 19
<212> TYPE: RNA
<213> ORGANISM: Artificial Sequence
<220> FEATURE:
<223> OTHER INFORMATION: Chemically synthesized

<400> SEQUENCE: 156
uagaacuguu uacaugaag                                                19

<210> SEQ ID NO 157
<211> LENGTH: 19
<212> TYPE: RNA
<213> ORGANISM: Artificial Sequence
<220> FEATURE:
<223> OTHER INFORMATION: Chemically synthesized

<400> SEQUENCE: 157
ucuuccaucu agaacuguu                                                19

<210> SEQ ID NO 158
<211> LENGTH: 19
<212> TYPE: RNA
<213> ORGANISM: Artificial Sequence
<220> FEATURE:
<223> OTHER INFORMATION: Chemically synthesized

<400> SEQUENCE: 158
caucuagaac uguuuacau                                                19

<210> SEQ ID NO 159
<211> LENGTH: 19
<212> TYPE: RNA
<213> ORGANISM: Artificial Sequence
<220> FEATURE:
<223> OTHER INFORMATION: Chemically synthesized

<400> SEQUENCE: 159
gggucuucca ucuagaacu                                                19
```

<210> SEQ ID NO 160
<211> LENGTH: 19
<212> TYPE: RNA
<213> ORGANISM: Artificial Sequence
<220> FEATURE:
<223> OTHER INFORMATION: Chemically synthesized

<400> SEQUENCE: 160
uccaucuaga acuguuuac                                               19

<210> SEQ ID NO 161
<211> LENGTH: 19
<212> TYPE: RNA
<213> ORGANISM: Artificial Sequence
<220> FEATURE:
<223> OTHER INFORMATION: Chemically synthesized

<400> SEQUENCE: 161
ucuagaacug uuuacauga                                               19

<210> SEQ ID NO 162
<211> LENGTH: 19
<212> TYPE: RNA
<213> ORGANISM: Artificial Sequence
<220> FEATURE:
<223> OTHER INFORMATION: Chemically synthesized

<400> SEQUENCE: 162
uuccaucuag aacuguuua                                               19

<210> SEQ ID NO 163
<211> LENGTH: 19
<212> TYPE: RNA
<213> ORGANISM: Artificial Sequence
<220> FEATURE:
<223> OTHER INFORMATION: Chemically synthesized

<400> SEQUENCE: 163
gucuuccauc uagaacugu                                               19

<210> SEQ ID NO 164
<211> LENGTH: 19
<212> TYPE: RNA
<213> ORGANISM: Artificial Sequence
<220> FEATURE:
<223> OTHER INFORMATION: Chemically synthesized

<400> SEQUENCE: 164
caaguauuaa gaccuaugc                                               19

<210> SEQ ID NO 165
<211> LENGTH: 19
<212> TYPE: RNA
<213> ORGANISM: Artificial Sequence
<220> FEATURE:
<223> OTHER INFORMATION: Chemically synthesized

<400> SEQUENCE: 165
guauuaagac cuaugcaau                                               19

<210> SEQ ID NO 166
<211> LENGTH: 19
<212> TYPE: RNA
<213> ORGANISM: Artificial Sequence
<220> FEATURE:

<223> OTHER INFORMATION: Chemically synthesized

<400> SEQUENCE: 166
aguauuaaga ccuaugcaa                                                19

<210> SEQ ID NO 167
<211> LENGTH: 19
<212> TYPE: RNA
<213> ORGANISM: Artificial Sequence
<220> FEATURE:
<223> OTHER INFORMATION: Chemically synthesized

<400> SEQUENCE: 167
auguucaagu auuaagacc                                                19

<210> SEQ ID NO 168
<211> LENGTH: 19
<212> TYPE: RNA
<213> ORGANISM: Artificial Sequence
<220> FEATURE:
<223> OTHER INFORMATION: Chemically synthesized

<400> SEQUENCE: 168
cacuugaugu ucaaguauu                                                19

<210> SEQ ID NO 169
<211> LENGTH: 19
<212> TYPE: RNA
<213> ORGANISM: Artificial Sequence
<220> FEATURE:
<223> OTHER INFORMATION: Chemically synthesized

<400> SEQUENCE: 169
ccaagaucca ggggcuguu                                                19

<210> SEQ ID NO 170
<211> LENGTH: 19
<212> TYPE: RNA
<213> ORGANISM: Artificial Sequence
<220> FEATURE:
<223> OTHER INFORMATION: Chemically synthesized

<400> SEQUENCE: 170
guucaaguau uaagaccua                                                19

<210> SEQ ID NO 171
<211> LENGTH: 19
<212> TYPE: RNA
<213> ORGANISM: Artificial Sequence
<220> FEATURE:
<223> OTHER INFORMATION: Chemically synthesized

<400> SEQUENCE: 171
ucaaguauua agaccuaug                                                19

<210> SEQ ID NO 172
<211> LENGTH: 19
<212> TYPE: RNA
<213> ORGANISM: Artificial Sequence
<220> FEATURE:
<223> OTHER INFORMATION: Chemically synthesized

<400> SEQUENCE: 172
aaguauuaag accuaugca                                                19

```
<210> SEQ ID NO 173
<211> LENGTH: 19
<212> TYPE: RNA
<213> ORGANISM: Artificial Sequence
<220> FEATURE:
<223> OTHER INFORMATION: Chemically synthesized

<400> SEQUENCE: 173
uguucaagua uuaagaccu                                              19

<210> SEQ ID NO 174
<211> LENGTH: 19
<212> TYPE: RNA
<213> ORGANISM: Artificial Sequence
<220> FEATURE:
<223> OTHER INFORMATION: Chemically synthesized

<400> SEQUENCE: 174
ugggucuucc aucuagaac                                              19

<210> SEQ ID NO 175
<211> LENGTH: 19
<212> TYPE: RNA
<213> ORGANISM: Artificial Sequence
<220> FEATURE:
<223> OTHER INFORMATION: Chemically synthesized

<400> SEQUENCE: 175
uggcuuacca acuggcuag                                              19

<210> SEQ ID NO 176
<211> LENGTH: 19
<212> TYPE: RNA
<213> ORGANISM: Artificial Sequence
<220> FEATURE:
<223> OTHER INFORMATION: Chemically synthesized

<400> SEQUENCE: 176
uuuccaacca cuggaauca                                              19

<210> SEQ ID NO 177
<211> LENGTH: 19
<212> TYPE: RNA
<213> ORGANISM: Artificial Sequence
<220> FEATURE:
<223> OTHER INFORMATION: Chemically synthesized

<400> SEQUENCE: 177
ucaguuuucc aaccacugg                                              19

<210> SEQ ID NO 178
<211> LENGTH: 19
<212> TYPE: RNA
<213> ORGANISM: Artificial Sequence
<220> FEATURE:
<223> OTHER INFORMATION: Chemically synthesized

<400> SEQUENCE: 178
uucuugauga cucggaagc                                              19

<210> SEQ ID NO 179
<211> LENGTH: 19
<212> TYPE: RNA
<213> ORGANISM: Artificial Sequence
<220> FEATURE:
<223> OTHER INFORMATION: Chemically synthesized
```

```
<400> SEQUENCE: 179
cacaacucaa ugagcuucc                                               19

<210> SEQ ID NO 180
<211> LENGTH: 19
<212> TYPE: RNA
<213> ORGANISM: Artificial Sequence
<220> FEATURE:
<223> OTHER INFORMATION: Chemically synthesized

<400> SEQUENCE: 180
agauggaaga cccagaugg                                               19

<210> SEQ ID NO 181
<211> LENGTH: 19
<212> TYPE: RNA
<213> ORGANISM: Artificial Sequence
<220> FEATURE:
<223> OTHER INFORMATION: Chemically synthesized

<400> SEQUENCE: 181
acaugcuaca cacacaucc                                               19

<210> SEQ ID NO 182
<211> LENGTH: 19
<212> TYPE: RNA
<213> ORGANISM: Artificial Sequence
<220> FEATURE:
<223> OTHER INFORMATION: Chemically synthesized

<400> SEQUENCE: 182
aguacugagg gguaugugu                                               19

<210> SEQ ID NO 183
<211> LENGTH: 19
<212> TYPE: RNA
<213> ORGANISM: Artificial Sequence
<220> FEATURE:
<223> OTHER INFORMATION: Chemically synthesized

<400> SEQUENCE: 183
acaguacuga gggguaugu                                               19

<210> SEQ ID NO 184
<211> LENGTH: 19
<212> TYPE: RNA
<213> ORGANISM: Artificial Sequence
<220> FEATURE:
<223> OTHER INFORMATION: Chemically synthesized

<400> SEQUENCE: 184
aguguauuca ugaacagug                                               19

<210> SEQ ID NO 185
<211> LENGTH: 19
<212> TYPE: RNA
<213> ORGANISM: Artificial Sequence
<220> FEATURE:
<223> OTHER INFORMATION: Chemically synthesized

<400> SEQUENCE: 185
uacacacaca uccagcugg                                               19

<210> SEQ ID NO 186
<211> LENGTH: 19
```

```
<212> TYPE: RNA
<213> ORGANISM: Artificial Sequence
<220> FEATURE:
<223> OTHER INFORMATION: Chemically synthesized

<400> SEQUENCE: 186
ucaaugagca gcguuccg                                                    19

<210> SEQ ID NO 187
<211> LENGTH: 19
<212> TYPE: RNA
<213> ORGANISM: Artificial Sequence
<220> FEATURE:
<223> OTHER INFORMATION: Chemically synthesized

<400> SEQUENCE: 187
acacaacuca augagcuuc                                                   19

<210> SEQ ID NO 188
<211> LENGTH: 19
<212> TYPE: RNA
<213> ORGANISM: Artificial Sequence
<220> FEATURE:
<223> OTHER INFORMATION: Chemically synthesized

<400> SEQUENCE: 188
uacugagggg uaugugucc                                                   19

<210> SEQ ID NO 189
<211> LENGTH: 19
<212> TYPE: RNA
<213> ORGANISM: Artificial Sequence
<220> FEATURE:
<223> OTHER INFORMATION: Chemically synthesized

<400> SEQUENCE: 189
uuucaagugu caaagaucc                                                   19

<210> SEQ ID NO 190
<211> LENGTH: 19
<212> TYPE: RNA
<213> ORGANISM: Artificial Sequence
<220> FEATURE:
<223> OTHER INFORMATION: Chemically synthesized

<400> SEQUENCE: 190
auaauaaggu acaugcuac                                                   19

<210> SEQ ID NO 191
<211> LENGTH: 19
<212> TYPE: RNA
<213> ORGANISM: Artificial Sequence
<220> FEATURE:
<223> OTHER INFORMATION: Chemically synthesized

<400> SEQUENCE: 191
uuccaugcua caguacuga                                                   19

<210> SEQ ID NO 192
<211> LENGTH: 19
<212> TYPE: RNA
<213> ORGANISM: Artificial Sequence
<220> FEATURE:
<223> OTHER INFORMATION: Chemically synthesized

<400> SEQUENCE: 192
```
auaagguaca ugcuacaca                                                   19

<210> SEQ ID NO 193
<211> LENGTH: 19
<212> TYPE: RNA
<213> ORGANISM: Artificial Sequence
<220> FEATURE:
<223> OTHER INFORMATION: Chemically synthesized

<400> SEQUENCE: 193
augcuacaca cacauccag                                                   19

<210> SEQ ID NO 194
<211> LENGTH: 19
<212> TYPE: RNA
<213> ORGANISM: Artificial Sequence
<220> FEATURE:
<223> OTHER INFORMATION: Chemically synthesized

<400> SEQUENCE: 194
auacuugaac aucaagugu                                                   19

<210> SEQ ID NO 195
<211> LENGTH: 19
<212> TYPE: RNA
<213> ORGANISM: Artificial Sequence
<220> FEATURE:
<223> OTHER INFORMATION: Chemically synthesized

<400> SEQUENCE: 195
ccuacucuua cauucaugc                                                   19

<210> SEQ ID NO 196
<211> LENGTH: 19
<212> TYPE: RNA
<213> ORGANISM: Artificial Sequence
<220> FEATURE:
<223> OTHER INFORMATION: Chemically synthesized

<400> SEQUENCE: 196
cgaagccacu guugcugcu                                                   19

<210> SEQ ID NO 197
<211> LENGTH: 19
<212> TYPE: RNA
<213> ORGANISM: Artificial Sequence
<220> FEATURE:
<223> OTHER INFORMATION: Chemically synthesized

<400> SEQUENCE: 197
uuccuacucu uacauucau                                                   19

<210> SEQ ID NO 198
<211> LENGTH: 19
<212> TYPE: RNA
<213> ORGANISM: Artificial Sequence
<220> FEATURE:
<223> OTHER INFORMATION: Chemically synthesized

<400> SEQUENCE: 198
gaagccacug uugcugcug                                                   19

<210> SEQ ID NO 199
<211> LENGTH: 19
<212> TYPE: RNA
<213> ORGANISM: Artificial Sequence

```
<220> FEATURE:
<223> OTHER INFORMATION: Chemically synthesized

<400> SEQUENCE: 199
uccuacucuu acauucaug                                                   19

<210> SEQ ID NO 200
<211> LENGTH: 19
<212> TYPE: RNA
<213> ORGANISM: Artificial Sequence
<220> FEATURE:
<223> OTHER INFORMATION: Chemically synthesized

<400> SEQUENCE: 200
gucuuaauac uugaacauc                                                   19

<210> SEQ ID NO 201
<211> LENGTH: 19
<212> TYPE: RNA
<213> ORGANISM: Artificial Sequence
<220> FEATURE:
<223> OTHER INFORMATION: Chemically synthesized

<400> SEQUENCE: 201
uccugcagca gcugcauca                                                   19

<210> SEQ ID NO 202
<211> LENGTH: 19
<212> TYPE: RNA
<213> ORGANISM: Artificial Sequence
<220> FEATURE:
<223> OTHER INFORMATION: Chemically synthesized

<400> SEQUENCE: 202
uugaacauca aguguauuc                                                   19

<210> SEQ ID NO 203
<211> LENGTH: 19
<212> TYPE: RNA
<213> ORGANISM: Artificial Sequence
<220> FEATURE:
<223> OTHER INFORMATION: Chemically synthesized

<400> SEQUENCE: 203
ugaacaucaa guguauuca                                                   19

<210> SEQ ID NO 204
<211> LENGTH: 19
<212> TYPE: RNA
<213> ORGANISM: Artificial Sequence
<220> FEATURE:
<223> OTHER INFORMATION: Chemically synthesized

<400> SEQUENCE: 204
acuugaacau caaguguau                                                   19

<210> SEQ ID NO 205
<211> LENGTH: 19
<212> TYPE: RNA
<213> ORGANISM: Artificial Sequence
<220> FEATURE:
<223> OTHER INFORMATION: Chemically synthesized

<400> SEQUENCE: 205
aacaucaagu guauucaug                                                   19
```

```
<210> SEQ ID NO 206
<211> LENGTH: 19
<212> TYPE: RNA
<213> ORGANISM: Artificial Sequence
<220> FEATURE:
<223> OTHER INFORMATION: Chemically synthesized

<400> SEQUENCE: 206
cacuguugcu gcuguccag                                                19

<210> SEQ ID NO 207
<211> LENGTH: 19
<212> TYPE: RNA
<213> ORGANISM: Artificial Sequence
<220> FEATURE:
<223> OTHER INFORMATION: Chemically synthesized

<400> SEQUENCE: 207
aucaagugua uucaugaac                                                19

<210> SEQ ID NO 208
<211> LENGTH: 19
<212> TYPE: RNA
<213> ORGANISM: Artificial Sequence
<220> FEATURE:
<223> OTHER INFORMATION: Chemically synthesized

<400> SEQUENCE: 208
acaucaagug uauucauga                                                19

<210> SEQ ID NO 209
<211> LENGTH: 19
<212> TYPE: RNA
<213> ORGANISM: Artificial Sequence
<220> FEATURE:
<223> OTHER INFORMATION: Chemically synthesized

<400> SEQUENCE: 209
ccacuguugc ugcugucca                                                19

<210> SEQ ID NO 210
<211> LENGTH: 19
<212> TYPE: RNA
<213> ORGANISM: Artificial Sequence
<220> FEATURE:
<223> OTHER INFORMATION: Chemically synthesized

<400> SEQUENCE: 210
ugcaucaggu uggcacaca                                                19

<210> SEQ ID NO 211
<211> LENGTH: 19
<212> TYPE: RNA
<213> ORGANISM: Artificial Sequence
<220> FEATURE:
<223> OTHER INFORMATION: Chemically synthesized

<400> SEQUENCE: 211
caucaagugu auucaugaa                                                19

<210> SEQ ID NO 212
<211> LENGTH: 19
<212> TYPE: RNA
<213> ORGANISM: Artificial Sequence
<220> FEATURE:
<223> OTHER INFORMATION: Chemically synthesized
```

```
<400> SEQUENCE: 212
gcagcagcug caucagguu                                                  19

<210> SEQ ID NO 213
<211> LENGTH: 19
<212> TYPE: RNA
<213> ORGANISM: Artificial Sequence
<220> FEATURE:
<223> OTHER INFORMATION: Chemically synthesized

<400> SEQUENCE: 213
uugcugcugu ccagggacu                                                  19

<210> SEQ ID NO 214
<211> LENGTH: 19
<212> TYPE: RNA
<213> ORGANISM: Artificial Sequence
<220> FEATURE:
<223> OTHER INFORMATION: Chemically synthesized

<400> SEQUENCE: 214
caugcuacag uacugaggg                                                  19

<210> SEQ ID NO 215
<211> LENGTH: 19
<212> TYPE: RNA
<213> ORGANISM: Artificial Sequence
<220> FEATURE:
<223> OTHER INFORMATION: Chemically synthesized

<400> SEQUENCE: 215
acuguugcug cuguccagg                                                  19

<210> SEQ ID NO 216
<211> LENGTH: 19
<212> TYPE: RNA
<213> ORGANISM: Artificial Sequence
<220> FEATURE:
<223> OTHER INFORMATION: Chemically synthesized

<400> SEQUENCE: 216
gcugcaucag guuggcaca                                                  19

<210> SEQ ID NO 217
<211> LENGTH: 19
<212> TYPE: RNA
<213> ORGANISM: Artificial Sequence
<220> FEATURE:
<223> OTHER INFORMATION: Chemically synthesized

<400> SEQUENCE: 217
cuugaacauc aaguguauu                                                  19

<210> SEQ ID NO 218
<211> LENGTH: 19
<212> TYPE: RNA
<213> ORGANISM: Artificial Sequence
<220> FEATURE:
<223> OTHER INFORMATION: Chemically synthesized

<400> SEQUENCE: 218
gaacaucaag uguauucau                                                  19

<210> SEQ ID NO 219
```

```
<211> LENGTH: 19
<212> TYPE: RNA
<213> ORGANISM: Artificial Sequence
<220> FEATURE:
<223> OTHER INFORMATION: Chemically synthesized

<400> SEQUENCE: 219
uccugcagca gcugcauca                                                    19

<210> SEQ ID NO 220
<211> LENGTH: 19
<212> TYPE: RNA
<213> ORGANISM: Artificial Sequence
<220> FEATURE:
<223> OTHER INFORMATION: Chemically synthesized

<400> SEQUENCE: 220
ucuucaugua aacaguucu                                                    19

<210> SEQ ID NO 221
<211> LENGTH: 19
<212> TYPE: RNA
<213> ORGANISM: Artificial Sequence
<220> FEATURE:
<223> OTHER INFORMATION: Chemically synthesized

<400> SEQUENCE: 221
cauguaaaca guucuagau                                                    19

<210> SEQ ID NO 222
<211> LENGTH: 19
<212> TYPE: RNA
<213> ORGANISM: Artificial Sequence
<220> FEATURE:
<223> OTHER INFORMATION: Chemically synthesized

<400> SEQUENCE: 222 ucccaaggc uaggcaugg                                                     19

<210> SEQ ID NO 223
<211> LENGTH: 19
<212> TYPE: RNA
<213> ORGANISM: Artificial Sequence
<220> FEATURE:
<223> OTHER INFORMATION: Chemically synthesized

<400> SEQUENCE: 223
uucauguaaa caguucuag                                                    19

<210> SEQ ID NO 224
<211> LENGTH: 19
<212> TYPE: RNA
<213> ORGANISM: Artificial Sequence
<220> FEATURE:
<223> OTHER INFORMATION: Chemically synthesized

<400> SEQUENCE: 224
aucuucaugu aaacaguuc                                                    19

<210> SEQ ID NO 225
<211> LENGTH: 19
<212> TYPE: RNA
<213> ORGANISM: Artificial Sequence
<220> FEATURE:
<223> OTHER INFORMATION: Chemically synthesized

<400> SEQUENCE: 225
```
caguucuaga uggaagacc                                          19

<210> SEQ ID NO 226
<211> LENGTH: 19
<212> TYPE: RNA
<213> ORGANISM: Artificial Sequence
<220> FEATURE:
<223> OTHER INFORMATION: Chemically synthesized

<400> SEQUENCE: 226
uguaaacagu ucuagaugg                                          19

<210> SEQ ID NO 227
<211> LENGTH: 19
<212> TYPE: RNA
<213> ORGANISM: Artificial Sequence
<220> FEATURE:
<223> OTHER INFORMATION: Chemically synthesized

<400> SEQUENCE: 227
aaacaguucu agauggaag                                          19

<210> SEQ ID NO 228
<211> LENGTH: 19
<212> TYPE: RNA
<213> ORGANISM: Artificial Sequence
<220> FEATURE:
<223> OTHER INFORMATION: Chemically synthesized

<400> SEQUENCE: 228
cuucauguaa acaguucua                                          19

<210> SEQ ID NO 229
<211> LENGTH: 19
<212> TYPE: RNA
<213> ORGANISM: Artificial Sequence
<220> FEATURE:
<223> OTHER INFORMATION: Chemically synthesized

<400> SEQUENCE: 229
aacaguucua gauggaaga                                          19

<210> SEQ ID NO 230
<211> LENGTH: 19
<212> TYPE: RNA
<213> ORGANISM: Artificial Sequence
<220> FEATURE:
<223> OTHER INFORMATION: Chemically synthesized

<400> SEQUENCE: 230
auguaaacag uucuagaug                                          19

<210> SEQ ID NO 231
<211> LENGTH: 19
<212> TYPE: RNA
<213> ORGANISM: Artificial Sequence
<220> FEATURE:
<223> OTHER INFORMATION: Chemically synthesized

<400> SEQUENCE: 231
aguucuagau ggaagaccc                                          19

<210> SEQ ID NO 232
<211> LENGTH: 19
<212> TYPE: RNA

-continued

<213> ORGANISM: Artificial Sequence
<220> FEATURE:
<223> OTHER INFORMATION: Chemically synthesized

<400> SEQUENCE: 232
guaaacaguu cuagaugga                                              19

<210> SEQ ID NO 233
<211> LENGTH: 19
<212> TYPE: RNA
<213> ORGANISM: Artificial Sequence
<220> FEATURE:
<223> OTHER INFORMATION: Chemically synthesized

<400> SEQUENCE: 233
ucauguaaac aguucuaga                                              19

<210> SEQ ID NO 234
<211> LENGTH: 19
<212> TYPE: RNA
<213> ORGANISM: Artificial Sequence
<220> FEATURE:
<223> OTHER INFORMATION: Chemically synthesized

<400> SEQUENCE: 234
uaaacaguuc uagauggaa                                              19

<210> SEQ ID NO 235
<211> LENGTH: 19
<212> TYPE: RNA
<213> ORGANISM: Artificial Sequence
<220> FEATURE:
<223> OTHER INFORMATION: Chemically synthesized

<400> SEQUENCE: 235
acaguucuag auggaagac                                              19

<210> SEQ ID NO 236
<211> LENGTH: 19
<212> TYPE: RNA
<213> ORGANISM: Artificial Sequence
<220> FEATURE:
<223> OTHER INFORMATION: Chemically synthesized

<400> SEQUENCE: 236
gcauaggucu uaauacuug                                              19

<210> SEQ ID NO 237
<211> LENGTH: 19
<212> TYPE: RNA
<213> ORGANISM: Artificial Sequence
<220> FEATURE:
<223> OTHER INFORMATION: Chemically synthesized

<400> SEQUENCE: 237
auugcauagg ucuuaauac                                              19

<210> SEQ ID NO 238
<211> LENGTH: 19
<212> TYPE: RNA
<213> ORGANISM: Artificial Sequence
<220> FEATURE:
<223> OTHER INFORMATION: Chemically synthesized

<400> SEQUENCE: 238
uugcauaggu cuuaauacu                                              19

<210> SEQ ID NO 239
<211> LENGTH: 19
<212> TYPE: RNA
<213> ORGANISM: Artificial Sequence
<220> FEATURE:
<223> OTHER INFORMATION: Chemically synthesized

<400> SEQUENCE: 239
ggucuuaaua cuugaacau                                               19

<210> SEQ ID NO 240
<211> LENGTH: 19
<212> TYPE: RNA
<213> ORGANISM: Artificial Sequence
<220> FEATURE:
<223> OTHER INFORMATION: Chemically synthesized

<400> SEQUENCE: 240
aauacuugaa caucaagug                                               19

<210> SEQ ID NO 241
<211> LENGTH: 19
<212> TYPE: RNA
<213> ORGANISM: Artificial Sequence
<220> FEATURE:
<223> OTHER INFORMATION: Chemically synthesized

<400> SEQUENCE: 241
aacagccccu ggaucuugg                                               19

<210> SEQ ID NO 242
<211> LENGTH: 19
<212> TYPE: RNA
<213> ORGANISM: Artificial Sequence
<220> FEATURE:
<223> OTHER INFORMATION: Chemically synthesized

<400> SEQUENCE: 242
uaggucuuaa uacuugaac                                               19

<210> SEQ ID NO 243
<211> LENGTH: 19
<212> TYPE: RNA
<213> ORGANISM: Artificial Sequence
<220> FEATURE:
<223> OTHER INFORMATION: Chemically synthesized

<400> SEQUENCE: 243
cauaggucuu aauacuuga                                               19

<210> SEQ ID NO 244
<211> LENGTH: 19
<212> TYPE: RNA
<213> ORGANISM: Artificial Sequence
<220> FEATURE:
<223> OTHER INFORMATION: Chemically synthesized

<400> SEQUENCE: 244
ugcauagguc uuaauacuu                                               19

<210> SEQ ID NO 245
<211> LENGTH: 19
<212> TYPE: RNA
<213> ORGANISM: Artificial Sequence
<220> FEATURE:

```
<223> OTHER INFORMATION: Chemically synthesized

<400> SEQUENCE: 245
aggucuuaau acugaaca                                                     19

<210> SEQ ID NO 246
<211> LENGTH: 19
<212> TYPE: RNA
<213> ORGANISM: Artificial Sequence
<220> FEATURE:
<223> OTHER INFORMATION: Chemically synthesized

<400> SEQUENCE: 246
guucuagaug gaagaccca                                                    19

<210> SEQ ID NO 247
<211> LENGTH: 21
<212> TYPE: RNA
<213> ORGANISM: Artificial Sequence
<220> FEATURE:
<223> OTHER INFORMATION: Chemically synthesized

<400> SEQUENCE: 247
ccaggaagcu cauugaguug u                                                 21

<210> SEQ ID NO 248
<211> LENGTH: 21
<212> TYPE: RNA
<213> ORGANISM: Artificial Sequence
<220> FEATURE:
<223> OTHER INFORMATION: Chemically synthesized

<400> SEQUENCE: 248
ccaucugggu cuuccaucua g                                                 21

<210> SEQ ID NO 249
<211> LENGTH: 21
<212> TYPE: RNA
<213> ORGANISM: Artificial Sequence
<220> FEATURE:
<223> OTHER INFORMATION: Chemically synthesized

<400> SEQUENCE: 249
ggaugugugu guagcaugua c                                                 21

<210> SEQ ID NO 250
<211> LENGTH: 21
<212> TYPE: RNA
<213> ORGANISM: Artificial Sequence
<220> FEATURE:
<223> OTHER INFORMATION: Chemically synthesized

<400> SEQUENCE: 250
caaguguguu uguuguuugu u                                                 21

<210> SEQ ID NO 251
<211> LENGTH: 21
<212> TYPE: RNA
<213> ORGANISM: Artificial Sequence
<220> FEATURE:
<223> OTHER INFORMATION: Chemically synthesized

<400> SEQUENCE: 251
ccucaguacu guagcaugga a                                                 21
```

```
<210> SEQ ID NO 252
<211> LENGTH: 21
<212> TYPE: RNA
<213> ORGANISM: Artificial Sequence
<220> FEATURE:
<223> OTHER INFORMATION: Chemically synthesized

<400> SEQUENCE: 252
gaccaagugu guuuguuguu u                                          21

<210> SEQ ID NO 253
<211> LENGTH: 21
<212> TYPE: RNA
<213> ORGANISM: Artificial Sequence
<220> FEATURE:
<223> OTHER INFORMATION: Chemically synthesized

<400> SEQUENCE: 253
gcuuccgagu caucaagaag a                                          21

<210> SEQ ID NO 254
<211> LENGTH: 21
<212> TYPE: RNA
<213> ORGANISM: Artificial Sequence
<220> FEATURE:
<223> OTHER INFORMATION: Chemically synthesized

<400> SEQUENCE: 254
ggaggugggg gaauaguguu u                                          21

<210> SEQ ID NO 255
<211> LENGTH: 21
<212> TYPE: RNA
<213> ORGANISM: Artificial Sequence
<220> FEATURE:
<223> OTHER INFORMATION: Chemically synthesized

<400> SEQUENCE: 255
caguacugua gcauggaaca a                                          21

<210> SEQ ID NO 256
<211> LENGTH: 21
<212> TYPE: RNA
<213> ORGANISM: Artificial Sequence
<220> FEATURE:
<223> OTHER INFORMATION: Chemically synthesized

<400> SEQUENCE: 256
gaauacacuu gauguucaag u                                          21

<210> SEQ ID NO 257
<211> LENGTH: 21
<212> TYPE: RNA
<213> ORGANISM: Artificial Sequence
<220> FEATURE:
<223> OTHER INFORMATION: Chemically synthesized

<400> SEQUENCE: 257
caaguauuaa gaccuaugca a                                          21

<210> SEQ ID NO 258
<211> LENGTH: 21
<212> TYPE: RNA
<213> ORGANISM: Artificial Sequence
<220> FEATURE:
<223> OTHER INFORMATION: Chemically synthesized
```

<400> SEQUENCE: 258
gaacuuuugg gguggagacu a                                              21

<210> SEQ ID NO 259
<211> LENGTH: 21
<212> TYPE: RNA
<213> ORGANISM: Artificial Sequence
<220> FEATURE:
<223> OTHER INFORMATION: Chemically synthesized

<400> SEQUENCE: 259
ggacacauac cccucaguac u                                              21

<210> SEQ ID NO 260
<211> LENGTH: 21
<212> TYPE: RNA
<213> ORGANISM: Artificial Sequence
<220> FEATURE:
<223> OTHER INFORMATION: Chemically synthesized

<400> SEQUENCE: 260
ggaggugguu uguguaucuu a                                              21

<210> SEQ ID NO 261
<211> LENGTH: 21
<212> TYPE: RNA
<213> ORGANISM: Artificial Sequence
<220> FEATURE:
<223> OTHER INFORMATION: Chemically synthesized

<400> SEQUENCE: 261
ggaucuuuga cacugaaaa a                                               21

<210> SEQ ID NO 262
<211> LENGTH: 21
<212> TYPE: RNA
<213> ORGANISM: Artificial Sequence
<220> FEATURE:
<223> OTHER INFORMATION: Chemically synthesized

<400> SEQUENCE: 262
ggucuuccau cuagaacugu u                                              21

<210> SEQ ID NO 263
<211> LENGTH: 21
<212> TYPE: RNA
<213> ORGANISM: Artificial Sequence
<220> FEATURE:
<223> OTHER INFORMATION: Chemically synthesized

<400> SEQUENCE: 263
uguguagcau guaccuuauu a                                              21

<210> SEQ ID NO 264
<211> LENGTH: 21
<212> TYPE: RNA
<213> ORGANISM: Artificial Sequence
<220> FEATURE:
<223> OTHER INFORMATION: Chemically synthesized

<400> SEQUENCE: 264
caacaaggcu uccagcugga u                                              21

<210> SEQ ID NO 265
<211> LENGTH: 21

```
<212> TYPE: RNA
<213> ORGANISM: Artificial Sequence
<220> FEATURE:
<223> OTHER INFORMATION: Chemically synthesized

<400> SEQUENCE: 265
cacuugggau cuuugacacu u                                              21

<210> SEQ ID NO 266
<211> LENGTH: 21
<212> TYPE: RNA
<213> ORGANISM: Artificial Sequence
<220> FEATURE:
<223> OTHER INFORMATION: Chemically synthesized

<400> SEQUENCE: 266
caucacuacu gaccuguugu a                                              21

<210> SEQ ID NO 267
<211> LENGTH: 21
<212> TYPE: RNA
<213> ORGANISM: Artificial Sequence
<220> FEATURE:
<223> OTHER INFORMATION: Chemically synthesized

<400> SEQUENCE: 267
guguguguag cauguaccuu a                                              21

<210> SEQ ID NO 268
<211> LENGTH: 21
<212> TYPE: RNA
<213> ORGANISM: Artificial Sequence
<220> FEATURE:
<223> OTHER INFORMATION: Chemically synthesized

<400> SEQUENCE: 268
gcaugaaugu aagaguagga a                                              21

<210> SEQ ID NO 269
<211> LENGTH: 21
<212> TYPE: RNA
<213> ORGANISM: Artificial Sequence
<220> FEATURE:
<223> OTHER INFORMATION: Chemically synthesized

<400> SEQUENCE: 269
gacagcagca acaguggcuu c                                              21

<210> SEQ ID NO 270
<211> LENGTH: 21
<212> TYPE: RNA
<213> ORGANISM: Artificial Sequence
<220> FEATURE:
<223> OTHER INFORMATION: Chemically synthesized

<400> SEQUENCE: 270
ugaugcagcu gcugcaggag a                                              21

<210> SEQ ID NO 271
<211> LENGTH: 21
<212> TYPE: RNA
<213> ORGANISM: Artificial Sequence
<220> FEATURE:
<223> OTHER INFORMATION: Chemically synthesized

<400> SEQUENCE: 271
```
ugaauacacu ugauguucaa g                                             21

<210> SEQ ID NO 272
<211> LENGTH: 21
<212> TYPE: RNA
<213> ORGANISM: Artificial Sequence
<220> FEATURE:
<223> OTHER INFORMATION: Chemically synthesized

<400> SEQUENCE: 272
caugaauaca cuugauguuc a                                             21

<210> SEQ ID NO 273
<211> LENGTH: 21
<212> TYPE: RNA
<213> ORGANISM: Artificial Sequence
<220> FEATURE:
<223> OTHER INFORMATION: Chemically synthesized

<400> SEQUENCE: 273
ggacagcagc aacaguggcu u                                             21

<210> SEQ ID NO 274
<211> LENGTH: 21
<212> TYPE: RNA
<213> ORGANISM: Artificial Sequence
<220> FEATURE:
<223> OTHER INFORMATION: Chemically synthesized

<400> SEQUENCE: 274
guucaugaau acacuugaug u                                             21

<210> SEQ ID NO 275
<211> LENGTH: 21
<212> TYPE: RNA
<213> ORGANISM: Artificial Sequence
<220> FEATURE:
<223> OTHER INFORMATION: Chemically synthesized

<400> SEQUENCE: 275
ucaugaauac acuugauguu c                                             21

<210> SEQ ID NO 276
<211> LENGTH: 21
<212> TYPE: RNA
<213> ORGANISM: Artificial Sequence
<220> FEATURE:
<223> OTHER INFORMATION: Chemically synthesized

<400> SEQUENCE: 276
ucccuggaca gcagcaacag u                                             21

<210> SEQ ID NO 277
<211> LENGTH: 21
<212> TYPE: RNA
<213> ORGANISM: Artificial Sequence
<220> FEATURE:
<223> OTHER INFORMATION: Chemically synthesized

<400> SEQUENCE: 277
agucccugga cagcagcaac a                                             21

<210> SEQ ID NO 278
<211> LENGTH: 21
<212> TYPE: RNA
<213> ORGANISM: Artificial Sequence

```
<220> FEATURE:
<223> OTHER INFORMATION: Chemically synthesized

<400> SEQUENCE: 278
gaauacacuu gauguucaag u                                              21

<210> SEQ ID NO 279
<211> LENGTH: 21
<212> TYPE: RNA
<213> ORGANISM: Artificial Sequence
<220> FEATURE:
<223> OTHER INFORMATION: Chemically synthesized

<400> SEQUENCE: 279
cuagaacugu uuacaugaag a                                              21

<210> SEQ ID NO 280
<211> LENGTH: 21
<212> TYPE: RNA
<213> ORGANISM: Artificial Sequence
<220> FEATURE:
<223> OTHER INFORMATION: Chemically synthesized

<400> SEQUENCE: 280
ccaucuagaa cuguuuacau g                                              21

<210> SEQ ID NO 281
<211> LENGTH: 21
<212> TYPE: RNA
<213> ORGANISM: Artificial Sequence
<220> FEATURE:
<223> OTHER INFORMATION: Chemically synthesized

<400> SEQUENCE: 281
cuuccaucua gaacuguuua c                                              21

<210> SEQ ID NO 282
<211> LENGTH: 21
<212> TYPE: RNA
<213> ORGANISM: Artificial Sequence
<220> FEATURE:
<223> OTHER INFORMATION: Chemically synthesized

<400> SEQUENCE: 282
ucuuccaucu agaacuguuu a                                              21

<210> SEQ ID NO 283
<211> LENGTH: 21
<212> TYPE: RNA
<213> ORGANISM: Artificial Sequence
<220> FEATURE:
<223> OTHER INFORMATION: Chemically synthesized

<400> SEQUENCE: 283
caucuagaac uguuuacaug a                                              21

<210> SEQ ID NO 284
<211> LENGTH: 21
<212> TYPE: RNA
<213> ORGANISM: Artificial Sequence
<220> FEATURE:
<223> OTHER INFORMATION: Chemically synthesized

<400> SEQUENCE: 284
gggucuucca ucuagaacug u                                              21
```

```
<210> SEQ ID NO 285
<211> LENGTH: 21
<212> TYPE: RNA
<213> ORGANISM: Artificial Sequence
<220> FEATURE:
<223> OTHER INFORMATION: Chemically synthesized

<400> SEQUENCE: 285
uccaucuaga acuguuuaca u                                          21

<210> SEQ ID NO 286
<211> LENGTH: 21
<212> TYPE: RNA
<213> ORGANISM: Artificial Sequence
<220> FEATURE:
<223> OTHER INFORMATION: Chemically synthesized

<400> SEQUENCE: 286
ucuagaacug uuuacaugaa g                                          21

<210> SEQ ID NO 287
<211> LENGTH: 21
<212> TYPE: RNA
<213> ORGANISM: Artificial Sequence
<220> FEATURE:
<223> OTHER INFORMATION: Chemically synthesized

<400> SEQUENCE: 287
uuccaucuag aacuguuuac a                                          21

<210> SEQ ID NO 288
<211> LENGTH: 21
<212> TYPE: RNA
<213> ORGANISM: Artificial Sequence
<220> FEATURE:
<223> OTHER INFORMATION: Chemically synthesized

<400> SEQUENCE: 288
gucuuccauc uagaacuguu u                                          21

<210> SEQ ID NO 289
<211> LENGTH: 21
<212> TYPE: RNA
<213> ORGANISM: Artificial Sequence
<220> FEATURE:
<223> OTHER INFORMATION: Chemically synthesized

<400> SEQUENCE: 289
ugauguucaa guauuaagac c                                          21

<210> SEQ ID NO 290
<211> LENGTH: 21
<212> TYPE: RNA
<213> ORGANISM: Artificial Sequence
<220> FEATURE:
<223> OTHER INFORMATION: Chemically synthesized

<400> SEQUENCE: 290
guucaaguau uaagaccuau g                                          21

<210> SEQ ID NO 291
<211> LENGTH: 21
<212> TYPE: RNA
<213> ORGANISM: Artificial Sequence
<220> FEATURE:
<223> OTHER INFORMATION: Chemically synthesized
```

-continued

```
<400> SEQUENCE: 291
ucaaguauua agaccuaugc a                                              21

<210> SEQ ID NO 292
<211> LENGTH: 21
<212> TYPE: RNA
<213> ORGANISM: Artificial Sequence
<220> FEATURE:
<223> OTHER INFORMATION: Chemically synthesized

<400> SEQUENCE: 292
gauguucaag uauuaagacc u                                              21

<210> SEQ ID NO 293
<211> LENGTH: 21
<212> TYPE: RNA
<213> ORGANISM: Artificial Sequence
<220> FEATURE:
<223> OTHER INFORMATION: Chemically synthesized

<400> SEQUENCE: 293
uucaaguauu aagaccuaug c                                              21

<210> SEQ ID NO 294
<211> LENGTH: 21
<212> TYPE: RNA
<213> ORGANISM: Artificial Sequence
<220> FEATURE:
<223> OTHER INFORMATION: Chemically synthesized

<400> SEQUENCE: 294
cugggucuuc caucuagaac u                                              21

<210> SEQ ID NO 295
<211> LENGTH: 21
<212> TYPE: RNA
<213> ORGANISM: Artificial Sequence
<220> FEATURE:
<223> OTHER INFORMATION: Chemically synthesized

<400> SEQUENCE: 295
ugggucuucc aucuagaacu g                                              21

<210> SEQ ID NO 296
<211> LENGTH: 21
<212> TYPE: RNA
<213> ORGANISM: Artificial Sequence
<220> FEATURE:
<223> OTHER INFORMATION: Chemically synthesized

<400> SEQUENCE: 296
acaacucaau gagcuuccug g                                              21

<210> SEQ ID NO 297
<211> LENGTH: 21
<212> TYPE: RNA
<213> ORGANISM: Artificial Sequence
<220> FEATURE:
<223> OTHER INFORMATION: Chemically synthesized

<400> SEQUENCE: 297
cuagauggaa gacccagaug g                                              21

<210> SEQ ID NO 298
```

```
<211> LENGTH: 21
<212> TYPE: RNA
<213> ORGANISM: Artificial Sequence
<220> FEATURE:
<223> OTHER INFORMATION: Chemically synthesized

<400> SEQUENCE: 298
guacaugcua cacacacauc c                                          21

<210> SEQ ID NO 299
<211> LENGTH: 21
<212> TYPE: RNA
<213> ORGANISM: Artificial Sequence
<220> FEATURE:
<223> OTHER INFORMATION: Chemically synthesized

<400> SEQUENCE: 299
aacaaacaac aaacacacuu g                                          21

<210> SEQ ID NO 300
<211> LENGTH: 21
<212> TYPE: RNA
<213> ORGANISM: Artificial Sequence
<220> FEATURE:
<223> OTHER INFORMATION: Chemically synthesized

<400> SEQUENCE: 300
uuccaugcua caguacugag g                                          21

<210> SEQ ID NO 301
<211> LENGTH: 21
<212> TYPE: RNA
<213> ORGANISM: Artificial Sequence
<220> FEATURE:
<223> OTHER INFORMATION: Chemically synthesized

<400> SEQUENCE: 301
aaacaacaaa cacacuuggu c                                          21

<210> SEQ ID NO 302
<211> LENGTH: 21
<212> TYPE: RNA
<213> ORGANISM: Artificial Sequence
<220> FEATURE:
<223> OTHER INFORMATION: Chemically synthesized

<400> SEQUENCE: 302
ucuucuugau gacucggaag c                                          21

<210> SEQ ID NO 303
<211> LENGTH: 21
<212> TYPE: RNA
<213> ORGANISM: Artificial Sequence
<220> FEATURE:
<223> OTHER INFORMATION: Chemically synthesized

<400> SEQUENCE: 303
aaacacuauu cccccaccuc c                                          21

<210> SEQ ID NO 304
<211> LENGTH: 21
<212> TYPE: RNA
<213> ORGANISM: Artificial Sequence
<220> FEATURE:
<223> OTHER INFORMATION: Chemically synthesized

<400> SEQUENCE: 304
```
uuguuccaug cuacaguacu g    21

<210> SEQ ID NO 305
<211> LENGTH: 21
<212> TYPE: RNA
<213> ORGANISM: Artificial Sequence
<220> FEATURE:
<223> OTHER INFORMATION: Chemically synthesized

<400> SEQUENCE: 305
acuugaacau caaguguauu c    21

<210> SEQ ID NO 306
<211> LENGTH: 21
<212> TYPE: RNA
<213> ORGANISM: Artificial Sequence
<220> FEATURE:
<223> OTHER INFORMATION: Chemically synthesized

<400> SEQUENCE: 306
uugcauaggu cuuaauacuu g    21

<210> SEQ ID NO 307
<211> LENGTH: 21
<212> TYPE: RNA
<213> ORGANISM: Artificial Sequence
<220> FEATURE:
<223> OTHER INFORMATION: Chemically synthesized

<400> SEQUENCE: 307
uagucuccac cccaaaaguu c    21

<210> SEQ ID NO 308
<211> LENGTH: 21
<212> TYPE: RNA
<213> ORGANISM: Artificial Sequence
<220> FEATURE:
<223> OTHER INFORMATION: Chemically synthesized

<400> SEQUENCE: 308
aguacugagg gguauguguc c    21

<210> SEQ ID NO 309
<211> LENGTH: 21
<212> TYPE: RNA
<213> ORGANISM: Artificial Sequence
<220> FEATURE:
<223> OTHER INFORMATION: Chemically synthesized

<400> SEQUENCE: 309
uaagauacac aaaccaccuc c    21

<210> SEQ ID NO 310
<211> LENGTH: 21
<212> TYPE: RNA
<213> ORGANISM: Artificial Sequence
<220> FEATURE:
<223> OTHER INFORMATION: Chemically synthesized

<400> SEQUENCE: 310
uuuuucaagu gucaaagauc c    21

<210> SEQ ID NO 311
<211> LENGTH: 21
<212> TYPE: RNA

```
<213> ORGANISM: Artificial Sequence
<220> FEATURE:
<223> OTHER INFORMATION: Chemically synthesized

<400> SEQUENCE: 311
aacaguucua gauggaagac c                                              21

<210> SEQ ID NO 312
<211> LENGTH: 21
<212> TYPE: RNA
<213> ORGANISM: Artificial Sequence
<220> FEATURE:
<223> OTHER INFORMATION: Chemically synthesized

<400> SEQUENCE: 312
uaauaaggua caugcuacac a                                              21

<210> SEQ ID NO 313
<211> LENGTH: 21
<212> TYPE: RNA
<213> ORGANISM: Artificial Sequence
<220> FEATURE:
<223> OTHER INFORMATION: Chemically synthesized

<400> SEQUENCE: 313
auccagcugg aagccuuguu g                                              21

<210> SEQ ID NO 314
<211> LENGTH: 21
<212> TYPE: RNA
<213> ORGANISM: Artificial Sequence
<220> FEATURE:
<223> OTHER INFORMATION: Chemically synthesized

<400> SEQUENCE: 314
aagugucaaa gaucccaagu g                                              21

<210> SEQ ID NO 315
<211> LENGTH: 21
<212> TYPE: RNA
<213> ORGANISM: Artificial Sequence
<220> FEATURE:
<223> OTHER INFORMATION: Chemically synthesized

<400> SEQUENCE: 315
uacaacaggu caguagugau g                                              21

<210> SEQ ID NO 316
<211> LENGTH: 21
<212> TYPE: RNA
<213> ORGANISM: Artificial Sequence
<220> FEATURE:
<223> OTHER INFORMATION: Chemically synthesized

<400> SEQUENCE: 316
uaagguacau gcuacacaca c                                              21

<210> SEQ ID NO 317
<211> LENGTH: 21
<212> TYPE: RNA
<213> ORGANISM: Artificial Sequence
<220> FEATURE:
<223> OTHER INFORMATION: Chemically synthesized

<400> SEQUENCE: 317
uuccuacucu uacauucaug c                                              21
```

<210> SEQ ID NO 318
<211> LENGTH: 21
<212> TYPE: RNA
<213> ORGANISM: Artificial Sequence
<220> FEATURE:
<223> OTHER INFORMATION: Chemically synthesized

<400> SEQUENCE: 318
gaagccacug uugcugcugu c                                              21

<210> SEQ ID NO 319
<211> LENGTH: 21
<212> TYPE: RNA
<213> ORGANISM: Artificial Sequence
<220> FEATURE:
<223> OTHER INFORMATION: Chemically synthesized

<400> SEQUENCE: 319
ucuccugcag cagcugcauc a                                              21

<210> SEQ ID NO 320
<211> LENGTH: 21
<212> TYPE: RNA
<213> ORGANISM: Artificial Sequence
<220> FEATURE:
<223> OTHER INFORMATION: Chemically synthesized

<400> SEQUENCE: 320
cuugaacauc aaguguauuc a                                              21

<210> SEQ ID NO 321
<211> LENGTH: 21
<212> TYPE: RNA
<213> ORGANISM: Artificial Sequence
<220> FEATURE:
<223> OTHER INFORMATION: Chemically synthesized

<400> SEQUENCE: 321
ugaacaucaa guguauucau g                                              21

<210> SEQ ID NO 322
<211> LENGTH: 21
<212> TYPE: RNA
<213> ORGANISM: Artificial Sequence
<220> FEATURE:
<223> OTHER INFORMATION: Chemically synthesized

<400> SEQUENCE: 322
aagccacugu ugcugcuguc c                                              21

<210> SEQ ID NO 323
<211> LENGTH: 21
<212> TYPE: RNA
<213> ORGANISM: Artificial Sequence
<220> FEATURE:
<223> OTHER INFORMATION: Chemically synthesized

<400> SEQUENCE: 323
acaucaagug uauucaugaa c                                              21

<210> SEQ ID NO 324
<211> LENGTH: 21
<212> TYPE: RNA
<213> ORGANISM: Artificial Sequence
<220> FEATURE:

<223> OTHER INFORMATION: Chemically synthesized

<400> SEQUENCE: 324
gaacaucaag uguauucaug a                                          21

<210> SEQ ID NO 325
<211> LENGTH: 21
<212> TYPE: RNA
<213> ORGANISM: Artificial Sequence
<220> FEATURE:
<223> OTHER INFORMATION: Chemically synthesized

<400> SEQUENCE: 325
acuguugcug cguccaggg a                                           21

<210> SEQ ID NO 326
<211> LENGTH: 21
<212> TYPE: RNA
<213> ORGANISM: Artificial Sequence
<220> FEATURE:
<223> OTHER INFORMATION: Chemically synthesized

<400> SEQUENCE: 326
uguugcugcu guccagggac u                                          21

<210> SEQ ID NO 327
<211> LENGTH: 21
<212> TYPE: RNA
<213> ORGANISM: Artificial Sequence
<220> FEATURE:
<223> OTHER INFORMATION: Chemically synthesized

<400> SEQUENCE: 327
acuugaacau caaguguauu c                                          21

<210> SEQ ID NO 328
<211> LENGTH: 21
<212> TYPE: RNA
<213> ORGANISM: Artificial Sequence
<220> FEATURE:
<223> OTHER INFORMATION: Chemically synthesized

<400> SEQUENCE: 328
ucuucaugua aacaguucua g                                          21

<210> SEQ ID NO 329
<211> LENGTH: 21
<212> TYPE: RNA
<213> ORGANISM: Artificial Sequence
<220> FEATURE:
<223> OTHER INFORMATION: Chemically synthesized

<400> SEQUENCE: 329
cauguaaaca guucuagaug g                                          21

<210> SEQ ID NO 330
<211> LENGTH: 21
<212> TYPE: RNA
<213> ORGANISM: Artificial Sequence
<220> FEATURE:
<223> OTHER INFORMATION: Chemically synthesized

<400> SEQUENCE: 330
guaaacaguu cuagauggaa g                                          21

```
<210> SEQ ID NO 331
<211> LENGTH: 21
<212> TYPE: RNA
<213> ORGANISM: Artificial Sequence
<220> FEATURE:
<223> OTHER INFORMATION: Chemically synthesized

<400> SEQUENCE: 331
uaaacaguuc uagauggaag a                                              21

<210> SEQ ID NO 332
<211> LENGTH: 21
<212> TYPE: RNA
<213> ORGANISM: Artificial Sequence
<220> FEATURE:
<223> OTHER INFORMATION: Chemically synthesized

<400> SEQUENCE: 332
ucauguaaac aguucuagau g                                              21

<210> SEQ ID NO 333
<211> LENGTH: 21
<212> TYPE: RNA
<213> ORGANISM: Artificial Sequence
<220> FEATURE:
<223> OTHER INFORMATION: Chemically synthesized

<400> SEQUENCE: 333
acaguucuag auggaagacc c                                              21

<210> SEQ ID NO 334
<211> LENGTH: 21
<212> TYPE: RNA
<213> ORGANISM: Artificial Sequence
<220> FEATURE:
<223> OTHER INFORMATION: Chemically synthesized

<400> SEQUENCE: 334
auguaaacag uucuagaugg a                                              21

<210> SEQ ID NO 335
<211> LENGTH: 21
<212> TYPE: RNA
<213> ORGANISM: Artificial Sequence
<220> FEATURE:
<223> OTHER INFORMATION: Chemically synthesized

<400> SEQUENCE: 335
cuucauguaa acaguucuag a                                              21

<210> SEQ ID NO 336
<211> LENGTH: 21
<212> TYPE: RNA
<213> ORGANISM: Artificial Sequence
<220> FEATURE:
<223> OTHER INFORMATION: Chemically synthesized

<400> SEQUENCE: 336
uguaaacagu ucuagaugga a                                              21

<210> SEQ ID NO 337
<211> LENGTH: 21
<212> TYPE: RNA
<213> ORGANISM: Artificial Sequence
<220> FEATURE:
<223> OTHER INFORMATION: Chemically synthesized
```

```
<400> SEQUENCE: 337
aaacaguucu agauggaaga c                                              21

<210> SEQ ID NO 338
<211> LENGTH: 21
<212> TYPE: RNA
<213> ORGANISM: Artificial Sequence
<220> FEATURE:
<223> OTHER INFORMATION: Chemically synthesized

<400> SEQUENCE: 338
ggucuuaaua cuugaacauc a                                              21

<210> SEQ ID NO 339
<211> LENGTH: 21
<212> TYPE: RNA
<213> ORGANISM: Artificial Sequence
<220> FEATURE:
<223> OTHER INFORMATION: Chemically synthesized

<400> SEQUENCE: 339
cauaggucuu aauacuugaa c                                              21

<210> SEQ ID NO 340
<211> LENGTH: 21
<212> TYPE: RNA
<213> ORGANISM: Artificial Sequence
<220> FEATURE:
<223> OTHER INFORMATION: Chemically synthesized

<400> SEQUENCE: 340
ugcauagguc uuaauacuug a                                              21

<210> SEQ ID NO 341
<211> LENGTH: 21
<212> TYPE: RNA
<213> ORGANISM: Artificial Sequence
<220> FEATURE:
<223> OTHER INFORMATION: Chemically synthesized

<400> SEQUENCE: 341
aggucuuaau acuugaacau c                                              21

<210> SEQ ID NO 342
<211> LENGTH: 21
<212> TYPE: RNA
<213> ORGANISM: Artificial Sequence
<220> FEATURE:
<223> OTHER INFORMATION: Chemically synthesized

<400> SEQUENCE: 342
gcauaggucu uaauacuuga a                                              21

<210> SEQ ID NO 343
<211> LENGTH: 21
<212> TYPE: RNA
<213> ORGANISM: Artificial Sequence
<220> FEATURE:
<223> OTHER INFORMATION: Chemically synthesized

<400> SEQUENCE: 343
aguucuagau ggaagaccca g                                              21

<210> SEQ ID NO 344
<211> LENGTH: 21
```

```
<212> TYPE: RNA
<213> ORGANISM: Artificial Sequence
<220> FEATURE:
<223> OTHER INFORMATION: Chemically synthesized

<400> SEQUENCE: 344
caguucuaga uggaagaccc a                                              21

<210> SEQ ID NO 345
<211> LENGTH: 19
<212> TYPE: RNA
<213> ORGANISM: Artificial Sequence
<220> FEATURE:
<223> OTHER INFORMATION: Chemically synthesized

<400> SEQUENCE: 345
ugaaaaauua caccuggca                                                 19

<210> SEQ ID NO 346
<211> LENGTH: 19
<212> TYPE: RNA
<213> ORGANISM: Artificial Sequence
<220> FEATURE:
<223> OTHER INFORMATION: Chemically synthesized

<400> SEQUENCE: 346
gacacuugaa aaauuacac                                                 19

<210> SEQ ID NO 347
<211> LENGTH: 19
<212> TYPE: RNA
<213> ORGANISM: Artificial Sequence
<220> FEATURE:
<223> OTHER INFORMATION: Chemically synthesized

<400> SEQUENCE: 347
cacuugaaaa auuacaccu                                                 19

<210> SEQ ID NO 348
<211> LENGTH: 19
<212> TYPE: RNA
<213> ORGANISM: Artificial Sequence
<220> FEATURE:
<223> OTHER INFORMATION: Chemically synthesized

<400> SEQUENCE: 348
uuaggggcca acaaggcuu                                                 19

<210> SEQ ID NO 349
<211> LENGTH: 19
<212> TYPE: RNA
<213> ORGANISM: Artificial Sequence
<220> FEATURE:
<223> OTHER INFORMATION: Chemically synthesized

<400> SEQUENCE: 349
acacuugaaa aauuacacc                                                 19

<210> SEQ ID NO 350
<211> LENGTH: 19
<212> TYPE: RNA
<213> ORGANISM: Artificial Sequence
<220> FEATURE:
<223> OTHER INFORMATION: Chemically synthesized

<400> SEQUENCE: 350
```
acccugagga ugaacacuu                                                    19

<210> SEQ ID NO 351
<211> LENGTH: 19
<212> TYPE: RNA
<213> ORGANISM: Artificial Sequence
<220> FEATURE:
<223> OTHER INFORMATION: Chemically synthesized

<400> SEQUENCE: 351
guacugcaga guugagcug                                                    19

<210> SEQ ID NO 352
<211> LENGTH: 19
<212> TYPE: RNA
<213> ORGANISM: Artificial Sequence
<220> FEATURE:
<223> OTHER INFORMATION: Chemically synthesized

<400> SEQUENCE: 352
guguacugca gaguugagc                                                    19

<210> SEQ ID NO 353
<211> LENGTH: 19
<212> TYPE: RNA
<213> ORGANISM: Artificial Sequence
<220> FEATURE:
<223> OTHER INFORMATION: Chemically synthesized

<400> SEQUENCE: 353
guguguuugu uguuuguuu                                                    19

<210> SEQ ID NO 354
<211> LENGTH: 19
<212> TYPE: RNA
<213> ORGANISM: Artificial Sequence
<220> FEATURE:
<223> OTHER INFORMATION: Chemically synthesized

<400> SEQUENCE: 354
uugugugcca accugaugc                                                    19

<210> SEQ ID NO 355
<211> LENGTH: 19
<212> TYPE: RNA
<213> ORGANISM: Artificial Sequence
<220> FEATURE:
<223> OTHER INFORMATION: Chemically synthesized

<400> SEQUENCE: 355
aucguguacu gcagaguug                                                    19

<210> SEQ ID NO 356
<211> LENGTH: 19
<212> TYPE: RNA
<213> ORGANISM: Artificial Sequence
<220> FEATURE:
<223> OTHER INFORMATION: Chemically synthesized

<400> SEQUENCE: 356
ccaucgugua cugcagagu                                                    19

<210> SEQ ID NO 357
<211> LENGTH: 19
<212> TYPE: RNA
<213> ORGANISM: Artificial Sequence

```
<220> FEATURE:
<223> OTHER INFORMATION: Chemically synthesized

<400> SEQUENCE: 357
acuugaaaaa uuacaccug                                                 19

<210> SEQ ID NO 358
<211> LENGTH: 19
<212> TYPE: RNA
<213> ORGANISM: Artificial Sequence
<220> FEATURE:
<223> OTHER INFORMATION: Chemically synthesized

<400> SEQUENCE: 358
ugaggaugaa cacugugu                                                  19

<210> SEQ ID NO 359
<211> LENGTH: 19
<212> TYPE: RNA
<213> ORGANISM: Artificial Sequence
<220> FEATURE:
<223> OTHER INFORMATION: Chemically synthesized

<400> SEQUENCE: 359
accuggcagc ugcguuuaa                                                 19

<210> SEQ ID NO 360
<211> LENGTH: 19
<212> TYPE: RNA
<213> ORGANISM: Artificial Sequence
<220> FEATURE:
<223> OTHER INFORMATION: Chemically synthesized

<400> SEQUENCE: 360
cagagacgac ugaacuuuu                                                 19

<210> SEQ ID NO 361
<211> LENGTH: 19
<212> TYPE: RNA
<213> ORGANISM: Artificial Sequence
<220> FEATURE:
<223> OTHER INFORMATION: Chemically synthesized

<400> SEQUENCE: 361
aagacagaga cgacugaac                                                 19

<210> SEQ ID NO 362
<211> LENGTH: 19
<212> TYPE: RNA
<213> ORGANISM: Artificial Sequence
<220> FEATURE:
<223> OTHER INFORMATION: Chemically synthesized

<400> SEQUENCE: 362
gcagcugcgu uuaagccuu                                                 19

<210> SEQ ID NO 363
<211> LENGTH: 19
<212> TYPE: RNA
<213> ORGANISM: Artificial Sequence
<220> FEATURE:
<223> OTHER INFORMATION: Chemically synthesized

<400> SEQUENCE: 363
aggaagcuca uugaguugu                                                 19
```

<210> SEQ ID NO 364
<211> LENGTH: 19
<212> TYPE: RNA
<213> ORGANISM: Artificial Sequence
<220> FEATURE:
<223> OTHER INFORMATION: Chemically synthesized

<400> SEQUENCE: 364
guguuuccca ggaagcuca					19

<210> SEQ ID NO 365
<211> LENGTH: 19
<212> TYPE: RNA
<213> ORGANISM: Artificial Sequence
<220> FEATURE:
<223> OTHER INFORMATION: Chemically synthesized

<400> SEQUENCE: 365
gacgacugaa cuuuugggg					19

<210> SEQ ID NO 366
<211> LENGTH: 19
<212> TYPE: RNA
<213> ORGANISM: Artificial Sequence
<220> FEATURE:
<223> OTHER INFORMATION: Chemically synthesized

<400> SEQUENCE: 366
acagagacga cugaacuuu					19

<210> SEQ ID NO 367
<211> LENGTH: 19
<212> TYPE: RNA
<213> ORGANISM: Artificial Sequence
<220> FEATURE:
<223> OTHER INFORMATION: Chemically synthesized

<400> SEQUENCE: 367
aggaugaaca cuugugugc					19

<210> SEQ ID NO 368
<211> LENGTH: 19
<212> TYPE: RNA
<213> ORGANISM: Artificial Sequence
<220> FEATURE:
<223> OTHER INFORMATION: Chemically synthesized

<400> SEQUENCE: 368
cugaggauga acacuugug					19

<210> SEQ ID NO 369
<211> LENGTH: 19
<212> TYPE: RNA
<213> ORGANISM: Artificial Sequence
<220> FEATURE:
<223> OTHER INFORMATION: Chemically synthesized

<400> SEQUENCE: 369
ucugggucuu ccaucuaga					19

<210> SEQ ID NO 370
<211> LENGTH: 19
<212> TYPE: RNA
<213> ORGANISM: Artificial Sequence
<220> FEATURE:
<223> OTHER INFORMATION: Chemically synthesized

```
<400> SEQUENCE: 370
aucugggucu uccaucuag                                                    19

<210> SEQ ID NO 371
<211> LENGTH: 19
<212> TYPE: RNA
<213> ORGANISM: Artificial Sequence
<220> FEATURE:
<223> OTHER INFORMATION: Chemically synthesized

<400> SEQUENCE: 371
gaagggacca aguguguuu                                                    19

<210> SEQ ID NO 372
<211> LENGTH: 19
<212> TYPE: RNA
<213> ORGANISM: Artificial Sequence
<220> FEATURE:
<223> OTHER INFORMATION: Chemically synthesized

<400> SEQUENCE: 372
aaggcuuagg ggccaacaa                                                    19

<210> SEQ ID NO 373
<211> LENGTH: 19
<212> TYPE: RNA
<213> ORGANISM: Artificial Sequence
<220> FEATURE:
<223> OTHER INFORMATION: Chemically synthesized

<400> SEQUENCE: 373
uucccaggaa gcucauuga                                                    19

<210> SEQ ID NO 374
<211> LENGTH: 19
<212> TYPE: RNA
<213> ORGANISM: Artificial Sequence
<220> FEATURE:
<223> OTHER INFORMATION: Chemically synthesized

<400> SEQUENCE: 374
ugggcaaaga acuacugcg                                                    19

<210> SEQ ID NO 375
<211> LENGTH: 19
<212> TYPE: RNA
<213> ORGANISM: Artificial Sequence
<220> FEATURE:
<223> OTHER INFORMATION: Chemically synthesized

<400> SEQUENCE: 375
ggugggcaaa gaacuacug                                                    19

<210> SEQ ID NO 376
<211> LENGTH: 19
<212> TYPE: RNA
<213> ORGANISM: Artificial Sequence
<220> FEATURE:
<223> OTHER INFORMATION: Chemically synthesized

<400> SEQUENCE: 376
gugggcaaag aacuacugc                                                    19

<210> SEQ ID NO 377
```

-continued

```
<211> LENGTH: 19
<212> TYPE: RNA
<213> ORGANISM: Artificial Sequence
<220> FEATURE:
<223> OTHER INFORMATION: Chemically synthesized

<400> SEQUENCE: 377
ugccuagcca guugguaag                                                19

<210> SEQ ID NO 378
<211> LENGTH: 19
<212> TYPE: RNA
<213> ORGANISM: Artificial Sequence
<220> FEATURE:
<223> OTHER INFORMATION: Chemically synthesized

<400> SEQUENCE: 378
aagccaggug ggcaaagaa                                                19

<210> SEQ ID NO 379
<211> LENGTH: 19
<212> TYPE: RNA
<213> ORGANISM: Artificial Sequence
<220> FEATURE:
<223> OTHER INFORMATION: Chemically synthesized

<400> SEQUENCE: 379
augccuagcc aguugguaa                                                19

<210> SEQ ID NO 380
<211> LENGTH: 19
<212> TYPE: RNA
<213> ORGANISM: Artificial Sequence
<220> FEATURE:
<223> OTHER INFORMATION: Chemically synthesized

<400> SEQUENCE: 380
uuccgaguca ucaagaaga                                                19

<210> SEQ ID NO 381
<211> LENGTH: 19
<212> TYPE: RNA
<213> ORGANISM: Artificial Sequence
<220> FEATURE:
<223> OTHER INFORMATION: Chemically synthesized

<400> SEQUENCE: 381
gacgcaugaa uguaagagu                                                19

<210> SEQ ID NO 382
<211> LENGTH: 19
<212> TYPE: RNA
<213> ORGANISM: Artificial Sequence
<220> FEATURE:
<223> OTHER INFORMATION: Chemically synthesized

<400> SEQUENCE: 382
uacagacgca ugaauguaa                                                19

<210> SEQ ID NO 383
<211> LENGTH: 19
<212> TYPE: RNA
<213> ORGANISM: Artificial Sequence
<220> FEATURE:
<223> OTHER INFORMATION: Chemically synthesized

<400> SEQUENCE: 383
```

-continued gughguagca uguaccuua                                    19

<210> SEQ ID NO 384
<211> LENGTH: 19
<212> TYPE: RNA
<213> ORGANISM: Artificial Sequence
<220> FEATURE:
<223> OTHER INFORMATION: Chemically synthesized

<400> SEQUENCE: 384
acgcaugaau guaagagua                                    19

<210> SEQ ID NO 385
<211> LENGTH: 19
<212> TYPE: RNA
<213> ORGANISM: Artificial Sequence
<220> FEATURE:
<223> OTHER INFORMATION: Chemically synthesized

<400> SEQUENCE: 385
aucuuacaga cgcaugaau                                    19

<210> SEQ ID NO 386
<211> LENGTH: 19
<212> TYPE: RNA
<213> ORGANISM: Artificial Sequence
<220> FEATURE:
<223> OTHER INFORMATION: Chemically synthesized

<400> SEQUENCE: 386
agacgcauga auguaagag                                    19

<210> SEQ ID NO 387
<211> LENGTH: 19
<212> TYPE: RNA
<213> ORGANISM: Artificial Sequence
<220> FEATURE:
<223> OTHER INFORMATION: Chemically synthesized

<400> SEQUENCE: 387
cuaucuuaca gacgcauga                                    19

<210> SEQ ID NO 388
<211> LENGTH: 19
<212> TYPE: RNA
<213> ORGANISM: Artificial Sequence
<220> FEATURE:
<223> OTHER INFORMATION: Chemically synthesized

<400> SEQUENCE: 388
gcaucacuac ugaccuguu                                    19

<210> SEQ ID NO 389
<211> LENGTH: 19
<212> TYPE: RNA
<213> ORGANISM: Artificial Sequence
<220> FEATURE:
<223> OTHER INFORMATION: Chemically synthesized

<400> SEQUENCE: 389
ggagcaucac uacugaccu                                    19

<210> SEQ ID NO 390
<211> LENGTH: 19
<212> TYPE: RNA

```
<213> ORGANISM: Artificial Sequence
<220> FEATURE:
<223> OTHER INFORMATION: Chemically synthesized

<400> SEQUENCE: 390
augaaacaaa ggcuuaggg                                               19

<210> SEQ ID NO 391
<211> LENGTH: 19
<212> TYPE: RNA
<213> ORGANISM: Artificial Sequence
<220> FEATURE:
<223> OTHER INFORMATION: Chemically synthesized

<400> SEQUENCE: 391
agcuaucuua cagacgcau                                               19

<210> SEQ ID NO 392
<211> LENGTH: 19
<212> TYPE: RNA
<213> ORGANISM: Artificial Sequence
<220> FEATURE:
<223> OTHER INFORMATION: Chemically synthesized

<400> SEQUENCE: 392
uaggcagcua ucuuacaga                                               19

<210> SEQ ID NO 393
<211> LENGTH: 19
<212> TYPE: RNA
<213> ORGANISM: Artificial Sequence
<220> FEATURE:
<223> OTHER INFORMATION: Chemically synthesized

<400> SEQUENCE: 393
accuguugua ggcagcuau                                               19

<210> SEQ ID NO 394
<211> LENGTH: 19
<212> TYPE: RNA
<213> ORGANISM: Artificial Sequence
<220> FEATURE:
<223> OTHER INFORMATION: Chemically synthesized

<400> SEQUENCE: 394
agcaucacua cugaccugu                                               19

<210> SEQ ID NO 395
<211> LENGTH: 19
<212> TYPE: RNA
<213> ORGANISM: Artificial Sequence
<220> FEATURE:
<223> OTHER INFORMATION: Chemically synthesized

<400> SEQUENCE: 395
ucugaucgga gcaucacua                                               19

<210> SEQ ID NO 396
<211> LENGTH: 19
<212> TYPE: RNA
<213> ORGANISM: Artificial Sequence
<220> FEATURE:
<223> OTHER INFORMATION: Chemically synthesized

<400> SEQUENCE: 396
ugacaguuaa caguggugu                                               19
```

<210> SEQ ID NO 397
<211> LENGTH: 19
<212> TYPE: RNA
<213> ORGANISM: Artificial Sequence
<220> FEATURE:
<223> OTHER INFORMATION: Chemically synthesized

<400> SEQUENCE: 397
cugacaguua acaguggug                                              19

<210> SEQ ID NO 398
<211> LENGTH: 19
<212> TYPE: RNA
<213> ORGANISM: Artificial Sequence
<220> FEATURE:
<223> OTHER INFORMATION: Chemically synthesized

<400> SEQUENCE: 398
guuacugaca guuaacagu                                              19

<210> SEQ ID NO 399
<211> LENGTH: 19
<212> TYPE: RNA
<213> ORGANISM: Artificial Sequence
<220> FEATURE:
<223> OTHER INFORMATION: Chemically synthesized

<400> SEQUENCE: 399
uuguuacuga caguuaaca                                              19

<210> SEQ ID NO 400
<211> LENGTH: 19
<212> TYPE: RNA
<213> ORGANISM: Artificial Sequence
<220> FEATURE:
<223> OTHER INFORMATION: Chemically synthesized

<400> SEQUENCE: 400
uacucacugu ucaugaaua                                              19

<210> SEQ ID NO 401
<211> LENGTH: 19
<212> TYPE: RNA
<213> ORGANISM: Artificial Sequence
<220> FEATURE:
<223> OTHER INFORMATION: Chemically synthesized

<400> SEQUENCE: 401
ucacuuggga ucuuugaca                                              19

<210> SEQ ID NO 402
<211> LENGTH: 19
<212> TYPE: RNA
<213> ORGANISM: Artificial Sequence
<220> FEATURE:
<223> OTHER INFORMATION: Chemically synthesized

<400> SEQUENCE: 402
acagacgcau gaauguaag                                              19

<210> SEQ ID NO 403
<211> LENGTH: 19
<212> TYPE: RNA
<213> ORGANISM: Artificial Sequence
<220> FEATURE:

<223> OTHER INFORMATION: Chemically synthesized

<400> SEQUENCE: 403
cagcuaucuu acagacgca                                          19

<210> SEQ ID NO 404
<211> LENGTH: 19
<212> TYPE: RNA
<213> ORGANISM: Artificial Sequence
<220> FEATURE:
<223> OTHER INFORMATION: Chemically synthesized

<400> SEQUENCE: 404
ucacuacuga ccuguugua                                          19

<210> SEQ ID NO 405
<211> LENGTH: 19
<212> TYPE: RNA
<213> ORGANISM: Artificial Sequence
<220> FEATURE:
<223> OTHER INFORMATION: Chemically synthesized

<400> SEQUENCE: 405
gagcaucacu acugaccug                                          19

<210> SEQ ID NO 406
<211> LENGTH: 19
<212> TYPE: RNA
<213> ORGANISM: Artificial Sequence
<220> FEATURE:
<223> OTHER INFORMATION: Chemically synthesized

<400> SEQUENCE: 406
guguaucuua cuggucuga                                          19

<210> SEQ ID NO 407
<211> LENGTH: 19
<212> TYPE: RNA
<213> ORGANISM: Artificial Sequence
<220> FEATURE:
<223> OTHER INFORMATION: Chemically synthesized

<400> SEQUENCE: 407
gugguuugug uaucuuacu                                          19

<210> SEQ ID NO 408
<211> LENGTH: 19
<212> TYPE: RNA
<213> ORGANISM: Artificial Sequence
<220> FEATURE:
<223> OTHER INFORMATION: Chemically synthesized

<400> SEQUENCE: 408
acaguuaaca gugguguga                                          19

<210> SEQ ID NO 409
<211> LENGTH: 19
<212> TYPE: RNA
<213> ORGANISM: Artificial Sequence
<220> FEATURE:
<223> OTHER INFORMATION: Chemically synthesized

<400> SEQUENCE: 409
aacugaggca gccaccuaa                                          19

```
<210> SEQ ID NO 410
<211> LENGTH: 19
<212> TYPE: RNA
<213> ORGANISM: Artificial Sequence
<220> FEATURE:
<223> OTHER INFORMATION: Chemically synthesized

<400> SEQUENCE: 410
uguucaugaa uacacuuga                                                  19

<210> SEQ ID NO 411
<211> LENGTH: 19
<212> TYPE: RNA
<213> ORGANISM: Artificial Sequence
<220> FEATURE:
<223> OTHER INFORMATION: Chemically synthesized

<400> SEQUENCE: 411
cuguucauga auacacuug                                                  19

<210> SEQ ID NO 412
<211> LENGTH: 19
<212> TYPE: RNA
<213> ORGANISM: Artificial Sequence
<220> FEATURE:
<223> OTHER INFORMATION: Chemically synthesized

<400> SEQUENCE: 412
agauacucac uguucauga                                                  19

<210> SEQ ID NO 413
<211> LENGTH: 19
<212> TYPE: RNA
<213> ORGANISM: Artificial Sequence
<220> FEATURE:
<223> OTHER INFORMATION: Chemically synthesized

<400> SEQUENCE: 413
cagacgcaug aauguaaga                                                  19

<210> SEQ ID NO 414
<211> LENGTH: 19
<212> TYPE: RNA
<213> ORGANISM: Artificial Sequence
<220> FEATURE:
<223> OTHER INFORMATION: Chemically synthesized

<400> SEQUENCE: 414
gcagcuaucu uacagacgc                                                  19

<210> SEQ ID NO 415
<211> LENGTH: 19
<212> TYPE: RNA
<213> ORGANISM: Artificial Sequence
<220> FEATURE:
<223> OTHER INFORMATION: Chemically synthesized

<400> SEQUENCE: 415
ggcagcuauc uuacagacg                                                  19

<210> SEQ ID NO 416
<211> LENGTH: 19
<212> TYPE: RNA
<213> ORGANISM: Artificial Sequence
<220> FEATURE:
<223> OTHER INFORMATION: Chemically synthesized
```

```
<400> SEQUENCE: 416
gguuugugua ucuuacugg                                              19

<210> SEQ ID NO 417
<211> LENGTH: 19
<212> TYPE: RNA
<213> ORGANISM: Artificial Sequence
<220> FEATURE:
<223> OTHER INFORMATION: Chemically synthesized

<400> SEQUENCE: 417
gaggugguuu guguaucuu                                              19

<210> SEQ ID NO 418
<211> LENGTH: 19
<212> TYPE: RNA
<213> ORGANISM: Artificial Sequence
<220> FEATURE:
<223> OTHER INFORMATION: Chemically synthesized

<400> SEQUENCE: 418
guggaggugg uuuguguau                                              19

<210> SEQ ID NO 419
<211> LENGTH: 19
<212> TYPE: RNA
<213> ORGANISM: Artificial Sequence
<220> FEATURE:
<223> OTHER INFORMATION: Chemically synthesized

<400> SEQUENCE: 419
uacugacagu uaacagugg                                              19

<210> SEQ ID NO 420
<211> LENGTH: 19
<212> TYPE: RNA
<213> ORGANISM: Artificial Sequence
<220> FEATURE:
<223> OTHER INFORMATION: Chemically synthesized

<400> SEQUENCE: 420
guguagcaug uaccuuauu                                              19

<210> SEQ ID NO 421
<211> LENGTH: 19
<212> TYPE: RNA
<213> ORGANISM: Artificial Sequence
<220> FEATURE:
<223> OTHER INFORMATION: Chemically synthesized

<400> SEQUENCE: 421 agguggggcaa agaacuacu                                             19

<210> SEQ ID NO 422
<211> LENGTH: 19
<212> TYPE: RNA
<213> ORGANISM: Artificial Sequence
<220> FEATURE:
<223> OTHER INFORMATION: Chemically synthesized

<400> SEQUENCE: 422
gugacccuga ggaugaaca                                              19

<210> SEQ ID NO 423
<211> LENGTH: 19
```

```
<212> TYPE: RNA
<213> ORGANISM: Artificial Sequence
<220> FEATURE:
<223> OTHER INFORMATION: Chemically synthesized

<400> SEQUENCE: 423
caggugggca aagaacuac                                                19

<210> SEQ ID NO 424
<211> LENGTH: 19
<212> TYPE: RNA
<213> ORGANISM: Artificial Sequence
<220> FEATURE:
<223> OTHER INFORMATION: Chemically synthesized

<400> SEQUENCE: 424
ccaggugggc aaagaacua                                                19

<210> SEQ ID NO 425
<211> LENGTH: 19
<212> TYPE: RNA
<213> ORGANISM: Artificial Sequence
<220> FEATURE:
<223> OTHER INFORMATION: Chemically synthesized

<400> SEQUENCE: 425
auccaggggc uguuuagcu                                                19

<210> SEQ ID NO 426
<211> LENGTH: 19
<212> TYPE: RNA
<213> ORGANISM: Artificial Sequence
<220> FEATURE:
<223> OTHER INFORMATION: Chemically synthesized

<400> SEQUENCE: 426
aagauccagg ggcuguuua                                                19

<210> SEQ ID NO 427
<211> LENGTH: 19
<212> TYPE: RNA
<213> ORGANISM: Artificial Sequence
<220> FEATURE:
<223> OTHER INFORMATION: Chemically synthesized

<400> SEQUENCE: 427
gcaugaaaca aaggcuuag                                                19

<210> SEQ ID NO 428
<211> LENGTH: 19
<212> TYPE: RNA
<213> ORGANISM: Artificial Sequence
<220> FEATURE:
<223> OTHER INFORMATION: Chemically synthesized

<400> SEQUENCE: 428
agcaugaaac aaaggcuua                                                19

<210> SEQ ID NO 429
<211> LENGTH: 19
<212> TYPE: RNA
<213> ORGANISM: Artificial Sequence
<220> FEATURE:
<223> OTHER INFORMATION: Chemically synthesized

<400> SEQUENCE: 429
```
uacuguagca ugaaacaaa                                            19

<210> SEQ ID NO 430
<211> LENGTH: 19
<212> TYPE: RNA
<213> ORGANISM: Artificial Sequence
<220> FEATURE:
<223> OTHER INFORMATION: Chemically synthesized

<400> SEQUENCE: 430
uagcaugaaa caaaggcuu                                            19

<210> SEQ ID NO 431
<211> LENGTH: 19
<212> TYPE: RNA
<213> ORGANISM: Artificial Sequence
<220> FEATURE:
<223> OTHER INFORMATION: Chemically synthesized

<400> SEQUENCE: 431
guagcaugaa acaaaggcu                                            19

<210> SEQ ID NO 432
<211> LENGTH: 19
<212> TYPE: RNA
<213> ORGANISM: Artificial Sequence
<220> FEATURE:
<223> OTHER INFORMATION: Chemically synthesized

<400> SEQUENCE: 432
caguacugua gcaugaaac                                            19

<210> SEQ ID NO 433
<211> LENGTH: 19
<212> TYPE: RNA
<213> ORGANISM: Artificial Sequence
<220> FEATURE:
<223> OTHER INFORMATION: Chemically synthesized

<400> SEQUENCE: 433
guacuguagc augaaacaa                                            19

<210> SEQ ID NO 434
<211> LENGTH: 19
<212> TYPE: RNA
<213> ORGANISM: Artificial Sequence
<220> FEATURE:
<223> OTHER INFORMATION: Chemically synthesized

<400> SEQUENCE: 434
ucaguacugu agcaugaaa                                            19

<210> SEQ ID NO 435
<211> LENGTH: 19
<212> TYPE: RNA
<213> ORGANISM: Artificial Sequence
<220> FEATURE:
<223> OTHER INFORMATION: Chemically synthesized

<400> SEQUENCE: 435
uguagcauga aacaaaggc                                            19

<210> SEQ ID NO 436
<211> LENGTH: 19
<212> TYPE: RNA
<213> ORGANISM: Artificial Sequence

```
<220> FEATURE:
<223> OTHER INFORMATION: Chemically synthesized

<400> SEQUENCE: 436
acuguagcau gaaacaaag                                                  19

<210> SEQ ID NO 437
<211> LENGTH: 19
<212> TYPE: RNA
<213> ORGANISM: Artificial Sequence
<220> FEATURE:
<223> OTHER INFORMATION: Chemically synthesized

<400> SEQUENCE: 437
cuguagcaug aaacaaagg                                                  19

<210> SEQ ID NO 438
<211> LENGTH: 19
<212> TYPE: RNA
<213> ORGANISM: Artificial Sequence
<220> FEATURE:
<223> OTHER INFORMATION: Chemically synthesized

<400> SEQUENCE: 438
aguacuguag caugaaaca                                                  19

<210> SEQ ID NO 439
<211> LENGTH: 19
<212> TYPE: RNA
<213> ORGANISM: Artificial Sequence
<220> FEATURE:
<223> OTHER INFORMATION: Chemically synthesized

<400> SEQUENCE: 439
ccucaguacu guagcauga                                                  19

<210> SEQ ID NO 440
<211> LENGTH: 19
<212> TYPE: RNA
<213> ORGANISM: Artificial Sequence
<220> FEATURE:
<223> OTHER INFORMATION: Chemically synthesized

<400> SEQUENCE: 440
cucaguacug uagcaugaa                                                  19

<210> SEQ ID NO 441
<211> LENGTH: 19
<212> TYPE: RNA
<213> ORGANISM: Artificial Sequence
<220> FEATURE:
<223> OTHER INFORMATION: Chemically synthesized

<400> SEQUENCE: 441
ugccaggugu aauuuuuca                                                  19

<210> SEQ ID NO 442
<211> LENGTH: 19
<212> TYPE: RNA
<213> ORGANISM: Artificial Sequence
<220> FEATURE:
<223> OTHER INFORMATION: Chemically synthesized

<400> SEQUENCE: 442
guguaauuuu ucaaguguc                                                  19
```

```
<210> SEQ ID NO 443
<211> LENGTH: 19
<212> TYPE: RNA
<213> ORGANISM: Artificial Sequence
<220> FEATURE:
<223> OTHER INFORMATION: Chemically synthesized

<400> SEQUENCE: 443
agguguaauu uuucaagug                                                    19

<210> SEQ ID NO 444
<211> LENGTH: 19
<212> TYPE: RNA
<213> ORGANISM: Artificial Sequence
<220> FEATURE:
<223> OTHER INFORMATION: Chemically synthesized

<400> SEQUENCE: 444
aagccuuguu ggccccuaa                                                    19

<210> SEQ ID NO 445
<211> LENGTH: 19
<212> TYPE: RNA
<213> ORGANISM: Artificial Sequence
<220> FEATURE:
<223> OTHER INFORMATION: Chemically synthesized

<400> SEQUENCE: 445
gguguaauuu uucaagugu                                                    19

<210> SEQ ID NO 446
<211> LENGTH: 19
<212> TYPE: RNA
<213> ORGANISM: Artificial Sequence
<220> FEATURE:
<223> OTHER INFORMATION: Chemically synthesized

<400> SEQUENCE: 446
aaguguucau ccucagggu                                                    19

<210> SEQ ID NO 447
<211> LENGTH: 19
<212> TYPE: RNA
<213> ORGANISM: Artificial Sequence
<220> FEATURE:
<223> OTHER INFORMATION: Chemically synthesized

<400> SEQUENCE: 447
cagcucaacu cugcaguac                                                    19

<210> SEQ ID NO 448
<211> LENGTH: 19
<212> TYPE: RNA
<213> ORGANISM: Artificial Sequence
<220> FEATURE:
<223> OTHER INFORMATION: Chemically synthesized

<400> SEQUENCE: 448
gcucaacucu gcaguacac                                                    19

<210> SEQ ID NO 449
<211> LENGTH: 19
<212> TYPE: RNA
<213> ORGANISM: Artificial Sequence
<220> FEATURE:
<223> OTHER INFORMATION: Chemically synthesized
```

<400> SEQUENCE: 449
aaacaaacaa caaacacac                                                    19

<210> SEQ ID NO 450
<211> LENGTH: 19
<212> TYPE: RNA
<213> ORGANISM: Artificial Sequence
<220> FEATURE:
<223> OTHER INFORMATION: Chemically synthesized

<400> SEQUENCE: 450
gcaucagguu ggcacacaa                                                    19

<210> SEQ ID NO 451
<211> LENGTH: 19
<212> TYPE: RNA
<213> ORGANISM: Artificial Sequence
<220> FEATURE:
<223> OTHER INFORMATION: Chemically synthesized

<400> SEQUENCE: 451
caacucugca guacacgau                                                    19

<210> SEQ ID NO 452
<211> LENGTH: 19
<212> TYPE: RNA
<213> ORGANISM: Artificial Sequence
<220> FEATURE:
<223> OTHER INFORMATION: Chemically synthesized

<400> SEQUENCE: 452
acucugcagu acacgaugg                                                    19

<210> SEQ ID NO 453
<211> LENGTH: 19
<212> TYPE: RNA
<213> ORGANISM: Artificial Sequence
<220> FEATURE:
<223> OTHER INFORMATION: Chemically synthesized

<400> SEQUENCE: 453
cagguguaau uuuucaagu                                                    19

<210> SEQ ID NO 454
<211> LENGTH: 19
<212> TYPE: RNA
<213> ORGANISM: Artificial Sequence
<220> FEATURE:
<223> OTHER INFORMATION: Chemically synthesized

<400> SEQUENCE: 454
acacaagugu ucauccuca                                                    19

<210> SEQ ID NO 455
<211> LENGTH: 19
<212> TYPE: RNA
<213> ORGANISM: Artificial Sequence
<220> FEATURE:
<223> OTHER INFORMATION: Chemically synthesized

<400> SEQUENCE: 455
uuaaacgcag cugccaggu                                                    19

<210> SEQ ID NO 456

```
<211> LENGTH: 19
<212> TYPE: RNA
<213> ORGANISM: Artificial Sequence
<220> FEATURE:
<223> OTHER INFORMATION: Chemically synthesized

<400> SEQUENCE: 456
aaaaguucag ucgucucug                                                   19

<210> SEQ ID NO 457
<211> LENGTH: 19
<212> TYPE: RNA
<213> ORGANISM: Artificial Sequence
<220> FEATURE:
<223> OTHER INFORMATION: Chemically synthesized

<400> SEQUENCE: 457
guucagucgu cucugucuu                                                   19

<210> SEQ ID NO 458
<211> LENGTH: 19
<212> TYPE: RNA
<213> ORGANISM: Artificial Sequence
<220> FEATURE:
<223> OTHER INFORMATION: Chemically synthesized

<400> SEQUENCE: 458
aaggcuuaaa cgcagcugc                                                   19

<210> SEQ ID NO 459
<211> LENGTH: 19
<212> TYPE: RNA
<213> ORGANISM: Artificial Sequence
<220> FEATURE:
<223> OTHER INFORMATION: Chemically synthesized

<400> SEQUENCE: 459
acaacucaau gagcuuccu                                                   19

<210> SEQ ID NO 460
<211> LENGTH: 19
<212> TYPE: RNA
<213> ORGANISM: Artificial Sequence
<220> FEATURE:
<223> OTHER INFORMATION: Chemically synthesized

<400> SEQUENCE: 460
ugagcuuccu gggaaacac                                                   19

<210> SEQ ID NO 461
<211> LENGTH: 19
<212> TYPE: RNA
<213> ORGANISM: Artificial Sequence
<220> FEATURE:
<223> OTHER INFORMATION: Chemically synthesized

<400> SEQUENCE: 461
ccccaaaagu ucagucguc                                                   19

<210> SEQ ID NO 462
<211> LENGTH: 19
<212> TYPE: RNA
<213> ORGANISM: Artificial Sequence
<220> FEATURE:
<223> OTHER INFORMATION: Chemically synthesized

<400> SEQUENCE: 462
```
aaaguucagu cgucucugu                                               19

<210> SEQ ID NO 463
<211> LENGTH: 19
<212> TYPE: RNA
<213> ORGANISM: Artificial Sequence
<220> FEATURE:
<223> OTHER INFORMATION: Chemically synthesized

<400> SEQUENCE: 463
gcacacaagu guucauccu                                               19

<210> SEQ ID NO 464
<211> LENGTH: 19
<212> TYPE: RNA
<213> ORGANISM: Artificial Sequence
<220> FEATURE:
<223> OTHER INFORMATION: Chemically synthesized

<400> SEQUENCE: 464
cacaaguguu cauccucag                                               19

<210> SEQ ID NO 465
<211> LENGTH: 19
<212> TYPE: RNA
<213> ORGANISM: Artificial Sequence
<220> FEATURE:
<223> OTHER INFORMATION: Chemically synthesized

<400> SEQUENCE: 465
ucuagaugga agacccaga                                               19

<210> SEQ ID NO 466
<211> LENGTH: 19
<212> TYPE: RNA
<213> ORGANISM: Artificial Sequence
<220> FEATURE:
<223> OTHER INFORMATION: Chemically synthesized

<400> SEQUENCE: 466
cuagauggaa gacccagau                                               19

<210> SEQ ID NO 467
<211> LENGTH: 19
<212> TYPE: RNA
<213> ORGANISM: Artificial Sequence
<220> FEATURE:
<223> OTHER INFORMATION: Chemically synthesized

<400> SEQUENCE: 467
aaacacacuu ggucccuuc                                               19

<210> SEQ ID NO 468
<211> LENGTH: 19
<212> TYPE: RNA
<213> ORGANISM: Artificial Sequence
<220> FEATURE:
<223> OTHER INFORMATION: Chemically synthesized

<400> SEQUENCE: 468
uuguuggccc cuaagccuu                                               19

<210> SEQ ID NO 469
<211> LENGTH: 19
<212> TYPE: RNA

```
<213> ORGANISM: Artificial Sequence
<220> FEATURE:
<223> OTHER INFORMATION: Chemically synthesized

<400> SEQUENCE: 469
ucaaugagcu uccugggaa                                                19

<210> SEQ ID NO 470
<211> LENGTH: 19
<212> TYPE: RNA
<213> ORGANISM: Artificial Sequence
<220> FEATURE:
<223> OTHER INFORMATION: Chemically synthesized

<400> SEQUENCE: 470
cgcaguaguu cuuugccca                                                19

<210> SEQ ID NO 471
<211> LENGTH: 19
<212> TYPE: RNA
<213> ORGANISM: Artificial Sequence
<220> FEATURE:
<223> OTHER INFORMATION: Chemically synthesized

<400> SEQUENCE: 471
caguaguucu uugcccacc                                                19

<210> SEQ ID NO 472
<211> LENGTH: 19
<212> TYPE: RNA
<213> ORGANISM: Artificial Sequence
<220> FEATURE:
<223> OTHER INFORMATION: Chemically synthesized

<400> SEQUENCE: 472
gcaguaguuc uuugcccac                                                19

<210> SEQ ID NO 473
<211> LENGTH: 19
<212> TYPE: RNA
<213> ORGANISM: Artificial Sequence
<220> FEATURE:
<223> OTHER INFORMATION: Chemically synthesized

<400> SEQUENCE: 473
cuuaccaacu ggcuaggca                                                19

<210> SEQ ID NO 474
<211> LENGTH: 19
<212> TYPE: RNA
<213> ORGANISM: Artificial Sequence
<220> FEATURE:
<223> OTHER INFORMATION: Chemically synthesized

<400> SEQUENCE: 474
uucuuugccc accuggcuu                                                19

<210> SEQ ID NO 475
<211> LENGTH: 19
<212> TYPE: RNA
<213> ORGANISM: Artificial Sequence
<220> FEATURE:
<223> OTHER INFORMATION: Chemically synthesized

<400> SEQUENCE: 475
uuaccaacug gcuaggcau                                                19
```

<210> SEQ ID NO 476
<211> LENGTH: 19
<212> TYPE: RNA
<213> ORGANISM: Artificial Sequence
<220> FEATURE:
<223> OTHER INFORMATION: Chemically synthesized

<400> SEQUENCE: 476
ucuucuugau gacucggaa                                                  19

<210> SEQ ID NO 477
<211> LENGTH: 19
<212> TYPE: RNA
<213> ORGANISM: Artificial Sequence
<220> FEATURE:
<223> OTHER INFORMATION: Chemically synthesized

<400> SEQUENCE: 477
acucuuacau ucaugcguc                                                  19

<210> SEQ ID NO 478
<211> LENGTH: 19
<212> TYPE: RNA
<213> ORGANISM: Artificial Sequence
<220> FEATURE:
<223> OTHER INFORMATION: Chemically synthesized

<400> SEQUENCE: 478
uuacauucau gcgucugua                                                  19

<210> SEQ ID NO 479
<211> LENGTH: 19
<212> TYPE: RNA
<213> ORGANISM: Artificial Sequence
<220> FEATURE:
<223> OTHER INFORMATION: Chemically synthesized

<400> SEQUENCE: 479
uaagguacau gcuacacac                                                  19

<210> SEQ ID NO 480
<211> LENGTH: 19
<212> TYPE: RNA
<213> ORGANISM: Artificial Sequence
<220> FEATURE:
<223> OTHER INFORMATION: Chemically synthesized

<400> SEQUENCE: 480
uacucuuaca uucaugcgu                                                  19

<210> SEQ ID NO 481
<211> LENGTH: 19
<212> TYPE: RNA
<213> ORGANISM: Artificial Sequence
<220> FEATURE:
<223> OTHER INFORMATION: Chemically synthesized

<400> SEQUENCE: 481
auucaugcgu cuguaagau                                                  19

<210> SEQ ID NO 482
<211> LENGTH: 19
<212> TYPE: RNA
<213> ORGANISM: Artificial Sequence
<220> FEATURE:

<223> OTHER INFORMATION: Chemically synthesized

<400> SEQUENCE: 482
cucuuacauu caugcgucu                                                    19

<210> SEQ ID NO 483
<211> LENGTH: 19
<212> TYPE: RNA
<213> ORGANISM: Artificial Sequence
<220> FEATURE:
<223> OTHER INFORMATION: Chemically synthesized

<400> SEQUENCE: 483
ucaugcgucu guaagauag                                                    19

<210> SEQ ID NO 484
<211> LENGTH: 19
<212> TYPE: RNA
<213> ORGANISM: Artificial Sequence
<220> FEATURE:
<223> OTHER INFORMATION: Chemically synthesized

<400> SEQUENCE: 484
aacaggucag uagugaugc                                                    19

<210> SEQ ID NO 485
<211> LENGTH: 19
<212> TYPE: RNA
<213> ORGANISM: Artificial Sequence
<220> FEATURE:
<223> OTHER INFORMATION: Chemically synthesized

<400> SEQUENCE: 485
aggucaguag ugaugcucc                                                    19

<210> SEQ ID NO 486
<211> LENGTH: 19
<212> TYPE: RNA
<213> ORGANISM: Artificial Sequence
<220> FEATURE:
<223> OTHER INFORMATION: Chemically synthesized

<400> SEQUENCE: 486
cccuaagccu uuguuucau                                                    19

<210> SEQ ID NO 487
<211> LENGTH: 19
<212> TYPE: RNA
<213> ORGANISM: Artificial Sequence
<220> FEATURE:
<223> OTHER INFORMATION: Chemically synthesized

<400> SEQUENCE: 487
augcgucugu aagauagcu                                                    19

<210> SEQ ID NO 488
<211> LENGTH: 19
<212> TYPE: RNA
<213> ORGANISM: Artificial Sequence
<220> FEATURE:
<223> OTHER INFORMATION: Chemically synthesized

<400> SEQUENCE: 488
ucuguaagau agcugccua                                                    19

```
<210> SEQ ID NO 489
<211> LENGTH: 19
<212> TYPE: RNA
<213> ORGANISM: Artificial Sequence
<220> FEATURE:
<223> OTHER INFORMATION: Chemically synthesized

<400> SEQUENCE: 489
auagcugccu acaacaggu                                                    19

<210> SEQ ID NO 490
<211> LENGTH: 19
<212> TYPE: RNA
<213> ORGANISM: Artificial Sequence
<220> FEATURE:
<223> OTHER INFORMATION: Chemically synthesized

<400> SEQUENCE: 490
acaggucagu agugaugcu                                                    19

<210> SEQ ID NO 491
<211> LENGTH: 19
<212> TYPE: RNA
<213> ORGANISM: Artificial Sequence
<220> FEATURE:
<223> OTHER INFORMATION: Chemically synthesized

<400> SEQUENCE: 491
uagugaugcu ccgaucaga                                                    19

<210> SEQ ID NO 492
<211> LENGTH: 19
<212> TYPE: RNA
<213> ORGANISM: Artificial Sequence
<220> FEATURE:
<223> OTHER INFORMATION: Chemically synthesized

<400> SEQUENCE: 492
acaccacugu uaacuguca                                                    19

<210> SEQ ID NO 493
<211> LENGTH: 19
<212> TYPE: RNA
<213> ORGANISM: Artificial Sequence
<220> FEATURE:
<223> OTHER INFORMATION: Chemically synthesized

<400> SEQUENCE: 493
caccacuguu aacugucag                                                    19

<210> SEQ ID NO 494
<211> LENGTH: 19
<212> TYPE: RNA
<213> ORGANISM: Artificial Sequence
<220> FEATURE:
<223> OTHER INFORMATION: Chemically synthesized

<400> SEQUENCE: 494
acuguuaacu gucaguaac                                                    19

<210> SEQ ID NO 495
<211> LENGTH: 19
<212> TYPE: RNA
<213> ORGANISM: Artificial Sequence
<220> FEATURE:
<223> OTHER INFORMATION: Chemically synthesized
```

<400> SEQUENCE: 495
uguuaacugu caguaacaa                                          19

<210> SEQ ID NO 496
<211> LENGTH: 19
<212> TYPE: RNA
<213> ORGANISM: Artificial Sequence
<220> FEATURE:
<223> OTHER INFORMATION: Chemically synthesized

<400> SEQUENCE: 496
uauucaugaa cagugagua                                          19

<210> SEQ ID NO 497
<211> LENGTH: 19
<212> TYPE: RNA
<213> ORGANISM: Artificial Sequence
<220> FEATURE:
<223> OTHER INFORMATION: Chemically synthesized

<400> SEQUENCE: 497
ugucaaagau cccaaguga                                          19

<210> SEQ ID NO 498
<211> LENGTH: 19
<212> TYPE: RNA
<213> ORGANISM: Artificial Sequence
<220> FEATURE:
<223> OTHER INFORMATION: Chemically synthesized

<400> SEQUENCE: 498
cuuacauuca ugcgucugu                                          19

<210> SEQ ID NO 499
<211> LENGTH: 19
<212> TYPE: RNA
<213> ORGANISM: Artificial Sequence
<220> FEATURE:
<223> OTHER INFORMATION: Chemically synthesized

<400> SEQUENCE: 499
ugcgucugua agauagcug                                          19

<210> SEQ ID NO 500
<211> LENGTH: 19
<212> TYPE: RNA
<213> ORGANISM: Artificial Sequence
<220> FEATURE:
<223> OTHER INFORMATION: Chemically synthesized

<400> SEQUENCE: 500
uacaacaggu caguaguga                                          19

<210> SEQ ID NO 501
<211> LENGTH: 19
<212> TYPE: RNA
<213> ORGANISM: Artificial Sequence
<220> FEATURE:
<223> OTHER INFORMATION: Chemically synthesized

<400> SEQUENCE: 501
caggucagua gugaugcuc                                          19

<210> SEQ ID NO 502
<211> LENGTH: 19

```
<212> TYPE: RNA
<213> ORGANISM: Artificial Sequence
<220> FEATURE:
<223> OTHER INFORMATION: Chemically synthesized

<400> SEQUENCE: 502
ucagaccagu aagauacac                                              19

<210> SEQ ID NO 503
<211> LENGTH: 19
<212> TYPE: RNA
<213> ORGANISM: Artificial Sequence
<220> FEATURE:
<223> OTHER INFORMATION: Chemically synthesized

<400> SEQUENCE: 503
aguaagauac acaaaccac                                              19

<210> SEQ ID NO 504
<211> LENGTH: 19
<212> TYPE: RNA
<213> ORGANISM: Artificial Sequence
<220> FEATURE:
<223> OTHER INFORMATION: Chemically synthesized

<400> SEQUENCE: 504
ucacaccacu guuaacugu                                              19

<210> SEQ ID NO 505
<211> LENGTH: 19
<212> TYPE: RNA
<213> ORGANISM: Artificial Sequence
<220> FEATURE:
<223> OTHER INFORMATION: Chemically synthesized

<400> SEQUENCE: 505
uuagguggcu gccucaguu                                              19

<210> SEQ ID NO 506
<211> LENGTH: 19
<212> TYPE: RNA
<213> ORGANISM: Artificial Sequence
<220> FEATURE:
<223> OTHER INFORMATION: Chemically synthesized

<400> SEQUENCE: 506
ucaaguguau ucaugaaca                                              19

<210> SEQ ID NO 507
<211> LENGTH: 19
<212> TYPE: RNA
<213> ORGANISM: Artificial Sequence
<220> FEATURE:
<223> OTHER INFORMATION: Chemically synthesized

<400> SEQUENCE: 507
caaguguauu caugaacag                                              19

<210> SEQ ID NO 508
<211> LENGTH: 19
<212> TYPE: RNA
<213> ORGANISM: Artificial Sequence
<220> FEATURE:
<223> OTHER INFORMATION: Chemically synthesized

<400> SEQUENCE: 508
```
ucaugaacag ugaguaucu                                                    19

<210> SEQ ID NO 509
<211> LENGTH: 19
<212> TYPE: RNA
<213> ORGANISM: Artificial Sequence
<220> FEATURE:
<223> OTHER INFORMATION: Chemically synthesized

<400> SEQUENCE: 509
ucuuacauuc augcgucug                                                    19

<210> SEQ ID NO 510
<211> LENGTH: 19
<212> TYPE: RNA
<213> ORGANISM: Artificial Sequence
<220> FEATURE:
<223> OTHER INFORMATION: Chemically synthesized

<400> SEQUENCE: 510
gcgucuguaa gauagcugc                                                    19

<210> SEQ ID NO 511
<211> LENGTH: 19
<212> TYPE: RNA
<213> ORGANISM: Artificial Sequence
<220> FEATURE:
<223> OTHER INFORMATION: Chemically synthesized

<400> SEQUENCE: 511
cgucuguaag auagcugcc                                                    19

<210> SEQ ID NO 512
<211> LENGTH: 19
<212> TYPE: RNA
<213> ORGANISM: Artificial Sequence
<220> FEATURE:
<223> OTHER INFORMATION: Chemically synthesized

<400> SEQUENCE: 512
ccaguaagau acacaaacc                                                    19

<210> SEQ ID NO 513
<211> LENGTH: 19
<212> TYPE: RNA
<213> ORGANISM: Artificial Sequence
<220> FEATURE:
<223> OTHER INFORMATION: Chemically synthesized

<400> SEQUENCE: 513
aagauacaca aaccaccuc                                                    19

<210> SEQ ID NO 514
<211> LENGTH: 19
<212> TYPE: RNA
<213> ORGANISM: Artificial Sequence
<220> FEATURE:
<223> OTHER INFORMATION: Chemically synthesized

<400> SEQUENCE: 514
auacacaaac caccuccac                                                    19

<210> SEQ ID NO 515
<211> LENGTH: 19
<212> TYPE: RNA
<213> ORGANISM: Artificial Sequence

```
<220> FEATURE:
<223> OTHER INFORMATION: Chemically synthesized

<400> SEQUENCE: 515
ccacuguuaa cugucagua                                          19

<210> SEQ ID NO 516
<211> LENGTH: 19
<212> TYPE: RNA
<213> ORGANISM: Artificial Sequence
<220> FEATURE:
<223> OTHER INFORMATION: Chemically synthesized

<400> SEQUENCE: 516
aauaagguac augcuacac                                          19

<210> SEQ ID NO 517
<211> LENGTH: 19
<212> TYPE: RNA
<213> ORGANISM: Artificial Sequence
<220> FEATURE:
<223> OTHER INFORMATION: Chemically synthesized

<400> SEQUENCE: 517
aguaguucuu ugcccaccu                                          19

<210> SEQ ID NO 518
<211> LENGTH: 19
<212> TYPE: RNA
<213> ORGANISM: Artificial Sequence
<220> FEATURE:
<223> OTHER INFORMATION: Chemically synthesized

<400> SEQUENCE: 518
uguucauccu cagggucac                                          19

<210> SEQ ID NO 519
<211> LENGTH: 19
<212> TYPE: RNA
<213> ORGANISM: Artificial Sequence
<220> FEATURE:
<223> OTHER INFORMATION: Chemically synthesized

<400> SEQUENCE: 519
guaguucuuu gcccaccug                                          19

<210> SEQ ID NO 520
<211> LENGTH: 19
<212> TYPE: RNA
<213> ORGANISM: Artificial Sequence
<220> FEATURE:
<223> OTHER INFORMATION: Chemically synthesized

<400> SEQUENCE: 520
uaguucuuug cccaccugg                                          19

<210> SEQ ID NO 521
<211> LENGTH: 19
<212> TYPE: RNA
<213> ORGANISM: Artificial Sequence
<220> FEATURE:
<223> OTHER INFORMATION: Chemically synthesized

<400> SEQUENCE: 521
agcuaaacag ccccuggau                                          19
```

```
<210> SEQ ID NO 522
<211> LENGTH: 19
<212> TYPE: RNA
<213> ORGANISM: Artificial Sequence
<220> FEATURE:
<223> OTHER INFORMATION: Chemically synthesized

<400> SEQUENCE: 522
uaaacagccc cuggaucuu                                              19

<210> SEQ ID NO 523
<211> LENGTH: 19
<212> TYPE: RNA
<213> ORGANISM: Artificial Sequence
<220> FEATURE:
<223> OTHER INFORMATION: Chemically synthesized

<400> SEQUENCE: 523
cuaagccuuu guuucaugc                                              19

<210> SEQ ID NO 524
<211> LENGTH: 19
<212> TYPE: RNA
<213> ORGANISM: Artificial Sequence
<220> FEATURE:
<223> OTHER INFORMATION: Chemically synthesized

<400> SEQUENCE: 524
uaagccuuug uuucaugcu                                              19

<210> SEQ ID NO 525
<211> LENGTH: 19
<212> TYPE: RNA
<213> ORGANISM: Artificial Sequence
<220> FEATURE:
<223> OTHER INFORMATION: Chemically synthesized

<400> SEQUENCE: 525
uuuguuucau gcuacagua                                              19

<210> SEQ ID NO 526
<211> LENGTH: 19
<212> TYPE: RNA
<213> ORGANISM: Artificial Sequence
<220> FEATURE:
<223> OTHER INFORMATION: Chemically synthesized

<400> SEQUENCE: 526
aagccuuugu uucaugcua                                              19

<210> SEQ ID NO 527
<211> LENGTH: 19
<212> TYPE: RNA
<213> ORGANISM: Artificial Sequence
<220> FEATURE:
<223> OTHER INFORMATION: Chemically synthesized

<400> SEQUENCE: 527
agccuuuguu ucaugcuac                                              19

<210> SEQ ID NO 528
<211> LENGTH: 19
<212> TYPE: RNA
<213> ORGANISM: Artificial Sequence
<220> FEATURE:
<223> OTHER INFORMATION: Chemically synthesized
```

```
<400> SEQUENCE: 528
guuucaugcu acaguacug                                                    19

<210> SEQ ID NO 529
<211> LENGTH: 19
<212> TYPE: RNA
<213> ORGANISM: Artificial Sequence
<220> FEATURE:
<223> OTHER INFORMATION: Chemically synthesized

<400> SEQUENCE: 529
uuguuucaug cuacaguac                                                    19

<210> SEQ ID NO 530
<211> LENGTH: 19
<212> TYPE: RNA
<213> ORGANISM: Artificial Sequence
<220> FEATURE:
<223> OTHER INFORMATION: Chemically synthesized

<400> SEQUENCE: 530
uuucaugcua caguacuga                                                    19

<210> SEQ ID NO 531
<211> LENGTH: 19
<212> TYPE: RNA
<213> ORGANISM: Artificial Sequence
<220> FEATURE:
<223> OTHER INFORMATION: Chemically synthesized

<400> SEQUENCE: 531
gccuuuguuu caugcuaca                                                    19

<210> SEQ ID NO 532
<211> LENGTH: 19
<212> TYPE: RNA
<213> ORGANISM: Artificial Sequence
<220> FEATURE:
<223> OTHER INFORMATION: Chemically synthesized

<400> SEQUENCE: 532
cuuuguuuca ugcuacagu                                                    19

<210> SEQ ID NO 533
<211> LENGTH: 19
<212> TYPE: RNA
<213> ORGANISM: Artificial Sequence
<220> FEATURE:
<223> OTHER INFORMATION: Chemically synthesized

<400> SEQUENCE: 533
ccuuuguuuc augcuacag                                                    19

<210> SEQ ID NO 534
<211> LENGTH: 19
<212> TYPE: RNA
<213> ORGANISM: Artificial Sequence
<220> FEATURE:
<223> OTHER INFORMATION: Chemically synthesized

<400> SEQUENCE: 534
uguuucaugc uacaguacu                                                    19

<210> SEQ ID NO 535
```

```
<211> LENGTH: 19
<212> TYPE: RNA
<213> ORGANISM: Artificial Sequence
<220> FEATURE:
<223> OTHER INFORMATION: Chemically synthesized

<400> SEQUENCE: 535
ucaugcuaca guacugagg                                                  19

<210> SEQ ID NO 536
<211> LENGTH: 19
<212> TYPE: RNA
<213> ORGANISM: Artificial Sequence
<220> FEATURE:
<223> OTHER INFORMATION: Chemically synthesized

<400> SEQUENCE: 536
uucaugcuac aguacugag                                                  19
```

THERAPEUTIC USES OF INHIBITORS OF RTP801

This application is a divisional of U.S. Ser. No. 11/655,636, filed Jan. 18, 2007 now U.S. Pat. No. 8,067,570, which claims the benefit of U.S. Provisional patent application No. 60/851,000, filed Oct. 10, 2006, of U.S. Provisional patent application No. 60/796,901, filed May 1, 2006 and of U.S. Provisional patent application No. 60/760,586, filed Jan. 20, 2006, each of which is hereby incorporated by reference in its entirety into this application.

Throughout this application, various publications and patents, including United States patents, are referenced by author and year and patents by number. The disclosures of these publications and patents and patent applications in their entireties are hereby incorporated by reference into to this application in order to more fully describe the state of the art to which this invention pertains.

FIELD OF THE INVENTION

The present invention relates to novel siRNA molecules which inhibit the RTP801 gene and to the use of such molecules to treat respiratory disorders of all types (including pulmonary disorders), eye diseases and conditions, microvascular disorders, angiogenesis- and apoptosis-related conditions, and hearing impairments.

BACKGROUND OF THE INVENTION

Chronic Obstructive Pulmonary Disease (COPD)

Chronic obstructive pulmonary disease (COPD), affects more than 16 million Americans and is the fourth highest cause of death in the United States. Cigarette smoking causes most occurrences of the debilitating disease but other environmental factors cannot be excluded (Petty T L. 2003. *Definition, epidemiology, course, and prognosis of COPD.* Clin. Cornerstone, 5-10).

Pulmonary emphysema is a major manifestation of COPD. Permanent destruction of peripheral air spaces, distal to terminal bronchioles, is the hallmark of emphysema (Tuder R M, et al. *Oxidative stress and apoptosis interact and cause emphysema due to vascular endothelial growth factor blocade. Am J Respir Cell Mol Biol,* 29:88-97; 2003.). Emphysema is also characterized by accumulation of inflammatory cells such as macrophages and neutrophils in bronchioles and alveolar structures (Petty, 2003).

The pathogenesis of emphysema is complex and multifactorial. In humans, a deficiency of inhibitors of proteases produced by inflammatory cells, such as alpha1-antitrypsin, has been shown to contribute to protease/antiprotease imbalance, thereby favoring destruction of alveolar extracellular matrix in cigarette-smoke (CS) induced emphysema (Eriksson, S. 1964. *Pulmonary Emphysema and Alpha1-Antitrypsin Deficiency. Acta Med Scand* 175: 197-205. Joos, L., Pare, P. D., and Sandford, A. J. 2002. *Genetic risk factors of chronic obstructive pulmonary disease. Swiss Med Wkly* 132:27-37). Matrix metalloproteinases (MMPs) play a central role in experimental emphysema, as documented by resistance of macrophage metalloelastase knockout mice against emphysema caused by chronic inhalation of CS (Hautamaki, et al: *Requirement for macrophage elastase for cigarette smoke-induced emphysema in mice. Science* 277:2002-2004). Moreover, pulmonary overexpression of interleukin-13 in transgenic mice results in MMP- and cathepsin-dependent emphysema (Zheng, T., et al 2000. *Inducible targeting of IL-13 to the adult lung causes matrix metalloproteinase-and cathepsin-dependent emphysema. J Clin Invest* 106:1081-1093). Recent works describe involvement of septal cell apoptosis in lung tissue destruction leading to emphysema (Rangasami T, et al. *Genetic ablation of Nrf2 enhances susceptibility to cigarette smoke-induced emphysema in mice. Submitted to Journal of Clinical Investigation.*; Tuder R M et al. *Oxidative stress and apoptosis interact and cause emphysema due to vascular endothelial growth factor blocade. Am J Respir Cell Mol Biol,* 29:88-97; 2003.; Yokohori N, Aoshiba K, Nagai A, *Increased levels of cell death and proliferation in alveolar wall cells in patients with pulmonary emphysema. Chest,* 2004 February; 125(2):626-32.; Aoshiba K, Yokohori N, Nagai A., *Alveolar wall apoptosis causes lung destruction and emphysematous changes. Am J Respir Cell Mol Biol.* 2003 May; 28(5):555-62.).

Among the mechanisms that underlie both pathways of lung destruction in emphysema, excessive formation of reactive oxygen species (ROS) should be first of all mentioned. It is well established that prooxidant/antioxidant imbalance exists in the blood and in the lung tissue of smokers (Hulea S A, et al: *Cigarette smoking causes biochemical changes in blood that are suggestive of oxidative stress: a case-control study. J Environ Pathol Toxicol Oncol.* 1995; 14(3-4):173-80.; Rahman I, MacNee W. *Lung glutathione and oxidative stress: implications in cigarette smoke-induced airway disease. Am J. Physiol.* 1999 December; 277(6 Pt 1):L1067-88.; MacNee W. Oxidants/antioxidants and COPD. *Chest.* 2000 May; 117(5 Suppl 1):303S-17S.; Marwick J A, Kirkham P, Gilmour P S, Donaldson K, MacNEE W, Rahman I. *Cigarette smoke-induced oxidative stress and TGF-beta1 increase p21waf1/cip1 expression in alveolar epithelial cells. Ann N Y Acad. Sci.* 2002 November; 973:278-83.; Aoshiba K, Koinuma M, Yokohori N, Nagai A. *Immunohistochemical evaluation of oxidative stress in murine lungs after cigarette smoke exposure. Inhal Toxicol.* 2003 September; 15(10):1029-38.; Dekhuijzen P N. *Antioxidant properties of N-acetylcysteine: their relevance in relation to chronic obstructive pulmonary disease. Eur Respir* 1 2004 April, 23(4):629-36.; Tuder R M, Zhen L, Cho C Y, Taraseviciene-Stewart L, Kasahara Y, Salvemini D, Voelkel N F, and Flores S C. *Oxidative stress and apoptosis interact and cause emphysema due to vascular endothelial growth factor blocade. Am J Respir Cell Mol Biol,* 29:88-97; 2003.). After one hour exposure of mice to CS, there is a dramatic increase of 8-hydroxy-2'-deoxyguanosine (8-OHdG) in the alveolar epithelial cells, particularly of type II (see *Inhal Toxicol.* 2003 September; 15(10):1029-38. above).

Overproduced reactive oxygen species are known for their cytotoxic activity, which stems from a direct DNA damaging effect and from the activation of apoptotic signal transduction pathways (Takahashi A, Masuda A, Sun M, Centonze V E, Herman B. *Oxidative stress-induced apoptosis is associated with alterations in mitochondrial caspase activity and Bcl-2-dependent alterations in mitochondrial pH (pHm). Brain Res Bull.* 2004 Feb. 15; 62(6):497-504.; Taniyama Y, Griendling K K. *Reactive oxygen species in the vasculature: molecular and cellular mechanisms. Hypertension.* 2003 December; 42(6):1075-81. Epub 2003 Oct. 27.; Higuchi Y. *Chromosomal DNA fragmentation in apoptosis and necrosis induced by oxidative stress. Biochem Pharmacol.* 2003 Oct. 15; 66(8): 1527-35.; Punj V, Chakrabarty A M. *Redox proteins in mammalian cell death: an evolutionarily conserved fraction in mitochondria and prokaryotes. Cell Microbiol.* 2003 April; 5(4):225-31.; Ueda S, Masutani H, Nakamura H, Tanaka T, Ueno M, Yodoi J. *Redox control of cell death. Antioxid Redox Signal.* 2002 June; 4(3):405-14.).

ROS's are not only cytotoxic per se but are also proinflammatory stimuli, being prominent activators of redox-sensitive transcription factors NFkB and AP-1 (reviewed in Rahman I. *Oxidative stress and gene transcription in asthma and chronic obstructive pulmonary disease: antioxidant therapeutic targets. Curr Drug Targets Inflamm Allergy.* 2002 September; 1(3):291-315.). Both transcription factors are, in turn, strongly implicated in stimulation of transcription of proinflammatory cytokines (reviewed in Renard P, Raes M. *The proinflammatory transcription factor NFkappaB: a potential target for novel therapeutical strategies. Cell Biol Toxicol.* 1999; 15(6):341-4.; Lentsch A B, Ward P A. *The NFkappaBb/IkappaB system in acute inflammation. Arch Immunol Ther Exp* (Warsz). 2000; 48(2):59-63) and matrix degrading proteinases (Andela V B, Gordon A H, Zotalis G, Rosier R N, Goater J J, Lewis G D, Schwarz E M, Puzas J E, O'Keefe R J. *NFkappaB: a pivotal transcription factor in prostate cancer metastasis to bone. Clin Orthop.* 2003 October; (415 Suppl):S75-85.; Fleenor D L, Pang I H, Clark A F. *Involvement of AP-1 in interleukin-1alpha-stimulated MMP-3 expression in human trabecular meshwork cells. Invest Ophthalmol Vis Sci.* 2003 August; 44(8):3494-501.; Ruhul Amin A R, Senga T, Oo M L, Thant A A, Hamaguchi M. *Secretion of matrix metalloproteinase-9 by the proinflammatory cytokine, IL-1beta: a role for the dual signalling pathways, Akt and Erk. Genes Cells.* 2003 June; 8(6):515-23.). Proinflammatory cytokines, in turn, serve as attractors of inflammatory cells that also secrete matrix degrading enzymes, cytokines and reactive oxygen species. Thus, it appears that a pathogenic factor, like e.g. CS, triggers a pathological network where reactive oxygen species act as major mediators of lung destruction.

Both reactive oxygen species (ROS) from inhaled cigarette smoke and those endogenously formed by inflammatory cells contribute to an increased intrapulmonary oxidant burden.

One additional pathogenic factor with regards to COPD pathogenesis is the observed decreased expression of VEGF and VEGFRII in lungs of emphysematous patients (Yasunori Kasahara, Rubin M. Tuder, Carlyne D. Cool, David A. Lynch, Sonia C. Flores, and Norbert F. Voelkel. *Endothelial Cell Death and Decreased Expression of Vascular Endothelial Growth Factor and Vascular Endothelial Growth Factor Receptor 2 in Emphysema.* Am J Respir Crit. Care Med Vol 163. pp 737-744, 2001). Moreover, inhibition of VEGF signaling using chemical VEGFR inhibitor leads to alveolar septal endothelial and then to epithelial cell apoptosis, probably due to disruption of intimate structural/functional connection of both types of cells within alveoli (Yasunori Kasahara, Rubin M. Tuder, Laimute Taraseviciene-Stewart, Timothy D. Le Cras, Steven Abman, Peter K. Hirth, Johannes Waltenberger, and Norbert F. Voelkel. *Inhibition of VEGF receptors causes lung cell apoptosis and emphysema. J. Clin. Invest.* 106:1311-1319 (2000).; Voelkel N F, Cool C D. *Pulmonary vascular involvement in chronic obstructive pulmonary disease. Eur Respir J. Suppl.* 2003 November; 46:28s-32s).

Macular Degeneration

The most common cause of decreased best-corrected vision in individuals over 65 years of age in the US is the retinal disorder known as age-related macular degeneration (AMD). As AMD progresses, the disease is characterized by loss of sharp, central vision. The area of the eye affected by AMD is the Macula—a small area in the center of the retina, composed primarily of photoreceptor cells. So-called "dry" AMD, accounting for about 85%-90% of AMD patients, involves alterations in eye pigment distribution, loss of photoreceptors and diminished retinal function due to overall atrophy of cells. So-called "wet" AMD involves proliferation of abnormal choroidal vessels leading to clots or scars in the sub-retinal space. Thus, the onset of wet AMD occurs because of the formation of an abnormal choroidal neovascular network (choroidal neovascularization, CNV) beneath the neural retina. The newly formed blood vessels are excessively leaky. This leads to accumulation of subretinal fluid and blood leading to loss of visual acuity. Eventually, there is total loss of functional retina in the involved region, as a large disciform scar involving choroids and retina forms. While dry AMD patients may retain vision of decreased quality, wet AMD often results in blindness. (Hamdi & Kenney, *Age-related Macular degeneration—a new viewpoint, Frontiers in Bioscience*, e305-314, May 2003). CNV occurs not only in wet AMD but also in other ocular pathologies such as ocular histoplasmosis syndrome, angiod streaks, ruptures in Bruch's membrane, myopic degeneration, ocular tumors and some retinal degenerative diseases.

Various studies conducted have determined several risk factors for AMD, such as smoking, aging, family history (Milton, *Am J Ophthalmol* 88, 269 (1979); Mitchell et al., *Ophthalmology* 102, 1450-1460 (1995); Smith et al., *Ophthalmology* 108, 697-704 (2001)) sex (7-fold higher likelihood in females: Klein et al., *Ophthalmology* 99, 933-943 (1992) and race (whites are most susceptible). Additional risk factors may include eye characteristics such as farsightedness (hyperopia) and light-colored eyes, as well as cardiovascular disease and hypertension. Evidence of genetic involvement in the onset progression of the disease has also been documented (see Hamdi & Kenney above).

Two companies, Acuity Pharmaceuticals and Sima Therapeutics, have both recently filed an IND for siRNA molecules inhibiting VEGF and VEGF-R1 (Flt-1), respectively, for treatment of AMD. These molecules are termed Cand5 inhibitor and 027 inhibitor respectively.

Microvascular Disorders

Microvascular disorders are composed of a broad group of conditions that primarily affect the microscopic capillaries and lymphatics and are therefore outside the scope of direct surgical intervention. Microvascular disease can be broadly grouped into the vasospastic, the vasculitis and lymphatic occlusive. Additionally, many of the known vascular conditions have a microvascular element to them.

Vasospastic Disease—Vasospastic diseases are a group of relatively common conditions where, for unknown reasons, the peripheral vasoconstrictive reflexes are hypersensitive. This results in inappropriate vasoconstriction and tissue ischaemia, even to the point of tissue loss. Vasospastic symptoms are usually related to temperature or the use of vibrating machinery but may be secondary to other conditions.

Vasculitic Disease—Vasculitic diseases are those that involve a primary inflammatory process in the microcirculation. Vasculitis is usually a component of an autoimmune or connective tissue disorder and is not generally amenable to surgical treatment but requires immunosuppressive treatment if the symptoms are severe.

Lymphatic Occlusive Disease—Chronic swelling of the lower or upper limb (lymphoedema) is the result of peripheral lymphatic occlusion. This is a relatively rare condition that has a large number of causes, some inherited, some acquired. The mainstays of treatment are correctly fitted compression garments and the use of intermittent compression devices.

Microvascular Pathologies Associated with Diabetes

Diabetes is the leading cause of blindness, the number one cause of amputations and impotence, and one of the most frequently occurring chronic childhood diseases. Diabetes is also the leading cause of end-stage renal disease in the United States, with a prevalence rate of 31% compared with other renal diseases. Diabetes is also the most frequent indication for kidney transplantation, accounting for 22% of all transplantation operations.

In general, diabetic complications can be classified broadly as microvascular or macrovascular disease. Microvascular complications include neuropathy (nerve damage), nephropathy (kidney disease) and vision disorders (eg retinopathy, glaucoma, cataract and corneal disease). In the retina, glomerulus, and vasa nervorum, similar pathophysiologic features characterize diabetes-specific microvascular disease.

Microvascular pathologies associated with diabetes are defined as a disease of the smallest blood vessels (capillaries) that may occur e.g. in people who have had diabetes for a long time. The walls of the vessels become abnormally thick but weak. They, therefore, bleed, leak protein and slow the flow of blood through the body.

Clinical and animal model data indicate that chronic hyperglycemia is the central initiating factor for all types of diabetic microvascular disease. Duration and magnitude of hyperglycemia are both strongly correlated with the extent and rate of progression of diabetic microvascular disease. Although all diabetic cells are exposed to elevated levels of plasma glucose, hyperglycemic damage is limited to those cell types (e.g., endothelial cells) that develop intracellular hyperglycemia. Endothelial cells develop intracellular hyperglycemia because, unlike many other cells, they cannot down-regulate glucose transport when exposed to extracellular hyperglycemia. That intracellular hyperglycemia is necessary and sufficient for the development of diabetic pathology is further demonstrated by the fact that overexpression of the GLUT1 glucose transporter in mesangial cells cultured in a normal glucose milieu mimics the diabetic phenotype, inducing the same increases in collagen type IV, collagen type I, and fibronectin gene expression as diabetic hyperglycemia.

Abnormal Endothelial Cell Function: Early in the course of diabetes mellitus, before structural changes are evident, hyperglycemia causes abnormalities in blood flow and vascular permeability in the retina, glomerulus, and peripheral nerve vasa nervorum. The increase in blood flow and intracapillary pressure is thought to reflect hyperglycemia-induced decreased nitric oxide (NO) production on the efferent side of capillary beds, and possibly an increased sensitivity to angiotensin II. As a consequence of increased intracapillary pressure and endothelial cell dysfunction, retinal capillaries exhibit increased leakage of fluorescein and glomerular capillaries have an elevated albumin excretion rate (AER). Comparable changes occur in the vasa vasorum of peripheral nerve. Early in the course of diabetes, increased permeability is reversible; as time progresses, however, it becomes irreversible.

Increased Vessel Wall Protein Accumulation

The common pathophysiologic feature of diabetic microvascular disease is progressive narrowing and eventual occlusion of vascular lumina, which results in inadequate perfusion and function of the affected tissues. Early hyperglycemia-induced microvascular hypertension and increased vascular permeability contribute to irreversible microvessel occlusion by three processes:

The first is an abnormal leakage of periodic acid-Schiff (PAS)-positive, carbohydrate-containing plasma proteins, which are deposited in the capillary wall and which may stimulate perivascular cells such as pericytes and mesangial cells to elaborate growth factors and extracellular matrix.

The second is extravasation of growth factors, such as transforming growth factor β1 (TGF-β1), which directly stimulates overproduction of extracellular matrix components, and may induce apoptosis in certain complication-relevant cell types.

The third is hypertension-induced stimulation of pathologic gene expression by endothelial cells and supporting cells, which include glut-1 glucose transporters, growth factors, growth factor receptors, extracellular matrix components, and adhesion molecules that can activate circulating leukocytes. The observation that unilateral reduction in the severity of diabetic microvascular disease occurs on the side with ophthalmic or renal artery stenosis is consistent with this concept.

Microvascular Cell Loss and Vessel Occlusion

The progressive narrowing and occlusion of diabetic microvascular lumina are also accompanied by microvascular cell loss. In the retina, diabetes mellitus induces programmed cell death of Müller cells and ganglion cells, pericytes, and endothelial cells. In the glomerulus, declining renal function is associated with widespread capillary occlusion and podocyte loss, but the mechanisms underlying glomerular cell loss are not yet known. In the vasa nervorum, endothelial cell and pericyte degeneration occur, and these microvascular changes appear to precede the development of diabetic peripheral neuropathy. The multifocal distribution of axonal degeneration in diabetes supports a causal role for microvascular occlusion, but hyperglycemia-induced decreases in neurotrophins may contribute by preventing normal axonal repair and regeneration.

Another common feature of diabetic microvascular disease has been termed hyperglycemic memory, or the persistence or progression of hyperglycemia-induced microvascular alterations during subsequent periods of normal glucose homeostasis. The most striking example of this phenomenon is the development of severe retinopathy in histologically normal eyes of diabetic dogs that occurred entirely during a 2.5-year period of normalized blood glucose that followed 2.5 years of hyperglycemia. Hyperglycemia-induced increases in selected matrix gene transcription also persist for weeks after restoration of normoglycemia in vivo, and a less pronounced, but qualitatively similar, prolongation of hyperglycemia-induced increase in selected matrix gene transcription occurs in cultured endothelial cells.

For further information, see "Shared pathophysiologic features of microvascular complications of diabetes" (Larsen: Williams Textbook of Endocrinology, 10th ed., Copyright © 2003 Elsevier).

Microvascular complications occur not only in overt diabetes but are also due to Impaired Glucose Tolerance (IGT). Microvascular complications of IGT: neuropathy, retinopathy, and renal microproteinuria.

Diabetic Neuropathy

Diabetic neuropathies are neuropathic disorders (peripheral nerve damage) that are associated with diabetes mellitus. These conditions usually result from diabetic microvascular injury involving small blood vessels that supply nerves (vasa nervorum). Relatively common conditions which may be associated with diabetic neuropathy include third nerve palsy; mononeuropathy; mononeuropathy multiplex; diabetic amyotrophy; a painful polyneuropathy; autonomic neuropathy; and thoracoabdominal neuropathy and the most common form, peripheral neuropathy, which mainly affects the feet and legs. There are four factors involved in the development of diabetic neuropathy: microvascular disease, advanced glycated end products, protein kinase C, and the polyol pathway.

Microvascular Disease in Diabetic Neuropathy

Vascular and neural diseases are closely related and intertwined. Blood vessels depend on normal nerve function, and nerves depends on adequate blood flow. The first pathological change in the microvasculature is vasoconstriction. As the disease progresses, neuronal dysfunction correlates closely with the development of vascular abnormalities, such as capillary basement membrane thickening and endothelial hyperplasia, which contribute to diminished oxygen tension and hypoxia. Neuronal ischemia is a well-established characteristic of diabetic neuropathy. Vasodilator agents (e.g., angiotensin-converting-enzyme inhibitors, alpha1-antagonists) can lead to substantial improvements in neuronal blood flow, with corresponding improvements in nerve conduction velocities. Thus, microvascular dysfunction occurs early in diabetes, parallels the progression of neural dysfunction, and may be sufficient to support the severity of structural, functional, and clinical changes observed in diabetic neuropathy. Peripheral neuropathy (legs), sensorimotor neuropathy is a significant component in the pathogenesis of leg ulcers in diabetes.

Neuropathy is a common complication of diabetes occurring over time in more than half of patients with type 2 diabetes. Nerve conduction studies demonstrate that neuropathy is already present in 10-18% of patients at the time of diabetes diagnosis, suggesting that peripheral nerve injury occurs at early stages of disease and with milder glycemic dysregulation. The concept that neuropathy is an early clinical sign of diabetes was proposed >40 years ago, and most studies report an association between IGT and neuropathy. Most patients with IGT and associated neuropathy have a symmetric, distal sensory polyneuropathy with prominent neuropathic pain. IGT neuropathy (*Microvascular complications of impaired glucose tolerance—Perspectives in Diabetes*, J. Robinson Singleton, in *Diabetes Dec.* 1, 2003) is phenotypically similar to early diabetic neuropathy, which also causes sensory symptoms, including pain, and autonomic dysfunction. In a survey of 669 patients with early diabetic neuropathy, sensory symptoms were present in >60%, impotence in nearly 40%, and other autonomic involvement in 33%, but evidence of motor involvement in only 12%. These clinical findings suggest prominent early involvement of the small unmyelinated nerve fibers that carry pain, temperature, and autonomic signals. Direct quantitation of unmyelinated intraepidermal nerve fibers from skin biopsies shows similar fiber loss and altered morphology in patients with neuropathy associated with IGT and early diabetes.

Autonomic dysfunction, particularly erectile dysfunction and altered cardiac vagal response, are common early features of neuropathic injury in diabetes. Work with IGT patients also suggests prevalent vagal dysautonoinia: separate studies have found abnormal heart rate recovery following exercise, blunted R—R interval variability to deep breathing, and reduced expiration to inspiration ratio (all measures of vagal dysautonomia) in a greater fraction of IGT patients than age-matched normoglycemic control subjects.

Nerve damage in diabetes affects the motor, sensory, and autonomic fibers. Motor neuropathy causes muscle weakness, atrophy, and paresis. Sensory neuropathy leads to loss of the protective sensations of pain, pressure, and heat. The absence of pain leads to many problems in the insensate foot, including ulceration, unperceived trauma, and Charcot neuroarthropathy. The patient may not seek treatment until after the wound has advanced. A combination of sensory and motor dysfunction can cause the patient to place abnormal stresses on the foot, resulting in trauma, which may lead to infection. Autonomic sympathetic neuropathy causes vasodilation and decreased sweating, which results in warm, overly dry feet that are particularly prone to skin breakdown, as well as functional alterations in microvascular flow. Autonomic dysfunction (and denervation of dermal structures) also results in loss of skin integrity, which provides an ideal site for microbial invasion. The neuropathic foot does not ulcerate spontaneously; rather, it is the combination of some form of trauma accompanied by neuropathy.

Microvascular dysfunction occurs early in diabetes, parallels the progression of neural dysfunction, and may be sufficient to support the severity of structural, functional, and clinical changes observed in diabetic neuropathy.

Advanced glycated end products—Elevated intracellular levels of glucose cause a nonenzymatic covalent bonding with proteins, which alters their structure and destroys their function. Certain of these glycated proteins are implicated in the pathology of diabetic neuropathy and other long term complications of diabetes.

Protein kinase C (PKC)—PKC is implicated in the pathology of diabetic neuropathy. Increased levels of glucose cause an increase in intracellular diacylglycerol, which activates PKC. PKC inhibitors in animal models will increase nerve conduction velocity by increasing neuronal blood flow.

Sensorimotor Polyneuropathy

Longer nerve fibers are affected to a greater degree than shorter ones, because nerve conduction velocity is slowed in proportion to a nerve's length. In this syndrome, decreased sensation and loss of reflexes occurs first in the toes bilaterally, then extends upward. It is usually described as glove-stocking distribution of numbness, sensory loss, dysesthesia and nighttime pain. The pain can feel like burning, pricking sensation, achy or dull. Pins and needles sensation is common. Loss of proprioception, that is, the sense of where a limb is in space, is affected early. These patients cannot feel when they are stepping on a foreign body, like a splinter, or when they are developing a callous from an ill-fitting shoe. Consequently, they are at risk for developing ulcers and infections on the feet and legs, which can lead to amputation. Similarly, these patients can get multiple fractures of the knee, ankle or foot, and develop a Charcot joint. Loss of motor function results on dorsiflexion contractures of the toes, so called hammertoes. These contractures occur not only in the foot but also in the hand.

Autonomic Neuropathy

The autonomic nervous system is composed of nerves serving the heart, GI tract and urinary system. Autonomic neuropathy can affect any of these organ systems. The most commonly recognized autonomic dysfuction in diabetics is orthostatic hypotension, or the uncomfortable sensation of fainting when a patient stands up. In the case of diabetic autonomic neuropathy, it is due to the failure of the heart and arteries to appropriately adjust heart rate and vascular tone to keep blood continually and fully flowing to the brain. This symptom is usually accompanied by a loss of sinus respiratory variation, that is, the usual change in heart rate seen with normal breathing. When these two findings are present, cardiac autonomic neuropathy is present.

GI tract manifestations include delayed gastric emptying, gastroparesis, nausea, bloating, and diarrhea. Because many diabetics take oral medication for their diabetes, absorption of these medicines is greatly affected by the delayed gastric emptying. This can lead to hypoglycemia when an oral diabetic agent is taken before a meal and does not get absorbed until hours, or sometimes days later, when there is normal or low blood sugar already. Sluggish movement of the small instestine can cause bacterial overgrowth, made worse by the presence of hyperglycemia. This leads to bloating, gas and diarrhea.

Urinary symptoms include urinary frequency, urgency, incontinence and retention. Again, because of the retention of sweet urine, urinary tract infections are frequent. Urinary retention can lead to bladder diverticula, stones, reflux nephropathy.

Cranial Neuropathy

When cranial nerves are affected, oculomotor (3rd) neuropathies are most common. The oculomotor nerve controls all of the muscles that move the eye with the exception of the lateral rectus and superior oblique muscles. It also serves to constrict the pupil and open the eyelid. The onset of a diabetic third nerve palsy is usually abrupt, beginning with frontal or periorbital pain and then diplopia. All of the oculomotor muscles innervated by the third nerve may be affected, except for those that control pupil size. The sixth nerve, the abducens nerve, which innervates the lateral rectus muscle of the eye (moves the eye laterally), is also commonly affected but fourth nerve, the trochlear nerve, (innervates the superior oblique muscle, which moves the eye downward) involvement is unusual. Mononeuropathies of the thoracic or lumbar spinal nerves can occur and lead to painful syndromes that mimic myocardial infarction, cholecystitis or appendicitis. Diabetics have a higher incidence of entrapment neuropathies, such as carpal tunnel syndrome.

Diabetic Limb Ischemia and Diabetic Foot Ulcers

Diabetes and pressure can impair microvascular circulation and lead to changes in the skin on the lower extremities, which in turn, can lead to formation of ulcers and subsequent infection. Microvascular changes lead to limb muscle microangiopathy, as well as a predisposition to develop peripheral ischemia and a reduced angiogenesis compensatory response to ischemic events. Microvascular pathology exacerbates Peripheral Vascular Disease (PVD) (or Peripheral Arterial Disease (PAD) or Lower Extremity Arterial Disease (LEAD)—a MACROvascular complication—narrowing of the arteries in the legs due to atherosclerosis. PVD occurs earlier in diabetics, is more severe and widespread, and often involves intercurrent microcirculatory problems affecting the legs, eyes, and kidneys.

Foot ulcers and gangrene are frequent comorbid conditions of PAD. Concurrent peripheral neuropathy with impaired sensation make the foot susceptible to trauma, ulceration, and infection. The progression of PAD in diabetes is compounded by such comorbidity as peripheral neuropathy and insensitivity of the feet and lower extremities to pain and trauma. With impaired circulation and impaired sensation, ulceration and infection occur. Progression to osteomyelitis and gangrene may necessitate amputation.

Persons with diabetes are up to 25 times more likely than nondiabetic persons to sustain a lower limb amputation, underscoring the need to prevent foot ulcers and subsequent limb loss.

Diabetic foot ulcers may occur not only in conjunction with PAD but may also be associated with neuropathy, venous insufficiency (varicose veins), trauma, and infection. PAD contributes to these other conditions in producing or precipitating foot ulcers. Foot ulcers do not necessarily represent progression of PAD, as they may occur in the presence of adequate clinical peripheral arterial perfusion. Patient-based studies indicate an increased risk of foot ulceration in diabetic patients who have peripheral neuropathy and a high plantar foot pressure. The prevalence of a history of ulcers or sores on the foot or ankles was 15% of all diabetic patients in the population-based study in southern Wisconsin. The prevalence was higher for diabetic individuals diagnosed at age<30 years, was slightly higher in men (16%) than in women (13%), and was greater in insulin-treated diabetic patients (17%) than in patients not taking insulin (10%). The prevalence increased with age, especially in diabetic patients diagnosed at age<30 years. In patient studies from Europe, prevalence of foot ulcers in diabetic patients was 3% in those age<50 years, 7% in those age<60 years, and 14% in those age<80 years. Prevalence was greater in males than in females at age 70 years.

In diabetic patients, foot ischemia and infection are serious and even life-threatening occurrences; however, neuropathy is the most difficult condition to treat. The medical and surgical literature concerning all aspects of the clinical and pathological manifestations of the diabetic foot is overwhelming. Neuropathy, angiopathy, retinopathy, and nephropathy, alone or in combination and in varying degrees of severity, may influence the treatment of the diabetic foot.

Every year, 82,000 limb amputations are performed in patients with diabetes mellitus. The majority of these amputations are performed in the elderly population. Amputations resulting from diabetes may arise from multiple etiologies, including foot ulcers, ischemia, venous leg ulcers (ie, those secondary to venous reflux), and heel ulcers (ie, those resulting from untreated pressure ulcers in the heel). The majority of these amputations originate from ulcers. The prevalence of foot ulcers among patients with diabetes is 12%. In addition, the 20-year cumulative incidence of lower-extremity ulcers in patients with type I diabetes is 9.9%. Diabetes-induced limb amputations result in a 5-year mortality rate of 39% to 68% and are associated with an increased risk of additional amputations. The length of hospital stay is approximately 60% longer among patients with diabetic foot ulcers, as compared with those without ulcers.

Diabetic neuropathy impairs the nerve axon reflex that depends on healthy C-fiber nociceptor function and causes local vasodilation in response to a painful stimulus. This condition further compromises the vasodilatory response present in conditions of stress, such as injury or inflammation, in the diabetic neuropathic foot. This impairment may partially explain why some ulcers in the diabetic neuropathic foot are either slow to heal or fail to heal at all, despite successful lower-extremity revascularization.

The most common causal pathway to diabetic foot ulceration can thus be identified as the combination of neuropathy (sensory loss), deformity (eg, prominent metatarsal heads), and trauma (eg, ill-fitting footwear).

Most surgeons prefer to perform popliteal or tibial arterial bypass because of inferior rates of limb salvage and patency compared with more proximal procedures. If popliteal or tibial arterial bypass is unable to restore a palpable foot pulse, pedal bypass has been reported to provide a more durable and effective limb-salvage procedure for patients with diabetes and ischemic foot wounds]. Even extensive multisegment occlusive disease in patients with diabetes does not present an impediment to foot salvage. Whereas serious wound complications may have disastrous results, they are uncommon after pedal bypass grafting. Adequate control of preexisting foot infection and careful graft tunneling have been shown to be effective in avoiding further complications. Angioplasty in the lower extremity is becoming more progressively utilized. However, it must be emphasized that for angioplasty to be effective, a distal vessel or feeding vessel must be patent if the more proximal angioplasty is to succeed.

While diabetic ulcers/limb pathologies may be managed in some patients (by Debridement, antibiotic treatment, use of preparations to stimulate granulation tissue (new collagen and angiogenesis) and reduction of bacterial burden in the wound), it would be beneficial to have a pharmaceutical composition that could better treat these conditions and/or alleviate the symptoms.

For further information, see American Journal of Surgery, Volume 187 •Number 5 Suppl 1 •May 1, 2004, Copyright 2004 Elsevier.

Coronary Microvascular Dysfunction in Diabetes

The correlation between histopathology and microcirculatory dysfunction in diabetes is well known from old experimental studies and from autopsy, where thickening of the basal membrane, perivascular fibrosis, vascular rarefication, and capillary hemorrhage are frequently found. It remains difficult to confirm these data in vivo, although a recent paper demonstrated a correlation between pathology and ocular microvascular dysfunction (Am J Physiol 2003; 285). A large amount of clinical studies, however, indicate that not only overt diabetes but also impaired metabolic control may affect coronary microcirculation (Hypert Res 2002; 25:893). Werner alluded to the important paper by Sambuceti et al (Circulation 2001; 104:1129) showing the persistence of microvascular dysfunction in patients after successful reopening of the infarct related artery, and which may explain the increased cardiovascular morbidity and mortality in these patients. There is mounting evidence from large acute reperfusion studies that morbidity and mortality are unrelated to the reopening itself of the infarct related artery, but much more dependent on the TIMI flow+/−myocardial blush (Stone 2002; Feldmann Circulation 2003). Herrmann indicated, among others, that the integrity of the coronary microcirculation is probably the most important clinical and prognostic factor in this context (Circulation 2001). The neutral effect of protection devices (no relevant change for TIMI flow, for ST resolution, or for MACE) may indicate that a functional impairment of microcirculation is the major determinant of prognosis. There is also increasing evidence that coronary microvascular dysfunction plays a major role in non obstructive CAD. Coronary endothelial dysfunction remains a strong prognostic predictor in these patients.

Diabetic Nephropathy (Renal Dysfunction in Patients with Diabetes)

Diabetic nephropathy encompasses microalbuminuria (a microvascular disease effect), proteinuria and ESRD. Diabetes is the most common cause of kidney failure, accounting for more than 40 percent of new cases. Even when drugs and diet are able to control diabetes, the disease can lead to nephropathy and kidney failure. Most people with diabetes do not develop nephropathy that is severe enough to cause kidney failure. About 16 million people in the United States have diabetes, and about 100,000 people have kidney failure as a result of diabetes.

Diabetic Retinopathy

In the diabetic state, hyperglycemia leads to decreased retinal blood flow, retinal hyperpermeability, delays in photoreceptor nerve conduction, and retinal neuronal cell death. In short duration diabetes, neuronal cell death has been identified within the inner nuclear layer of the retina. Specifically, apoptosis has been localized to glial cells such as Mueller cells and astrocytes and has been shown to occur within 1 month of diabetes in the STZ-induced diabetic rat model. The cause of these events is multi-factorial including activation of the diacylglycerol/PKC pathway, oxidative stress, and non-enzymatic glycosylation. The combination of these events renders the retina hypoxic and ultimately leads to the development of diabetic retinopathy. One possible connection between retinal ischemia and the early changes in the diabetic retina is the hypoxia-induced production of growth factors such as VEGF. The master regulator of the hypoxic response has been identified as hypoxia inducible factor-1 (HIF-1), which controls genes that regulate cellular proliferation and angiogenesis. Prior studies have demonstrated that inhibition of HIF-1 ubiquitination leads to binding with hypoxia responsive elements (HRE) and production of VEGF mRNA.

Diabetic Retinopathy is defined as the progressive dysfunction of the retinal vasculature caused by chronic hyperglycemia. Key features of diabetic retinopathy include microaneurysms, retinal hemorrhages, retinal lipid exudates, cotton-wool spots, capillary nonperfusion, macular edema and neovascularization. Associated features include vitreous hemorrhage, retinal detachment, neovascular glaucoma, premature cataract and cranial nerve palsies.

There are 16 million people in the US with Type 1 and Type 2 diabetes. Within 15 years, 80% of Type 1 patients have developed diabetic retinopathy while 84% of Type 2 diabetic patients develop retinopathy within 19 years. These numbers constitute a significant market for therapeutic agents aimed at ocular diseases of neovasculature. The development of diabetic retinopathy is time-dependent. Despite optimal blood sugar control, patients with long-standing disease can be expected to eventually develop some form of retinopathy. The National Society to Prevent Blindness has estimated that 4 to 6 million diabetics in the U.S. have diabetic retinopathy. The estimated annual incidence of new cases of proliferative diabetic retinopathy and diabetic macular edema are 65,000 and 75,000, respectively, with a prevalence of 700,000 and 500,000 respectively. Diabetic retinopathy causes from 12,000 to 24,000 new cases of blindness in the US every year. Retinopathy is treated by surgical methods, effective in reducing severe vision loss, but the lasered portions of the retina are irreversibly destroyed. There are no drug treatments available.

A microvascular disease that primarily affects the capillaries, diabetes mellitus affects the eye by destroying the vasculature in the conjunctiva, retina and central nervous system. Patients may present with histories of long-standing injected bulbar conjunctivae along with systemic complaints of weight loss despite larger than normal appetite (polyphasia), abnormal thirst (polydypsia) and abnormally frequent urination (polyuria).

Fluctuating visual acuity secondary to unstable blood sugar is a common ocular sign. Swelling within the crystalline lens results in large sudden shifts in refraction as well as premature cataract formation. Changes in visual acuity will depend upon the severity and stage of the disease.

In the retina, weakening of the arterioles and capillaries may result in the characteristic appearance of intraretinal dot and blot hemorrhages, exudates, intraretinal microvascular abnormalities (IRMA) microaneurysms, edema and cotton wool infarcts. Proliferative diabetic retinopathy is the result of severe vascular compromise and is visible as neovascularization of the disc (NVD), neovascularization elsewhere (NVE) and neovascularization of the iris (NVI, or rubeosis irides). Neurological complications include palsies of the third, fourth and sixth cranial nerves as well as diabetic papillitis and facial nerve paralysis.

Diabetes mellitus is a genetically influenced group of diseases that share glucose intolerance. It is characterized as a disorder of metabolic regulation as a result of deficient or malfunctioning insulin or deficient or malfunctioning cellular insulin receptors.

Biochemistry involving the formation of sorbitol plays a role in the destruction of pericytes, which are cells that support the vascular endothelium. As the supportive pericytes perish, capillary endothelium becomes compromised, resulting in the vascular leakage of blood, protein and lipid. This, in combination with thickened, glucose-laden blood, produces vascular insufficiency, capillary nonperfusion, retinal hypoxia, altered structure and decreased function. The formation and release of vasoproliferative factors which play a role in the genesis of retinal neovascularization are poorly understood.

Most non-vision threatening sequelae of diabetes resolve spontaneously over the course of weeks to months following medical control. In cases where there are large refractive changes, patients may require a temporary spectacle prescription until the refraction stabilizes. When retinopathy threatens the macula or when new blood vessels proliferate, the patient may be referred for laser photocoagulation. The Diabetic Retinopathy Study (DRS) has conclusively proven that panretinal photocoagulation was successful in reducing the risk of severe vision loss in high-risk patients. It defined the high-risk characteristics as: (1) Neovascularization of the optic disc (NVD) one-quarter to one-third of a disc diameter in size and (2) Neovascularization elsewhere (NVE) with any vitreous hemorrhage.

Diabetic Macular Edema (DME)

DME is a complication of diabetic retinopathy, a disease affecting the blood vessels of the retina. Diabetic retinopathy results in multiple abnormalities in the retina, including retinal thickening and edema, hemorrhages, impeded blood flow, excessive leakage of fluid from blood vessels and, in the final stages, abnormal blood vessel growth. This blood vessel growth can lead to large hemorrhages and severe retinal damage. When the blood vessel leakage of diabetic retinopathy causes swelling in the macula, it is referred to as DME. The principal symptom of DME is a loss of central vision. Risk factors associated with DME include poorly controlled blood glucose levels, high blood pressure, abnormal kidney function causing fluid retention, high cholesterol levels and other general systemic factors.

According to the World Health Organization, diabetic retinopathy is the leading cause of blindness in working age adults and a leading cause of vision loss in diabetics. The American Diabetes Association reports that there are approximately 18 million diabetics in the United States and approximately 1.3 million newly diagnosed cases of diabetes in the United States each year. Prevent Blindness America and the National Eye Institute estimate that in the United States there are over 5.3 million people aged 18 or older with diabetic retinopathy, including approximately 500,000 with DME. The CDC estimates that there are approximately 75,000 new cases of DME in the United States each year.

Additional Neuropathies

In addition to diabetes, the common causes of neuropathy are herpes zoster infection, chronic or acute trauma (including surgery) and various neurotoxins. Neuropathic pain is common in cancer as a direct result of the cancer on peripheral nerves (e.g., compression by a tumor) and as a side effect of many chemotherapy drugs.

Microvascular disease—Vascular and neural diseases are closely related and intertwined. Blood vessels depend on normal nerve function, and nerves depends on adequate blood flow. The first pathological change in the microvasculature is vasoconstriction. As the disease progresses, neuronal dysfunction correlates closely with the development of vascular abnormalities, such as capillary basement membrane thickening and endothelial hyperplasia, which contribute to diminished oxygen tension and hypoxia. Vasodilator agents (e.g., angiotensin-converting-enzyme inhibitors, al-antagonists) can lead to substantial improvements in neuronal blood flow, with corresponding improvements in nerve conduction velocities.

Clinical Manifestations

Neuropathy affects all peripheral nerves: pain fibers, motor neurons, autonomic nerves. It therefore necessarily can affect all organs and systems since all are innervated. There are several distinct syndromes based on the organ systems and members affected, but these are by no means exclusive. A patient can have sensorimotor and autonomic neuropathy or any other combination.

Despite advances in the understanding of the metabolic causes of neuropathy, treatments aimed at interrupting these pathological processes have been limited by side effects and lack of efficacy. Thus, treatments are symptomatic and do not address the underlying problems. Agents for pain caused by sensorimotor neuropathy include tricyclic antidepressants (TCAs), serotonin reuptake inhibitors (SSRIs) and antiepileptic drugs (AEDs). None of these agents reverse the pathological processes leading to diabetic neuropathy and none alter the relentless course of the illness. Thus, it would be useful to have a pharmaceutical composition that could better treat these conditions and/or alleviate the symptoms.

Additional Retinopathies

Retinal Microvasculopathy (AIDS Retinonathy)

Retinal microvasculopathy is seen in 100% of AIDS patients. It is characterized by intraretinal hemorrhages, microaneurysms, Roth spots, cotton-wool spots (microinfarctions of the nerve fiber layer) and perivascular sheathing. The etiology of the retinopathy is unknown though it has been thought to be due to circulating immune complexes, local release of cytotoxic substances, abnormal hemorheology, and HIV infection of endothelial cells. AIDS retinopathy is now so common that cotton wool spots in a patient without diabetes or hypertension but at risk for HIV should prompt the physician to consider viral testing. There is no specific treatment for AIDS retinopathy but its continued presence may prompt a physician to reexamine the efficacy of the HIV therapy and patient compliance.

Bone Marrow Transplantation (BMT) Retinopathy

Bone marrow transplantation retinopathy was first reported in 1983. It typically occurs within six months, but it can occur as late as 62 months after BMT. Risk factors such as diabetes and hypertension may facilitate the development of BMT retinopathy by heightening the ischemic microvasculopathy. There is no known age, gender or race predilection for development of BMT retinopathy. Patients present with decreased visual acuity and/or visual field deficit. Posterior segment findings are typically bilateral and symmetric. Clinical manifestations include multiple cotton wool spots, telangiectasia, microaneurysms, macular edema, hard exudates and retinal hemorrhages. Fluorescein angiography demonstrates capillary nonperfusion and dropout, intraretinal microvascular abnormalities, microaneurysms and macular edema. Although the precise etiology of BMT retinopathy has not been elucidated, it appears to be affected by several factors: cyclosporine toxicity, total body irradiation (TBI), and chemotherapeutic agents. Cyclosporine is a powerful immunomodulatory agent that suppresses graft-versus-host immune response. It may lead to endothelial cell injury and neurologic side effects, and as a result, it has been suggested as the cause of BMT retinopathy. However, BMT retinopathy can develop in the absence of cyclosporine use, and cyclosporine has not been shown to cause BMT retinopathy in autologous or syngeneic bone marrow recipients. Cyclosporine does not, therefore, appear to be the sole cause of BMT retinopathy. Total body irradiation (TBI) has also been implicated as the cause of BMT retinopathy. Radiation injures the retinal microvasculature and leads to ischemic vasculopathy. Variables such as the total dose of radiation and the time interval between radiation and bone marrow ablation appear to be important. However, BMT retinopathy can occur in patients who did not receive TBI, and BMT retinopathy is not observed in solid organ transplant recipients who received similar doses of radiation. Thus, TBI is not the sole cause, but it is another contributing factor in development of BMT retinopathy. Chemotherapeutic agents have been suggested as a potential contributing factor in BMT retinopathy. Medications such as cisplatin, carmustine, and cyclophosphamide can cause ocular side effects including papilledema, optic neuritis, visual field deficit and cortical blindness. It has been suggested that these chemotherapeutic drugs may predispose patients to radiation-induced retinal damages and enhance the deleterious effect of radiation. In general, patients with BMT retinopathy have a good prognosis. The retinopathy usually resolves within two to four months after stopping or lowering the dosage of cyclosporine. In one report, 69 percent of patients experienced complete resolution of the retinal findings, and 46 percent of patients fully recovered their baseline visual acuity. Because of the favorable prognosis and relatively non-progressive nature of BMT retinopathy, aggressive intervention is usually not necessary.

Ischemic Conditions

Ischemia can be divided into 2 categories: the first involves the accelerated atherosclerosis that occurs commonly in patients with diabetes, i.e., in the femoral, popliteal, and posterior tibial arteries. These vessels, often only 1 or 2 cm in diameter, can develop atherosclerotic plaque, which seriously decreases blood flow. After large vessels become completely occluded, stroke, myocardial infarction, ischemia, and non-healing diabetic foot ulcers can occur. This form of ischemia is essentially a large-vessel disease.

Post Stroke Dementia

25% of people have dementia after a stroke with many others developing dementia over the following 5 to 10 years. In addition, many individuals experience more subtle impairments of their higher brain functions (such as planning skills and speed of processing information) and are at very high risk of subsequently developing dementia. Very small strokes in the deep parts of the brain in this process (called microvascular disease) seem to be essential in the process leading to an identified pattern of brain atrophy specific to post-stroke dementia.

Ocular Ischemic Syndrome

Patients suffering from ocular ischemic syndrome (OIS) are generally elderly, ranging in age from the 50s to 80s. Males are affected twice as commonly as females. The patient is only rarely asymptomatic. Decreased vision occurs at presentation in 90 percent of cases, and 40 percent of patients have attendant eye pain. There may also be an attendant or antecedent history of transient ischemic attacks or amaurosis fugax. Patients also have significant known or unknown systemic disease at the time of presentation. The most commonly encountered systemic diseases are hypertension, diabetes, ischemic heart disease, stroke, and peripheral vascular disease. To a lesser extent, patients manifest OIS as a result of giant cell arteritis (GCA).

Unilateral findings are present in 80 percent of cases. Common findings may include advanced unilateral cataract, anterior segment inflammation, asymptomatic anterior chamber reaction, macular edema, dilated but non-tortuous retinal veins, mid-peripheral dot and blot hemorrhages, cotton wool spots, exudates, and neovascularization of the disc and retina. There may also be spontaneous arterial pulsation, elevated intraocular pressure, and neovascularization of the iris and angle with neovascular glaucoma (NVG). While the patient may exhibit anterior segment neovascularization, ocular hypotony may occur due to low arterial perfusion to the ciliary body. Occasionally, there is visible retinal emboli (Hollenhorst plaques).

The findings in OIS are caused by internal carotid artery atheromatous ulceration and stenosis at the bifurcation of the common carotid artery. Five percent of patients with internal artery stenosis develop OIS. However, OIS only occurs if the degree of stenosis exceeds 90 percent. Stenosis of the carotid artery reduces perfusion pressure to the eye, resulting in the above-mentioned ischemic phenomena. Once stenosis reaches 90 percent, the perfusion pressure in the central retinal artery (CRA) drops only to 50 percent. Often, the reduced arterial pressure manifests as spontaneous pulsation of the CRA. The findings are variable and may include any or all of the above findings.

Patients with OIS have significant systemic disease that must be assessed. Cardiac death is the primary cause of mortality in patients with OIS—the five-year mortality rate is 40 percent. For this reason, patients with OIS must be referred to a cardiologist for complete serology, EKG, ECG, and carotid evaluation.

Microvascular Diseases of the Kidney

The kidney is involved in a number of discreet clinicopathologic conditions that affect systemic and renal microvasculature. Certain of these conditions are characterized by primary injury to endothelial cells, such as:

hemolytic-uremic syndrome (HUS) and thrombotic thrombocytopenic purpura (TTP) HUS and ITP are closely related diseases characterized by microangiopathic hemolytic anemia and variable organ impairment Traditionally, the diagnosis of HUS is made when renal failure is a predominant feature of the syndrome, as is common in children. In adults, neurologic impairment frequently predominates and the syndrome is then referred to as TTP. Thrombotic microangiopathy is the underlying pathologic lesion in both syndromes, and the clinical and laboratory findings in patients with either HUS or TTP overlap to a large extent. This has prompted several investigators to regard the two syndromes as a continuum of a single disease entity. Pathogenesis; Experimental data strongly suggest that endothelial cell injury is the primary event in the pathogenesis of HUS/TTP. Endothelial damage triggers a cascade of events that includes local intravascular coagulation, fibrin deposition, and platelet activation and aggregation. The end result is the histopathologic finding of thrombotic microangiopathy common to the different forms of the HUS/TTP syndrome. If HUS/TTP is left untreated, the mortality rate approaches 90%. Supportive therapy—including dialysis, antihypertensive medications, blood transfusions, and management of neurologic complications—contributes to the improved survival of patients with HUS/TTP. Adequate fluid balance and bowel rest are important in treating typical HUS associated with diarrhea.

radiation nephritis—The long-term consequences of renal irradiation in excess of 2500 rad can be divided into five clinical syndromes:
(i) Acute radiation nephritis occurs in approximately 40% of patients after a latency period of 6 to 13 months. It is characterized clinically by abrupt onset of hypertension, proteinuria, edema, and progressive renal failure in most cases leading to end-stage kidneys.

(ii) Chronic radiation nephritis, conversely, has a latency period that varies between 18 months and 14 years after the initial insult. It is insidious in onset and is characterized by hypertension, proteinuria, and gradual loss of renal function.

(iii) The third syndrome manifests 5 to 19 years after exposure to radiation as benign proteinuria with normal renal function (iv) A fourth group of patients exhibits only benign hypertension 2 to 5 years later and may have variable proteinuria. Late malignant hypertension arises 18 months to 11 years after irradiation in patients with either chronic radiation nephritis or benign hypertension. Removal of the affected kidney reversed the hypertension. Radiation-induced damage to the renal arteries with subsequent renovascular hypertension has been reported.

(v) A syndrome of renal insufficiency analogous to acute radiation nephritis has been observed in bone marrow transplantation (BMT) patients who were treated with total-body irradiation (TBI).

It has been reported that irradiation causes endothelial dysfunction but spares vascular smooth muscle cells in the early postradiation phase. Radiation could directly damage DNA, leading to decreased regeneration of these cells and denudement of the basement membrane in the glomerular capillaries and tubules. How this initial insult eventually leads to glomerulosclerosis, tubule atrophy, and interstitial fibrosis is unclear. It is postulated that degeneration of the endothelial cell layer may result in intravascular thrombosis in capillaries and smaller arterioles. This intrarenal angiopathy would then explain the progressive renal fibrosis and the hypertension that characterize radiation nephritis. A recent study of irradiated mouse kidneys showed a dose-dependent increase in leukocytes in the renal cortex, suggesting a role for inflammatory processes in radiation-induced nephritis.

In other kidney diseases, the microvasculature of the kidney is involved in autoimmune disorders, such as systemic sclerosis (scleroderma). Kidney involvement in systemic sclerosis manifests as a slowly progressing chronic renal disease or as scleroderma renal crisis (SRC), which is characterized by malignant hypertension and acute azotemia. It is postulated that SRC is caused by a Raynaud-like phenomenon in the kidney. Severe vasospasm leads to cortical ischemia and enhanced production of renin and angiotensin II, which in turn perpetuate renal vasoconstriction. Hormonal changes (pregnancy), physical and emotional stress, or cold temperature may trigger the Raynaud-like arterial vasospasm. The role of the renin-angiotensin system in perpetuating renal ischemia is underscored by the significant benefit of ACE inhibitors in treating SRC. In patients with SRC who progress to severe renal insufficiency despite antihypertensive treatment, dialysis becomes a necessity. Both peritoneal dialysis and hemodialysis have been employed. The End-Stage Renal Disease (ESRD) Network report on 311 patients with systemic sclerosis-induced ESRD dialyzed between 1983 and 1985 revealed a 33% survival rate at 3 years.

The renal microcirculation can also be affected in sickle cell disease, to which the kidney is particularly susceptible because of the low oxygen tension attained in the deep vessels of the renal medulla as a result of countercurrent transfer of oxygen along the vasa recta. The smaller renal arteries and arterioles can also be the site of thromboembolic injury from cholesterol-containing material dislodged from the walls of the large vessels.

Taken as a group, diseases that cause transient or permanent occlusion of renal microvasculature uniformly result in disruption of glomerular perfusion, and hence of the glomerular filtration rate, thereby constituting a serious threat to systemic homeostasis.

Acute Renal Failure (ARF)

ARF can be caused by microvascular or macrovascular disease (major renal artery occlusion or severe abdominal aortic disease). The classic microvascular diseases often present with microangiopathic hemolysis and acute renal failure occurring because of glomerular capillary thrombosis or occlusion, often with accompanying thrombocytopenia. Typical examples of these diseases include:

a) Thrombotic thrombocytopenic Purpura—The classic pentad in thrombotic thrombocytopenic purpura includes fever, neurologic changes, renal failure, microangiopathic hemolytic anemia and thrombocytopenia.

b) Hemolytic Uremic Syndrome—Hemolytic uremic syndrome is similar to thrombotic thrombocytopenic purpura but does not present with neurologic changes.

c) HELLP syndrome (hemolysis, elevated liver enzymes and low platelets). HELLP syndrome is a type of hemolytic uremic syndrome that occurs in pregnant women with the addition of transaminase elevations.

Acute renal failure can present in all medical settings but is predominantly acquired in hospitals. The condition develops in 5 percent of hospitalized patients, and approximately 0.5 percent of hospitalized patients require dialysis. Over the past 40 years, the survival rate for acute renal failure has not improved, primarily because affected patients are now older and have more comorbid conditions. Infection accounts for 75 percent of deaths in patients with acute renal failure, and cardio-respiratory complications are the second most common cause of death. Depending on the severity of renal failure, the mortality rate can range from 7 percent to as high as 80 percent. Acute renal failure can be divided into three categories: Prerenal, intrinsic and postrenal ARF. Intrinsic ARF is subdivided into four categories: tubular disease, glomerular disease, vascular disease (includes microvascular) and interstitial disease.

Progressive Renal Disease

There is evidence that progressive renal disease is characterized by a progressive loss of the microvasculature. The loss of the microvasculature correlates directly with the development of glomerular and tubulointerstitial scarring. The mechanism is mediated in part by a reduction in the endothelial proliferative response, and this impairment in capillary repair is mediated by alteration in the local expression of both angiogenic (vascular endothelial growth factor) and antiangiogenic (thrombospondin 1) factors in the kidney. The alteration in balance of angiogenic growth factors is mediated by both macrophage-associated cytokines (interleukin-1β) and vasoactive mediators. Finally, there is intriguing evidence that stimulation of angiogenesis and/or capillary repair may stabilize renal function and slow progression and that this benefit occurs independently of effects on BP or proteinuria.

For further information see Brenner & Rector's The Kidney, 7th ed., Copyright © 2004 Elsevier: Chapter 33 —*Microvascular diseases of the kidney* and also Tiwari and Vikrant Journal of Indian Academy of Clinical Medicine Vol. 5, No. 1 *Review Article-Sepsis and the Kidney.*

Hearing Disorders

Chemical-Induced Ototoxicity

The toxic effects of various ototoxic therapeutic drugs on auditory cells and spiral ganglion neurons are often the limiting factor for their therapeutic usefulness. Main ototoxic drugs include the widely used chemotherapeutic agent cisplatin and its analogs, commonly used aminoglycoside antibiotics, e.g. gentamicin, for the treatment of infections caused by gram-negative bacteria, quinine and its analogs, salicylate and its analogs, and loop-diuretics.

For example, antibacterial aminoglycosides such as gentamicins, streptomycins, kanamycins, tobramycins, and the like are known to have serious toxicity, particularly ototoxicity and nephrotoxicity, which reduce the usefulness of such antimicrobial agents (see Goodman and Gilman's The Pharmacological Basis of Therapeutics, 6th ed., A. Goodman Gilman et al., eds; Macmillan Publishing Co., Inc., New York, pp. 1169-71 (1980)). Clearly, ototoxicity is a dose-limiting side-effect of antibiotic administration. From 4 to 15% of patients receiving I gram per day for greater than 1 week develop measurable hearing loss, which slowly becomes worse and can lead to complete permanent deafness if treatment continues.

Ototoxicity is also a serious dose-limiting side-effect for cisplatin, a platinum coordination complex, that has proven effective on a variety of human cancers including testicular, ovarian, bladder, and head and neck cancer. Cisplatin (Platinol®) damages auditory and vestibular systems. Salicylates, such as aspirin, are the most commonly used therapeutic drugs for their anti-inflammatory, analgesic, anti-pyretic and anti-thrombotic effects. Unfortunately, they too have ototoxic side effects. They often lead to tinnitus ("ringing in the ears") and temporary hearing loss. Moreover, if the drug is used at high doses for a prolonged time, the hearing impairment can become persistent and irreversible.

Accordingly, there exists a need for means to prevent, reduce or treat the incidence and/or severity of inner ear disorders and hearing impairments involving inner ear tissue, particularly inner ear hair cells. Of particular interest are those conditions arising as an unwanted side-effect of ototoxic therapeutic drugs including cisplatin and its analogs, aminoglycoside antibiotics, salicylate and its analogs, or loop diuretics. In addition, there exits a need for methods which will allow higher and thus more effective dosing with these ototoxicity-inducing pharmaceutical drugs, while concomitantly preventing or reducing ototoxic effects caused by these drugs. What is needed is a method that provides a safe, effective, and prolonged means for prophylactic or curative treatment of hearing impairments related to inner ear tissue damage, loss, or degeneration, particularly ototoxin-induced and particularly involving inner ear hair cells. In addition, there is required a method and composition for the treatment of damage and deafness resulting from inner ear trauma (acoustic trauma).

Without being bound by theory, it is believed that cisplatin drugs and other drugs that induce ototoxicity (such as aminoglycoside antibiotics), as well as acoustic trauma, may induce the ototoxic effects via programmed cell death or apoptosis in inner ear tissue, particularly inner ear hair cells (Zhang et al., Neuroscience 120 (2003) 191-205; Wang et al., J. Neuroscience 23((24):8596-8607). In mammals, auditory hair cells are produced only during embryonic development and do not regenerate if lost during postnatal life, therefore, a loss of hair cells will result in profound and irreversible deafness. Unfortunately, at present, there are no effective therapies to treat the cochlea and reverse this condition. Thus, an effective therapy to prevent cell death of auditory hair cells would be of great therapeutic value.

Pressure Sores

Pressure sores or pressure ulcers, are areas of damaged skin and tissue that develop when sustained pressure (usually from a bed or wheelchair) cuts off circulation to vulnerable parts of the body, especially the skin on the buttocks, hips and heels. The lack of adequate blood flow leads to ischemic necrosis and ulceration of the affected tissue. Pressure sores occur most often in patients with diminished or absent sensation or who are debilitated, emaciated, paralyzed, or long bedridden. Tissues over the sacrum, ischia, greater trochanters, external malleoli, and heels are especially susceptible; other sites may be involved depending on the patient's position.

Pressure sores are wounds which normally only heal very slowly and especially in such cases an improved and more rapid healing is of course of great importance for the patient. Furthermore, the costs involved in the treatment of patients suffering from such wounds are markedly reduced when the healing is improved and takes place more rapidly.

Ischemic Conditions

Ischemic injury is the most common clinical expression of cell injury by oxygen deprivation. The most useful models for studying ischemic injury involve complete occlusion of one of the end-arteries to an organ (e.g., a coronary artery) and examination of the tissue (e.g., cardiac muscle) in areas supplied by the artery. Complex pathologic changes occur in diverse cellular systems during ischemia. Up to a certain point, for a duration that varies among different types of cells, the injury may be amenable to repair, and the affected cells may recover if oxygen and metabolic substrates are again made available by restoration of blood flow. With further extension of the ischemic duration, cell structure continues to deteriorate, owing to relentless progression of ongoing injury mechanisms. With time, the energetic machinery of the cell—the mitochondrial oxidative powerhouse and the glycolytic pathway—becomes irreparably damaged, and restoration of blood flow (reperfusion) cannot rescue the damaged cell. Even if the cellular energetic machinery were to remain intact, irreparable damage to the genome or to cellular membranes will ensure a lethal outcome regardless of reperfusion. This irreversible injury is usually manifested as necrosis, but apoptosis may also play a role. Under certain circumstances, when blood flow is restored to cells that have been previously made ischemic but have not died, injury is often paradoxically exacerbated and proceeds at an accelerated pace—this is reperfusion injury.

Reperfusion injury may occur in a variety of conditions, especially during medical intervention, including but not limited to angioplasty, cardiac surgery or thrombolysis; organ transplant (lung, heart, kidney, liver, etc.), resulting possibly in transplant rejection as a result of ischemia-reperfusion following the renewal of blood flow to the transplanted organ; as a result of plastic surgery; during severe compartment syndrome; during re-attachment of severed limbs; as a result of multiorgan failure syndrome; in the brain as a result of stroke or brain trauma; in connection with chronic wounds such as a pressure sore, a venous ulcer and a diabetic ulcer; during skeletal muscle ischemia or limb transplantation; as a result of mesenteric ischemia or acute ischemic bowel disease; respiratory failure as a result of lower torso ischemia, leading to pulmonary hypertension, hypoxemia, and noncardiogenic pulmonary edema; acute renal failure as observed after renal transplantation, major surgery, trauma, and septic as well as hemorrhagic shock; sepsis; retinal ischemia occurring as a result of acute vascular occlusion, leading to loss of vision in a number of ocular diseases such as acute glaucoma, diabetic retinopathy, hypertensive retinopathy, and retinal vascular occlusion; cochlear ischemia; flap failure in microvascular surgery for head and neck defects; Raynaud's phenomenon and the associated digital ischemic lesions in scleroderma; spinal cord injury; vascular surgery; traumatic rhabdomyolysis (crush syndrome); and myoglobinuria.

Further, ischemia/reperfusion may be involved in the following conditions: hypertension, hypertensive cerebral vascular disease, rupture of aneurysm, a constriction or obstruction of a blood vessel—as occurs in the case of a thrombus or embolus, angioma, blood dyscrasias, any form of compromised cardiac function including cardiac arrest or failure, systemic hypotension, cardiac arrest, cardiogenic shock, septic shock, spinal cord trauma, head trauma, seizure, bleeding from a tumor; and diseases such as stroke, Parkinson's disease, epilepsy, depression, ALS, Alzheimer's disease, Huntington's disease and any other disease-induced dementia (such as HIV induced dementia for example).

Additionally, an ischemic episode may be caused by a mechanical injury to the Central Nervous System, such as results from a blow to the head or spine. Trauma can involve a tissue insult such as an abrasion, incision, contusion, puncture, compression, etc., such as can arise from traumatic contact of a foreign object with any locus of or appurtenant to the head, neck, or vertebral column. Other forms of traumatic injury can arise from constriction or compression of CNS tissue by an inappropriate accumulation of fluid (for example, a blockade or dysfunction of normal cerebrospinal fluid or vitreous humor fluid production, turnover, or volume regulation, or a subdural or intracamial hematoma or edema). Similarly, traumatic constriction or compression can arise from the presence of a mass of abnormal tissue, such as a metastatic or primary tumor.

In conclusion, current modes of therapy for the prevention and/or treatment of COPD, macular degeneration microvascular diseases and ototoxic conditions are unsatisfactory and there is a need therefore to develop novel compounds for this purpose. There is also a need to develop a therapy and a medicament which can treat the ototoxic effects currently associated with certain drugs and conditions, in particular with cisplatin chemotherapeutics and certain antibiotics without sacrificing the effectiveness of the drugs. Additionally, there is a need to develop a therapy and medicament which can treat the ototoxic effects associated with acoustic trauma or mechanical trauma within the inner ear. Furthermore, there is a need to develop a therapy and a medicament for the treatment of pressure sores, ischemia and ischemia-reperfusion related conditions. All the diseases and indications disclosed herein above, as well as other diseases and conditions described herein such as MI may also be treated by the novel compounds of this invention.

RTP801

Gene RTP801, was first reported by a co-assignee of the instant application. U.S. Pat. Nos. 6,455,674, 6,555,667, and 6740738, all assigned to one of the co-assignees of the instant application, disclose and claim per se the RTP801 polynucleotide and polypeptide, and antibodies directed toward the polypeptide. RTP801 represents a unique gene target for hypoxia-inducible factor-1 (HIF-1) that may regulate hypoxia-induced pathogenesis independent of growth factors such as VEGF.

The Following patent applications and Publications Give Aspects of Background Information.

WO 2001070979 relates to nucleic acid markers which are overexpressed in ovarian cancer cells.

U.S. Pat. No. 6,673,549 discloses a combination comprising cDNAs that are differentially expressed in response to steroid treatment.

US application 2003165864 relates to cDNAs that are differentially expressed in cells treated with a DNA demethylating agent.

US application 2003108871 relates to a composition comprising several cDNAs that are differentially expressed in treated human C3A liver cell cultures.

US application 2002119463 discloses a new composition, useful for treating and diagnosing prostate cancer, said composition comprising human cDNAs that are differentially expressed in prostate cancer.

WO 2004018999 discloses a method for assessing, characterizing, monitoring, preventing and treating cervical cancer.

EP 1394274 relates to a method of testing for bronchial asthma or chronic obstructive pulmonary disease by comparing the expression level of a marker gene in a biological sample from a subject with the expression level of the gene in a sample from a healthy subject.

WO 2002101075 relates to an isolated nucleic acid molecule useful for detecting, characterizing, preventing and treating human cervical cancers.

WO 2003010205 relates to inhibiting angiogenesis for treating wound healing, retinopathy, ischemia, inflammation, microvasculopathy, bone healing and skin inflammation.

WO 2002046465 relates to identifying a gene involved in disease for treating hypoxia-regulated conditions.

WO 2002031111 relates to polypeptides and their encoded proteins, and many uses therefore are provided.

WO 2001012659 relates to nucleic acids useful in recombinant DNA methodologies.

WO 2001077289 discloses six hundred and twenty three polynucleotides derived from a variety of human tissue sources.

WO 2003101283 relates to a combination which comprises many cDNAs and proteins

JP 2003259877 relates to many hepatic fibrosis disease markers.

Tzipora Shoshani, et al. *Identification of a Novel Hypoxia-Inducible Factor I-Responsive Gene. RTP801, Involved in Apoptosis. MOLECULAR AND CELLULAR BIOLOGY*, April 2002, p. 2283-2293; this paper, co-authored by the inventors of the present invention, details the discovery of the RTP801 gene (a then novel HIF-1-dependent gene Anat Brafman, et al. Inhibition of Oxygen-Induced Retinopathy in RTP801-Deficient Mice. Invest Ophthalmol V is Sci. 2004 October; 45 (10): 3796-805; also co-authored by the inventors of the present invention, this paper demonstrates that in RTP801 knock out mice, hyperoxia does not cause degeneration of the retinal capillary network.

Leif W. Ellisen, et al. *REDD1, a Developmentally Regulated Transcriptional Target of p63 and p53, Links p63 to Regulation of Reactive Oxygen Species*. Molecular Cell, Vol. 10, 995-1005, November, 2002; this paper demonstrates that overexpression of RTP801 (referred to therein as REDD1) leads to increased production of reactive oxygen species.

Richard D R, Berra E, and Pouyssegur J. *Non-hypoxic pathway mediates the induction of hypoxia-inducible factor I alpha in vascular smooth muscle cells*. J. Biol. Chem. 2000, Sep. 1; 275(35): 26765-71. This paper demonstrates that HIF-1-dependent transcription may be induced by excessive production of reactive oxygen species.

Rangasami T, et al., *Genetic ablation of Nrf2 enhances susceptibility to cigarette smoke-induced emphysema in mice*. Submitted to *Journal of Clinical Investigation*. This work relates to mice with a compromised antioxidant defence.

SUMMARY OF THE INVENTION

The present invention provides novel methods and compositions for treating microvascular disorders, macular degeneration, respiratory disorders, and spinal cord injury or disease.

In one embodiment, novel molecules which inhibit RTP801 and can be used to treat various diseases and indications are provided.

In another embodiment, the present invention provides a method of treating a patient suffering from a microvascular disorder, macular degeneration or a respiratory disorder, comprising administering to the patient a pharmaceutical composition comprising an RTP801 inhibitor.

Another embodiment of the present invention concerns a method for treating a patient suffering from COPD, comprising administering to the patient a pharmaceutical composition comprising a therapeutically effective amount of an RTP801 inhibitor. In one embodiment the inhibitor is an siRNA molecule, an antisense molecule, an antibody (such as a neutralizing antibody), a dominant negative peptide or a ribozyme.

Another embodiment of the present invention concerns a method for treating a patient suffering from macular degeneration, comprising administering to the patient a pharmaceutical composition comprising a therapeutically effective amount of an RTP801 inhibitor. In one embodiment the inhibitor is an siRNA molecule, an antisense molecule, an antibody (such as a neutralizing antibody), a dominant negative peptide or a ribozyme.

Another embodiment of the present invention concerns a method for treating a patient suffering from a microvascular disorder, comprising administering to the patient a pharmaceutical composition comprising a therapeutically effective amount of an RTP801 inhibitor. In one embodiment the inhibitor is an siRNA molecule, an antisense molecule, an antibody (such as a neutralizing antibody), a dominant negative peptide or a ribozyme.

An additional embodiment of the present invention provides for the use of a therapeutically effective amount of an RTP801 inhibitor for the preparation of a medicament for promoting recovery in a patient suffering from a respiratory disorder. In one embodiment the respiratory disorder is COPD and the inhibitor is preferably an siRNA.

An additional embodiment of the present invention provides for the use of a therapeutically effective dose of an RTP801 inhibitor for the preparation of a medicament for promoting recovery in a patient suffering from macular degeneration. In one embodiment the macular degeneration is AMD and the inhibitor is preferably an siRNA.

An additional embodiment of the present invention provides for the use of a therapeutically effective amount of an RTP801 inhibitor for the preparation of a medicament for promoting recovery in a patient suffering from a microvascular disorder. In one embodiment the microvascular disorder is diabetic retinopathy and the inhibitor is preferably an siRNA.

The present invention relates generally to methods and compositions for treating or preventing the incidence or severity of hearing impairment (or balance impairment), particularly hearing impairment associated with cell death of the inner ear hair cells. The methods and compositions involve administering to a mammal in need of such treatment a prophylactically or therapeutically effective amount of one or more compounds which down-regulate expression of the RTP801 gene, particularly novel small interfering RNAs (siRNAs).

More specifically, the present invention provides methods and compositions for treating a patient suffering from hearing impairment, or other oto-pathologies associated with cell death of inner ear hair cells. Such oto-pathologies may be the result of acoustic trauma, mechanical trauma, or ototoxin-induced hearing loss. The methods of the invention comprising administering to the patient one or more compounds which down-regulate expression of the RTP801 gene, particularly siRNAs that inhibit RTP801 typically as a pharmaceutical composition, in a therapeutically effective dose so as to thereby treat the patient.

In one embodiment, the present invention provides for improved compositions and methods for treatments requiring administration of a pharmaceutical drug having an ototoxic, hearing-impairing side-effect, in combination with a therapeutically effective amount of one or more siRNA molecules that inhibit RTP801, to treat or prevent the ototoxicity induced by the pharmaceutical drug. The compositions of the invention can be administered at a suitable interval(s) either prior to, subsequent to, or substantially concurrent with the administration of the ototoxic, hearing-impairing drug that induces inner ear apoptotic tissue damage. Similarly, this treatment can be effective as a prophalactic treatment prior to or in conjunction with conditions which cause acoustic trauma.

Accordingly, it is an object of the invention to provide an improved composition containing a therapeutically effective amount of one or more siRNA molecules that inhibit RTP801 in combination with an ototoxic, hearing-impairing pharmaceutical drug for administration to a mammal. Said combination drugs may be administered separately; the siRNA molecules that inhibit RTP801 would then be administered locally while the ototoxic, hearing-impairing pharmaceutical drug is administered systemically. The siRNA molecules may be administered prior to, simultaneously with or subsequent to the ototoxic drug. Such combination compositions can further contain a pharmaceutically acceptable carrier. The pharmaceutical composition will have lower ototoxicity than the ototoxic pharmaceutical alone, and preferably, will have a higher dosage of the ototoxic pharmaceutical than typically used. Examples of such improved compositions include cisplatin or other ototoxic neoplastic agent or an aminoglycoside antibiotic(s) in combination with the therapeutically effective amount of one or more siRNA molecules that inhibit RTP801.

Still further, the invention relates to the use of the compositions of the invention in cases where diuretics are needed. The present invention provides a solution to the art that has long sought a therapy and a medicament which can treat the ototoxic effects currently associated with certain diuretics, and particular with the more popular and commonly used loop-diuretics, without sacrificing their diuretic effectiveness.

Still further, the invention relates to the use of the compositions of the invention in cases where quinine or quinine-like compounds are needed. The present invention provides a solution to the art that has long sought a therapy and a medicament which can treat the ototoxic effects currently associated with certain quinines without sacrificing their effectiveness.

The present invention further relates to methods and compositions for treating or preventing the incidence or severity of pressure sores. The methods and compositions involve administering to a mammal in need of such treatment a prophylactically or therapeutically effective amount of one or more compounds which down-regulate expression of the RTP801 gene, particularly novel small interfering RNAs (siRNAs).

Further, the present invention relates to methods and compositions for the treatment of any ischemic or ischemia-reperfusion injuries or conditions, as described herein. Said methods and compositions involve administering to a mammal in need of such treatment a prophylactically or therapeutically effective amount of one or more compounds which down-regulate expression of the RTP801 gene, particularly novel small interfering RNAs (siRNAs).

DETAILED DESCRIPTION OF THE INVENTION

The present invention, in some of its embodiments, concerns inhibition of the RTP801 gene or polypeptide for the treatment of eye diseases, respiratory disorders, microvascular disorders, hearing disorders and ischemic conditions, inter alia. As will be described herein, the preferred inhibitors to be used with the present invention are biological molecules.

Without being bound by theory, the inventors of the present invention have found that RTP801 is involved in various disease states including microvascular disorders, eye diseases, respiratory disorders, hearing disorders, pressure sores, ischemic conditions and spinal cord injury and disease, and it would be beneficial to inhibit RTP801 in order to treat any of said diseases or disorders. Methods, molecules and compositions which inhibit RTP801 are discussed herein at length, and any of said molecules and/or compositions may be beneficially employed in the treatment of a patient suffering from any of said conditions.

The present invention provides methods and compositions for inhibiting expression of the RTP801 gene in vivo. In general, the method includes administering oligoribonucleotides, such as small interfering RNAs (i.e., siRNAs) that are targeted to a particular mRNA and hybridise to it, or nucleic acid material that can produce siRNAs in a cell, in an amount sufficient to down-regulate expression of a target gene by an RNA interference mechanism. In particular, the subject method can be used to inhibit expression of the RTP801 gene for treatment of respiratory disorders, microvascular disorders, eye disorders and hearing impairments.

Thus, in one embodiment the present invention provides for a method of treating a patient suffering from a condition selected from a microvascular disorder, an eye disease, a respiratory disorder, a hearing disorder, pressure sores or a spinal cord injury or other wound, comprising administering to the patient a pharmaceutical composition comprising an RTP801 inhibitor in a therapeutically effective amount so as to thereby treat the patient. The invention further provides a method of treating a patient suffering from a microvascular disorder, an eye disease a respiratory disorder, a hearing disorder, pressure sores or a spinal cord injury or other wound, comprising administering to the patient a pharmaceutical composition comprising an RTP801 inhibitor, in a dosage and over a period of time sufficient to promote recovery. The eye disease may be macular degeneration such as age-related macular degeneration (AMD), inter alia. The microvascular disorder may be diabetic retinopathy or acute renal failure, inter alia. The respiratory disorder may be chronic obstructive pulmonary disease (COPD), emphysema, chronic bronchitis, asthma and lung cancer, inter alia. The hearing disorder may be acoustic trauma or cisplatin-induced deafness, inter alia. The RTP801 inhibitor may be selected from a large variety of molecules, including but not limited to compounds such as polynucleotides, antisense fragments, RNA in molecules which target the RTP801 gene mRNA such as ribozymes or siRNAs (such as the siRNAs of Tables A-D and in particular, siRNA Nos:14, 22, 23, 25, 27, 39, 41, 42, 49 and 50 of Table A or siRNA Nos: 257, 260-262, and 264-268 of Table D), or expression vectors comprising them; polypeptides such as dominant negatives, antibodies (such as an antibody which specifically binds to an epitope present within a polypeptide which comprises consecutive amino acids, the sequence of which is set forth in FIG. 2 (SEQ ID No:2)), or, in some cases, enzymes. Additionally, the RTP801 inhibitor may be a chemical inhibitor such as a small molecule, e.g., chemical molecules with a low molecular weight e.g. a molecular weight below 2000 daltons. Specific RTP801 inhibitors are given below.

The present invention further provides a method for treating a patient suffering from macular degeneration, COPD, diabetic retinopathy or acoustic trauma-induced deafness, comprising administering to the patient a pharmaceutical composition comprising a therapeutically effective dose of an RTP801 inhibitor comprising a polynucleotide which specifically hybridizes to mRNA transcribed from the RTP801 gene and down regulates the expression of the RTP801 gene so as to thereby treat the patient. The polynucleotide may be an siRNA comprising consecutive nucleotides having a sequence identical to any sequence set forth in Tables A-D (SEQ ID NOs:3-536) and in particular, siRNA Nos: 14, 22, 23, 25, 27, 39, 41, 42, 49 and 50 of Table A or siRNA Nos: 257, 260-262, and 264-268 of Table D.

Further, an additional embodiment of the present invention concerns a method for treating a patient suffering from a microvascular disorder, an eye disease, a respiratory disorder, a hearing disorder, pressure sores or a spinal cord injury or other wound, comprising administering to the patient a pharmaceutical composition comprising a therapeutically effective dose of an RTP801 inhibitor comprising an siRNA molecule, optionally an siRNA molecule detailed in any one of Tables A-D, in a dosage and over a period of time so as to thereby treat the patient.

An additional method for treating a patient suffering from a microvascular disorder, an eye disease, a respiratory disorder, a hearing disorder, pressure sores or a spinal cord injury or other wound is provided, comprising administering to the patient a pharmaceutical composition comprising a therapeutically effective dose of an RNA molecule which targets the RTP801 gene mRNA in a dosage and over a period of time so as to thereby treat the in patient. The RNA molecule may be an siRNA molecule, such as an siRNA molecule detailed in Tables A-D and in particular, siRNA Nos:14, 22, 23, 25, 27, 39, 41, 42, 49 and 50 of Table A or siRNA Nos: 257, 260-262, and 264-268 of Table D, or a ribozyme.

The present invention further provides a method for treating a patient suffering from a microvascular disorder, an eye disease, a respiratory disorder, a hearing disorder, pressure sores or a spinal cord injury or other wound or any of the conditions disclosed herein, comprising administering to the patient a pharmaceutical composition comprising a therapeutically effective dose of an siRNA molecule which targets the RTP801 gene mRNA, optionally an siRNA molecule detailed in Tables A-D, in a dosage and over a period of time so as to thereby treat the patient. Further, the eye disease may be macular degeneration such as age-related macular degeneration (AMD); the microvascular disorder may be diabetic retinopathy or acute renal failure; the respiratory disorder may be COPD and the aspects of COPD being treated may comprise, but are not limited to, emphysema, chronic bronchitis, or both; and the hearing disorder may be acoustic trauma-induced deafness.

The present invention additionally relates to the use of the novel siRNAs disclosed herein in the treatment of hearing impairment in which inhibition of RTP801 expression is beneficial. In one embodiment, the present invention constitutes a method for treating a mammal having or prone to a hearing (or balance) impairment or treating a mammal prophylactically in conditions where inhibition of RTP801 expression is beneficial. The method of this embodiment of the present invention would prevent or reduce the occurrence or severity of a hearing (or balance) impairment that would result from inner ear cell injury, loss, or degeneration, in particular caused by acoustic trauma or an ototoxic agent. In this embodiment, the method of the invention includes administering a therapeutically effective amount of one or more compounds which down-regulate expression of the RTP801 gene, particularly the novel siRNAs of the present invention.

In one embodiment, it is the object of the present invention to provide a method for treating a mammal, to prevent, reduce, or treat a hearing impairment, disorder or imbalance, preferably acoustic trauma or an ototoxin-induced hearing condition, by administering to a mammal in need of such treatment a composition of the invention. One embodiment is a method for treating a hearing disorder or impairment wherein the acoustic trauma results from a one-time exposure to an extremely loud sound or continuous exposure to a noisy environment which can cause deafness over time. The hearing impairment may also be caused by physical trauma to the ear. Another embodiment is a method for treating a hearing disorder or impairment wherein the ototoxicity results from administration of a therapeutically effective amount of an ototoxic pharmaceutical drug. Typical ototoxic drugs are chemotherapeutic agents, e.g. antineoplastic agents, and antibiotics. Other possible candidates include loop-diuretics, quinines or a quinine-like compound, and salicylate or salicylate-like compounds. These methods are especially effective when the ototoxic compound is an antibiotic, preferably an aminoglycoside antibiotic. Ototoxic aminoglycoside antibiotics include but are not limited to neomycin, paromomycin, ribostamycin, lividomycin, kanamycin, amikacin, tobramycin, viomycin, gentamicin, sisomicin, netilmicin, streptomycin, dibekacin, fortimicin, and dihydrostreptomycin, or combinations thereof. Particular antibiotics include neomycin B, kanamycin A, kanamycin B, gentamicin C1, gentamicin C1a, and gentamicin C2. The methods of the invention are also effective when the ototoxic compound is a neoplastic agent such as vincristine, vinblastine, cisplatin and cisplatin-like compounds and taxol and taxol-like compounds In some embodiments aimed at treating or preventing a hearing disorder, the composition of the invention is co-administered with an ototoxin. For example, an improved method is provided for treatment of infection of a mammal by administration of an aminoglycoside antibiotic, the improvement comprising administering a therapeutically effective amount of one or more compounds which down-regulate expression of the RTP801 gene particularly novel siRNAs, to the patient in need of such treatment to reduce or prevent ototoxin-induced hearing impairment associated with the antibiotic. The compounds which reduce or prevent the ototoxin-induced hearing impairment, particularly the novel siRNAs are preferably administered locally within the inner ear, optionally by trans-tympanic injection.

In yet another embodiment is provided an improved method for treatment of cancer in a mammal by administration of a chemotherapeutic compound, the improvement comprises administering a therapeutically effective amount of a composition of the invention to the patient in need of such treatment to reduce or prevent ototoxin-induced hearing impairment associated with the chemotherapeutic drug. In another embodiment the methods of treatment are applied to hearing impairments resulting from the administration of a chemotherapeutic agent to treat its ototoxic side-effect. Ototoxic chemotherapeutic agents amenable to the methods of the invention include, but are not limited to an antineoplastic agent, including cisplatin or cisplatin-like compounds, taxol or taxol-like compounds, and other chemotherapeutic agents believed to cause ototoxin-induced hearing impairments, e.g., vincristine, an antineoplastic drug used to treat hematological malignancies and sarcomas. Cisplatin-like compounds include carboplatin (Paraplatin®), tetraplatin, oxaliplatin, aroplatin and transplatin inter alia. In another embodiment the methods of the invention are applied to hearing impairments resulting from the administration of quinine and its synthetic substitutes, typically used in the treatment of malaria, to treat its ototoxic side-effect. In another embodiment the methods of the invention are applied to hearing impairments resulting from administration of a diuretic. Diuretics, particularly "loop" diuretics, i.e. those that act primarily in the Loop of Henle, are candidate ototoxins. Illustrative examples, not limiting to the invention method, include furosemide, ethacrylic acid, and mercurials. Diuretics are typically used to prevent or eliminate edema. Diuretics are also used in nonedematous states for example hypertension, hypercalcemia, idiopathic hypercalciuria, and nephrogenic diabetes insipidus.

In another embodiment, the methods of the invention are applied to treating or preventing the incidence or severity of pressure sores. The methods and compositions involve administering to a mammal in need of such treatment a prophylactically or therapeutically effective amount of one or more compounds which down-regulate expression of the RTP801 gene, particularly novel small interfering RNAs (siRNAs). The compounds which treat or prevent the incidence or severity of pressure sores, particularly the novel siRNAs are preferably administered locally within the damaged area. The methods and compositions of the present invention are effective in the treatment and prevention of pressure sores or pressure ulcers developed when sustained pressure (usually from a bed or wheelchair) cuts off circulation to vulnerable parts of the body. The methods and compositions are effective in patients with diminished or absent sensation or who are debilitated, emaciated, paralyzed, or long bedridden. The compositions of the present invention are effective also in improving the healing of pressure sores using the compositions. The compositions may be used at any particular stage in the healing process including the stage before any healing has initiated or even before a specific sore is formed (prophylactic treatment).

Other kinds of wounds to be treated according to the invention include also i) general wounds such as, e.g., surgical, traumatic, infectious, ischemic, thermal, chemical and bullous wounds; ii) wounds specific for the oral cavity such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and iii) wounds on the skin such as, e.g., neoplasm, burns (e.g. chemical, thermal), lesions (bacterial, viral, autoimmunological), bites and surgical incisions.

The methods and compositions of the present invention are also effective in the treatment and prevention of any chronic wounds including inter alia pressure sores, venous ulcers, and diabetic ulcers. In all these chronic wound types, the underlying precipitating event is a period of ischemia followed by a period of reperfusion. These ischemia-reperfusion events are usually repetitive, which means the deleterious effects of ischemia-reperfusion are potentiated and eventually sufficient to cause ulceration. For both pressure sores and diabetic foot ulcers, the ischemic event is the result of prolonged pressure sufficient to prevent tissue perfusion, and when the pressure is finally relieved, the reperfusion injury occurs. The present compositions are effective in inhibiting the damage caused by ischemia-reperfusion in chronic wounds.

The present compositions are also effective in other conditions associated with ischemia-reperfusion such as but not limited to: organ transplantation, intestinal and colon anastamoses, operations on large blood vessels, stitching detached limbs, balloon angioplasty or any cardiac surgery, stroke or brain trauma, limb transplantation, pulmonary hypertension, hypoxemia, and noncardiogenic pulmonary edema, acute renal failure, acute glaucoma, diabetic retinopathy, hypertensive retinopathy, retinal vascular occlusion, cochlear ischemia, microvascular surgery and ischemic lesions in scleroderma.

The methods and compositions of the present invention are also effective in the treatment of acoustic trauma or mechanical trauma, preferably acoustic or mechanical trauma that leads to inner ear hair cell loss. Acoustic trauma to be treated in the present invention may be caused by a single exposure to an extremely loud sound, or following long-term exposure to everyday loud sounds above about 85 decibels. Mechanical inner ear trauma to be treated in the present invention is for example the inner ear trauma following an operation of electronic device insertion in the inner ear. The compositions of the present invention prevent or minimize the damage to inner ear hair cells associated with the operation. The compounds which reduce or prevent the ototoxin-induced hearing impairment, particularly the novel siRNAs are preferably administered locally within the inner ear, optionally by trans-tympanic injection.

Additionally, the compound of the present invention can be used to treat any condition in which ischemia is involved, optionally ischemia-reperfusion. Such condition include ischmia or ischemia-reperfusion resulting from an angioplasty, cardiac surgery or thrombolysis; organ transplant; as a result of plastic surgery; during severe compartment syndrome; during re-attachment of severed limbs; as a result of multiorgan failure syndrome; in the brain as a result of stroke or brain trauma; in connection with chronic wounds such as pressure sores, venous ulcers and diabetic ulcers; during skeletal muscle ischemia or limb transplantation; as a result of mesenteric ischemia or acute ischemic bowel disease; respiratory failure as a result of lower torso ischemia, leading to pulmonary hypertension, hypoxemia, and noncardiogenic pulmonary edema; acute renal, failure as observed after renal transplantation, major surgery, trauma, and septic as well as hemorrhagic shock; sepsis; retinal ischemia occurring as a result of acute vascular occlusion, leading to loss of vision in a number of ocular diseases such as acute glaucoma, diabetic retinopathy, hypertensive retinopathy, and retinal vascular occlusion; cochlear ischemia; flap failure in microvascular surgery for head and neck defects; Raynaud's phenomenon and the associated digital ischemic lesions in scleroderma; spinal cord injury; vascular surgery; traumatic rhabdomyolysis (crush syndrome); and myoglobinuria. Further, ischemia/reperfusion may be involved in the following conditions: hypertension, hypertensive cerebral vascular disease, rupture of aneurysm, a constriction or obstruction of a blood vessel—as occurs in the case of a thrombus or embolus, angioma, blood dyscrasias, any form of compromised cardiac function including cardiac arrest or failure, systemic hypotension, cardiac arrest, cardiogenic shock, septic shock, spinal cord trauma, head trauma, seizure, bleeding from a tumor, and diseases such as stroke, Parkinson's disease, epilepsy, depression, ALS, Alzheimer's disease, Huntington's disease and any other disease-induced dementia (such as HIV induced dementia for example). Additionally, an ischemic episode may be caused by a mechanical injury to the Central Nervous System, such as results from a blow to the head or spine. Trauma can involve a tissue insult such as an abrasion, incision, contusion, puncture, compression, etc., such as can arise from traumatic contact of a foreign object with any locus of or appurtenant to the head, neck, or vertebral column. Other forms of traumatic injury can arise from constriction or compression of CNS tissue by an inappropriate accumulation of fluid (for example, a blockade or dysfunction of normal cerebrospinal fluid or vitreous humor fluid production, turnover, or volume regulation, or a subdural or intracamial hematoma or edema). Similarly, traumatic constriction or compression can arise from the presence of a mass of abnormal tissue, such as a metastatic or primary tumor.

"Treating a disease" refers to administering a therapeutic substance effective to ameliorate symptoms associated with a disease, to lessen the severity or cure the disease, or to prevent the disease from occurring. "Treatment" refers to both therapeutic treatment and prophylactic or preventative measures, wherein the object is to prevent or slow down (lessen) a disease or disorder.

A "therapeutically effective dose" refers to an amount of a pharmaceutical compound or composition which is effective to achieve an improvement in a patient or his physiological systems including, but not limited to, improved survival rate, more rapid recovery, or improvement or elimination of symptoms, and other indicators as are selected as appropriate determining measures by those skilled in the art.

The methods of treating the diseases disclosed herein and included in the present invention may include administering an RTP801 inhibitor in conjunction with an additional RTP801 inhibitor, a substance which improves the pharmacological properties of the active ingredient as detailed below, or an additional compound known to be effective in the treatment of the disease to be treated, such as macular degeneration, COPD, ARF, DR, cisplatin or acoustic trauma-induced deafness, inter alia. By "in conjunction with" is meant prior to, simultaneously or subsequent to. Further detail on exemplary conjoined therapies is given below.

In another embodiment, the present invention provides for the use of a therapeutically effective dose of an RTP801 inhibitor for the preparation of a medicament for promoting recovery in a patient suffering from macular degeneration, COPD, ARF, DR, cisplatin or acoustic trauma-induced deafness or any other eye disease, microvascular or respiratory condition or hearing disorder as detailed above, and the use of a therapeutically effective dose of an RTP801 inhibitor for the preparation of a medicament for treating said diseases and conditions. In this embodiment, the RTP801 inhibitor may comprise a polynucleotide which comprises consecutive nucleotides having a sequence which comprises an antisense sequence to the sequence set forth in FIG. 1 (SEQ ID No: 1). Additionally, the RTP801 inhibitor may be an expression vector comprising a polynucleotide having a sequence which is an antisense sequence to the sequence set forth in FIG. 1 (SEQ ID No:1). The RTP801 inhibitor according to said uses may also be an antibody, such as a neutralizing antibody which specifically binds to an epitope present within a polypeptide which comprises consecutive amino acids, the sequence of which is set forth in FIG. 2 (SEQ ID No:2). Additionally, the RTP801 inhibitor may be an RNA molecule which targets the RTP801 gene mRNA optionally an siRNA, optionally an siRNA comprising consecutive nucleotides having a sequence identical to any sequence set forth in Tables A-D (SEQ ID NOs:3-536) and in particular, siRNA Nos: 14, 22, 23, 25, 27, 39, 41, 42, 49 and 50 of Table A or siRNA Nos: 257, 260-262, and 264-268 of Table D, or a ribozyme.

Thus, according to the information disclosed herein, the RTP801 inhibitor to be used with any of the methods disclosed herein, in any of the uses disclosed herein and in any of the pharmaceutical compositions disclosed herein, may be selected from the group consisting of an siRNA, a vector comprising an siRNA, a vector which expresses an siRNA and any molecule which is endogenously processed into an siRNA. As detailed herein, said siRNA is preferably an siRNA comprising consecutive nucleotides having a sequence identical to any sequence set forth in Tables A-D (SEQ ID NOs:3-536) and in particular, siRNA Nos: 14, 22, 23, 25, 27, 39, 41, 42, 49 and 50 of Table A or siRNA Nos: 257, 260-262, and 264-268 of Table D.

"Respiratory disorder" refers to conditions, diseases or syndromes of the respiratory system including but not limited to pulmonary disorders of all types including chronic obstructive pulmonary disease (COPD), emphysema, chronic bronchitis, asthma and lung cancer, inter alia. Emphysema and chronic bronchitis may occur as part of COPD or independently.

"Microvascular disorder" refers to any condition that affects microscopic capillaries and lymphatics, in particular vasospastic diseases, vasculitic diseases and lymphatic occlusive diseases. Examples of microvascular disorders include, inter alia: eye disorders such as Amaurosis Fugax (embolic or secondary to SLE), apla syndrome, Prot CS and ATIII deficiency, microvascular pathologies caused by IV drug use, dysproteinemia, temporal arteritis, anterior ischemic optic neuropathy, optic neuritis (primary or secondary to autoimmune diseases), glaucoma, von hippel lindau syndrome, corneal disease, corneal transplant rejection cataracts, Eales' disease, frosted branch angiitis, encircling buckling operation, uveitis including pars planitis, choroidal melanoma, choroidal hemangioma, optic nerve aplasia; retinal conditions such as retinal artery occlusion, retinal vein occlusion, retinopathy of prematurity, HIV retinopathy, Purtscher retinopathy, retinopathy of systemic vasculitis and autoimmune diseases, diabetic retinopathy, hypertensive retinopathy, radiation retinopathy, branch retinal artery or vein occlusion, idiopathic retinal vasculitis, aneurysms, neuroretinitis, retinal embolization, acute retinal necrosis, birdshot retinochoroidopathy, long-standing retinal detachment; systemic conditions such as diabetes mellitus, diabetic retinopathy (DR), diabetes-related microvascular pathologies (as detailed herein), hyperviscosity syndromes, aortic arch syndromes and ocular ischemic syndromes, carotid-cavernous fistula, multiple sclerosis, systemic lupus erythematosus, arteriolitis with SS-A autoantibody, acute multifocal hemorrhagic vasculitis, vasculitis resulting from infection, vasculitis resulting from Behçet's disease, sarcoidosis, coagulopathies, neuropathies, nephropathies, microvascular diseases of the kidney, and ischemic microvascular conditions, inter alia.

Microvascular disorders may comprise a neovascular element. The term "neovascular disorder" refers to those conditions where the formation of blood vessels (neovascularization) is harmful to the patient. Examples of ocular neovascularization include: retinal diseases (diabetic retinopathy, diabetic Macular Edema, chronic glaucoma, retinal detachment, and sickle cell retinopathy); rubeosis iritis; proliferative vitreo-retinopathy, inflammatory diseases; chronic uveitis; neoplasms (retinoblastoma, pseudoglioma and melanoma); Fuchs' heterochromic iridocyclitis; neovascular glaucoma; corneal neovascularization (inflammatory, transplantation and developmental hypoplasia of the iris); neovascularization following a combined vitrectomy and lensectomy; vascular diseases (retinal ischemia, choroidal vascular insufficiency, choroidal thrombosis and carotid artery ischemia); neovascularization of the optic nerve; and neovascularization due to penetration of the eye or contusive ocular injury. All these neovascular conditions may be treated using the compounds and pharmaceutical compositions of the present invention.

"Eye disease" refers to refers to conditions, diseases or syndromes of the eye including but not limited to any conditions involving choroidal neovascularization (CNV), wet and dry AMD, ocular histoplasmosis syndrome, angiod streaks, ruptures in Bruch's membrane, myopic degeneration, ocular tumors, retinal degenerative diseases and retinal vein occlusion (RVO). Some conditions disclosed herein, such as DR, which may be treated according to the methods of the present invention have been regarded as either a microvascular disorder and an eye disease, or both, under the definitions presented herein.

Hearing impairments relevant to the invention may be due to end-organ lesions involving inner ear hair cells, e.g., acoustic trauma, viral endolymphatic labyrinthitis, Meniere's disease. Hearing impairments include tinnitus, which is a perception of sound in the absence of an acoustic stimulus, and may be intermittent or continuous, wherein there is diagnosed a sensorineural loss. Hearing loss may be due to bacterial or viral infection, such as in herpes zoster oticus, purulent labyrinthitis arising from acute otitis media, purulent meningitis, chronic otitis media, sudden deafness including that of viral origin, e.g., viral endolymphatic labyrinthitis caused by viruses including mumps, measles, influenza, chicken pox, mononucleosis and adenoviruses. The hearing loss can be congenital, such as that caused by rubella, anoxia during birth, bleeding into the inner ear due to trauma during delivery, ototoxic drugs administered to the mother, erythroblastosis fetalis, and hereditary conditions including Waardenburg's syndrome and Hurler's syndrome. The hearing loss can be noise-induced, generally due to a noise greater than about 85 decibels (db) that damages the inner ear. Preferably, the hearing loss is caused by acoustic trauma or an ototoxic drug that effects the auditory portion of the inner ear, particularly inner ear hair cells. Incorporated herein by reference are Chapters 196, 197, 198 and 199 of The Merck Manual of Diagnosis and Therapy, 14th Edition, (1982), Merck Sharp & Dome Research Laboratories, N.J. and corresponding chapters in the most recent 16th edition, including Chapters 207 and 210) relating to description and diagnosis of hearing and balance impairments.

Hearing disorders or impairments (or balance impairment) to be treated or prevented in the context of the present invention are preferably, without being bound by theory, ototoxin- or trauma-induced apoptotic damage to inner ear hair cells. Those in need of treatment include those already experiencing a hearing impairment, those prone to having the impairment, and those in which the impairment is to be prevented. Without being bound by theory, the hearing impairments may be due to apoptotic inner ear hair cell damage or loss, wherein the damage or loss is caused by infection, mechanical injury, loud sound, aging, or chemical-induced ototoxicity. Ototoxins include therapeutic drugs including antineoplastic agents, salicylates, quinines, and aminoglycoside antibiotics, contaminants in foods or medicinals, and environmental or industrial pollutants. Typically, treatment is performed to prevent or reduce ototoxicity or acoustic trauma, especially resulting from or expected to result from administration of therapeutic drugs or exposure to acoustic-trauma including environments. Preferably a therapeutically effective composition is given immediately after the exposure to prevent or reduce the ototoxic effect or traumatic effect. More preferably, treatment is provided prophylactically, either by administration of the composition prior to or concomitantly with the ototoxic pharmaceutical or the exposure to the ototoxin or to the acoustic-trauma inducing environment.

The hearing impairment may be induced by chemotherapy. In more detail, hearing impairment may be caused by chemotherapeutic agents such as etoposide, 5-FU (5-fluorouracil), cis-platinum, doxorubicin, a vinca alkaloid, vincristine, vinblastine, vinorelbine, taxol, cyclophosphamide, Ifosfamide, chlorambucil, busulfan, mechlorethamine, mitomycin, dacarbazine, carboplatinum, thiotepa, daunorubicin, idarubicin, mitoxantrone, bleomycin, esperamicin A1, dactinomycin, plicamycin, carmustine, lomustine, tauromustine, streptozocin, melphalan, dactinomycin, procarbazine, dexamethasone, prednisone, 2-chlorodeoxyadenosine, cytarabine, docetaxel, fludarabine, gemcitabine, herceptin, hydroxyurea, irinotecan, methotrexate, oxaliplatin, rituxin, semustine, epirubicin, etoposide, tomudex and topotecan, or a chemical analog of one of these chemotherapeutic agents. The chemotherapeutic agents most likely to cause hearing impairment are cis-platinum (cisplatin) and cisplatin-like compounds By "ototoxin" in the context of the present invention is meant a substance that through its chemical action injures, impairs or inhibits the activity of the sound receptors of the nervous system related to hearing, which in turn impairs hearing (and/or balance). In the context of the present invention, ototoxicity includes a deleterious effect on the inner ear hair cells. Ototoxic agents that cause hearing impairments include, but are not limited to, neoplastic agents such as vincristine, vinblastine, cisplatin and cisplatin-like compounds, taxol and taxol-like compounds, dideoxy-compounds, e.g., dideoxyinosine; alcohol; metals; industrial toxins involved in occupational or environmental exposure; contaminants of food or medicinals; and over-doses of vitamins or therapeutic drugs, e.g., antibiotics such as penicillin or chloramphenicol, and megadoses of vitamins A, D, or B6, salicylates, quinines and loop diuretics. By "exposure to an ototoxic agent" is meant that the ototoxic agent is made available to, or comes into contact with, a mammal. Exposure to an ototoxic agent can occur by direct administration, e.g., by ingestion or administration of a food, medicinal, or therapeutic agent, e.g., a chemotherapeutic agent, by accidental contamination, or by environmental exposure, e.g., aerial or aqueous exposure.

"RTP801 gene" refers to the RTP801 coding sequence open reading frame, as shown in FIG. 1 (SEQ ID NO:1), or any homologous sequence thereof preferably having at least 70% identity, more preferable 80% identity, even more preferably 90% or 95% identity. This encompasses any sequences derived from SEQ ID NO:1 which have undergone mutations, alterations or modifications as described herein. Thus, in a preferred embodiment RTP801 is encoded by a nucleic acid sequence according to SEQ. ID. NO. I. It is also within the present invention that the nucleic acids according to the present invention are only complementary and identical, respectively, to a part of the nucleic acid coding for RTP801 as, preferably, the first stretch and first strand is typically shorter than the nucleic acid according to the present invention. It is also to be acknowledged that based on the amino acid sequence of RTP801 any nucleic acid sequence coding for such amino acid sequence can be perceived by the one skilled in the art based on the genetic code. However, due to the assumed mode of action of the nucleic acids according to the present invention, it is most preferred that the nucleic acid coding for RTP801, preferably the mRNA thereof, is the one present in the organism, tissue and/or cell, respectively, where the expression of RTP801 is to be reduced.

"RTP801 polypeptide" refers to the polypeptide of the RTP801 gene, and is understood to include, for the purposes of the instant invention, the terms "RTP779", "REDD1", "Ddit4", "FLJ20500", "Dig2", and "PRF1", derived from any organism, optionally man, splice variants and fragments thereof retaining biological activity, and homologs thereof, preferably having at least 70%, more preferably at least 80%, even more preferably at least 90% or 95% homology thereto. In addition, this term is understood to encompass polypeptides resulting from minor alterations in the RTP801 coding sequence, such as, inter alia, point mutations, substitutions, deletions and insertions which may cause a difference in a few amino acids between the resultant polypeptide and the naturally occurring RTP801. Polypeptides encoded by nucleic acid sequences which bind to the RTP801 coding sequence or genomic sequence under conditions of highly stringent hybridization, which are well-known in the art (for example Ausubel et al., Current Protocols in Molecular Biology, John Wiley and Sons, Baltimore, Md. (1988), updated in 1995 and 1998), are also encompassed by this term. Chemically modified RTP801 or chemically modified fragments of RTP801 are also included in the term, so long as the biological activity is retained. RTP801 preferably has or comprises an amino acid sequence according to SEQ. ID. NO. 2. It is acknowledged that there might be differences in the amino acid sequence among various tissues of an organism and among different organisms of one species or among different species to which the nucleic acid according to the present invention can be applied in various embodiments of the present invention. However, based on the technical teaching provided herein, the respective sequence can be taken into consideration accordingly when designing any of the nucleic acids according to the present invention. Particular fragments of RTP801 include amino acids 1-50, 51-100, 101-150, 151-200 and 201-232 of the sequence shown in FIG. 2. Further particular fragments of RTP801 include amino acids 25-74, 75-124, 125-174, 175-224 and 225-232 of the sequence shown in FIG. 2.

RTP801 as used herein is a protein described, among others, in WO 99/09046. RTP801 which is also referred to as RTP801, has been described as a transcriptional target of HIF-1α by Shoshani T et al. (Shoshani et al., 2002, Mol Cell Biol, 22, 2283-93). Furthermore the study by Ellisen et al. (Ellisen et al., Mol Cell, 10, 995-1005) has identified RTP801 as a p53-dependent DNA damage response gene and as a p63-dependent gene involved in epithelial differentiation. Also, RTP801 mirrors the tissue-specific pattern of the p53 family member p63, is effective similar to or in addition to TP 63, is an inhibitor to in vitro differentiation, and is involved in the regulation of reactive oxygen species. Apart from that, RTP801 is responsive to hypoxia-responsive transcription factor hypoxia-inducible factor 1 (HIF-1) and is typically up-regulated during hypoxia both in vitro and in vivo in an animal model of ischemic stroke. RTP801 appears to function in the regulation of reactive oxygen species (ROS) and ROS levels and reduced sensitivity to oxidative stress are both increased following ectopic expression RTP801 (Ellisen et al. 2002, supra; Soshani et al. 2002, supra). Preferably, RTP801 is a biologically active RTP801 protein which preferably exhibits at least one of those characteristics, preferable two or more and most preferably each and any of these characteristics.

Without being bound by theory, RTP801 being a stress-inducible protein (responding to hypoxia, oxidative stress, termal stress, ER stress) is a factor acting in fine-tuning of cell response to energy disbalance. As such, it is a target suitable for treatment of any disease where cells should be rescued from apoptosis due to stressful conditions (e.g. diseases accompanied by death of normal cells) or where cells, which are adapted to stressful conditions due to changes in RTP801 expression (e.g. cancer cells), should be killed. In the latter case, RTP801 may be viewed as a survival factor for cancer cells and its inhibitors may treat cancer as a monotherapy or as sensitising drugs in combination with chemotherapy or radiotherapy.

The term "polynucleotide" refers to any molecule composed of DNA nucleotides, RNA nucleotides or a combination of both types, i.e. that comprises two or more of the bases guanidine, cytosine, thymidine, adenine, uracil or inosine, inter alia. A polynucleotide may include natural nucleotides, chemically modified nucleotides and synthetic nucleotides, or chemical analogs thereof. The term includes "oligonucleotides" and encompasses "nucleic acids".

The term "amino acid" refers to a molecule which consists of any one of the 20 naturally occurring amino acids, amino acids which have been chemically modified (see below), or synthetic amino acids.

The term "polypeptide" refers to a molecule composed of two or more amino acids residues. The term includes peptides, polypeptides, proteins and peptidomimetics.

A "peptidomimetic" is a compound containing non-peptidic structural elements that is capable of mimicking the biological action(s) of a natural parent peptide. Some of the classical peptide characteristics such as enzymatically scissile peptidic bonds are normally not present in a peptidomimetic.

By the term "dominant negative peptide" is meant a polypeptide encoded by a cDNA fragment that encodes for a part of a protein (see Herskowitz I.: *Functional inactivation of genes by dominant negative mutations. Nature.* 1987 Sep. 17-23; 329(6136):219-22. Review; Roninson I B et al., *Genetic suppressor elements: new tools for molecular oncology—thirteenth Cornelius P. Rhoads Memorial Award Lecture. Cancer Res.* 1995 Sep. 15; 55(18):4023). This peptide can have a different function from the protein from which it was derived. It can interact with the full protein and inhibit its activity or it can interact with other proteins and inhibit their activity in response to the full-length (parent) protein. Dominant negative means that the peptide is able to overcome the natural parent protein and inhibit its activity to give the cell a different characteristic, such as resistance or sensitization to death or any cellular phenotype of interest. For therapeutic intervention the peptide itself may be delivered as the active ingredient of a pharmaceutical composition, or the cDNA can be delivered to the cell utilizing known methods.

Preparation of Peptides and Polypeptides

Polypeptides may be produced via several methods, for example:

1) Synthetically:

Synthetic polypeptides can be made using a commercially available machine, using the known sequence of RTP801 or a portion thereof.

2) Recombinant Methods:

A preferred method of making the RTP801 polypeptides of fragments thereof is to clone a polynucleotide comprising the cDNA of the RTP801 gene into an expression vector and culture the cell harboring the vector so as to express the encoded polypeptide, and then purify the resulting polypeptide, all performed using methods known in the art as described in, for example, Marshak et al., *"Strategies for Protein Purification and Characterization. A laboratory course manual."* CSHL Press (1996). (in addition, see *Bibl Haematol.* 1965; 23:1165-74 *Appl Microbiol.* 1967 July; 15(4):851-6; *Can J. Biochem.* 1968 May; 46(5):441-4; *Biochemistry.* 1968 July; 7(7):2574-80; *Arch Biochem Biophys.* 1968 Sep. 10; 126(3):746-72; *Biochem Biophys Res Commun.* 1970 Feb. 20; 38(4):825-30).).

The expression vector can include a promoter for controlling transcription of the heterologous material and can be either a constitutive or inducible promoter to allow selective transcription. Enhancers that can be required to obtain necessary transcription levels can optionally be included. The expression vehicle can also include a selection gene.

Vectors can be introduced into cells or tissues by any one of a variety of methods known within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Vega et al., *Gene Targeting*, CRC Press, Ann Arbor, Mich. (1995), *Vectors: A Survey of Molecular Cloning Vectors and Their Uses*, Butterworths, Boston Mass. (1988) and Gilboa et al. (1986).

3) Purification from Natural Sources:

RTP801 polypeptide, or naturally occurring fragments thereof, can be purified from natural sources (such as tissues) using many methods known to one of ordinary skill in the art, such as for example: immuno-precipitation with anti-RTP801 antibody, or matrix-bound affinity chromatography with any molecule known to bind RTP801.

Protein purification is practiced as is known in the art as described in, for example, Marshak et al., *"Strategies for Protein Purification and Characterization. A laboratory course manual."* CSHL Press (1996).

By "biological effect of RTP801" or "RTP801 biological activity" is meant the effect of RTP801 in respiratory disorders, which may be direct or indirect, and includes, without being bound by theory, the effect of RTP801 on apoptosis of alveolar cells induced by hypoxic or hyperoxic conditions. The indirect effect includes, but is not limited to, RTP801 binding to or having an effect on one of several molecules, which are involved in a signal transduction cascade resulting in apoptosis.

"Apoptosis" refers to a physiological type of cell death which results from activation of some cellular mechanisms, i.e. death that is controlled by the machinery of the cell. Apoptosis may, for example, be the result of activation of the cell machinery by an external trigger, e.g. a cytokine or anti-FAS antibody, which leads to cell death or by an internal signal. The term "programmed cell death" may also be used interchangeably with "apoptosis".

"Apoptosis-related disease" refers to a disease whose etiology is related either wholly or partially to the process of apoptosis. The disease may be caused either by a malfunction of the apoptotic process (such as in cancer or an autoimmune disease) or by overactivity of the apoptotic process (such as in certain neurodegenerative diseases). Many diseases in which RTP801 is involved are apoptosis-related diseases. For example, apoptosis is a significant mechanism in dry AMD, whereby slow atrophy of photoreceptor and pigment epithelium cells, primarily in the central (macular) region of retina takes place. Neuroretinal apoptosis is also a significant mechanism in diabetic retinopathy.

An "inhibitor" is a compound which is capable of inhibiting the activity of a gene or the product of such gene to an extent sufficient to achieve a desired biological or physiological effect. An "RTP801 inhibitor" is a compound which is capable of inhibiting the activity of the RTP801 gene or RTP801 gene product, particularly the human RTP801 gene or gene product. Such inhibitors include substances that affect the transcription or translation of the gene as well as substances that affect the activity of the gene product. An RTP801 inhibitor may also be an inhibitor of the RTP801 promoter. Examples of such inhibitors may include, inter alia: polynucleotides such as AS fragments, siRNA, or vectors comprising them; polypeptides such as dominant negatives, antibodies, and enzymes; catalytic RNAs such as ribozymes; and chemical molecules with a low molecular weight e.g. a molecular weight below 2000 daltons. Specific RTP801 inhibitors are given below.

"Expression vector" refers to a vector that has the ability to incorporate and express heterologous DNA fragments in a foreign cell. Many prokaryotic and eukaryotic expression vectors are known and/or commercially available. Selection of appropriate expression vectors is within the knowledge of those having skill in the art.

The term "antibody" refers to IgG, IgM, IgD, IgA, and IgE antibody, inter alia. The definition includes polyclonal antibodies or monoclonal antibodies. This term refers to whole antibodies or fragments of antibodies comprising an antigen-binding domain, e.g. antibodies without the Fc portion, single chain antibodies, miniantibodies, fragments consisting of essentially only the variable, antigen-binding domain of the antibody, etc. The term "antibody" may also refer to antibodies against polynucleotide sequences obtained by cDNA vaccination. The term also encompasses antibody fragments which retain the ability to selectively bind with their antigen or receptor and are exemplified as follows, inter alia:

(1) Fab, the fragment which contains a monovalent antigen-binding fragment of an antibody molecule which can be produced by digestion of whole antibody with the enzyme papain to yield a light chain and a portion of the heavy chain;

(2) (Fab')$_2$, the fragment of the antibody that can be obtained by treating whole antibody with the enzyme pepsin without subsequent reduction; F(ab'$_2$) is a dimer of two Fab fragments held together by two disulfide bonds;

(3) Fv, defined as a genetically engineered fragment containing the variable region of the light chain and the variable region of the heavy chain expressed as two chains; and (4) Single chain antibody (SCA), defined as a genetically engineered molecule containing the variable region of the light chain and the variable region of the heavy chain linked by a suitable polypeptide linker as a genetically fused single chain molecule.

Minibodies and Microbodies are also included in this term. Microbodies are very small (typically about 28-45 amino acids) proteins with pseudo-knot structures, which are highly selective and stable. Any of the applications and novel compounds disclosed herein which include antibodies may therefore include instead a minibody or microbody as the antibody portion of the molecule.

By the term "epitope" as used in this invention is meant an antigenic determinant on an antigen to which the antibody binds. Epitopic determinants usually consist of chemically active surface groupings of molecules such as amino acids or sugar side chains and usually have specific three-dimensional structural characteristics, as well as specific charge characteristics.

Preparation of Anti-RTP801 Antibodies

Antibodies which bind to RTP801 or a fragment derived therefrom may be prepared using an intact polypeptide or fragments containing smaller polypeptides as the immunizing antigen. For example, it may be desirable to produce antibodies that specifically bind to the N- or C-terminal or any other suitable domains of the RTP801. The polypeptide used to immunize an animal can be derived from translated cDNA or chemical synthesis and can be conjugated to a carrier protein, if desired. Such commonly used carriers which are chemically coupled to the polypeptide include keyhole limpet hemocyanin (KLH), thyroglobulin, bovine serum albumin (BSA) and tetanus toxoid. The coupled polypeptide is then used to immunize the animal.

If desired, polyclonal or monoclonal antibodies can be further purified, for example by binding to and elution from a matrix to which the polypeptide or a peptide to which the antibodies were raised is bound. Those skilled in the art know various techniques common in immunology for purification and/or concentration of polyclonal as well as monoclonal antibodies (Coligan et al, Unit 9, *Current Protocols in Immunology*, Wiley Interscience, 1994).

Methods for making antibodies of all types, including fragments, are known in the art (See for example, Harlow and Lane, *Antibodies: A Laboratory Manual*, Cold Spring Harbor Laboratory, New York (1988)). Methods of immunization, including all necessary steps of preparing the immunogen in a suitable adjuvant, determining antibody binding, isolation of antibodies, methods for obtaining monoclonal antibodies, and humanization of monoclonal antibodies are all known to the skilled artisan The antibodies may be humanized antibodies or human antibodies. Antibodies can be humanized using a variety of techniques known in the art including CDR-grafting (EP239, 400: PCT publication WO.91/09967; U.S. Pat. Nos. 5,225, 539; 5,530,101; and 5,585,089, veneering or resurfacing (EP 592,106; EP 519,596; Padlan, Molecular Immunology 28(415):489-498 (1991); Studnicka et al., Protein Engineering 7(6):805-814 (1994); Roguska et al., PNAS 91:969-973 (1994)), and chain shuffling (U.S. Pat. No. 5,565,332).

The monoclonal antibodies as defined include antibodies derived from one species (such as murine, rabbit, goat, rat, human, etc.) as well as antibodies derived from two (or more) species, such as chimeric and humanized antibodies.

Completely human antibodies are particularly desirable for therapeutic treatment of human patients. Human antibodies can be made by a variety of methods known in the art including phage display methods using antibody libraries derived from human immunoglobulin sequences. See also U.S. Pat. Nos. 4,444,887 and 4,716,111; and PCT publications WO 98/46645, WO 98/50433, WO 98/24893, WO 98/16654, WO 96/34096, WO 96/33735, and WO 91/10741, each of which is incorporated herein by reference in its entirety.

Additional information regarding all types of antibodies, including humanized antibodies, human antibodies and antibody fragments can be found in WO 01/05998, which is incorporated herein by reference in its entirety.

Neutralizing antibodies can be prepared by the methods discussed above, possibly with an additional step of screening for neutralizing activity by, for example, a survival assay.

The terms "chemical compound", "small molecule", "chemical molecule" "small chemical molecule" and "small chemical compound" are used interchangeably herein and are understood to refer to chemical moieties of any particular type which may be synthetically produced or obtained from natural sources and usually have a molecular weight of less than 2000 daltons, less than 1000 daltons or even less than 600 daltons.

The present invention also relates to functional nucleic acids comprising a double-stranded structure, their use for the manufacture of a medicament, a pharmaceutical composition comprising such functional nucleic acids and a method for the treatment of a patient.

Hypoxia has been recognised as a key element in the pathomechanism of quite a number of diseases such as stroke, emphysema and infarct which are associated with sub-optimum oxygen availability and tissue damaging responses to the hypoxia conditions. In fast-growing tissues, including tumor, a sub-optimum oxygen availability is compensated by undesired neo-angiogenesis. Therefore, at least in case of cancer diseases, the growth of vasculature is undesired.

In view of this, the inhibition of angiogenesis and vascular growth, respectively, is subject to intense research. Already today some compounds are available which inhibit undesired angiogenesis and vascular growth. Some of the more prominent compounds are those inhibiting VEGF and the VEGF receptor. In both cases, the effect of VEGF is avoided by either blocking VEGF as such, for example by using an antibody directed against VEGF such as pursued by Genentech's AVASTIN (monoclonal AB specific for VEGF) (Ferrara N.; Endocr Rev. 2004 August; 25(4):581-611), or by blocking the corresponding receptor, i.e. the VEGF receptor (Traxler P; Cancer Res. 2004 July 15; 64(14):4931-41; or Stadler W M et al., Clin Cancer Res. 2004 May 15; 10(10):3365-70).

As, however, angiogenesis and the growth of vasculature is a very basic and vital process in any animal and human being, the effect of this kind of compound has to be focused at the particular site where angiogenesis and vascular growth is actually undesired which renders appropriate targeting or delivery a critical issue in connection with this kind of therapeutic approach.

It is thus an objective of the present invention to provide further means for the treatment of diseases involving undesired growth of vasculature and angiogenesis, respectively.

By "small interfering RNA" (siRNA) is meant an RNA molecule which decreases or silences (prevents) the expression of a gene/mRNA of its endogenous cellular counterpart. The term is understood to encompass "RNA interference" (RNAi). RNA interference (RNAi) refers to the process of sequence-specific post transcriptional gene silencing in mammals mediated by small interfering RNAs (siRNAs) (Fire et al, 1998, Nature 391, 806). The corresponding process in plants is commonly referred to as specific post transcriptional gene silencing or RNA silencing and is also referred to as quelling in fungi. The RNA interference response may feature an endonuclease complex containing an siRNA, commonly referred to as an RNA-induced silencing complex (RISC), which mediates cleavage of single-stranded RNA having sequence complementary to the antisense strand of the siRNA duplex. Cleavage of the target RNA may take place in the middle of the region complementary to the antisense strand of the siRNA duplex (Elbashir at 2001, Genes Dev., 15 188). For recent information on these terms and proposed mechanisms, see Bernstein E., Denli A M., Hannon G J: *The rest is silence*. *RNA*. 2001 November; 7(11):1509-21; and Nishikura K.: *A short primer on RNAi: RNA-directed RNA polymerase acts as a key catalyst*. *Cell*. 2001 November 16; 107(4):415-8. Examples of siRNA molecules which may be used in the present invention are given in Tables A-D.

During recent years, RNAi has emerged as one of the most efficient methods for inactivation of genes (Nature Reviews, 2002, v.3, p. 737-47; Nature, 2002, v.418, p. 244-51). As a method, it is based on the ability of dsRNA species to enter a specific protein complex, where it is then targeted to the complementary cellular RNA and specifically degrades it. In more detail, dsRNAs are digested into short (17-29 bp) inhibitory RNAs (siRNAs) by type III RNAses (DICER, Drosha, etc) (Nature, 2001, v.409, p. 363-6; Nature, 2003, 425, p. 415-9). These fragments and complementary mRNA are recognized by the specific RISC protein complex. The whole process is culminated by endonuclease cleavage of target mRNA (Nature Reviews, 2002, v.3, p. 737-47; Curr Opin Mol. Ther. 2003 June; 5(3):217-24).

For disclosure on how to design and prepare siRNA to known genes see for example Pei & Tuschl *On the Art of Identifying Effective and Specific siRNAs* Nature Methods 3 No. 9 Sep. 2006; Chalk A M, Wahlestedt C, Sonnhammer E L. *Improved and automated prediction of effective siRNA* Biochem. Biophys. Res. Commun. 2004 Jun. 18; 319(1):264-74; Sioud M, Leirdal M., *Potential design rules and enzymatic synthesis of siRNAs*, Methods Mol Biol. 2004; 252:457-69; Levenkova N, Gu Q, Rux J J.: Gene specific siRNA selector Bioinformatics. 2004 Feb. 12; 20(3):430-2. and Ui-Tei K, Naito Y, Takahashi F, Haraguchi T, Ohki-Hamazaki H, Juni A, Ueda R, Saigo K., *Guidelines for the selection of highly effective siRNA sequences for mammalian and chick RNA interference* Nucleic Acids Res. 2004 Feb. 9; 32(3):936-48. See also Liu Y, Braasch D A, Nulf C J, Corey D R. *Efficient and isoform-selective inhibition of cellular gene expression by peptide nucleic acids* Biochemistry, 2004 Feb. 24; 43(7): 1921-7. See also PCT publications WO 2004/015107 (Atugen) and WO 02/44321 (Tuschl et al), and also Chiu Y L, Rana T M. siRNA function in RNAi: a chemical modification analysis, RNA 2003 September; 9(9):1034-48 and U.S. Pat. Nos. 5,898,031 and 6,107,094 (Crooke) for production of modified/more stable siRNAs.

DNA-based vectors capable of generating siRNA within cells have been developed. The method generally involves transcription of short hairpin RNAs that are efficiently processed to form siRNAs within cells. Paddison et al. *PNAS* 2002, 99:1443-1448; Paddison et al. *Genes & Dev* 2002, 16:948-958; Sui et al. PNAS 2002, 8:5515-5520; and Brummelkamp et al. *Science* 2002, 296:550-553. These reports describe methods to generate siRNAs capable of specifically targeting numerous endogenously and exogenously expressed genes.

For delivery of siRNAs, see, for example, Shen et al (FEBS letters 539: 111-114 (2003)), Xia et al., Nature Biotechnology 20: 1006-1010 (2002), Reich et al., Molecular Vision 9: 210-216 (2003), Sorensen et al. (J. Mol. Biol. 327: 761-766 (2003), Lewis et al., Nature Genetics 32: 107-108 (2002) and Simeoni et al., Nucleic Acids Research 31, 11: 2717-2724 (2003). siRNA has recently been successfully used for inhibition in primates; for further details see Tolentino et al., Retina 24(1) February 2004 pp 132-138.

siRNAs of the Present Invention

General Specifications of siRNAs of the Present Invention

Generally, the siRNAs used in the present invention comprise a ribonucleic acid comprising a double stranded structure, whereby the double-stranded structure comprises a first strand and a second strand, whereby the first strand comprises a first stretch of contiguous nucleotides and whereby said first stretch is at least partially complementary to a target nucleic acid, and the second strand comprises a second stretch of contiguous nucleotides and whereby said second stretch is at least partially identical to a target nucleic acid, whereby said first strand and/or said second strand comprises a plurality of groups of modified nucleotides having a modification at the 2'-position whereby within the strand each group of modified nucleotides is flanked on one or both sides by a flanking group of nucleotides whereby the flanking nucleotides forming the flanking group of nucleotides is either an unmodified nucleotide or a nucleotide having a modification different from the modification of the modified nucleotides. Further, said first strand and/or said second strand may comprise said plurality of modified nucleotides and may comprises said plurality of groups of modified nucleotides.

The group of modified nucleotides and/or the group of flanking nucleotides may comprise a number of nucleotides whereby the number is selected from the group comprising one nucleotide to 10 nucleotides. In connection with any ranges specified herein it is to be understood that each range discloses any individual integer between the respective figures used to define the range including said two figures defining said range. In the present case the group thus comprises one nucleotide, two nucleotides, three nucleotides, four nucleotides, five nucleotides, six nucleotides, seven nucleotides, eight nucleotides, nine nucleotides and ten nucleotides.

The pattern of modified nucleotides of said first strand may be the same as the pattern of modified nucleotides of said second strand, and may align with the pattern of said second strand. Additionally, the pattern of said first strand may be shifted by one or more nucleotides relative to the pattern of the second strand.

The modifications discussed above may be selected from the group comprising amino, fluoro, methoxy, alkoxy and alkyl.

The double stranded structure of the siRNA may be blunt ended, on one or both sides. More specifically, the double stranded structure may be blunt ended on the double stranded structure's side which is defined by the 5'-end of the first strand and the 3'-end of the second strand, or the double stranded structure may be blunt ended on the double stranded structure's side which is defined by at the 3'-end of the first strand and the 5'-end of the second strand.

Additionally, at least one of the two strands may have an overhang of at least one nucleotide at the 5'-end; the overhang may consist of at least one deoxyribonucleotide. At least one of the strands may also optionally have an overhang of at least one nucleotide at the 3'-end.

The length of the double-stranded structure of the siRNA is typically from about 17 to 21 and more preferably 18 or 19 bases. Further, the length of said first strand and/or the length of said second strand may independently from each other be selected from the group comprising the ranges of from about 15 to about 23 bases, 17 to 21 bases and 18 or 19 bases.

Additionally, the complementarily between said first strand and the target nucleic acid may be perfect, or the duplex formed between the first strand and the target nucleic acid may comprise at least 15 nucleotides wherein there is one mismatch or two mismatches between said first strand and the target nucleic acid forming said double-stranded structure.

In some cases both the first strand and the second strand each comprise at least one group of modified nucleotides and at least one flanking group of nucleotides, whereby each group of modified nucleotides comprises at least one nucleotide and whereby each flanking group of nucleotides comprising at least one nucleotide with each group of modified nucleotides of the first strand being aligned with a flanking group of nucleotides on the second strand, whereby the most terminal 5' nucleotide of the first strand is a nucleotide of the group of modified nucleotides, and the most terminal 3' nucleotide of the second strand is a nucleotide of the flanking group of nucleotides. Each group of modified nucleotides may consist of a single nucleotide and/or each flanking group of nucleotides may consist of a single nucleotide.

Additionally, it is possible that on the first strand the nucleotide forming the flanking group of nucleotides is an unmodified nucleotide which is arranged in a 3' direction relative to the nucleotide forming the group of modified nucleotides, and on the second strand the nucleotide forming the group of modified nucleotides is a modified nucleotide which is arranged in 5' direction relative to the nucleotide forming the flanking group of nucleotides.

Further the first strand of the siRNA may comprise eight to twelve, preferably nine to eleven, groups of modified nucleotides, and the second strand may comprise seven to eleven, preferably eight to ten, groups of modified nucleotides.

The first strand and the second strand may be linked by a loop structure, which may be comprised of a non-nucleic acid polymer such as, inter alia, polyethylene glycol. Alternatively, the loop structure may be comprised of a nucleic acid.

Further, the 5'-terminus of the first strand of the siRNA may be linked to the 3'-terminus of the second strand, or the 3'-end of the first strand may be linked to the 5'-terminus of the second strand, said linkage being via a nucleic acid linker typically having a length between 10-2000 nucleobases.

Particular Specifications of siRNAs of the Present Invention

The invention provides a compound having the structure (structure A):

$$5'(N)_x\text{—}Z3' \quad \text{(antisense strand)}$$

$$3'Z'\text{—}(N')_y5' \quad \text{(sense strand)}$$

wherein each N and N' is a ribonucleotide which may be modified or unmodified in its sugar residue and $(N)_x$ and $(N')_y$ is oligomer in which each consecutive N or N' is joined to the next N or N' by a covalent bond;

wherein each of x and y is an integer between 19 and 40;

wherein each of Z and Z' may be present or absent, but if present may be dTdT and covalently attached at the 3' terminus of the strand in which it is present;

and wherein the sequence of $(N)_x$ comprises a complementary sequence to cDNA of the RTP801 gene.

In particular, the invention provides the above compound wherein the sequence of $(N)_x$ comprises one or more of the antisense sequences present in Tables A, B C and D, in particular Table D.

In particular, the invention provides the above compound wherein the covalent bond is a phosphodiester bond, wherein x=y, preferably wherein x=y=19, wherein Z and Z' are both absent, wherein at least one ribonucleotide is modified in its sugar residue at the 2' position, wherein the moiety at the 2' position is methoxy(2'-0-methyl) wherein alternating ribonucleotides are modified in both the antisense and the sense strands and wherein the ribonucleotides at the 5' and 3' termini of the antisense strand are modified in their sugar residues, and the ribonucleotides at the 5' and 3' termini of the sense strand are unmodified in their sugar residues.

In particular, the siRNA used in the present invention is an oligoribonucleotide wherein one strand comprises consecutive nucleotides having, from 5' to 3', the sequence set forth in SEQ ID NOS: 3-52 or in SEQ ID NOS: 103-174 or in SEQ ID NOS: 247-295 or in SEQ ID NOS 345-440 (which are sense strands) wherein a plurality of the bases may be modified, preferably by a 2-O-methyl modification, or a homolog thereof wherein in up to 2 of the nucleotides in each terminal region a base is altered.

Further, the present invention provides for a method of treating a patient suffering from a respiratory disorder, an eye disease, a microvascular disorder, a hearing disorder, pressure sores or other bedridden-associated flesh wounds or a spinal cord injury or disease comprising administering to the patient a pharmaceutical composition comprising a compound of the above structure (A) (having any of the specifics mentioned above) in a therapeutically effective amount so as to thereby treat the patient. Additionally, the invention provides for the use of a therapeutically effective amount of the above structure (A) (having any of the specifics mentioned above) for the preparation of a medicament for promoting recovery in a patient suffering from a respiratory disorder, an eye disease, a microvascular disorder, a hearing disorder, pressure sores or other bedridden-associated flesh wounds or spinal cord injury or disease.

An additional aspect of the present invention provides for a pharmaceutical composition comprising a compound of the above structure (A) for the treatment of any of the diseases and conditions mentioned herein.

Further, this aspect provides for a pharmaceutical composition comprising two or more compounds of the above structure (A) for the treatment of any of the diseases and conditions mentioned herein, whereby said two compounds may be physically mixed together in the pharmaceutical composition in amounts which generate equal or otherwise beneficial activity, or may be covalently or non-covalently bound, or joined together by a nucleic acid linker of a length ranging from 2-100, preferably 2-50 or 2-30 nucleotides. Such siRNA molecules are therefore comprised of a double-stranded nucleic acid structure as described herein, whereby two siRNA sequences selected from Tables A-D and preferably from Table A, ID Nos: 14, 22, 23, 25, 27, 39, 41, 42, 49 and 50 or siRNA Nos: 257, 260-262, and 264-268 of Table D are covalently or non-covalently bound or joined by a linker to form a tandem siRNA molecule. Such tandem siRNA molecules comprising two siRNA sequences would typically be of 38-150 nucleotides in length, more preferably 38 or 40-60 nucleotides in length, and longer accordingly if more than two siRNA sequences are included in the tandem molecule. A longer tandem molecule comprised of two or more longer sequences which encode siRNA produced via internal cellular processing, e.g., long dsRNAs, is also envisaged, as is a tandem molecule encoding two or more shRNAs. Such tandem molecules are also considered to be a part of the present invention, and further information concerning them is given below.

Said combined or tandem structures have the advantage that toxicity and/or off-target effects of each siRNA are minimized, while the efficacy is increased.

In particular the siRNA used in the Examples has been such modified such that a 2' O-Me group was present on the first, third, fifth, seventh, ninth, eleventh, thirteenth, fifteenth, seventeenth and nineteenth nucleotide of the antisense strand, whereby the very same modification, i.e. a 2'-O-Me group was present at the second, fourth, sixth, eighth, tenth, twelfth, fourteenth, sixteenth and eighteenth nucleotide of the sense strand. Additionally, it is to be noted that the in case of these particular nucleic acids according to the present invention the first stretch is identical to the first strand and the second stretch is identical to the second strand and these nucleic acids are also blunt ended. The siRNA used was phosphorylated but it is envisaged that an un-phosphorylated version may be simpler to prepare in large scale and said un-phosphorylated REDD14, termed REDD-14NP, was found to be just as biologically active as REDD-14 in a CNV model (see Example 6). The sequence of this siRNA used in the experiments in Examples 6-8 is that of REDD14, i.e., the sequence having internal reference No. 14 (see Table A). The siRNAs used in the experiments in Example 14 are termed 801__1 and 801__4; 801__1 has internal reference number 257 in Table D (SEQ ID NO: 429 [sense] and 525 [antisense]) and 801__4 has internal reference number 260 in Table D (SEQ ID NO: 432 [sense] and 528 [antisense]) (see Table D).

Such sRNAs may also be phosphorylated or un-phosphorylated.

The terminal region of the oligonucleotide refers to bases 1-4 and/or 16-19 in the 19-mer sequences (Tables A B and D below) and to bases 1-4 and/or 18-21 in the 21-mer sequences (Table C below).

Additionally, the siRNAs used in the present invention are oligoribonucleotides wherein one strand comprises consecutive nucleotides having, from 5' to 3', the sequence set forth SEQ ID NOS: 53-102 or SEQ ID NOS: 175-246 or SEQ ID NOS: 296-344 or SEQ ID NOS: 441-536 (antisense strands) or a homolog thereof wherein in up to 2 of the nucleotides in each terminal region a base is altered.

Thus, in particular aspects the oligonucleotide comprises a double-stranded structure, whereby such double-stranded structure comprises a first strand and a second strand, whereby the first strand comprises a first stretch of contiguous nucleotides and the second strand comprises a second stretch of contiguous nucleotides, whereby the first stretch is either complementary or identical to a nucleic acid sequence coding for gene RTP801 and whereby the second stretch is either identical or complementary to a nucleic acid sequence coding for RTP801. Said first stretch comprises at least 14 nucleotides, preferably at least 18 nucleotides and even more preferably 19 nucleotides or even at least 21 nucleotides. In an embodiment the first stretch comprises from about 14 to 40 nucleotides, preferably about 18 to 30 nucleotides, more preferably from about 19 to 27 nucleotides and most preferably from about 19 to 23 nucleotides. In an embodiment the second stretch comprises from about 14 to 40 nucleotides, preferably about 18 to 30 nucleotides, more preferably from about 19 to 27 nucleotides and most preferably from about 19 to 23 nucleotides or even about 19 to 21 nucleotides. In an embodiment the first nucleotide of the first stretch corresponds to a nucleotide of the nucleic acid sequence coding for RTP801, whereby the last nucleotide of the first stretch corresponds to a nucleotide of the nucleic acid sequence coding for RTP801. In an embodiment the first stretch comprises a sequence of at least 14 contiguous nucleotides of an oligonucleotide, whereby such oligonucleotide is selected from the group comprising SEQ. ID. Nos. 3-536, preferably from the group comprising the oligoribonucleotides of having the sequence of any of the serial numbers 14, 22, 23, 25, 27, 39, 41, 42, 49 and 50 in Table A or 260-262, and 264-268 in Table D. Additionally specifications of the siRNA molecules used in the present invention may provide an oligoribonucleotide wherein the dinucleotide dTdT is covalently attached to the 3' terminus, and/or in at least one nucleotide a sugar residue is modified, possibly with a modification comprising a 2'-O-methyl modification. Further, the 2' OH group may be replaced by a group or moiety selected from the group comprising —H—OCH$_3$, —OCH$_2$CH$_3$, —OCH$_2$CH$_2$CH$_3$, —NH$_2$, and F. Further, the preferable compounds of the present invention as disclosed above may be phosphorylated or non-phosphorylated.

Additionally, the siRNA used in the present invention may be an oligoribonucleotide wherein in alternating nucleotides modified sugars are located in both strands. Particularly, the oligoribonucleotide may comprise one of the sense strands wherein the sugar is unmodified in the terminal 5' and 3' nucleotides, or one of the antisense strands wherein the sugar is modified in the terminal 5' and 3' nucleotides.

Additionally, further nucleic acids to be used in the present invention comprise at least 14 contiguous nucleotides of any one of the SEQ. ID. NO. 3 to 536, and more preferably 14 contiguous nucleotide base pairs at any end of the double-stranded structure comprised of the first stretch and second stretch as described above. It will be understood by one skilled in the art that given the potential length of the nucleic acid according to the present invention and particularly of the individual stretches forming such nucleic acid according to the present invention, some shifts relative to the coding sequence of the RTP801 gene as detailed in SEQ ID NO:1 to each side is possible, whereby such shifts can be up to 1, 2, 3, 4, 5 and 6 nucleotides in both directions, and whereby the thus generated double-stranded nucleic acid molecules shall also be within the present invention.

An additional aspect of the present invention concerns a functional nucleic acid comprising a double-stranded structure, whereby such double-stranded structure comprises
a first strand and a second strand, whereby
the first strand comprises a first stretch of contiguous nucleotides and the second strand comprises a second stretch of contiguous nucleotides, whereby
the first stretch is either complementary or identical to a nucleic acid sequence coding for RTP801 and whereby the second stretch is either identical or complementary to a nucleic acid sequence coding for RTP801.

In an embodiment the nucleic acid is down-regulating RTP801, whereby the down-regulation of RTP801 is selected from the group comprising down-regulation of RTP801 function, down-regulation of RTP801 protein and down-regulation of RTP801 mRNA expression.

In an embodiment the first stretch comprises at least 14 nucleotides, preferably at least 18 nucleotides and even more preferably 19 nucleotides.

In an embodiment the first stretch comprises from about 14 to 40 nucleotides, preferably about 18 to 30 nucleotides, more preferably from about 19 to 27 nucleotides and most preferably from about 19 to 23 nucleotides.

In an embodiment the second stretch comprises from about 14 to 40 nucleotides, preferably about 18 to 30 nucleotides, more preferably from about 19 to 27 nucleotides and most preferably from about 19 to 23 nucleotides.

In an embodiment the first nucleotide of the first stretch corresponds to a nucleotide of the nucleic acid sequence coding for RTP801, whereby the last nucleotide of the first stretch corresponds to a nucleotide of the nucleic acid sequence coding for RTP801.

In an embodiment one stretch comprises a sequence of at least 14 contiguous nucleotides of a nucleic acid sequence, whereby such nucleic acid sequence is selected from the sequences disclosed in Tables A-D, preferably from the group comprising SEQ. ID. NOs 53, 66, 67, 72, 73, 74, 75, 76, 77, 91, 92, 93, 94, 96, 101 102, 525, 528, 529, 530, 532, 533, 534, 535 and 536, more preferably selected from the group comprising SEQ. ID. Nos 66, 75, 79, 91, 94, 101, 102, 525 and 528, and most preferably selected from the group comprising SEQ. ID. Nos 66, 74, 75, 79, 525 and 528.

In an embodiment the other stretch comprises a sequence of at least 14 contiguous nucleotides of a nucleic acid sequence, whereby such nucleic acid sequence is selected from the sequences disclosed in Tables A-D, preferably from the group comprising SEQ. ID. NOs. 3, 16, 22, 23, 24, 25, 26, 27, 29, 41, 42, 43, 44, 45, 46, 51 52, 429, 432, 433, 434, 436, 437, 438, 439, and 440, more preferably selected from the group comprising SEQ. ID. Nos 16, 24, 25, 29, 41, 44, 51, and 52, and most preferably selected from the group comprising SEQ. ID. Nos 16, 24, 25 and 29.

In an embodiment
the first stretch has a sequence according to SEQ. ID. NO. 53 and the second stretch has a sequence according to SEQ. ID. NO. 3;
the first stretch has a sequence according to SEQ. ID. NO. 66 and the second stretch has a sequence according to SEQ. ID. NO. 16;
the first stretch has a sequence according to SEQ. ID. NO. 67 and the second stretch has a sequence according to SEQ. ID. NO. 17;
the first stretch has a sequence according to SEQ. ID. NO. 72 and the second stretch has a sequence according to SEQ. ID. NO. 22;
the first stretch has a sequence according to SEQ. ID. NO. 73 and the second stretch has a sequence according to SEQ. ID. NO. 23;
the first stretch has a sequence according to SEQ. ID. NO. 74 and the second stretch has a sequence according to SEQ. ID. NO. 24;
the first stretch has a sequence according to SEQ. ID. NO. 75 and the second stretch has a sequence according to SEQ. ID. NO. 25;
the first stretch has a sequence according to SEQ. ID. NO. 76 and the second stretch has a sequence according to SEQ. ID. NO. 26;
the first stretch has a sequence according to SEQ. ID. NO. 77 and the second stretch has a sequence according to SEQ. ID. NO. 27;
the first stretch has a sequence according to SEQ. ID. NO. 79 and the second stretch has a sequence according to SEQ. ID. NO. 29;
the first stretch has a sequence according to SEQ. ID. NO. 91 and the second stretch has a sequence according to SEQ. ID. NO. 41;
the first stretch has a sequence according to SEQ. ID. NO. 92 and the second stretch has a sequence according to SEQ. ID. NO. 42;
the first stretch has a sequence according to SEQ. ID. NO. 93 and the second stretch has a sequence according to SEQ. ID. NO. 43;
the first stretch has a sequence according to SEQ. ID. NO. 94 and the second stretch has a sequence according to SEQ. ID. NO. 44;
the first stretch has a sequence according to SEQ. ID. NO. 95 and the second stretch has a sequence according to SEQ. ID. NO. 45;
the first stretch has a sequence according to SEQ. ID. NO. 96 and the second stretch has a sequence according to SEQ. ID. NO. 46;
the first stretch has a sequence according to SEQ. ID. NO. 101 and the second stretch has a sequence according to SEQ. ID. NO. 51; and
the first stretch has a sequence according to SEQ. ID. NO. 102 and the second stretch has a sequence according to SEQ. ID. NO. 52.

In an embodiment the first stretch has a nucleic acid sequence which is selected from the group comprising SEQ. ID. NO. 53, 66, 72, 73, 74, 75, 76, 77, 79, 91, 92, 93, 94, 95, 96, 101 102, 525, 528, 529, 530, 532, 533, 534, 535 and 536.

It is to be understood that while the terms "first" and "second" stretch are used in connection with the nucleic acids of the present invention, they are used for the sake of convenience alone, and any nucleic acid molecule of the invention that is described as having a first stretch with the sequence X and a second stretch with the sequence Y, could also equally be described as having a first stretch with the sequence Y and a second stretch with the sequence X, so long as it is understood that one stretch is comprised in the antisense strand, which must be antisense to a portion of the coding sequence of the RTP801 gene, and the other stretch is comprised in the sense strand, which must be complementary (although not 100% complementary) to the antisense strand, all according to the definitions and specifications presented herein.

In an embodiment the first and/or the second strand comprises at least one overhang nucleotide at the 3' end which is complementary or identical to the corresponding nucleotide of a nucleic acid sequence coding for RTP801.

In an embodiment the first and/or the second strand comprises from 1 to 15 overhang nucleotides at the 3' end, preferably the first and/or the second strand comprises from 1 to 10 overhang nucleotides at the 3' end, more preferably the first and/or the second strand comprises from 1 to 5 overhang nucleotides at the 3' end, and most preferably the first and/or the second strand comprises from 1 to 2 overhang nucleotides at the 3' end.

In an embodiment the first strand and/or the second strand comprises at least one overhang nucleotide which is different from the corresponding nucleotide of the nucleic acid sequence coding for RTP801.

In an embodiment the first strand comprises two overhang nucleotides which are different form the corresponding nucleotide of a nucleic acid sequence coding for RTP801.

In an embodiment the first strand consists of the first stretch only.

In an embodiment the second strand consists of the second stretch only.

In an embodiment the first stretch and/or the first strand comprise(s) ribonucleotides.

In an embodiment the second stretch and/or the second strand comprise(s) ribonucleotides.

In an embodiment the first stretch and/or the second strand consist(s) of ribonucleotides.

In an embodiment some or all of the nucleotides are modified.

In a preferred embodiment such modification is related to the nucleobase moiety of the nucleotide, to the sugar moiety of the nucleotide and/or to the phosphate moiety of the nucleotide.

In a more preferred embodiment the modification is a modification of a sugar moiety and the modification is a modification at the 2' position, whereby the 2' OH group is replaced by a group or moiety selected from the group comprising —H—OCH$_3$, —OCH$_2$CH$_3$, —OCH$_2$CH$_2$CH$_3$, —NH$_2$, and —F.

In an embodiment the modification is a modification of the nucleobase moiety and the modification or modified nucleobase is selected from the group comprising inosine, xanthine, hypoxanthine, 2-aminoadenine, 6-methyl, 2-propyl and other alkyladenines, 5-halo uracil, 5-halocytosine, 5-halo cytosine, 6-azacytosine, 6-aza thymine, pseudo-uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanine, 8-hydroxylguanine and other substituted guanines, other aza- and deaza adenines, other aza- and deaza guanines, 5-trifluoromethyl uracil and 5-trifluoro cytosine.

In an embodiment the modification is a modification of the phosphate moiety, whereby the modified phosphate moiety is selected from the group comprising phosphothioate.

In an embodiment the first stretch and/or the second stretch comprises a plurality of groups of modified nucleotides having a modification at the 2' position, whereby within the stretch each group of modified nucleotides is flanked on one or both sides by a flanking group of nucleotides, whereby the flanking nucleotides forming the flanking group of nucleotides are either a non-modified nucleotide or a nucleotide having a modification different from the modification of the modified nucleotides.

In a preferred embodiment the first stretch and/or the second stretch consists of ribonucleotides.

In a more preferred embodiment the first and the second stretch comprise a plurality of groups of modified nucleotides.

In an embodiment the first stretch comprises said plurality of groups of modified nucleotides.

In an embodiment the second stretch comprises said plurality of groups of modified nucleotides.

In an embodiment each group of modified nucleotides and/or each group of flanking nucleotides comprises a number of nucleotides, whereby the number is selected from the group comprising one nucleotide to ten nucleotides.

In an embodiment the first stretch comprises a first pattern of modified nucleotides and the second stretch comprises a second pattern of modified nucleotides.

In an embodiment the first pattern is the same pattern as the second pattern.

In another embodiment the first pattern aligns with the second pattern.

In a preferred embodiment the first pattern is shifted by one or more nucleotides relative to the second pattern.

In an embodiment each of the groups of modified nucleotides consists of one modified nucleotides and each of the groups of flanking nucleotides consists of one non-modified nucleotide or a nucleotide having a modification which is different from the modification of the modified nucleotides.

In a preferred embodiment the modified nucleotide has a —OMe group at the 2' position.

In a preferred embodiment the flanking nucleotide is a ribonucleotide which has a 2' OH group.

In an embodiment the first stretch starts with a modified nucleotide at the 5' end and every other nucleotide of the stretch is also a modified nucleotide, whereas a second nucleotide starting from the 5' end and every other nucleotide is a non-modified nucleotide or a nucleotide having a modification which is different from the modification of the modified nucleotide(s).

In an embodiment the first stretch is in antisense orientation to the nucleic acid sequence coding for RTP801.

An additional aspect of the present invention related to a pharmaceutical composition comprising a nucleic acid according to the first aspect of the present invention and/or a vector according to the second aspect of the present invention and preferably a pharmaceutically acceptable carrier; said composition optionally being for systemic or for local administration.

In an embodiment the composition is for the treatment of a disease, whereby the disease is selected from the group comprising tumor diseases.

In an additional aspect, the problem underlying the present invention is solved by a method for the prevention and/or treatment of a patient in need of such prevention and/or treatment comprising the administration of a nucleic acid according to the present invention and/or vector according to the present invention and/or a pharmaceutical composition according to the present invention.

In an additional embodiment, a nucleic acid according to the present invention and/or a vector according to the present invention are used for the manufacture of a medicament. The medicament may be for the prevention and/or treatment of a disease, whereby such disease is selected from the group comprising tumor diseases. The tumor disease may be selected from the group comprising solid tumors, metastatic tumors including PTEN negative tumors, tumors which are drug resistant and tumors where RTP801 inhibition can be used for sensitization. Further, the tumor disease may be a late-stage tumor disease, or may involve cells which are tumor suppressor negative; said tumor suppressor may be PTEN.

An additional aspect of the present invention is solved by a method for designing or screening a nucleic acid which is suitable to down-regulate RTP801, comprising the following steps:
a) designing or screening a nucleic acid which is suitable to down-regulate RTP801;
b) assessing defect of a nucleic acid according to any of the above aspects of the present invention; and
c) comparing the effect of the nucleic acid of step a) with the effect of the nucleic acid of step b).

In an embodiment the effect is the down-regulation of RTP801.

An additional aspect of the present invention is the use of a nucleic acid according to the present invention as a sensitizer, particularly as a sensitizer in the treatment of a disease, whereby such disease is preferably selected from the group comprising tumor and more particularly tumors which are resistant to a treatment using chemotherapeutics and/or radiotherapeutics. Additional diseases for which a nucleic acid of the present invention can serve as a sensitizer are disclosed herein.

This application discloses that a nucleic acid comprising a double-stranded structure which is specific for RTP801 is a suitable means of inhibiting angiogenesis/growth of vasculature and vascular leakage, (both from the existing vasculature and from growing vasculature). Additionally, this application discloses (without being bound by theory) that RTP801 being a stress-inducible protein (induced by hypoxia, oxidative stress, thermal stress, ER stress) is a factor acting in fine-tuning of cell response to energy disbalance. Thus inhibition of RTP801 by such double-stranded nucleic acid is suitable for treatment of any disease where cells should be rescued from apoptosis due to stressful conditions (e.g. diseases accompanied by death of normal cells) or where cells adapted to stressful conditions due to changes in RTP801 expression, should be killed (e.g. tumor cells). In the latter case, upon inhibiting RTP801 through such double-stranded nucleic acid, this survival factor with anti-apoptotic function in hypoxic cells, more particularly hypoxic cancer cells, is made ineffective thus allowing the cells devoid of RTP801-mediated protection to be driven into apoptosis. This can additionally occur when other apoptosis promoting factors are present. Such other apoptosis promoting factors include, among others, chemotherapy and radiation therapy. In other words, the double-stranded nucleic acid according to the present invention may be effective alone in cancer treatment (monotherapy) and also as a supplementary therapy.

Such double-stranded structure comprises a first strand and a second strand, whereby the first strand comprises a first stretch of contiguous nucleotides and the second strand comprises a second stretch of contiguous nucleotides, whereby the first stretch is either complementary or identical to a nucleic acid sequence coding for RTP801 and whereby the second stretch is either identical or complementary to a nucleic acid sequence coding for RTP801. By particularly using RTP801 as a target for such kind of double-stranded nucleic acid, it is thus also possible to immediately address a target in the cascade involved in the growth and development of vasculature and angiogenesis, respectively, and thus in a different way compared to the pathway used by VEGF inhibitors such as VEGF antibodies. Without wishing to be bound by any theory, the present inventors assume that the nucleic acid according to the present invention may exert its function in those cells which provide for a background which is involved in or observed in connection with any disease where undesired, particularly hypoxia induced angiogenesis and/or growth or development of vasculature occurs. This understanding is supported by the finding that RTP801 knock-out mice do not exhibit any phenotype different from wildtype mice under non-hypoxic conditions. Only upon induction of hypoxia as observed in a diseased condition such as, e.g., tumor growth, the RTP801 related knock-out results in a pathology similar to the one observed in humans suffering from this kind of disease.

It is to be understood that the nucleic acid according to the present invention is preferably a functional nucleic acid. As used herein, the term functional nucleic acid preferably means a nucleic acid the function of which is different from being active in the cell as a template for the transcription of any hnRNA, mRNA, or any other transcription product, whereby either said hnRNA, mRNA or any other transcription product, respectively, or the nucleic acid according to the present invention is subject to a translation process, preferably a cellular translation process, resulting in a biologically active RTP801 protein. It is to be acknowledged that a functional nucleic acid as preferably used herein is capable of reducing the expression of a target nucleic acid. More preferably, such reduction is based on a post-transcriptional gene silencing process of the target nucleic acid. Even more preferably such reduction is based on RNA interference. A most preferred form of the functional nucleic acid is an siRNA molecule or any further molecule having the same effect as an siRNA molecule. Such further molecule is selected from the group comprising siRNAs, synthetic siRNAs, shRNAs and synthetic shRNAs. As used herein siRNAs may additionally comprise expression vector derived siRNAs, whereby the expression vector is in a preferred embodiment a virus such as Adenoviruses, Adenoassociated viruses, Herpes viruses and Lentiviruses. As used herein shRNA preferably means short hairpin RNAs. Such shRNA can be made synthetically or can be generated using vector encoded expression systems, preferably using RNA polymerase III promoters. In connection therewith it is to be acknowledged that the functional nucleic acid according to the present invention is directed to RTP801 which is also preferably referred to herein as the target and the nucleic acid coding for said target as the target nucleic acid.

As preferably used herein, the double-stranded structure of the nucleic acid according to the present invention comprises any double-stranded structure, whereby such double-stranded structure is preferably generated by the first stretch and the second stretch provided by the nucleic acid having the basic design. The double-stranded structure may comprise one or several mismatches. Such double-stranded structure is formed by Watson-Crick-base pairing and/or Hoogsteen base pairing and/or similar base pairing mechanisms. Based on the basic design of the nucleic acid according to the present invention it is preferred that one stretch, is in antisense orientation to a nucleic acid sequence coding for RTP801 or a part thereof, whereas the other stretch is in the sense orientation to a nucleic acid sequence coding for RTP801 or a part thereof. Because of this, one stretch is complementary to a nucleic acid sequence coding for RTP801 or a part thereof, and the other stretch is identical to a nucleic acid sequence coding for RTP801 or a part thereof. In connection therewith it is to be acknowledged that the term identical, of course, means also partially identical, whereby the identity, expressed as homology, is at least 80%, preferably 90%, more preferably 95%, 96%, 97%, 98%, 99% or 100%. Similar to the definition of identity, complementarity can be defined in terms of homology, whereby such homology is of the same range as the identity if the complementary strand would be translated into the identical strand according to Watson-Crick base pairing rules. In an alternative embodiment, one stretch is identical to a nucleic acid sequence coding for RTP801 or a part thereof and the other stretch is complementary to a nucleic acid sequence coding for RTP801 or a part thereof.

In a preferred embodiment, the nucleic acid according to the present invention is down-regulating RTP801 function. Down-regulation of RTP801 function preferably happens by reduction in the level of expression at the protein level and/or the mRNA level, whereby such reduced level of expression, preferably at the protein level, can be as little as 5% and be as high as 100%, with reference to an expression under conditions where the nucleic acid according to the present invention is not administered or is not functionally active. Such conditions are preferably the conditions of or as present in an expression system, preferably an expression system for RTP801. Such expression system is preferably a translation system which can be an in vitro translation system, more preferably a cell, organ and/or organism. It is more preferred that the organism is a multicellular organism, more preferably a mammal, whereby such mammal is preferably selected from the group comprising man, monkey, mouse, rat, guinea pig, rabbit, cat, dog, sheep, cow, horse, cattle and pig. In connection with the down-regulation it is to be acknowledged that said down-regulation may be a function of time, i.e. the down-regulation effect is not necessarily observed immediately upon administration or functional activation of the nucleic acids according to the present invention, but may be deferred in time as well as in space, i.e. in various cells, tissues and/or organs. Such deferment may range from 5%-100%, preferably 10 to 50%. It will be acknowledged by the ones skilled in the art that a 5% reduction for a longer time period might be as effective as a 100% reduction over a shorter time period. It will also be acknowledged by the ones skilled in the art that such deferment strongly depends on the particular functional nucleic acid actually used, as well as on the target cell population and thus, ultimately, on the disease to be treated and/or prevented according to the technical teaching of the present application. Insofar, a 5% reduction over a longer time period might be as effective as 100% reduction over a shorter time period. It will also be acknowledged by the ones skilled in the art that the deferment can occur at any level as outlined above, i.e. a deferment in function, whereby such function is any function exhibited by RTP801, a deferment in protein expression or a deferment at mRNA expression level.

In a preferred embodiment the first stretch comprises at least 14 nucleotides, preferably 14 contiguous nucleotides. It will be acknowledged by the one skilled in the art that the first stretch should have a length which is suitable to allow for specifically addressing a nucleic acid sequence coding for RTP801 and more specifically the nucleic acid coding for RTP801 as present in the translation system where the expression of RTP801 is to be reduced. Again without wishing to be bound by any theory or any mode of action of the nucleic acid according to the present invention, it seems that there is an interaction between the nucleic acid according to the present invention and the nucleic acid sequence coding for RTP801, preferably at the transcript level, i.e. upon generation of an mRNA from the respective nucleic acid sequence coding for RTP801. Due to the likelihood of any sequence of the nucleic acid according to the present invention being identical to or complementary to a sequence contained in the genome or transcriptome of the translation system, the length of the first stretch should thus be as long as to make sure that, under the assumption that some kind of base pairing between the nucleic acid coding for RTP801 and one of the strands of the nucleic acid according to the present invention actually occurs, only the sequence coding for RTP801 but no other coding sequence, certainly no other essential coding sequence, of the genome or the transcriptome is addressed for or by such base pairing. By this length, the occurrence of off-target effects can be reduced and preferably eliminated. To increase the stringency of this kind of specifically addressing RTP801 and the nucleic acid sequence coding therefor, the first stretch preferably has a length of at least 18 or 19 nucleotides. The upper limit for the length of the first stretch is preferably less than 50 nucleotides, however, the length can be significantly longer and can comprise 100, 200 or even 500 nucleotides or any length in-between. Apart from this, one skilled in the art will prefer to have a rather short first stretch, particularly in case the nucleic acid according to the present invention is chemically synthesised as the shorter the sequence is, the less time and material consuming the synthesis thereof will be and the lower will be the rate at which incorrect nucleotides are inserted into the respective sequence. Another factor which is to be taken into consideration in connection with fixing the length of the first stretch is the fact that, typically at a length beyond 50 or more nucleotides, an unspecific interferon response may be observed. It depends on the particular condition to be treated whether this kind of unspecific interferon response is to be tolerated or not. For example, an interferon response could be tolerated if the interferon response and/or the expression of the interferon genes can be limited to the pathogenic cells.

In view of this, more preferred lengths of the first stretch are from about 14 to 40 nucleotides, 18 to 30 nucleotides, 19 to 27 nucleotides, 21 to 25 nucleotides and 19 to 23 nucleotides.

The same considerations as outlined above for the first stretch are applicable to the second stretch which may thus comprise any length as described herein in connection with the first stretch. It is also within the present invention that the length of the first stretch is different from the length of the second stretch, however, it is preferred that both stretches have the same length.

According to the basic design of the nucleic acid, the first stretch and second stretch are parts of the first strand and second strand, respectively, of the nucleic acid according to the present invention. It will be acknowledged that at either end, i.e. at the 5' end as well as the 3' end the first strand and/or second strand may comprise one or several nucleotides, preferably additional nucleotides, at any combination.

In connection therewith it is to be acknowledged that those nucleotides of the individual strand going beyond the end(s) of the stretch corresponding to the respective strand can be used to further contribute to the complementarity and identity, respectively, of the stretch and thus to the specific addressing of the nucleic acid sequence coding for RTP801.

It will be acknowledged that, basically, based on the technical teaching provided herein, the nucleic acid according to the present invention can address any part of the nucleic acid sequence coding for RTP801, preferably coding for RTP801 in the translation system where the expression of RTP801 is to be reduced. Insofar, the present invention comprises any nucleic acid having the characteristics as defined herein, whereby the complementary and identical strands and stretches of the nucleic acid according to the present invention can basically start from any nucleotide of the nucleic acid sequence coding for RTP801. Accordingly, under the proviso that the first stretch of the nucleic acid according to the present invention is complementary to the nucleic acid sequence coding for RTP801, i.e. is the antisense strand thereof or is in antisense orientation thereto, the first nucleotide of said stretch, i.e. the most 5' terminal nucleotide corresponds, i.e. aligns to the last nucleotide of the sequence coding for RTP801 at the 3' end. In a further embodiment such most 5' terminal nucleotide corresponds to the penultimate nucleotide of the nucleic acid coding for RTP801 and so on until the last position is reached which, given the length of the antisense stretch, still allows that the antisense strand of the nucleic acid according to the present invention is complementary to the nucleic acid sequence coding for RTP801. Insofar, any nucleic acid according to the present invention is within the present invention which could be generated by scanning the nucleic acid sequence coding for RTP801 starting from the most 5' terminal nucleotide thereof and laying over the basic design of the nucleic acid according to the present invention and realising the characteristics for such nucleic acid according to the present invention. The same considerations are applicable to the embodiments disclosed herein where the complementarity and identity of the nucleic acid according to the present invention is not only provided by the first stretch and second stretch, respectively, but such complementarity and identity also involves one or more nucleotides beyond the first stretch and second stretch, respectively, then being part of the first strand and second strand, respectively.

Of the various nucleic acids according to the present invention as disclosed herein, those with internal reference numbers 14, 22, 23, 25, 27, 39, 41, 42, 49 and 50 (see Table A) and 257, 260-262, and 264-268 (see Table D) are particularly preferred. In connection therewith it is to be noted that those nucleic acids according to the present invention which can be used in both human and an animal model such as rat and/or mouse are particularly useful. The surprising advantage of these particular nucleic acids according to the present invention resides in the fact that they are effective both in human and in an animal model which means that the test results obtained in the animal model can be immediately transferred from the animal model to the human being and more particularly without the necessity to make any changes to the human sequence which would otherwise become necessary in case the nucleic acid according to the present invention was designed such as to comprise (a) sequence(s) which differ(s) between the species, more particularly the species used for animal model testing and man as the ultimate preferred organisms or patient. It is further preferred that these nucleic acids have a modification pattern as also described in the examples.

However, it is also within the present invention that any of the sequences according to SEQ. ID. NOs. 3, 16-17, 22-27, 29, 41-46, 51-53, 66-67, 72-77, 79, 91-96 101-102, 525, 528-530, 532-536, and respective combinations resulting in the nucleic acid molecules according to the present invention having internal reference numbers 14, 22, 23, 25, 27, 39, 41, 42, 49 and 50 (of Table A) and 257, 260-262, and 264-268 (of Table D) is only partially contained in a further nucleic acid according to the present invention. Preferably, the further nucleic acids according to the present invention comprise at least 14 contiguous nucleotides of the SEQ. ID. NO.s 3, 16-17, 22-27, 29, 41-46, 51-53, 66-67, 72-77, 79, 91-96 101-102, 525, 528-530, 532-536, and more preferably 14 contiguous nucleotide base pairs at any end of the double-stranded structure comprised of the first stretch and second stretch as outlined in the preceding table. It will be understood by the ones skilled in the art that given the potential length of the nucleic acid according to the present invention and particularly of the individual stretches forming such nucleic acid according to the present invention, some shifts relative to the coding sequence of RTP801 to each side is possible, whereby such shifts can be up to 1, 2, 3, 4, 5 and 6 nucleotides in both directions, and whereby the thus generated double-stranded nucleic acid molecules shall also be within the present invention.

In a preferred embodiment of the present invention the first stretch and the first strand have the same length. Likewise it is preferred that the second strand has the same length as the second stretch, whereby it is even more preferred that the first stretch and the second stretch have the same length. In a still more preferred embodiment, the first strand only comprises the first stretch and the second strand only comprises the second stretch. In an even more preferred embodiment neither the first stretch, and thus the first strand, nor the second stretch, and thus the second strand, comprise an overhang. In other words, it is also within the present invention that the double-stranded nucleic acids according to the present invention are blunt ended, preferably at each end of the double-stranded structure of the nucleic acids according to the present invention. Such blunt ended structure can be realized in connection with any other embodiments of the nucleic acids according to the present invention, particularly those embodiments where the nucleic acids according to the present invention have a modification pattern, more preferably a modification pattern as described herein.

In a further aspect, the nucleic acid according to the present invention has thus a basic design which provides for blunt ends at both ends of the double-stranded structure of the nucleic acid according to the present invention. However, it is also within the present invention that there is a overhang, i.e. a stretch of one or more nucleotides protruding from the double-stranded structure. The overhang can be, in principle, at the 5' end of the antisense strand, at the 3' end of the antisense strand, at the 5' end of the sense strand and/or the 3' end of the sense strand. It is to be noted that realising any single of said options as well as any combination thereof is within the present invention. More preferred is a combination, whereby the overhang is located at the 3' end of the antisense strand and at the 3' end of the sense strand. It is also within the present invention that the overhang is at the 5' end of the antisense strand and at the 5' end of the sense strand. Furthermore it is within the present invention that the overhang is located only at the antisense strand of double-stranded structure, more preferably at the 3' end of the antisense strand of the double-stranded structure.

In connection with the overhangs, it is to be noted that the overhang plus the stretch preferably form the strand and the lengths provided for the stretches herein apply also to these embodiments. The individual overhang can, independent of its location, consist of at least one nucleotide. However, the individual overhang can comprise as many as 10 and is preferably two nucleotides long. It is within the present invention that the respective nucleotide(s) forming the overhang(s) is/are also complementary to the nucleic acid sequence coding for RTP801 in case of the first strand being complementary to said nucleic acid sequence coding for RTP801, and the overhang being at the 3' or 5' end of the antisense strand, or that the overhang(s) is/are identical to the nucleic acid sequence coding for RTP801 in case the First strand is identical to the nucleic acid sequence coding for RTP801. The same applies to any overhang located at the second stretch of the basic design of the nucleic acid according to the present invention, whereby it is to be acknowledged that the overhang design at the second stretch can be independent from the overhang design of the first stretch.

It is also within the present invention that the overhang forming nucleotides are neither complementary nor identical to the corresponding nucleotides of the nucleic acid sequence coding for RTP801. As used herein, and preferably in this embodiment, "corresponding" means the respective nucleotides which follow at the 5' end and/or the 3' end of the stretch having a nucleotide counterpart on the nucleic acid coding for RTP801.

Preferably, the first strand comprises at its 3' end two nucleotides, preferably deoxynucleotides and more preferably two TT and/or this kind of nucleotides also at the 3' end of the second strand, whereby more preferably the length of the first stretch and the second stretch is 19 nucleotides. The strands are thus comprised of the stretch and the overhang. In this embodiment the double-stranded structure consists of 19 base pairs and an overhang of two nucleotides at each end of 3' end of the individual stretch.

In a preferred embodiment, the first stretch and/or the first strand comprise(s) ribonucleotides, whereby it is particularly preferred that the first stretch consists in its entirety of ribonucleotides. The same applies to the second stretch and the second strand, respectively. In connection therewith, however, each and any of the nucleotides of the first stretch and second stretch, respectively, is modified in a preferred embodiment. The same applies to the first strand and second strand, respectively. Particularly the terminal nucleotides, irrespective whether they are ribonucleotides or deoxyribonucleotides, can have an OH-group which as such can be modified. Such OH-group may stem from either the sugar moiety of the nucleotide, more preferably from the 5' position in case of the 5'OH-group and/or from the 3' position in case of the 3'OH-group, or from a phosphate group attached to the sugar moiety of the respective terminal nucleotide. The phosphate group may in principle be attached to any OH-group of the sugar moiety of the nucleotide. Preferably, the phosphate group is attached to the 5'OH-group of the sugar moiety in case of the free 5'OH-group and/or to the 3'OH-group of the sugar moiety in case of the free 3'OH-group still providing what is referred to herein as free 5' or 3' OH-group.

As used herein with any strategy for the design of RNAi or any embodiment of RNAi disclosed herein, the term end modification means a chemical entity added to the most 5' or 3' nucleotide of the first and/or second strand. Examples for such end modifications include, but are not limited to, 3' or 5' phosphate, inverted (deoxy) abasics, amino, fluoro, chloro, bromo, CN, CF, methoxy, imidazole, carboxylate, thioate, $C_1$ to $C_{10}$ lower alkyl, substituted lower alkyl, alkaryl or aralkyl, $OCF_3$, OCN, O-, S-, or N-alkyl; O-, S-, or N-alkenyl; $SOCH_3$; $SO_2CH_3$; $ONO_2$; $NO_2$, $N_3$; heterocycloalkyl; heterocycloalkaryl; aminoalkylamino; polyalkylamino or substituted silyl, as, among others, described in European patents EP 0 586 520 B1 or EP 0 618 925 131.

As used herein, alkyl or any term comprising "alkyl" preferably means any carbon atom chain comprising 1 to 12, preferably 1 to 6 and more, preferably 1 to 2 C atoms.

A further end modification is a biotin group. Such biotin group may preferably be attached to either the most 5' or the most 3' nucleotide of the first and/or second strand or to both ends. In a more preferred embodiment the biotin group is coupled to a polypeptide or a protein. It is also within the scope of the present invention that the polypeptide or protein is attached through any of the other aforementioned end modifications. The polypeptide or protein may confer further characteristics to the nucleic acid molecules according to the present invention. Among others the polypeptide or protein may act as a ligand to another molecule. If said other molecule is a receptor the receptor's function and activity may be activated by the binding ligand. The receptor may show an internalization activity which allows an effective transfection of the ligand bound nucleic acid molecules according to the present invention. An example for the ligand to be coupled to the inventive nucleic acid molecule is VEGF and the corresponding receptor is the VEGF receptor.

Various possible embodiments of the RNAi of the present invention having different kinds of end modification(s) are presented in the following Table 1.

TABLE 1

VARIOUS EMBODIMENTS OF THE INTERFERING RIBONUCLEIC ACID ACCORDING TO THE PRESENT INVENTION

|   |   | $1^{st}$ strand/$1^{st}$ stretch | $2^{nd}$ strand/2nd stretch |
|---|---|---|---|
| 1.) | 5'-end | free OH | free OH |
|   | 3'-end | free OH | free OH |
| 2.) | 5'-end | free OH | free OH |
|   | 3'-end | end modification | end modification |
| 3.) | 5'-end | free OH | free OH |
|   | 3'-end | free OH | end modification |
| 4.) | 5'-end | free OH | free OH |
|   | 3'-end | end modification | free OH |
| 5.) | 5'-end | free OH | end modification |
|   | 3'-end | free OH | free OH |
| 6.) | 5'-end | free OH | end modification |
|   | 3'-end | end modification | free OH |
| 7.) | 5'-end | free OH | end modification |
|   | 3'-end | free OH | end modification |
| 8.) | 5'-end | free OH | end modification |
|   | 3'-end | end modification | end modification |

The various end modifications as disclosed herein are preferably located at the ribose moiety of a nucleotide of the nucleic acid according to the present invention. More particularly, the end modification may be attached to or replace any of the OH-groups of the ribose moiety, including but not limited to the 2'OH, 3'OH and 5'OH position, provided that the nucleotide thus modified is a terminal nucleotide. Inverted abasics are nucleotides, either desoxyribonucleotides or ribonucleotides which do not have a nucleobase moiety. This kind of compound is, among others, described in Sternberger, M., Schmiedeknecht, A., Kretschmer, A., Gebhardt, F., Leenders, F., Czauderna, F., Von Carlowitz, I., Engle, M., Giese, K., Beigelman, L. & Klippel, A. (2002). Antisense Nucleic Acid Drug Dev, 12, 131-43

Any of the aforementioned end modifications may be used in connection with the various embodiments of RNAi depicted in Table 1; it is to be noted that the 5' end modifications mentioned above are usually only present in the sense strand of the siRNA molecule Further modifications can be related to the nucleobase moiety, the sugar moiety or the phosphate moiety of the individual nucleotide.

Such modification of the nucleobase moiety can be such that the derivatives of adenine, guanine, cytosine and thymidine and uracil, respectively, are modified. Particularly preferred modified nucleobases are selected from the group comprising inosine, xanthine, hypoxanthine, 2-aminoadenine, 6-methyl, 2-propyl and other alkyladenines, 5-halo uracil, 5-halocytosine, 5-halo cytosine, 6-azacytosine, 6-aza thymine, pseudo-uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanine, 8-hydroxylguanine and other substituted guanines, other aza- and deaza adenines, other aza- and deaza guanines, 5-trifluoromethyl uracil and 5-trifluoro cytosine.

In another preferred embodiment, the sugar moiety of the nucleotide is modified, whereby such modification preferably is at the 2' position of the ribose and desoxyribose moiety, respectively, of the nucleotide. More preferably, the 2' OH group is replaced by a group or moiety selected from the group comprising amino, fluoro, alkoxy and alkyl. Preferably, alkoxy is either methoxy or ethoxy. Also preferably alkyl means methyl, ethyl, propyl, isobutyl, butyl and isobutyl. It is even more preferred that, regardless of the type of modification, the nucleotide is preferably a ribonucleotide.

The modification of the phosphate moiety is preferably selected from the group comprising phosphothioates.

It will be acknowledged by the one skilled in the art that the nucleic acid of the present invention which consists of a multitude of nucleotides may thus be formed by nucleotides which are linked through a phosphodiester linkage or through a phosphothioate linkage, or a combination of both along the length of the nucleotide sequence of the individual strand and stretch, respectively.

A further form of nucleotides used may actually be siRNA which is, among others, described in international patent application WO 03/070918.

The nucleotides forming the first stretch and first strand, respectively, of the nucleic acid according to the present invention can comprise one or more modified nucleotides, whereby the individual modified nucleotide has a modification which is preferably a modification as disclosed herein. In addition to the particular modification, the modification can be or comprise some sort of label, whereby the label is selected from the group chemiluminescent labels, fluorescent labels and radio labels. These kinds of labels are known to the one skilled in the art and, e.g., described in Ausubel et al., Current Protocols in Molecular Biology, John Wiley and Sons, Baltimore, Md., 1998. The thus labelled nucleic acid according to the present invention may be used also for diagnostic purposes or for monitoring the site of action as well as for the staging of any treatment, preferably related to any of the diseases disclosed herein.

In a preferred embodiment, the nucleic acid according to the present invention is modified such that the pyrimidine nucleotides in the sense stretch or strand are 2' O-methylpyrimidine nucleotides and, either additionally or alternatively, the purine nucleotides in the sense stretch or strand are 2'-deoxypurine nucleotides. In a further embodiment the pyrimidine nucleotides present in the sense stretch or sense strand are 2'-deoxy-2'-fluoro pyrimidine nucleotides.

In an alternative embodiment, the modification is not based on the chemistry of the nucleotide, i.e. the modification depends on whether the nucleotide to be modified is either a purine nucleotide or a pyrimidine nucleotide, but is predominantly based on the individual nucleotide's spatial arrangement in the overall double-stranded structure of the basic design of the nucleic acid according to the present invention.

More particularly, either the first strand and first stretch, respectively, or the second strand and second stretch, respectively, show a spatial pattern of modification of the nucleotides forming said stretches and strands, respectively.

Focusing on the first stretch first, there is a pattern of groups of modified nucleotides and groups of non-modified nucleotides. These groups of non-modified nucleotides are also referred to herein as flanking groups of nucleotides. More preferably, the pattern consists of groups of modified nucleotides and non-modified nucleotides. Even more preferably, the pattern is a regular pattern and even more preferably an alternating pattern along the length of the first stretch of the nucleic acid according to the present invention. The group of modified nucleotides may either consist of one or of several nucleotides which are and which are preferably nucleotides which are modified at the 2' position, i.e. have a modification at the sugar moiety. More preferably, this modification is a 2'-O-Me modification.

The group of non-modified nucleotides may either consist of one or of several nucleotides which are either not modified, whereby the not-modified nucleotides are preferably ribonucleotides, or the not modified nucleotides are nucleotides having a modification, whereby such modification is different from the modification shown by the nucleotides forming the group of modified nucleotides. Even more preferably, the not modified nucleotides are ribonucleotides. It is to be noted that the term not modified and non-modified nucleotide are used in an interchangeable manner if not indicated to the contrary. The first stretch of the nucleic acid according to the present invention may either start with a group of modified nucleotides or start with a group of non-modified nucleotides as defined herein. However, it is preferred that the first stretch starts with a group of modified nucleotides. Most preferably, the group of modified nucleotides consists of a single nucleotide. In connection with this embodiment the first stretch is preferably in antisense orientation to the nucleic acid coding for RTP801. It is also within the present invention that the modification as exhibited by the nucleotides forming the group of modified nucleotides is the same for all groups of modified nucleotides present on the first stretch. However, it is also within the present invention that some group of modified nucleotides have a different modification than one or several groups of modified nucleotides present on the first stretch.

On the second strand of the nucleic acid according to the present invention, a pattern as described for the first stretch can also be realised. The same characteristics as described in connection with the first stretch can be realized in an embodiment on the second stretch as well, whereby it is preferred that, under the proviso that the second stretch is in sense orientation relative to the nucleic acid sequence coding for RTP801, the second strand of the nucleic acid according to the present invention starts with a' group of non-modified nucleotides.

The nucleic acid according to the present invention comprising a double-stranded structure may comprise a first stretch having the modification pattern as described herein. Alternatively, the double-stranded nucleic acid according to the present invention may comprise a second stretch having the modification pattern as outlined above. It is, however, most preferred that the double-stranded nucleic acid according to the present invention consists of a first stretch and a second stretch, whereby both the first stretch and the second stretch have a spatial modification pattern as described herein.

It is within the present invention that the characteristics of the spatial modification pattern is the same on both stretches in terms of size of the groups of modified nucleotides and groups of non-modified nucleotides and the kind of modifications actually used. Preferably, the spatial pattern of modification on the first stretch is shifted such that a group of modified nucleotides on the first stretch is opposing a group of non-modified nucleotides on the second stretch and vice versa. However, it is also with the present invention that the patterns are exactly aligned, i.e. that a group of modified nucleotides on the first stretch is opposing a group of non-modified nucleotides on the second stretch and a group of non-modified nucleotides on the first stretch is opposing a group of non-modified nucleotides on the second stretch. It is still within the present invention that the spatial pattern of modification on the first stretch and the second stretch is shifted relative to each other so that only a first portion of a group of modified nucleotides on one stretch is opposing a portion of a group of non-modified nucleotides on the other stretch, whereas the second portion of the group of modified nucleotides is opposing another group of modified nucleotides. It is within the present invention that the disclosure provided herein on the spatial modification pattern of the stretch(es) of the nucleic acid according to the present invention applies also to the strand(s) of the nucleic acid according to the present invention. However, it is preferred that the stretches of the nucleic acid comprise the spatial modification pattern and the strands comprise such stretches and one or more overhang(s) as disclosed herein. It is particularly preferred that the overhang is a phosphate group at the 3' end of either the antisense strand, or the sense strand or both strands, whereby it is more preferred that the phosphate group is at the 3' end of both the antisense strand and the sense strand. In an even more preferred embodiment, the phosphate group is a phosphate group as defined herein.

It is also within the present invention that the nucleic acid according to the present invention may exhibit a linker connecting the first and the second strand. Such linker is preferably a polymer. The polymer can be any synthetic or natural polymer. Possible synthetic linkers are, among others, PEG or a polynucleotide. Such linker is preferably designed such as to allow the either partial or complete folding back of the first stretch onto the second stretch and vice versa.

Finally, it is within the present invention that the nucleic acid according to the present invention is a synthetic one, a chemically synthesised one, an isolated one, or one derived from any natural sources such as, for example, prepared by means of recombinant technology. In connection with the preparation of any nucleic acid according to the present invention any modification as disclosed herein can be introduced either prior, during or subsequent to the preparation of the respective nucleic acid according to the present invention as known to the ones skilled in the art.

The vector according to the present invention comprises a nucleic acid according to the present invention. Additionally, the vector may include elements to control targeting, expression and transcription of said nucleic acid in a cell selective manner as is known in the art. The plasmid can include a promoter for controlling transcription of the heterologous material, i.e. the nucleic acid according to the present invention, and can be either a constitutive or an inducible promoter to allow selective transcription. Enhancers that may be required to obtain necessary transcription levels can optionally be included. Enhancers are generally any non-translated DNA sequences which work contiguously with the coding sequence, thus in cis, to change the basal transcription level dictated by the promoter. The expression of such constructs is known to the one skilled in the art and may be done, e.g., by providing a respective tandem construct or by having different promoters transcribing for the first and second strand and first and second stretch, respectively, of the nucleic acid according to the present invention.

When the nucleic acid according to the present invention is manufactured or expressed, preferably expressed in vivo, more preferably in a patient who is in need of the nucleic acid according to the present invention, such manufacture or expression preferably uses an expression vector, preferably a mammalian expression vector. Expression vectors are known in the art and preferably comprise plasmids, cosmids, viral expression systems. Preferred viral expression systems include, but are not limited to, adenovirus, retrovirus and lentivirus.

Methods are known in the art to introduce the vectors into cells or tissues. Such methods can be found generally described in Sambrook et al., Molecular cloning: A Laboratory Manual, Cold Springs Harbour Laboratory, New York (1983, 1992), or in Ausubel et al., Current Protocols in Molecular Biology, John Wiley and Sons, Baltimore, Md., 1998.

Suitable methods comprise, among others, transfection, lipofection, electroporation and infection with recombinant viral vectors. In connection with the present invention, an additional feature of the vector is in one embodiment an expression limiting feature such as a promoter and regulatory element, respectively, that are specific for the desired cell type thus allowing the expression of the nucleic acid sequence according to the present invention only once the background is provided which allows the desired expression.

In a further aspect the present invention is related to a pharmaceutical composition comprising a nucleic acid according to the present invention and/or a vector according to the present invention and, optionally, a pharmaceutically acceptable carrier, diluent or adjuvants or other vehicle(s). Preferably, such carrier, diluents, adjuvants and vehicles are inert, and non-toxic. The pharmaceutical composition is in its various embodiments adapted for administration in various ways. Such administration comprises systemic and local administration as well as oral, subcutaneous, parenteral, intravenous, intraarterial, intramuscular, intraperitonial, intranasal, and intrategral.

It will be acknowledged by the ones skilled in the art that the amount of the pharmaceutical composition and the respective nucleic acid and vector, respectively, depends on the clinical condition of the individual patient, the site and method of administration, scheduling of administration, patient age, sex, bodyweight and other factors known to medical practitioners. The pharmaceutically effective amount for purposes of prevention and/or treatment is thus determined by such considerations as are known in the medical arts. Preferably, the amount is effective to achieve improvement including but limited to improve the diseased condition or to provide for a more rapid recovery, improvement or elimination of symptoms and other indicators as are selected as appropriate measures by those skilled in the medical arts.

In a preferred embodiment, the pharmaceutical composition according to the present invention may comprise other pharmaceutically active compounds. Preferably, such other pharmaceutically active compounds are selected from the group comprising compounds which allow for uptake intracellular cell delivery, compounds which allow for endosomal release, compounds which allow for, longer circulation time and compounds which allow for targeting of endothelial cells or pathogenic cells. Preferred compounds for endosomal release are chloroquine, and inhibitors of ATP dependent Er pumps.

The pharmaceutical composition is preferably formulated so as to provide for a single dosage administration or a multi-dosage administration.

It will be acknowledged that the pharmaceutical composition according to the present invention can be used for any disease which involves undesired development or growth of vasculature including angiogenesis, as well as any of the diseases and conditions described herein. Preferably, these kind of diseases are tumor diseases. Among tumor diseases, the following tumors are most preferred: endometrial cancer, colorectal carcinomas, gliomas, endometrial cancers, adenocarcinomas, endometrial hyperplasias, Cowden's syndrome, hereditary non-polyposis colorectal carcinoma, Li-Fraumene's syndrome, breast-ovarian cancer, prostate cancer (Ali, I. U., Journal of the National Cancer Institute, Vol. 92, no. 11, Jun. 7, 2000, page 861-863), Bannayan-Zonana syndrome, LDD (Lhermitte-Duklos' syndrome)

(Macleod, K., supra) hamartoma-macrocephaly diseases including Cow disease (CD) and Bannayan-Ruvalcaba-Rily syndrome (BRR), mucocutaneous lesions (e.g. trichilemmonmas), macrocephaly, mental retardation, gastrointestinal harmatomas, lipomas, thyroid adenomas, fibrocystic disease of the breast, cerebellar dysplastic gangliocytoma and breast and thyroid malignancies (Vazquez, F., Sellers, W. R., supra).

It is to be acknowledged that any of the tumor disease to be treated with the pharmaceutical composition according to the present invention is preferably a late stage tumor disease. In another embodiment, the tumor disease involves cells which are tumor suppressor negative, whereby more preferably the tumor suppressor is PTEN.

The pharmaceutical composition according to the present invention can also be used in a method for preventing and/or treating a disease as disclosed herein, whereby the method comprises the administration of a nucleic acid according to the present invention, a vector according to the present invention or a pharmaceutical composition or medicament according to the present invention for any of the diseases described herein.

In a further aspect, the present invention is related to a method for designing or screening a nucleic acid which is suitable to down-regulate RTP801, more particularly to down-regulate RTP801 function. This method comprises the use of a nucleic acid sequence as disclosed herein and the assessment of such nucleic acid in a suitable assay. Such assay is known in the art and, for example, described in the example part of this application. In a further step, a double-stranded nucleic acid is designed, preferably according to the design principles as laid down herein, which is suitable to down-regulate RTP801, preferably in connection with a post transcriptional gene silencing mechanism such as RNA interference. Also the thus obtained, i.e. designed or screened, nucleic acid is assessed in the respective assay and the result, i.e. the effect of both the nucleic acid according to the present invention as well as the newly designed or screened nucleic acid in such assay compared. Preferably, the designed or screened nucleic acid is more suitable in case it is either more stable or more effective, preferably both. It will be acknowledged that the method will be particularly effective if any of the nucleic acids according to the present invention is used as a starting point. It is thus within the present invention that new nucleic acid molecules will be designed based on the principles disclosed herein, whereby the target sequence on the RTP801 mRNA will be slightly shifted relative to the target sequence on the RTP801 mRNA for the corresponding nucleic acid according to the present invention. Preferably the new nucleic acid will be shifted by at least one or more nucleotides relative to the stretch on the target mRNA in either the 5' or the 3' direction of the mRNA coding for RTP801. It is however with in the present invention that the shift occurs in both directions simultaneously which means that the new nucleic acid incorporates the nucleic acid according to the present invention used as a starting point. It is also within the present invention that the elongation of the nucleic acid according to the present invention and used as a starting point is biased to either the 3' end or the 5' end. In case of such as bias either the 3' end or the 5' end of the new nucleic acid is longer, i.e more extended than the other end. When the new nucleic acid molecule is generated by extending either the 3' end of the 5' end of the antisense strand and/or the sense strand, the following sequence of steps is typically applied. If the shift is to the 5' end of the mRNA of RTP801, the 3' end of the antisense strand has to be extended by the number of nucleotides by which the 5' end of the mRNA of RTP801 is shifted. The nucleotide(s) thus to be added to the 3' end of the antisense strand of the new nucleic acid is/are complementary to those nucleotides following at the 5' end of the target sequence on the RTP801 mRNA used for the nucleic acid molecule according to the present invention used as a starting point. The same has to be done to the sense strand. However the nucleotides to be added to the sense strand have to correspond, i.e. be complementary to the nucleotides newly added to the 3' end of the antisense strand which means that they have to be added to the 5' end of the sense strand. The latter step on the sense strand, however has to be done only to the extent that apart from the antisense strand also the sense strand shall be shifted, which is the case in preferred embodiments of the present invention. Although this shifting can be done to an extent defined by the ones skilled in the art, more preferably the shift shall be done such that also the new nucleic acid still contains a stretch of at least 14 nucleotides, preferably 14 contiguous nucleotides as exhibited by any of the nucleic acid molecules disclosed herein.

The synthesis of any of the nucleic acids described herein is within the skills of the one of the art. Such synthesis is, among others, described in Beaucage S. L. and Iyer R. P., Tetrahedron 1992; 48: 2223-2311, Beaucage S. L. and Iyer R. P., Tetrahedron 1993; 49: 6123-6194 and Caruthers M. H. et. al., Methods Enzymol. 1987; 154: 287-313, the synthesis of thioates is, among others, described in Eckstein F., Annu. Rev. Biochem. 1985; 54: 367-402, the synthesis of RNA molecules is described in Sproat B., in Humana Press 2005 Edited by Herdewijn P.; Kap. 2: 17-31 and respective downstream processes are, among others, described in Pingoud A. et. al., in IRL Press 1989 Edited by Oliver R. W. A.; Kap. 7: 183-208 and Sproat B., in Humana Press 2005 Edited by Herdewijn P.; Kap. 2: 17-31 (supra).

siRNA for RTP801 can be made using methods known in the art as described above, based on the known sequence of RTP801 (SEQ ID NO:1), and can be made stable by various modifications as described above. For further information, see Example 9.

Further, in relation to the methods of the present invention as described herein, additional RNA molecules may be used with said methods e.g. inhibitory RNA molecules of the present invention include single stranded oligoribonucleotides preferably comprising stretches of at least 7-10 consecutive nucleotides present in the sequences detailed in Tables A-D, said oligoribonucleotides being capable of forming [and/or comprising] double stranded regions in particular conformations that are recognized by intracellular complexes, leading to the degradation of said oligoribonucleotides into smaller RNA molecules that are capable of exerting inhibition of their corresponding endogenous gene, and DNA molecules encoding such RNA molecules. The corresponding endogenous gene is preferably the 801 gene and may additionally be the VEGF gene and/or the VEGF-R1gene. The invention also provides a composition comprising the above single stranded oligoribonucleotide in a carrier, preferably a pharmaceutically acceptable carrier.

Additionally, the present invention provides for combination therapy for all the conditions disclosed herein and in particular conditions involving choroidal neovascularization. In said combination therapy, both the RTP801 and VEGFR genes are inhibited in order to ameliorate the symptoms of the disease being treated. These genes may be inhibited with a combination of one or more siRNAs or antibodies or aptamers. The present invention therefore also provides for a novel pharmaceutical composition comprising an RTP801 inhibitor and a VEGF or VEGFR-1 inhibitor, the RTP801 inhibitor preferable being an siRNA, more preferably an siRNA molecule detailed in Tables A-D and in particular, siRNA Nos: 14, 22, 23, 25, 27, 39, 41, 42, 49 and 50 of Table A or siRNA Nos: 257, 260-262, and 264-268 of Table D, and the VEGF/VEGFR-1 inhibitor optionally being an antibody or aptamer. The combined use of said compounds (i.e., RTP801 siRNA and VEGF antibody or any other combined example disclosed herein) in the preparation of a medicament is also part of the present invention.

Thus, RTP801 siRNA such as an siRNA molecule detailed in Tables A-D and in particular, siRNA Nos: 14, 22, 23, 25, 27, 39, 41, 42, 49 and 50 of Table A or siRNA Nos: 257, 260-262, and 264-268 of Table D may be administered in conjunction with agents which target VEGF or VEGF receptor 1 (VEGFR1). Such agents currently exist on the market or in various stages of approval and work through different mechanisms. Antibodies and antibody fragments such as ranibizumab (Lucentis, Genentech) attach to released VEGF to inhibit binding of VEGF to active receptors. An aptamer which can act like a ligand/antibody (Macugen, Eyetech/Pfizer, approved recently by the FDA for wet AMD) is also a possibility. Macugen bonds with extracellular VEGF to block its activity. These drugs are administered locally by intravitreal injection. Anti-VEGF siRNA based compounds (such as Acuity's Cand5 inhibitor of VEGF or SIRNA's 027 inhibitor of VEGFR-1) are also available. Additionally, the small molecule aminosterol Squalamine (Genaera) which is administered systemically reportedly interferes in multiple facets of the angiogenic process, including inhibiting VEGF and other growth factor signaling in endothelial cells.

The conjoined administration of an RTP801 inhibitor, preferably an siRNA, and any of the above VEGF/VEGFR-1 inhibitory agents can have a synergistic effect whereby said combined treatment is more effective than treatment by any of these individual compositions, irrespective of dosage in the single therapy option. This synergistic effect is also supported by preliminary results as detailed in Example 6.

RTP801i has a different mechanism of action and is potentially synergistic with VEGF-VEGFR inhibitors. A study in RTP801 KO mice indicates that protective phenotype in the KO mice persists in spite of the fact that expression of VEGF mRNA in the eye is as high as in the WT mice. Our additional preliminary data indicate that inhibition of RTP801 may be synergistic with the inhibition of VEGF-VEGFR regulatory axis in treatment of retinal pathology. The inventors of the present invention have found in appropriate experiments that administration of siRNA against RTP801 in the model of AMD (see Example 6 below) leads not only to downregulation of RTP801 itself but also, as a consequence, to upregulation of the antiangiogenic and neuroprotective factor PEDF as well as the downregulation of expression of MCP1, a macrophage chemoattractant protein. Thus, inhibition of RTP801 simultaneously confers antiangiogenic, neuroprotective and anti-inflammatory effects.

As disclosed herein, aptamers may also be used in the present invention in combination with the novel siRNAs disclosed herein. For example, an aptamer can be used with any one of the siRNAs disclosed herein in combination therapy for the treatment of any one of the conditions disclosed herein. The novel pharmaceutical composition employed for such a combination therapy, which is also part of the present invention, may comprise an siRNA of the present invention covalently or non-covalently attached to an aptamer. Aptamers are RNA or DNA single-strand or double-strand oligonucleic acids which bind to a target protein and do not generally exhibit non-specific effects. Aptamers can be modified for stability or other desired qualities in accordance with any nucleic acid modifications disclosed herein and/or known to one of skill in the art. Modifications to aptamers can be introduced anywhere in the molecule, such as the 5' or 3' termini, or at any internally defined modification site. For example, RNA aptamers can be stabilized with 2'-Fluoro or 2'-amino modified pyrimidines. Aptamers can also be linked to reporter molecules or linker chemistries and can be attached to beads or other solid support if necessary (e.g., 5' or 3' amino, thiol ester or biotin groups). Thioaptamers are aptamers which contain sulfur modifications at specific internucleoside phosphoryl sites, and may possess enhanced stability, nuclease resistance, target affinity and/or selectivity. Examples of thioaptamers include phosphoromonothioate (S-ODN) and phosphorodithioate (S2-ODN) oligodeoxy thioaptamers. For further information on aptamers and thioaptamers see U.S. Pat. Nos. 5,218,088 and 6,423,493.

It is to be understood that, in the context of the present invention, any of the siRNA molecules disclosed herein, or any long double-stranded RNA molecules (typically 25-500 nucleotides in length) which are processed by endogenous cellular complexes (such as DICER—see above) to form the siRNA molecules disclosed herein, or molecules which comprise the siRNA molecules disclosed herein, can be employed in the treatment of the diseases or disorders described herein.

Additional disorders which can be treated by the molecules and compositions of the present invention include all types of choroidal neovascularization (CNV), which occurs not only in wet AMD but also in other ocular pathologies such as ocular histoplasmosis syndrome, angiod streaks, ruptures in Bruch's membrane, myopic degeneration, ocular tumors and some retinal degenerative diseases.

An additional aspect of the present invention provides for methods of treating an apoptosis related disease. Methods for therapy of diseases or disorders associated with uncontrolled, pathological cell growth, e.g. cancer, psoriasis, autoimmune diseases, inter alia, and methods for therapy of diseases associated with ischemia and lack of proper blood flow, e.g. myocardial infarction (MI) and stroke, are provided. "Cancer" or "Tumor" refers to an uncontrolled growing mass of abnormal cells. These terms include both primary tumors, which may be benign or malignant, as well as secondary tumors, or metastases which have spread to other sites in the body. Examples of cancer-type diseases include, inter alia: carcinoma (e.g.: breast, colon and lung), leukemia such as B cell leukemia, lymphoma such as B-cell lymphoma, blastoma such as neuroblastoma and melanoma.

The invention also provides a composition comprising one or more of the compounds of the invention in a carrier, preferably a pharmaceutically acceptable carrier. This composition may comprise a mixture of two or more siRNAs for different genes or different siRNAs for the same gene. A composition comprising siRNA for the RTP801 gene and siRNA for the VEGF gene and/or the VEGF-R1 gene is envisaged.

Another compound of the invention comprises the above compound of the invention (structure A) covalently or non-covalently bound to one or more compounds of the invention (structure A). This compound may be delivered in a carrier, preferably a pharmaceutically acceptable carrier, and may be processed intracellularly by endogenous cellular complexes to produce one or more siRNAs of the invention. Another compound of the invention comprises the above compound of the invention (structure A) covalently or non-covalently bound to an siRNA for another gene, especially the VEGF gene and/or the VEGF-R1 gene.

This invention also comprises a novel chemical entity which is an RTP801 inhibitor, preferably an siRNA, chemically bound, covalently or non-covalently, to any of the above VEGF/VEGFR-1 inhibitory agents. A particular chemical entity envisaged is an siRNA RTP801 inhibitor covalently bound to an antibody to VEGF or VEGF receptor-1. An additional chemical entity envisaged is a modified or unmodified DNA aptamer which targets VEGF receptor-1 covalently bound to an RTP801 siRNA disclosed herein. Without being bound by theory, the aptamer portion of such a pharmaceutical composition would bind VEGF receptor-1 and internalize into the cell, whereupon the siRNA portion of the molecule would inhibit RTP801 expression in the cell. Such a pharmaceutical would thus have the benefit of increased selectivity and targeting, as well as the additional benefits of combination therapy as disclosed herein. Methods of production of such novel chemical entities are known to those skilled in the art.

This invention also comprises a tandem double-stranded structure which comprises two or more siRNA sequences, which is processed intracellularly to form two or more different siRNAs, one inhibiting 801 and a second inhibiting VEGF/VEGFR-1 In a related aspect, this invention also comprises a tandem double-stranded structure which comprises two or more siRNA sequences, which is degraded intracellularly to form two or more different siRNAs, both inhibiting 801.

In particular, it is envisaged that a long oligonucleotide (typically about 80-500 nucleotides in length) comprising one or more stem and loop structures, where stem regions comprise the sequences of the oligonucleotides of the invention, may be delivered in a carrier, preferably a pharmaceutically acceptable carrier, and may be processed intracellularly by endogenous cellular complexes (e.g. by DROSHA and DICER as described above) to produce one or more smaller double stranded oligonucleotides (siRNAs) which are oligonucleotides of the invention. This oligonucleotide can be termed a tandem shRNA construct. It is envisaged that this long oligonucleotide is a single stranded oligonucleotide comprising one or more stem and loop structures, wherein each stem region comprises a sense and corresponding antisense siRNA sequence of an 801 gene. In particular, it is envisaged that this oligonucleotide comprises sense and antisense siRNA sequences as depicted in any one of Tables A through D. Alternatively, the tandem shRNA construct may comprise sense and corresponding antisense siRNA sequence of an 801 gene and additionally sense and corresponding antisense siRNA sequence of a different gene such as VEGF or VEGF-R1.

As mentioned herein, siRNA against RTP801 may be the main active component in a pharmaceutical composition, or may be one active component of a pharmaceutical composition containing two or more siRNAs (or molecules which encode or endogenously produce two or more siRNAs, be it a mixture of molecules or one or more tandem molecule which encodes two or more siRNAs), said pharmaceutical composition further being comprised of one or more additional siRNA molecule which targets one or more additional gene. Simultaneous inhibition of RTP801 and said additional gene(s) will probably have an additive or synergistic effect for treatment of the diseases disclosed herein, according to the following:

Acute Renal Failure (ARF) and other microvascular disorders, as well as hearing disorders and pressure sores: the pharmaceutical composition for treatment of ARF may be comprised of the following compound combinations: 1) RTP801 siRNA and p53 siRNA dimers; 2) RTP801 and Fas siRNA dimers; 3) RTP801 and Bax siRNA dimers; 4) RTP801 and Fas siRNA dimers; 5) RTP801 and Bax siRNA dimers; 6) RTP801 and Noxa siRNA dimers; 7) RTP801 and Puma siRNA dimers; 8) RTP801 (REDD1) and RTP801L (REDD2) siRNA dimers; 9) RTP801 siRNA, Fas siRNA and any of RTP801L siRNA p53 siRNA, Bax siRNA, Noxa siRNA or Puma siRNA to form trimers or polymers (i.e., tandem molecules which encode three or more siRNAs).

Further, additional pharmaceutical compositions for combination therapies for ARF, hearing disorders, pressure sores and any other disease or condition disclosed herein may comprise two siRNAs wherein the first siRNA is an RTP801 siRNA, preferably selected from Tables A-D, and the second siRNA, which can be covalently or non-covalently bound to the first siRNA or admixed with the first siRNA, is an siRNA which targets a gene selected from the following group: tumor protein p53 binding protein, 2 (TP53BP2); leucine-rich repeats and death domain containing (LRDD); cytochrome b-245, alpha polypeptide (CYBA); activating transcription factor 3 (ATF3); caspase 2, apoptosis-related cysteine peptidase (neural precursor cell expressed, developmentally down-regulated 2) (CASP2); NADPH oxidase 3 (NOX3); harakiri, BCL2 interacting protein (HRK); complement component 1, q subcomponent binding protein (C1QBP); BCL2/adenovirus E1B 19 kDa interacting protein 3 (BNIP3); mitogen-activated protein kinase 8 (MAPK8); mitogen-activated protein kinase 14 (MAPK14); ras-related C3 botulinum toxin substrate 1 (rho family, small GTP binding protein Reel); glycogen synthase kinase 3 beta (GSK3B); purinergic receptor P2X, ligand-gated ion channel, 7 (P2RX7); transient receptor potential cation channel, subfamily M, member 2 (TRPM2); poly (ADP-ribose) glycohydrolase (PARG); CD38 molecule (CD38); STEAP family member 4 (STEAP4); bone morphogenetic protein 2—BMP2; gap junction protein, alpha 1, 43 kDa (connexin 43) (GJA1); TYRO protein tyrosine kinase binding protein (TYROBP); connective tissue growth factor (CTGF); secreted phosphoprotein 1 (osteopontin, bone sialoprotein I, early T-lymphocyte activation 1) (SPP1); reticulon 4 receptor (RTN4R); annexin A2 (ANXA2); ras homolog gene family, member A (RHOA); dual oxidase 1 (DUOX1); solute carrier family 5 (sodium/glucose cotransporter), member 1 (SLC5A1); solute carrier family 2 (facilitated glucose transporter), member 2 (SLC2A2); aldo-keto reductase family 1, member B1 (aldose reductase) (AKR1B1); sorbitol dehydrogenase (SORD); solute carrier family 2 (facilitated glucose transporter), member 1 (SLC2A1); and membrane metallo-endopeptidase (neutral endopeptidase, enkephalinase) (MME).

Macular degeneration (MD), diabetic retinopathy (DR), spinal cord injury: pharmaceutical compositions for treatment of MD, DR and spinal cord injury may be comprised of the following compound combinations: 1) RTP801 siRNA combined with either of VEGF siRNA, VEGF-R1 siRNA, VEGF R2 siRNA, PKCbeta siRNA, MCP1 siRNA, eNOS siRNA, KLF2 siRNA, RTP801L siRNA (either physically mixed or in a tandem molecule); 2) RTP801 siRNA in combination with two or more siRNAs of the above list (physically mixed or in a tandem molecule encoding three siRNAs, or a combination thereof).

COPD and respiratory disorders: the pharmaceutical composition for treatment of respiratory W disorders may be comprised of the following compound combinations: RTP801 siRNA combined with siRNA against one or more of the following genes: elastases, matrix metalloproteases, phospholipases, caspases, sphingomyelinase, and ceramide synthase.

Additionally, RTP801 siRNA or any nucleic acid molecule comprising or encoding RTP801 siRNA can be linked (covalently or non-covalently) to an antibody or aptamer, in order to achieve enhanced targeting for treatment of the diseases disclosed herein, according to the following:

ARF: anti-Fas antibody (preferably neutralizing antibodies).

Macular degeneration, diabetic retinopathy, spinal cord injury: anti-Fas antibody or aptamer, anti-MCP1 antibody or aptamer, anti-VEGFR1 and anti-VEGFR2 antibody or aptamer. The antibodies should be preferably be neutralizing antibodies.

Any molecules, such as, for example, antisense DNA molecules which comprise the siRNA sequences disclosed herein (with the appropriate nucleic acid modifications) are particularly desirable and may be used in the same capacity as their corresponding siRNAs for all uses and methods disclosed herein.

The invention also comprises a method of treating a patient suffering from a disorder such as the disorders described herein comprising administering to the patient the above composition or compound in a therapeutically effective dose so as to thereby treat the patient.

By the term "antisense" (AS) or "antisense fragment" is meant a polynucleotide fragment (comprising either deoxyribonucleotides, ribonucleotides or a mixture of both) having inhibitory antisense activity, said activity causing a decrease in the expression of the endogenous genomic copy of the corresponding gene (in this case RTP801). An RTP801 AS polynucleotide is a polynucleotide which comprises consecutive nucleotides having a sequence of sufficient length and homology to a sequence present within the sequence of the RTP801 gene set forth in SEQ ID NO:1 to permit hybridization of the AS to the gene. The sequence of the AS is designed to complement a target mRNA of interest and form an RNA:AS duplex. This duplex formation can prevent processing, splicing, transport or translation of the relevant mRNA. Moreover, certain AS nucleotide sequences can elicit cellular RNase H activity when hybridized with their target mRNA, resulting in mRNA degradation (Calabretta et al, 1996: Antisense strategies in the treatment of leukemias. Semin Oncol. 23(1):78-87). In that case, RNase H will cleave the RNA component of the duplex and can potentially release the AS to further hybridize with additional molecules of the target RNA. An additional mode of action results from the interaction of AS with genomic DNA to form a triple helix which can be transcriptionally inactive. Particular AS fragments are the AS of the DNA encoding the particular fragments of RTP801 described herein.

Many reviews have covered the main aspects of antisense (AS) technology and its therapeutic potential (Wright & Anazodo, 1995. *Antisense Molecules and Their Potential For The Treatment Of Cancer and AIDS. Cancer J.* 8:185-189.). There are reviews on the chemical (Crooke, 1995. *Progress in antisense therapeutics, Hematol. Pathol.* 2:59; Uhlmann and Peyman, 1990. *Antisense Oligonucleotides: A New Therapeutic Principle. Chem. Rev* 90(4):543-584.), cellular (Wagner, 1994. *Gene inhibition using antisense oligodeoxynucleotides. Nature* 372:333.) and therapeutic (Hanania, et al 1995. *Recent advances in the application of gene therapy to human disease. Am. J. Med.* 99:537.; Scanlon et al., 1995. *Oligonucleotides-mediated modulation of mammalian gene expression. FASEB J.* 9:1288.; Gewirtz, 1993. *Oligodeoxynucleotide-based therapeutics for human leukemias, Stem Cells Dayt.* 11:96.) aspects of this technology.

Antisense intervention in the expression of specific genes can be achieved by the use of synthetic AS oligonucleotide sequences (see Lefebvre-d'Hellencourt et al, 1995. *Immunomodulation by cytokine antisense oligonucleotides. Eur. Cytokine Netw.* 6:7.; Agrawal, 1996. *Antisense oligonucleotides: towards clinical trials, TIBTECH,* 14:376.; Lev-Lehman et al., 1997. *Antisense Oligomers in vitro and in vivo. In Antisense Therapeutics,* A. Cohen and S. Smicek, eds (Plenum Press, New York)). AS oligonucleotide sequences are designed to complement a target mRNA of interest and form an RNA:AS duplex. This duplex formation can prevent processing, splicing, transport or translation of the relevant mRNA. Moreover, certain AS nucleotide sequences can elicit cellular RNase H activity when hybridized with their target mRNA, resulting in mRNA degradation (Calabretta, et al, 1996. *Antisense strategies in the treatment of leukemias. Semin. Oncol.* 23:78.). In that case, RNase H will cleave the RNA component of the duplex and can potentially release the AS to further hybridize with additional molecules of the target RNA. An additional mode of action results from the interaction of AS with genomic DNA to form a triple helix which may be transcriptionally inactive.

The sequence target segment for the antisense oligonucleotide is selected such that the sequence exhibits suitable energy related characteristics important for oligonucleotide duplex formation with their complementary templates, and shows a low potential for self-dimerization or self-complementation (Anazodo et al., 1996). For example, the computer program OLIGO (Primer Analysis Software, Version 3.4), can be used to determine antisense sequence melting temperature, free energy properties, and to estimate potential self-dimer formation and self-complimentary properties. The program allows the determination of a qualitative estimation of these two parameters (potential self-dimer formation and self-complimentary) and provides an indication of "no potential" or "some potential" or "essentially complete potential". Using this program target segments are generally selected that have estimates of no potential in these parameters. However, segments can be used that have "some potential" in one of the categories. A balance of the parameters is used in the selection as is known in the art. Further, the oligonucleotides are also selected as needed so that analogue substitution do not substantially affect function.

Phosphorothioate antisense oligonucleotides do not normally show significant toxicity at concentrations that are effective and exhibit sufficient pharmacodynamic half-lives in animals (Agrawal, 1996. *Antisense oligonucleotides: towards clinical trials,* TIBTECH, 14:376.) and are nuclease resistant. Antisense induced loss-of-function phenotypes related with cellular development have been shown for the glial fibrillary acidic protein (GFAP), for the establishment of tectal plate formation in chick (Galileo et al., 1991. J. Cell. Biol., 112:1285.) and for the N-myc protein, responsible for the maintenance of cellular heterogeneity in neuroectodermal cultures (ephithelial vs. neuroblastic cells, which differ in their colony forming abilities, tumorigenicity and adherence) (Rosolen et al., 1990. Cancer Res. 50:6316.; Whitesell et al., 1991. *Episome-generated N-myc antisense RNA restricts the differentiation potential of primitive neuroectodermal cell lines.* Mol. Cell. Biol. 11:1360.). Antisense oligonucleotide inhibition of basic fibroblast growth factor (bFgF), having mitogenic and angiogenic properties, suppressed 80% of growth in glioma cells (Morrison, 1991. *Suppression of basic fibroblast growth factor expression by antisense oligonucleotides inhibits the growth of transformed human astrocytes.* J. Biol. Chem. 266:728.) in a saturable and specific manner. Being hydrophobic, antisense oligonucleotides interact well with phospholipid membranes (Akhter et al, 1991. *Interactions of antisense DNA oligonucleotide analogs with phospholipid membranes (liposomes)* Nuc. Res. 19:5551-5559.). Following their interaction with the cellular plasma membrane, they are actively (or passively) transported into living cells (Loke et al, 1989. *Characterization of oligonucleotide transport into living cells.* PNAS USA 86:3474.), in a saturable mechanism predicted to involve specific receptors (Yakubov et al, 1989. PNAS USA 86:6454.).

A "ribozyme" is an RNA molecule that possesses RNA catalytic ability (see Cech for review) and cleaves a specific site in a target RNA.

In accordance with the present invention, ribozymes which cleave RTP801 mRNA may be utilized as RTP801 inhibitors. This may be necessary in cases where antisense therapy is limited by stoichiometric considerations (Sarver et al., 1990, *Gene Regulation and Aids.* pp. 305-325). Ribozymes can then be used that will target the RTP801 sequence. The number of RNA molecules that are cleaved by a ribozyme is greater than the number predicted by stochiochemistry. (Hampel and Tritz, 1989; Uhlenbeck, 1987).

Ribozymes catalyze the phosphodiester bond cleavage of RNA. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (Sullivan, 1994; U.S. Pat. No. 5,225,347, columns 4-5). The latter two families are derived from viroids and virusoids, in which the ribozyme is believed to separate monomers from oligomers created during rolling circle replication (Symons, 1989 and 1992). Hammerhead and hairpin ribozyme motifs are most commonly adapted for trans-cleavage of mRNAs for gene therapy (Sullivan, 1994). The ribozyme type utilized in the present invention is selected as is Known in the art. Hairpin ribozymes are now in clinical trial and are the preferred type. In general the ribozyme is from 30-100 nucleotides in length. Delivery of ribozymes is similar to that of AS fragments and/or siRNA molecules.

It will be noted that all the polynucleotides to be used in the present invention may undergo modifications so as to possess improved therapeutic properties. Modifications or analogs of nucleotides can be introduced to improve the therapeutic properties of polynucleotides. Improved properties include increased nuclease resistance and/or increased ability to permeate cell membranes. Nuclease resistance, where needed, is provided by any method known in the art that does not interfere with biological activity of the AS polynucleotide, siRNA, cDNA and/or ribozymes as needed for the method of use and delivery (Iyer et al., 1990; Eckstein, 1985; Spitzer and Eckstein, 1988; Woolf et al., 1990; Shaw et al., 1991). Modifications that can be made to oligonucleotides in order to enhance nuclease resistance include modifying the phosphorous or oxygen heteroatom in the phosphate backbone. These include preparing methyl phosphonates, phosphorothioates, phosphorodithioates and morpholino oligomers. In one embodiment it is provided by having phosphorothioate bonds linking between the four to six 3'-terminus nucleotide bases. Alternatively, phosphorothioate bonds link all the nucleotide bases. Other modifications known in the art may be used where the biological activity is retained, but the stability to nucleases is substantially increased.

All analogues of, or modifications to, a polynucleotide may be employed with the present invention, provided that said analogue or modification does not substantially affect the function of the polynucleotide. The nucleotides can be selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiuracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine.

In addition, analogues of polynucleotides can be prepared wherein the structure of the nucleotide is fundamentally altered and that are better suited as therapeutic or experimental reagents. An example of a nucleotide analogue is a peptide nucleic acid (PNA) wherein the deoxyribose (or ribose) phosphate backbone in DNA (or RNA is replaced with a polyimide backbone which is similar to that found in peptides. PNA analogues have been shown to be resistant to degradation by enzymes and to have extended lives in vivo and in vitro. Further, PNAs have been shown to bind stronger to a complementary DNA sequence than a DNA molecule. This observation is attributed to the lack of charge repulsion between the PNA strand and the DNA strand. Other modifications that can be made to oligonucleotides include polymer backbones, cyclic backbones, or acyclic backbones.

The polypeptides employed in the present invention may also be modified, optionally chemically modified, in order to improve their therapeutic activity. "Chemically modified"—when referring to the polypeptides, means a polypeptide where at least one of its amino acid residues is modified either by natural processes, such as processing or other post-translational modifications, or by chemical modification techniques which are well known in the art. Among the numerous known modifications typical, but not exclusive examples include: acetylation, acylation, amidation, ADP-ribosylation, glycosylation, GPI anchor formation, covalent attachment of a lipid or lipid derivative, methylation, myristlyation, pegylation, prenylation, phosphorylation, ubiqutination, or any similar process.

Additional possible polypeptide modifications (such as those resulting from nucleic acid sequence alteration) include the following:

"Conservative substitution"—refers to the substitution of an amino acid in one class by an amino acid of the same class, where a class is defined by common physicochemical amino acid side chain properties and high substitution frequencies in homologous polypeptides found in nature, as determined, for example, by a standard Dayhoff frequency exchange matrix or BLOSUM matrix. Six general classes of amino acid side chains have been categorized and include: Class I (Cys); Class H (Ser, Thr, Pro, Ala, Gly); Class III (Asn, Asp, Gln, Glu); Class IV (H is, Arg, Lys); Class V (Ile, Leu, Val, Met); and Class VI (Phe, Tyr, Trp). For example, substitution of an Asp for another class III residue such as Asn, Gln, or Glu, is a conservative substitution.

"Non-conservative substitution"—refers to the substitution of an amino acid in one class with an amino acid from another class; for example, substitution of an Ala, a class II residue, with a class HI residue such as Asp, Asn, Glu, or Gln.

"Deletion"—is a change in either nucleotide or amino acid sequence in which one or more nucleotides or amino acid residues, respectively, are absent.

"Insertion" or "addition"—is that change in a nucleotide or amino acid sequence which has resulted in the addition of one or more nucleotides or amino acid residues, respectively, as compared to the naturally occurring sequence.

"Substitution"—replacement of one or more nucleotides or amino acids by different nucleotides or amino acids, respectively. As regards amino acid sequences the substitution may be conservative or non-conservative.

In an additional embodiment of the present invention, the RTP801 polypeptide or polynucleotide may be used to diagnose or detect macular degeneration in a subject. A detection method would typically comprise assaying for RTP801 mRNA or RTP801 polypeptide in a sample derived from a subject.

"Detection"—refers to a method of detection of a disease. This term may refer to detection of a predisposition to a disease, or to the detection of the severity of the disease.

By "homolog/homology", as utilized in the present invention, is meant at least about 70%, preferably at least about 75% homology, advantageously at least about 80% homology, more advantageously at least about 90% homology, even more advantageously at least about 95%, e.g., at least about 97%, about 98%, about 99% or even about 100% homology. The invention also comprehends that these polynucleotides and polypeptides can be used in the same fashion as the herein or aforementioned polynucleotides and polypeptides.

Alternatively or additionally, "homology", with respect to sequences, can refer to the number of positions with identical nucleotides or amino acid residues, divided by the number of nucleotides or amino acid residues in the shorter of the two sequences, wherein alignment of the two sequences can be determined in accordance with the Wilbur and Lipman algorithm ((1983) Proc. Natl. Acad. Sci. USA 80:726); for instance, using a window size of 20 nucleotides, a word length of 4 nucleotides, and a gap penalty of 4, computer-assisted analysis and interpretation of the sequence data, including alignment, can be conveniently performed using commercially available programs (e.g., Intelligenetics™ Suite, Intelligenetics Inc., CA). When RNA sequences are said to be similar, or to have a degree of sequence identity or homology with DNA sequences, thymidine (T) in the DNA sequence is considered equal to uracil (U) in the RNA sequence. RNA sequences within the scope of the invention can be derived from DNA sequences or their complements, by substituting thymidine (T) in the DNA sequence with uracil (U).

Additionally or alternatively, amino acid sequence similarity or homology can be determined, for instance, using the BlastP program (Altschul et al., Nucl. Acids Res. 25:3389-3402) and available at NCBI. The following references provide algorithms for comparing the relative identity or homology of amino acid residues of two polypeptides, and additionally, or alternatively, with respect to the foregoing, the teachings in these references can be used for determining percent homology: Smith et al., (1981) Adv. Appl. Math. 2:482-489; Smith et al., (1983) Nucl. Acids Res. 11:2205-2220; Devereux et al., (1984) Nucl. Acids Res. 12:387-395; Feng et al., (1987) J. Molec. Evol. 25:351-360; Higgins et al., (1989) CABIOS 5:151-153; and Thompson et al., (1994) Nucl. Acids Res. 22:4673-4680. "Having at least X % homolgy"—with respect to two amino acid or nucleotide sequences, refers to the percentage of residues that are identical in the two sequences when the sequences are optimally aligned. Thus, 90% amino acid sequence identity means that 90% of the amino acids in two or more optimally aligned polypeptide sequences are identical.

An additional embodiment of the present invention concerns a pharmaceutical composition comprising an RTP801 inhibitor in a therapeutically affective amount as an active ingredient and a pharmaceutically acceptable carrier. The inhibitor may be a biological inhibitor, an organic molecule, a chemical molecule, etc. said pharmaceutical composition may comprise an RTP801 inhibitor which is a polynucleotide which comprises consecutive nucleotides having a sequence which is an antisense sequence to the sequence set forth in FIG. 1 (SEQ ID No: 1). Further, the RTP801 inhibitor may be a vector comprising these polynucleotides. Additionally, the RTP801 inhibitor may be a monoclonal antibody which specifically binds to an epitope comprising 4-25 amino acids set forth in FIG. 2 (SEQ ID No:2), or an RNA molecule which targets the RTP801 gene mRNA such as an siRNA molecule (optionally depicted in Tables A-D and in particular, siRNA Nos: 22, 23, 25, 27, 39, 41, 42, 49 and 50 of Table A or siRNA Nos: 257, 260-262, and 264-268 of Table D) or a ribozyme. The active ingredients of the pharmaceutical composition can include oligonucleotides that are nuclease resistant needed for the practice of the invention or a fragment thereof shown to have the same effect targeted against the appropriate sequence(s) and/or ribozymes. Combinations of active ingredients as disclosed in the present invention can be used, including combinations of antisense sequences.

An additional embodiment of the present invention provides for the use of a therapeutically effective dose of an RTP801 inhibitor for the preparation of a medicament for promoting recovery in a patient suffering from spinal cord disease or injury. In one embodiment the inhibitor is preferably an siRNA. In another embodiment the inhibitor is preferably Structure A depicted herein.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

BRIEF DESCRIPTION OF THE FIGURES

FIG. 1 details the coding sequence of the RTP801 gene (SEQ ID NO:1);

FIG. 2 details the amino acid sequence of the RTP801 polypeptide (SEQ ID NO:2);

FIG. 4A-H depict a panel of Western Blot analysis results obtained upon applying various double-stranded nucleic acids according to the present invention to a first human cell line, whereby the experiment was carried out twice, referred to as experiment 1 and experiment 2, and whereby the expression level of p110a and p85 is represented as loading controls and the intensity (density) of the RTP801 band is a measure for the inhibitory activity of the particular double-stranded nucleic acid applied;

FIG. 5A-F depict a panel of Western Blot analysis results obtained upon applying various double-stranded nucleic acids according to the present invention to a second human cell line, whereby the experiment was carried out twice, referred to as experiment 1 and experiment 2, and whereby the expression level of p110a and p85 is represented as loading controls and the density of the RTP801 band is a measure for the inhibitory activity of the particular double-stranded nucleic acid applied;

FIG. 7 depicts a panel of Western Blot analysis results obtained applying various double-stranded nucleic acids according to the present invention to a mouse cell line, whereby the experiment was carried out twice, referred to as experiment 1 and experiment 2, and whereby the expression level of p110a and p85 is represented as loading controls and the density of the RTP801 band is a measure for the inhibitory activity of the particular double-stranded nucleic acid applied;

FIG. 11A-B shows the results of additional experiments in a non-human primate AMD model system;

FIG. 12A-B shows the results of further additional experiments in a non-human primate AMD model system;

FIG. 13A-B represents an analysis of the experimental results achieved in a non-human primate AMD model;

FIG. 26 A-B shows additional results of experiments studying effect of RTP801 siRNA on gene expression in RPE and neural retina.

EXAMPLES

Figure 3:
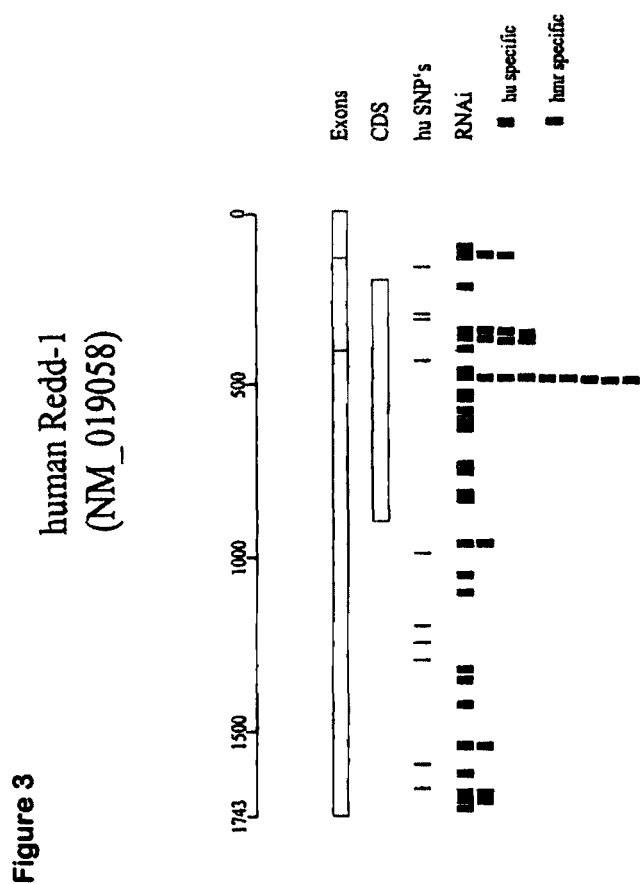
FIG. 3 is a diagram depicting the exons, CDS, human SNPs and the position of the various nucleic acid molecules which are either human specific or specific for human, mouse and rat in parallel.

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., *Molecular cloning: A laboratory manual*, Cold Springs Harbor Laboratory, New-York (1989, 1992), and in Ausubel et al., *Current Protocols in Molecular Biology*, John Wiley and Sons, Baltimore, Md. (1988).

Standard organic synthesis protocols known in the art not specifically described herein are generally followed essentially as in *Organic syntheses: Vol* 1-79, editors vary, J. Wiley, New York, (1941-2003); Gewert et al., *Organic synthesis workbook*, Wiley-VCH, Weinheim (2000); Smith & March, *Advanced Organic Chemistry*, Wiley-Interscience; 5th edition (2001).

Standard medicinal chemistry methods known in the art not specifically described herein are generally followed essentially as in the series "Comprehensive Medicinal Chemistry", by various authors and editors, published by Pergamon Press.

The features of the present invention disclosed in the specification, the claims and/or the drawings may both separately and in any combination thereof be material for realizing the invention in various forms thereof.

Example 1

General Materials and Methods

If not indicated to the contrary, the following materials and methods were used in Examples 1-5:

Cell Culture

The first human cell line, namely HeLa cells (American Type Culture Collection) were cultured as follows: Hela cells (American Type Culture Collection) were cultured as described in Czauderna F et al. (Czauderna, F., Fechtner, M., Aygun, H., Arnold, W., Klippel, A., Giese, K. & Kaufmann, J. (2003). Nucleic Acids Res, 31, 670-82).

The second human cell line was a human keratinozyte cell line which was cultivated as follows: Human keratinocytes were cultured at 37° C. in Dulbecco's modified Eagle medium (DMEM) containing 10% FCS.

The mouse cell line was B16V (American Type Culture Collection) cultured at 37° C. in Dulbecco's modified Eagle medium (DMEM) containing 10% FCS. Culture conditions were as described in Methods Find Exp Clin Pharmacol. 1997 May; 19(4):231-9:

In each case, the cells were subject to the experiments as described herein at a density of about 50,000 cells per well and the double-stranded nucleic acid according to the present invention was added at 20 nM, whereby the double-stranded nucleic acid was complexed using 1 μg/ml of a proprietary lipid.

Induction of Hypoxia-Like Condition

The cells were treated with $CoCl_2$ for inducing a hypoxia-like condition as follows: siRNA transfections were carried out in 10-cm plates (30-50% confluency) as described by (Czauderna et al., 2003; Kretschmer et al., 2003). Briefly, siRNA were transfected by adding a preformed 10× concentrated complex of GB and lipid in serum-free medium to cells in complete medium. The total transfection volume was 10 ml. The final lipid concentration was 1.0 μg/ml; the final siRNA concentration was 20 nM unless otherwise stated.

Induction of the hypoxic responses was carried out by adding CoCl$_2$ (100 μM) directly to the tissue culture medium 24 h before lysis.

Preparation of Cell Extracts and Immuno Blotting

The preparation of cell extracts and immuno blot analysis were carried out essentially as described by Klippel et al. (Klippel, A., Escobedo, M. A., Wachowicz, M. S., Apell, G., Brown, T. W., Giedlin, M. A., Kavanaugh, W. M. & Williams, L. T. (1998). Mol Cell Biol, 18, 5699-711; Klippel, A., Reinhard, C., Kavanaugh, W. M., Apell, G., Escobedo, M. A. & Williams, L. T. (1996). Mol Cell Biol, 16, 4117-27). Polyclonal antibodies against full length RTP801 were generated by immunising rabbits with recombinant RTP801 protein producing bacteria from pET19-b expression vector (Merck Biosciences GmbH, Schwalbach, Germany). The murine monoclonal anti-p110a and anti-p85 antibodies have been described by Klippel et al. (supra).

Example 2

Reduction of RTP801 Expression in a Lint Human Cell Line

Various double-stranded nucleic acids were prepared. Their location relative to the mRNA and CDS as well as human SNPs in the nucleic acid coding for human RTP801 (databank accession no. NM_019058) is depicted in FIG. 3. The first human cell line was contacted with said double-stranded nucleic acids as described in Example 1. Upon induction of a hypoxia-like condition and treatment with said double-stranded nucleic acids the cells were lysed and the cell lysates subjected to immunoblotting. p110a, which is a catalytic unit of the PI3-kinase, and p85 were used as loading controls. The intensity of the RTP801 band as visualised using the RTP801 polyclonal antibodies is a measure of the activity of the individual double-stranded nucleic acids in terms of reducing the expression level of RTP801.

Each and any of the double-stranded nucleic acids has been such modified such that a 2' O-Me group was present on the first, third, fifth, seventh, ninth, eleventh, thirteenth, fifteenth, seventeenth and nineteenth nucleotide of the antisense strand, whereby the very same modification, i.e. a 2'-O-Me group was present at the second, fourth, sixth, eighth, tenth, twelfth, fourteenth, sixteenth and eighteenth nucleotide of the sense strand. Additionally, it is to be noted that in case of these particular nucleic acids according to the present invention the first stretch is identical to the first strand and the second stretch is identical to the second strand and these nucleic acids are also blunt ended.

The experiments were performed twice and the individual results shown in FIGS. 4A to H, where they are designated as experiment 1 and experiment 2, respectively.

The representations h, hr and hmr in FIGS. 4A to H indicate that the respective double-stranded nucleic acid was designed such as to address a section of the RTP801 mRNA which is specific for human RTP801 mRNA (h), to address a section of the RTP801 mRNA which is specific for human and rat RTP801 mRNA (hr) and to address a section of the RTP801 mRNA which is specific for human, mouse and rat RTP801 mRNA (hmr). The double-stranded nucleic acid referred to as no. 40.1 was used as a positive control and untreated cells (UT+) were used as negative control.

In accordance with the results, the following double-stranded nucleic acids turned out to be particularly useful in down-regulating the expression of RTP801: no. 14, no. 15, no. 20, no. 21, no. 22, no. 23, no. 24, no. 25, no. 27, no. 39, no. 40, no. 41, no. 42, no. 43, no. 44, no. 49 and no. 50 (see Table A).

Example 3

Reduction of RTP801 Expression in a Second Human Cell Line

The experiments as described in connection with Example 2 were repeated using the second human cell line as specified in Example I and the results are depicted in FIGS. 5A to F.

As may be deduced from these figures, the results as obtained in connection with the experiments described in Example 2, were confirmed using this second human cell line.

Example 4

Dosage Effect of RTP801-Specific Double-Stranded Nucleic Acids

In this experiment, the dosage effect of RTP801-specific double-stranded nucleic acids was investigated.

For that purpose, the HeLa cells treated as in connection with Examples 2 and 3, whereby the concentration of double-stranded nucleic acid in the cultivation broth was 10 nM, 5 nM and 1 nM. As positive control, double-stranded nucleic acid no. 40.1 was used, as negative control untreated cells (UT+). The read out was the same as described in connection with Examples 2 and 3. The particular double-stranded nucleic acids used were those with internal reference numbers 14, 22, 23 and 27 which are directed to stretches on the RTP801 mRNA which are shared by humans, mice and rats, and double-stranded nucleic acid with internal reference numbers 39 and 42 which are directed to stretches of the RTP801 mRNA specific for human RTP801.

Figure 6:
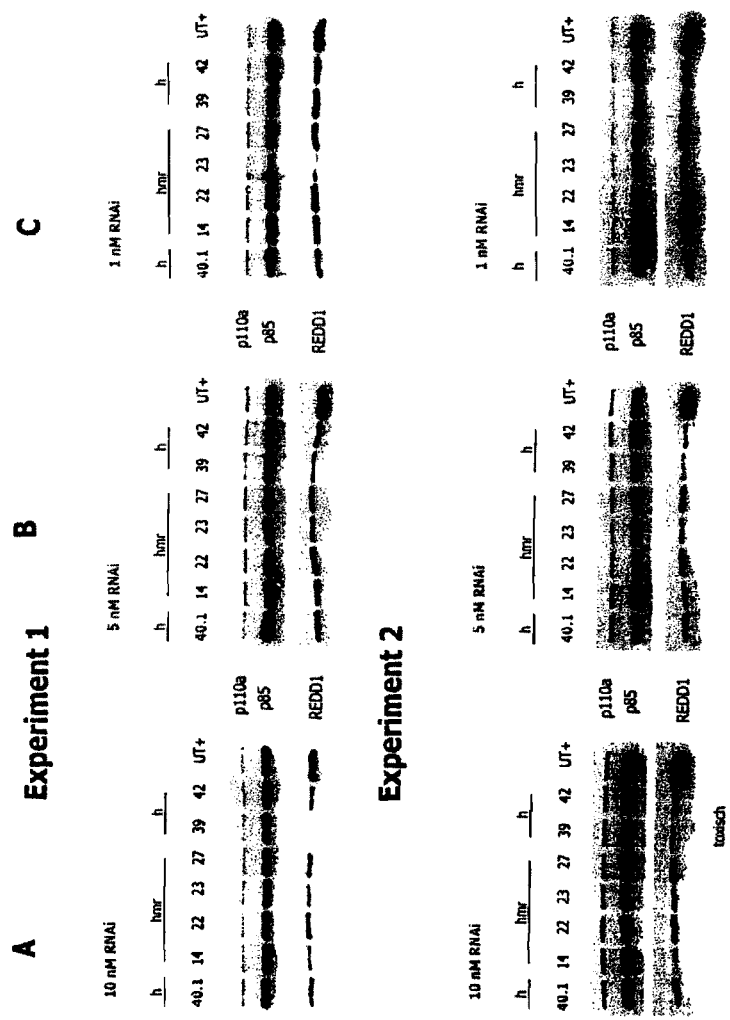
FIG. 6A-C depict a panel of Western Blot analysis results obtained upon applying various double-stranded nucleic acids according to the present invention to the first human cell line at different concentrations, namely 10 nM (5A), 5 nM (5B) and 1 nM (5C), whereby the experiment was carried out twice, referred to as experiment 1 and experiment 2, and whereby the expression level of p110a and p85 is represented as loading controls and the density of the RTP801 band is a measure for the inhibitory activity of the particular double-stranded nucleic acid applied.

The results are shown in FIG. 6A to C. From said figures it can be taken that there is a clear concentration dependency of the effect of the double-stranded nucleic acids specific for RTP801, whereby the nucleic acid molecules having internal reference numbers 1, 15, 20, 21, 24, 40, 41, 43, 44, 22, 23, 27, 39, 42, 40.1, 44.1, and 14, preferably 22, 23, 27, 39, 42, 40.1 and 44.1 and more preferably 14, 23 and 27 and preferably each of said nucleic acid molecule having the particular modification pattern as described for them in the example part herein are particularly effective Example 5

Species Specificity of the RTP801-Specific Double-Stranded Nucleic Acid

The double-stranded nucleic acids according to the present invention have been designed against stretches of the RTP801 mRNA which are the same or different in various species. To test whether there is a species specificity of a RTP801-specific double-stranded nucleic acid, the double-stranded nucleic acids with internal reference numbers 14, 22, 23 and 27 which address a stretch of the RTP801 mRNA which is conserved among human, mouse and rat RTP801 mRNA, and the double-stranded nucleic acids with internal reference numbers 39 and 42 which address a stretch of the RTP801 mRNA which is specific for human RTP801 mRNA, i.e. which addresses a stretch which as such is not present in mouse or rat, were compared in terms of down-regulating RTP801 using the same approach and read-out as specified in Examples 1 and 2.

Although all of the double-stranded nucleic acids used are in principle active against human mRNA and, as shown in the preceding examples, are also suitable to down-regulate the expression of RTP801, upon using a mouse cell line only those double-stranded nucleic acids which are also specific for mouse RTP801 mRNA effectively reduced RTP801 expression, namely double-stranded nucleic acids nos. 14, 22, 23 and 27.

From this result it can be concluded that it is possible to design RTP801 addressing double-stranded nucleic acids which are specific for one or several species. This allows use of the very same molecule in animal models as well as in man.

Example 6

Experimental Models, Methods and Results Relating to Macular Degeneration

The compounds of the present invention were tested in the following an animal model of Choroidal neovascularization (CNV). This hallmark of wet AMD is induced in model animals by laser treatment.

A) Mouse Model

Choroidal Neovascularization (CNV) Induction

Choroid neovascularization (CNV), a hallmark of wet AMD, was triggered by laser photocoagulation (532 nm, 200 mW, 100 ms, 75 μm) (OcuLight GL, Irides, Mountain View, Calif.) performed on both eyes of each mouse on day 0 by a single individual masked to drug group assignment. Laser spots were applied in a standardized fashion around the optic nerve, using a slit lamp delivery system and a cover slip as a contact lens.

Treatment Groups

CNV was induced in the following groups of mice (males 6-8 weeks of age):
(1) 12 WT mice;
(2) 12 RTP801 Knock-Out mice;
(3) 12 WT mice injected with 0.25 μg of synthetic stabilized active anti-RTP801 siRNA (REDD14) in one eye and inactive anti-RTP801 siRNA (REDD8—negative control) in the fellow eye, at days 0 and 7;
(4) 12 WT mice injected with 0.25 μg of synthetic stabilized active anti-RTP801 siRNA (REDD14) in one eye and inactive anti-GFP siRNA (negative control) in the fellow eye at days 0 and 7;
(5) 12 WT mice injected with either 0.1 μg of synthetic stabilized active anti-RTP801 siRNA (REDD14) in one eye and PBS (negative control) in the fellow eye at days 0 and 7;
(6) 12 WT mice injected with either 0.05 μg of synthetic stabilized active anti-RTP801 siRNA (REDD14) in one eye and PBS (negative control) in the fellow eye at days 0 and 7.

Both eyes of each mouse were laser-treated. The volume injected was 2 μl.

Evaluation
1. The experiment was terminated at day 14. For evaluation, the eyes were enucleated and fixed with 4% paraformaldehyde for 30 min at 4° C. The neurosensory retina was detached and severed from the optic nerve. The remaining RPE-choroid-sclera complex was flat mounted in Immu-Mount (Vectashield Mounting Medium, Vector) and coverslipped. Flat mounts were examined with a scanning laser confocal microscope (TCS SP, Leica, Germany). Vessels were visualized by exciting with blue argon laser. Horizontal optical sections (1 μm step) were obtained from the surface of the RPE-choroid-sclera complex. The deepest focal plane in which the surrounding choroidal vascular network connecting to the lesion could be identified was judged to be the floor of the lesion. Any vessel in the laser treated area and superficial to this reference plane was judged as CNV. Images of each section were digitally stored. The area of CNV-related fluorescence was measured by computerized image analysis using the Leica TCS SP software. The summation of whole fluorescent area in each horizontal section was used as an index for the volume of CNV.
2. Separate WT mice (5 eyes per group) were used for evaluating RTP801 mRNA expression in CNV (as well as the expression of other genes relevant to AMD) (untreated and treated with siRNA) using real-time PCR on RNA extracted from RPE/choroids, or from neural retina.

Figure 8:
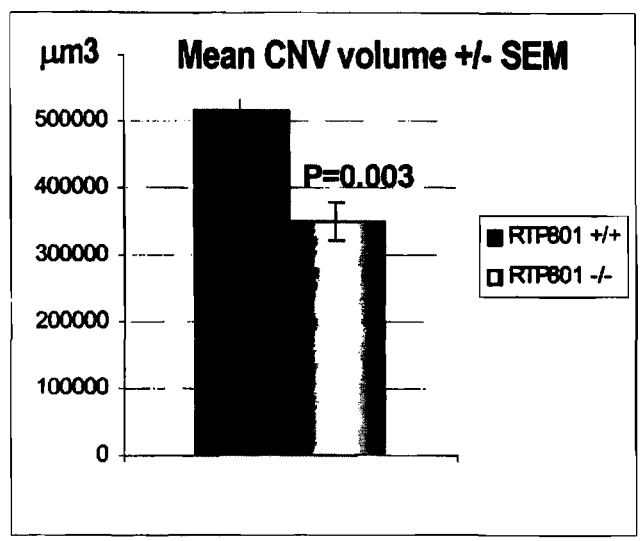
FIG. 8 shows the results of experiments in a mouse AMD model system.
Figure 9:
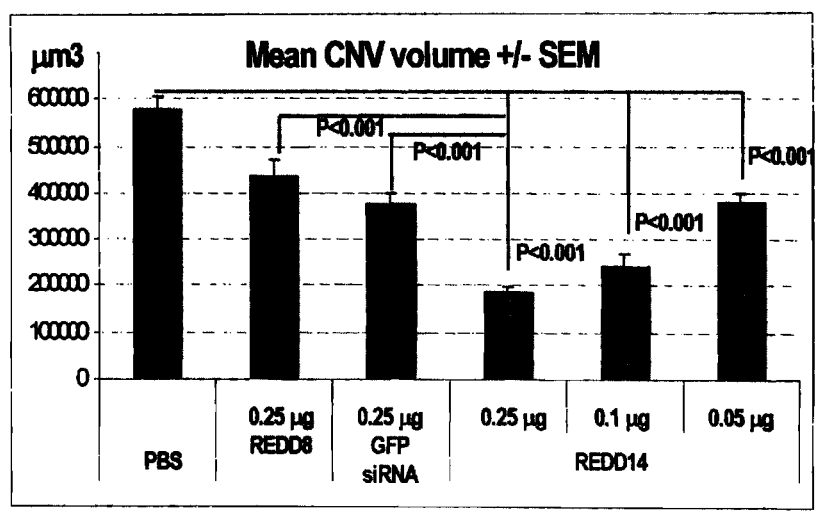
FIG. 9 shows the results of additional experiments in a mouse AMD model system.

Results
1. RTP801 KO mice displayed 30% less blood vessel leakage compared to WT mice following CNV induction; see FIG. 8.
2. Synthetic stabilized siRNA against RTP801, REDD14, elicited a dose-dependent reduction of the CNV volume. A maximum of ~70% inhibition compared to PBS-injected eyes was achieved at a REDD14 (sequence No. 14 in Table A, SEQ ID No.s 16 (sense) and 66 (antisense)) dose of 0.25 ug per eye. At the same dose, both negative control siRNAs, REDD8 and anti-GFP siRNA, displayed only 27% and 33% CNV volume reduction respectively, supporting both the superior efficacy of REDD14 and also the specificity of its effect.

B) Non-Human Primate Model

CNV Induction

Eight male cynomolgus monkeys (*Macaca fascicularis*) 2-6 years of age were used for the study. Choroidal neovascularization (CNV) was induced by perimacular laser treatment of both eyes prior to dose administration. Nine lesions were placed in the macula with a laser [OcuLight GL (532 nm) Laser Photo-coagulator with an IRIS Medical® Portable Slit Lamp Adaptor], and laser spots in the right eye were mirror the placement in the left eye. The approximate laser parameters were as follows: spot size: 50-100 μm diameter; laser power: 300-700 milliwatts; exposure time: 0.1 seconds.

Treatment

Immediately following laser treatment, both eyes of all animals were subjected to a single intravitreal injection. Left eye was dosed with 350 ug of synthetic stabilized siRNA against RTP801 (the same one used in the mouse study) in the final volume of 50 ul, whereas the contralateral eye received 50 ul of PBS (vehicle).

Evaluation
1. All the animals were subjected to daily examination of food consumption and body weight measurements.
2. 2 monkeys were euthanized at day 6 following CNV induction. Their eyes were enucleated and posterior pole was flattened. Then the fovea region was excised and separated into choroids and neuroretina which were separately (for every animal) frozen in liquid nitrogen to be subsequently used for RNA extraction and real time PCR evaluation of RTP801 expression.
3. Fluorescein angiograms were performed pre-study, and at the end of weeks 1, 2, and 3 following CNV induction. Photographs were taken, using a fundus camera (TRC-50EX Retina Camera). Images were captured using the TOPCON IMAGEnet™ system. Fluorescein dye (10% fluorescein sodium, approximately 0.1 mL/kg) was injected via vascular access ports. Photographs were taken at several timepoints following dye injection, to include the arterial phase, early arteriovenous phase and several late arteriovenous phases in order to evaluate neovascularization and to monitor leakage of fluorescein associated with CNV lesions. Interpretation and analysis of the fluorescein angiograms was independently conducted by two ophthalmologists.

Neovascularization (NV) was assessed in early angiograms and every spot was graded according to the following scheme:
0—no signs of NV
0.5—suspicious spot
1—"hot" spot
2—NV in the laser burn
3—evident NV Leakage was assessed according to the following scheme:
0—no leakage
0.5—suspicious spot
1—evident small spot leakage
2—leakage growing with time
3—leakage greater than previous borders (evidently)

In addition, the size of every spot was compared between the early and the late angiograms using morphometric measurements, and the increase in the spot's size resulting from the leakage was calculated.

4. Electroretinograms (ERGs) were recorded using an Epic 2000 electroretinograph according to Sierra's SOPs and the study-specific SOP, including the use of the Ganzfield apparatus, at prestudy and in the end of week 3 The tabulated ERG data were evaluated by a veterinary ophthalmologist.

The study was terminated at day 21 post CNV induction. Gross necropsy and histological examination were performed on organs and tissues including the eyes.

Figure 10:
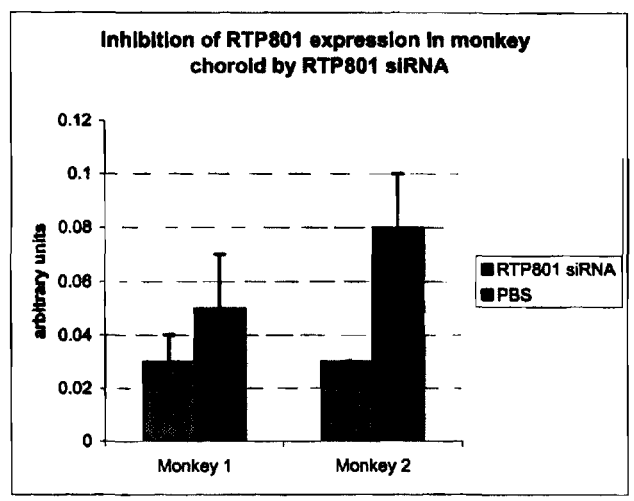
FIG. 10 shows the results of experiments in a non-human primate AMD model system.

Results 1. siRNA against RTP801 reduced RTP801 expression in the RPE/choroids of laser-treated animals, as measured at day 6 post CNV induction by real-time PCR (see FIG. 10).
2. Comparison of the spot grading for leakage and neovascularization between the fellow eyes in each individual monkey revealed that both of these pathological characteristics were diminished in the eyes injected with RTP801 siRNA as compared to the control (for leakage results, see FIG. 11; for neovascularization results, see FIG. 12).
3. Calculation of the overall number of spots with higher clinically-relevant grades (2 and 3) of leakage or neovascularization in all siRNA-injected eyes compared to all PBS-injected eyes again revealed that siRNA injected eyes were less affected (see FIG. 13, a+b).
4. The overall grading data for leakage of spots and neovascularisation was subjected to statistical evaluation. The existence of differences between the siRNA and control treatments was analyzed by calculating the delta between the mean spot ranks of the control right (R) eye and siRNA-injected left (L) eye (delta=R−L). The significance of the difference was calculated using a non-parametric statistical method, Wilcoxon signed ranks test—a one tail test. Different phases of angiograms (early arterial, arteriovenous and late venous) were analyzed separately for every week (1, 2, and 3).

Table 2 shows the significance (one tail test) of leakage rank difference from 0 for each group (p-values<0.05 are underlined). A significant leakage rank reduction was found in the left eyes (siRNA treated) with respect to the right (Placebo treated) in week 2 and 3 in the late angiograms.

TABLE 2

| Leakage | | P-Value Wilcoxon Signed Rank |
|---|---|---|
| Angiograms | Week | Test |
| Early | 1 | 0.2500 |
|  | 2 | 0.5000 |
|  | 3 | 0.5000 |
| Arterio-Venus | 1 | 0.3438 |
|  | 2 | 0.1250 |
|  | 3 | 0.2344 |
| Late | 1 | 0.1250 |
|  | 2 | 0.0313 |
|  | 3 | 0.0156 |

Note that late angiograms are usually utilized for evaluation of leakage parameters.

Table 3 shows the significance (one tail test) of neovascularization (NV) rank difference from 0 for each group (p-values<0.05 are underlined).

TABLE 3

| NV | | P-Value Wilcoxon Signed Rank |
|---|---|---|
| Angiograms | Week | Test |
| Early | 1 | 0.0781 |
|  | 2 | 0.0313 |
|  | 3 | 0.0313 |
| Arterio Venus | 1 | 0.0625 |
|  | 2 | 0.0313 |
|  | 3 | 0.1563 |
| Late | 1 | 0.2500 |
|  | 2 | 0.3438 |
|  | 3 | 0.2500 |

A significant NV rank reduction was found in the left eyes with respect to the right in week 2 and 3 in the early period and in the Arterio Venus period in week 2.

Note that early angiograms are usually utilized for evaluation of neovascularization parameters.

Figure 14:
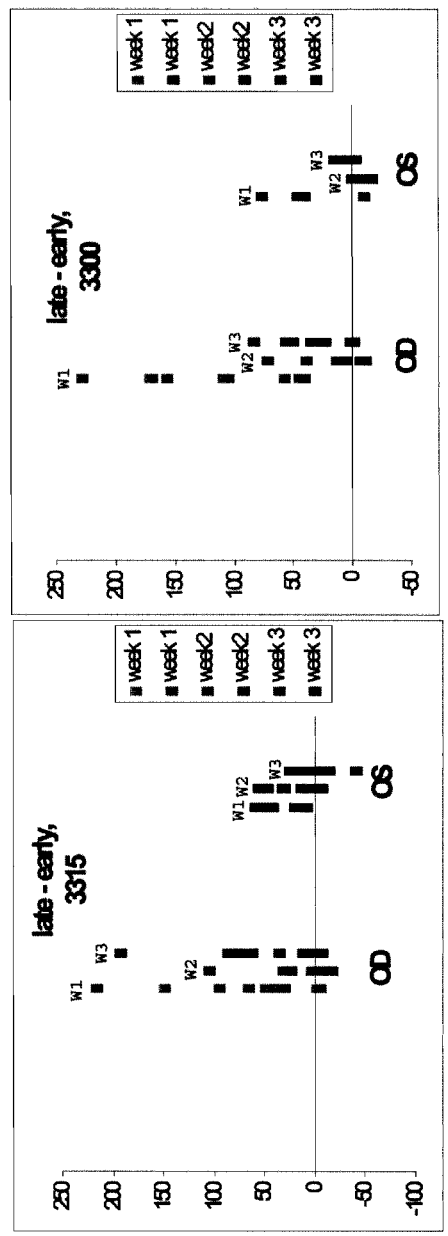
FIG. 14 represents an additional analysis of the experimental results achieved in a non-human primate AMD model.

5. Quantitative morphometric evaluation of the increase in area of the spots occurring between early (arterial phase) and late (venous phase) angiograms due to the leakage revealed that this parameter was significantly reduced in the laser spots within siRNA-injected eyes (left eyes, OS) compared to control (right eyes, OD). Two examples are shown in FIG. 14. The graphs demonstrate the relative increase (in %) in the area of every spot in the left and right eye of animals #3315 and 3300.

Additionally, it was noted throughout all the above studies that anti RTP-801 siRNA had no adverse effects on electroretinograms (ERG), on eye histology or on structure and function of other organs and systems.

To Summarize the Above Experiments and Results:
1. Both genetic (RTP801−/−) and therapeutic siRNA inhibition of RTP801 expression in the laser-induced CNV model of wet age-related macular degeneration (wet AMD) result in significant reduction of the CNV volume.
2. Positive results were obtained in mouse and non-human primate model.
3. Pathological and ERG examination in monkey did not reveal any siRNA-mediated toxicity either in eyes or in any other organs or systems.

C) Efficacy of Combination Therapy of RTP801 siRNA (REDD14) and Anti-VEGF Antibody The efficacy of combination therapy of RTP801 siRNA (REDD14) and anti-VEGF antibody in the treatment of diseases in which CNV occurs was tested in the above mouse CNV model.

A) CNV Volume Studies

The volume of choroidal neovascularization (CNV) 3 weeks after laser injury was computed byconfocal fluorescence microscopy as previously described (Sakurai et al. *IOVS* 2003; 44: 3578-85 & Sakurai et al. *IOVS* 2003; 44: 2743-2749).

In previous studies it was found that anti-VEGF-A antibody (Ab) reduced CNV volume in a dose dependent fashion. A dose of 1 ng of VEGF-A Ab was chosen for the REDD14+ VEGF-A Ab combination studies because this dose had an intermediate inhibitory effect: VEGF-A Ab (1 ng) reduced the size of CNV by 26±6%.

The principal findings of the REDD14+VEGF-A antibody (Ab) study are:
  The addition of REDD14 at the lower 0.05 μg dose reduced the size of CNV by 27±4% compared to VEGF-A Ab alone.
  The addition of REDD14 at the higher 0.25 μg dose reduced the size of CNV by 55±3% compared to VEGF-A Ab alone.

B) CNV Leakage Studies

Experiment 1

This experiment was designed in order to identify a potential additive or synergistic therapeutic effect of inhibition of VEGF and RTP801 in the model of laser-induced choroid neovascularization in mice Materials:
  REDD14 (RTP801 siRNA)
  REDD8 (negative control)
  Anti-VEGF antibodies
  Non-specific IgG (negative control)

CNV was induced on day zero as described above; the test material was injected to the subjects on day zero and day 7.

The results were evaluated by Fluorescein angiography on weeks 1, 2, 3, and by CNV volume measurement on week 3. Each test group was composed of 10 eyes.

Figure 23:
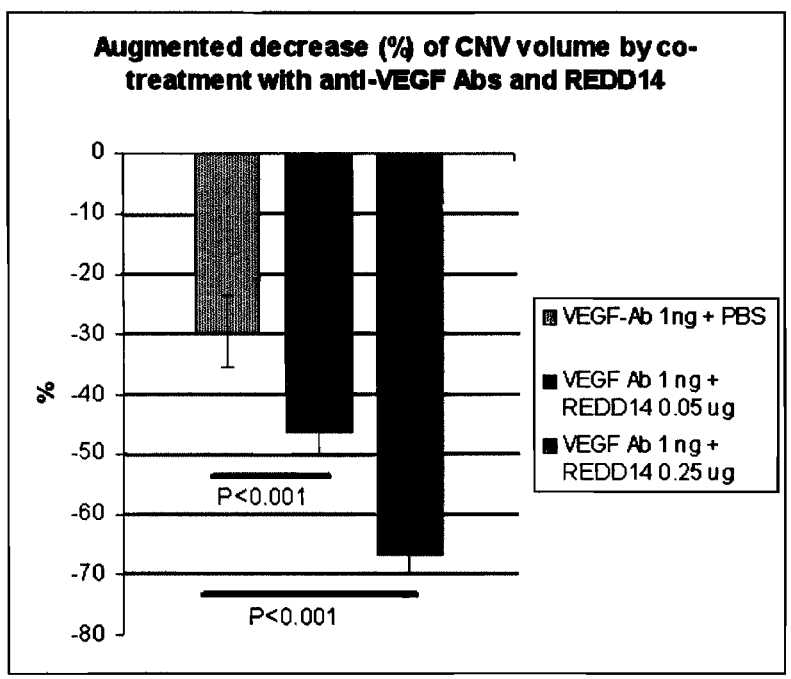
FIG. 23 shows the results of combined RTP801/VEGF inhibition experiments in a mouse CNV model system.
Figure 24:
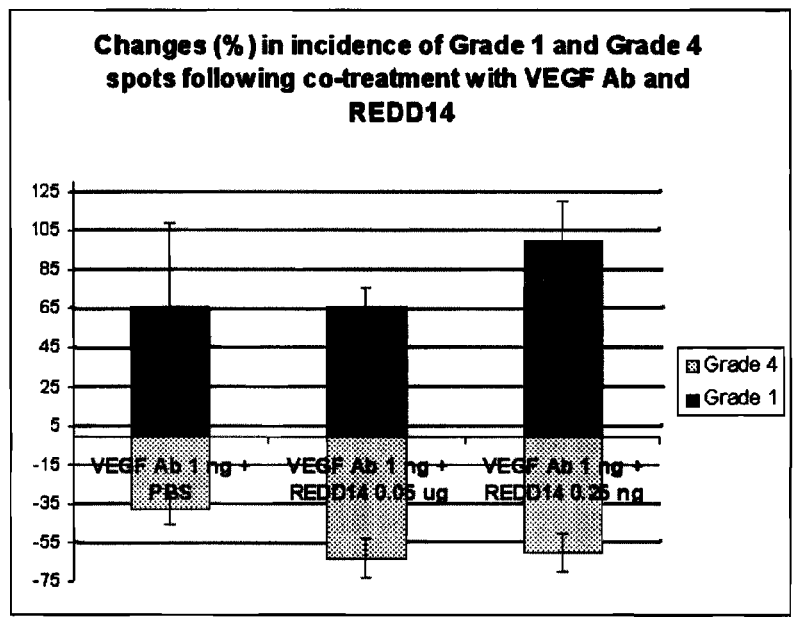
FIG. 24 shows the results of additional combined RTP801/VEGF inhibition experiments in a mouse CNV model system.

Experimental groups:
  VEGF Ab 0.5 ng/eye
  VEGF Ab 1 ng/eye
  VEGF Ab 2 ng/eye
  VEGF Ab 4 ng/eye
  REDD14 0.05 ug/eye
  REDD14 0.1 ug/eye
  REDD14 0.25 ug/eye
  REDD14 0.05 ug/eye+VEGF Ab 1 ng/eye
  REDD14 0.1 ug/eye+VEGF Ab 1 ng/eye
  REDD14 0.25 ug/eye+VEGF Ab 1 ng/eye Control groups
  PBS
  Non-specific IgG 2 ng/eye
  REDD8 0.1 ug/eye
  REDD8 0.1 ug/eye+VEGF Ab 1 ng/eye Results The results of the above experiment are presented in FIGS. 23-24. These results show that simultaneous intravitreal administration of VEGF Ab and REDD14 leads to augmented and dose-dependent inhibition of Choroid neovascularization and Choroid blood vessel leakage, as expressed in reduced incidence of Grade 4 spots and increased incidence of Grade 1 spots. Angiograms were graded using a modification of a semi-quantitative grading (1-4) scheme previously published (Sakurai et al. *IOVS* 2003; 44: 2743-2749). Grade 1 lesions are considered as never having formed, i.e., equivalent to complete prevention. Grade 4 lesions are considered pathologically significant, i.e., equivalent to lesions that would be treated in patients. VEGF-A Ab (1 ng) reduced the incidence of Grade 4 lesions per eye by 38+8% and increased the incidence of Grade 1 lesions per eye by 66+43%.

The principal findings of the REDD14+VEGF-A Ab combination leakage study are:
  The addition of REDD14 at the lower 0.05 μg dose reduced the incidence of Grade 4 lesions by 66±12% compared to VEGF-A Ab alone.
  The addition of REDD14 at the higher 0.25 μg dose reduced the incidence of Grade 4 lesions by 60+12% compared to VEGF-A Ab alone.
  The addition of REDD14 at the higher 0.25 μg dose doubled (100±34%) the incidence of Grade 1 lesions compared to VEGF-A Ab alone.

Experiment 2

This experiment was designed in order to study the effect of REDD14 on gene expression in RPE and neural retina.

Experimental Design

Groups:
  PBS
  REDD14 0.25 mg

The Group size was 5 eyes. CNV was induced by laser treatment as described above on day zero; the test material was also injected on day zero, and the effect evaluated by qPCR analysis of gene expression in RPE and neural retina on days zero and 5.

Results

Figure 25:
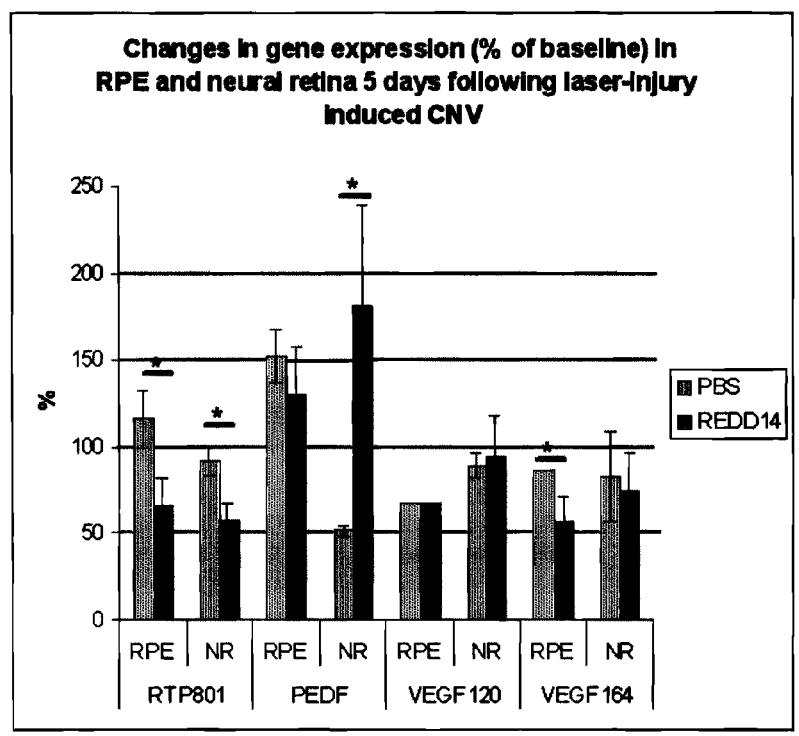
FIG. 25 shows the results of experiments studying effect of RTP801 siRNA on gene expression in RPE and neural retina.

The results of the above experiment are presented in FIG. 25. These results show that the administration of REDD14 causes:
  ~40% downregulation of RTP801 expression below the baseline both in RPE and in neural retina (see also FIG. 26);
  ~70% upregulation of PEDF expression over the baseline in neural retina (note: in PBS-injected eyes expression of PEDF is 40% downregulated below the baseline)
  ~40% downregulation of VEGF164 expression below the baseline in RPE (note: in PBS-injected eyes, expression of VEGF164 is 20% down-regulated)
  ~50% reduction of MCP1 expression in RPE/choroids (FIG. 26)

General Conclusions from Both Experiments:
  Simultaneous inhibition of RTP801 and VEGF has enhanced inhibitory effect on choroid neovascularization and neovascular leakage.
  Inhibition of RTP801 expression by REDD14 not only prevents PEDF downregulation in the CNV model but enhances its expression compared to the baseline.
  Inhibition of RTP801 expression leads to concomitant downregulation of MCP1 which should have an anti-inflammatory effect.
  Without being bound by theory, the increase of PEDF expression by REDD14 may underlie the observed cooperative effect of simultaneous inhibition of VEGF and RTP801. (PEDF is a well-known antiangiogenic and neuroprotective factor.)
  Without being bound by theory, the reduction of MCP1 expression by REDD14 may also underlie the observed cooperative effect of simultaneous inhibition of VEGF and RTP801. (MCP1 is a known pro-inflammatory chemokine involved in pathogenesis of AMD.)

Additional AMD models which may be used to test the methods of the present invention:

Ccl-2 or Ccr-2 deficient animals—deficiency in either of these proteins causes the development of some of the main features of AMD. Animals deficient in these proteins can be used to test the methods of the present invention.

For further information on AMD animal models, see: Chader, *Vision research* 42 (2002) 393-399; Ambati et al., *Nature Medicine* 9(11) (2003) 1390-1397; Tolentino et al., *Retina* 24 (2004) 132-138.

D) Comparison of Activity of REDD14 Anti RTP801 siRNA Possessing a 3' Phosphate Group on Each Strand with the Same Molecule Lacking 3' Phosphates (REDD14NP) in the Laser-Induced CNV Model.

The experiment was generally performed and evaluated as described above. One eye of each mouse (12 per group) was injected with 0.25 ug of REDD14 siRNA whereas another eye was injected with REDD14NP siRNA.

Results

Figure 27:
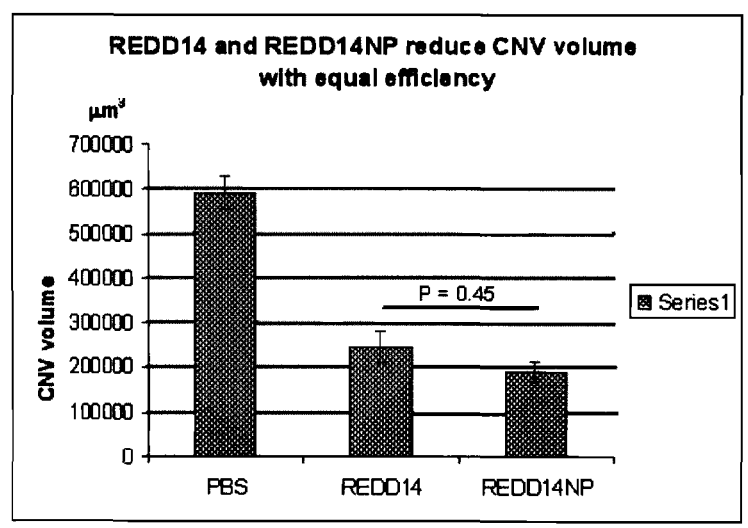
FIG. 27 shows the results of experiments demonstrating that RT801NP is as active as RTP801.

Both siRNAs equally efficiently reduced CNV volume (FIG. 27).

Example 7

Models and Results Relating to COPD and Emphysema

The compounds of the present invention were tested in the following an animal models:

Cigarette smoke-induced emphysema model: chronic exposure to cigarette smoke causes emphysema in several animals such as, inter alia, mouse, guinea pig.

Lung protease activity as a trigger of emphysema.

VEGFR inhibition model of emphysema.

Bronchial instillation with human neutrophil/pancreatic elastase in rodents.

MMP (matrix metalloprotease)-induced emphysema.

Inflammation-induced emphysema.

Additionally, emphysema models may be generated through genetic means (e.g., mice carrying the TSK mutation), and emphysematous animals may be generated by known modifiers of susceptibility to emphysema such as, inter alia, lung injury, alveolar hypoplasia, hyperoxia, glucocorticoid treatment and nutrition.

A. Evaluation of the Influence of Lack of RTP801 on Disease Development in Mouse Models of Emphysema (Using RTP801 Knockout Mice)

(1) Cigarette smoking (CS) induced inflammation and apoptosis is initiated in 5

RTP801 KO and 5 control wild type 4 months old male mice. The mice are subjected to intense CS (as described in Rangasamy et al., see above) for 7 days. KO and WT non-treated mice from the VEGFR inhibition experiment above can also serve as non-treated control groups for this experiment. The lungs are subsequently agarose-inflated, fixed and imbedded in paraffin, and development oxidative stress in the KO mice is assessed by:
 a) immunohistochemical localization and quantitation of 8-oxo-dG in the lung sections;
 b) immunohistochemical localization and quantitation of active caspase 3 in the lung sections using specific antibodies, or quantitative evaluation of the number of TUNEL-positive cells;
 c) measurement of ceramide concentration in the lung extracts;
 d) measurement of caspase activity in the lung extracts.

(2) Long-term cigarette smoking in the KO mice.

6 KO and 6 age-matched WT female mice were subjected to intense cigarette smoking (5 hrs a day) during a period of 6 months. The mice were then sacrificed, and average intersepal diameter (a parameter of emphysema development) was evaluated using a morphometric approach.

B. Evaluation of the Influence of Lack of RTP801 on Disease Progression in Mouse Models of Emphysema by Inhibiting Endogenous RTP801 Employing Intralung Delivery RTP801-Inactivating siRNA CS-induced inflammation was induced by 7 day smoking in 2 groups of C57BL6 mice, 10 mice per group. Group 1: CS+delivery of control siRNA (REDD8) siRNA; Group 2: CS+RTP801 siRNA (REDD14). Control groups of mice were instilled with either type of siRNA but kept in room air conditions. The animals were evaluated as in the above experiment with the Knock-Out mice.

Methods

Exposure to Cigarette Smoking (CS)

Exposure is carried out (7 h/day, 7 days/week) by burning 2R4F reference cigarettes (2.45 mg nicotine per cigarette; purchased from the Tobacco Research Institute, University of Kentucky, Lexington, Ky., USA) using a smoking machine (Model TE-10, Teague Enterprises, Davis, Calif., USA). Each smoldering cigarette was puffed for 2 s, once every minute for a total of eight puffs, at a flow rate of 1.05 L/min, to provide a standard puff of 35 cm$^3$. The smoke machine is adjusted to produce a mixture of sidestream smoke (89%) and mainstream smoke (11%) by burning five cigarettes at one time. Chamber atmosphere is monitored for total suspended particulates and carbon monoxide, with concentrations of 90 mg/m3 and 350 ppm, respectively.

Morphologic and Morphometric Analyses

After exposing the mice to CS or instillation of RTP801 expressing plasmid, the mice are anesthetized with halothane and the lungs are inflated with 0.5% low-melting agarose at a constant pressure of 25 cm as previously described[6]. The inflated lungs are fixed in 10% buffered formalin and embedded in paraffin. Sections (5 µm) are stained with hematoxylin and eosin. Mean alveolar diameter, alveolar length, and mean linear intercepts are determined by computer-assisted morphometry with the Image Pro Plus software (Media Cybernetics, Silver Spring, Md., USA). The lung sections in each group are coded and representative images (15 per lung section) are acquired by an investigator masked to the identity of the slides, with a Nikon E800 microscope, 20× lens.

Bronchoalveolar Lavage (BAL) and Phenotyping

Following exposure to CS or instillation of RTP801 expressing plasmid, the mice are anesthetized with sodium pentobarbital. The BAL fluid collected from the lungs of the mice is centrifuged (500 g at 4° C.), and the cell pellet is resuspended in phosphate-buffered saline. The total number of cells in the lavage fluid is determined, and 2×104 cells are cytocentrifuged (Shandon Southern Products, Pittsburgh, Pa., USA) onto glass slides and stained with Wright-Giemsa stain. Differential cell counts are performed on 300 cells, according to standard cytologic techniques.

Identification of Alveolar Apoptotic Cell Populations in the Lungs.

To identify the different alveolar cell types undergoing apoptosis in the lungs, an immunohistochemical staining of active caspase 3 is performed in the lung sections from the room air (RA) as well as CS exposed mice. To identify the apoptotic type II epithelial cells in the lungs, after active caspase 3 labeling, the lung sections are incubated first with anti-mouse surfactant protein C (SpC) antibody and then with an anti-rabbit Texas red antibody. Apoptotic endothelial cells are identified by incubating the sections first with the anti-mouse CD 31 antibody and then with the biotinylated rabbit anti-mouse secondary antibody. The lung sections are rinsed in PBS and then incubated with the streptavidin-Texas red conjugated complex. The apoptotic macrophages in the lungs are identified by incubating the sections first with the rat anti-mouse Mac-3 antibody and then with the anti-rat Texas red antibody. Finally, DAPI is applied to all lung sections, incubated for 5 minutes, washed and mounted with Vectashield HardSet mounting medium. DAPI and fluorescein are visualized at 330-380 nm and 465-495 nm, respectively. Images of the lung sections are acquired with the Nikon E800 microscope, 40× lens.

Immunohistochemical Localization of Active Caspase-3

Immunohistochemical staining of active caspase-3 assay is performed using anti-active caspase-3 antibody and the active caspase-3-positive cells are counted with a macro, using Image Pro Plus program. The counts are normalized by the sum of the alveolar profiles herein named as alveolar length and expressed in µm. Alveolar length correlates inversely with mean linear intercept, i.e., as the alveolar septa are destroyed, mean linear intercepts increases as total alveolar length, i.e., total alveolar septal length decreases.

Caspase 3 Activity Assay

The caspase-3/7 activity is measured in lung tissue extracts using a fluorometric assay according to the manufacturer's instructions. Snap-frozen lung tissue (n=3 per group) was homogenized with the assay buffer, followed by sonication and centrifugation at 800×g. After removal of nuclei and cellular debris, the supernatant (300 µg protein) is then incubated with the pro-fluorescent substrate at room temperature for 1 h and the fluorescence intensity was measured utilizing a Typhoon phosphoimager (Amersham Biosciences, Inc., Piscataway, N.J., USA). The results are expressed as the rate of specific caspase-3 substrate cleavage, expressed in units of caspase 3 enzymatic activity, normalized by total protein concentration. Active recombinant caspase 3 was utilized as the assay standard (0-4 U). Tissue lysates without substrate, assay buffer alone, and lysates with caspase 3 inhibitor were utilized as negative controls.

Immunohistochemical Localization of 8-oxo-dG

For the immunohistochemical localization and quantification of 8-oxo-dG, lung sections from the mice exposed to CS or instilled with RTP801 expressing plasmid are incubated with anti-8-oxo-dG antibody and stained using InnoGenex™ Iso-IHC DAB kit using mouse antibodies. The 8-oxo-dG-positive cells are counted with a macro (using Image Pro Plus), and the counts were normalized by alveolar length as described.

Instillation of Plasmid DNA into Mouse Lungs

Plasmid DNA of RTP801 expressing and control vectors were prepared using an endotoxin-free DNA isolation kit. For intra-tracheal instillation, 50 ug of plasmid DNA is delivered in 80 ul sterile perfluorocarbon. The oxygen carrying properties of perfluorocarbon make it well-tolerated at these volumes, while its physical-chemical properties allow for extremely efficient distal lung delivery when instilled intratracheally. Mice are anesthetized by brief inhalational halothane exposure, the tongue is gently pulled forward by forceps and the trachea instilled with perfluorocarbon solution applied at the base of the tongue via a blunt angiocatheter.

Instillation of siRNA into Mouse Lungs.

Mice are anesthetized with an intra-peritoneal injection of Ketamine/Xylazine (115/22 mg/kg). 50 µg of siRNA is instilled intranasally in 50 µl volume of 0.9% NaCl by delivering five consecutive 10 µl portions. At the end of the intra-nasal instillation, the mouse's head is held straight up for 1 minute to ensure that all the instilled solution drains inside.

For further information, see: Rangasamy T, Cho CY, Thimmulappa, R K, Zhen L, Srisuma S S, Kensler T W, Yamamoto M, Petrache I, Tuder R M, Biswal S. *Genetic ablation of Nrf2 enhances susceptibility to cigarette smoke-induced emphysema in mice*. Submitted to Journal of Clinical Investigation; Yasunori Kasahara, Rubin M. Tuder, Carlyne D. Cool, David A. Lynch, Sonia C. Flores, and Norbert F. Voelkel. *Endothelial Cell Death and Decreased Expression of Vascular Endothelial Growth Factor and Vascular Endothelial Growth Factor Receptor 2 in Emphysema*. Am J Respir Crit. Care Med Vol 163. pp 737-744, 2001; Yasunori Kasahara, Rubin M. Tuder, Laimute Taraseviciene-Stewart, Timothy D. Le Cras, Steven Abman, Peter K. Hirth, Johannes Waltenberger, and Norbert F. Voelkel. *Inhibition of VEGF receptors causes lung cell apoptosis and emphysema*. J. Clin. Invest. 106:1311-1319 (2000); and a review on the topic: Robin M. Tuder, Sharon McGrath and Enid Neptune, *The pathological mechanisms of emphysema models: what do they have in common?*, Pulmonary Pharmacology & Therpaeutics 2002.

Results

Figure 15:
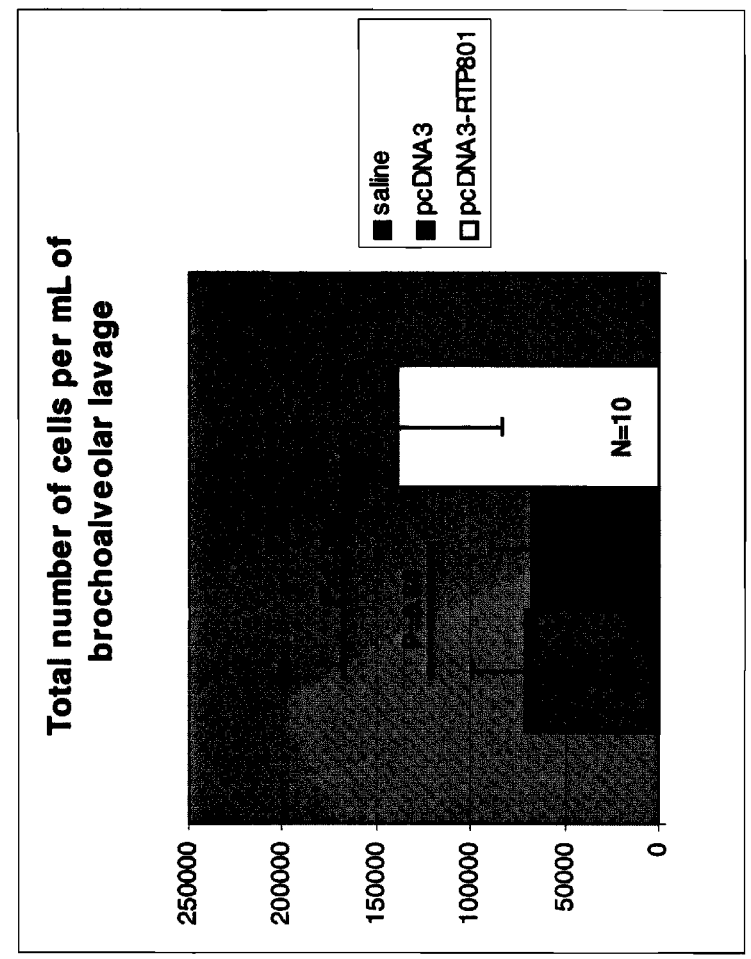
FIG. 15 A-C shows the results of an experiment involving the intratracheal instillation of an RTP801 expressing plasmid into mice.
Figure 15:
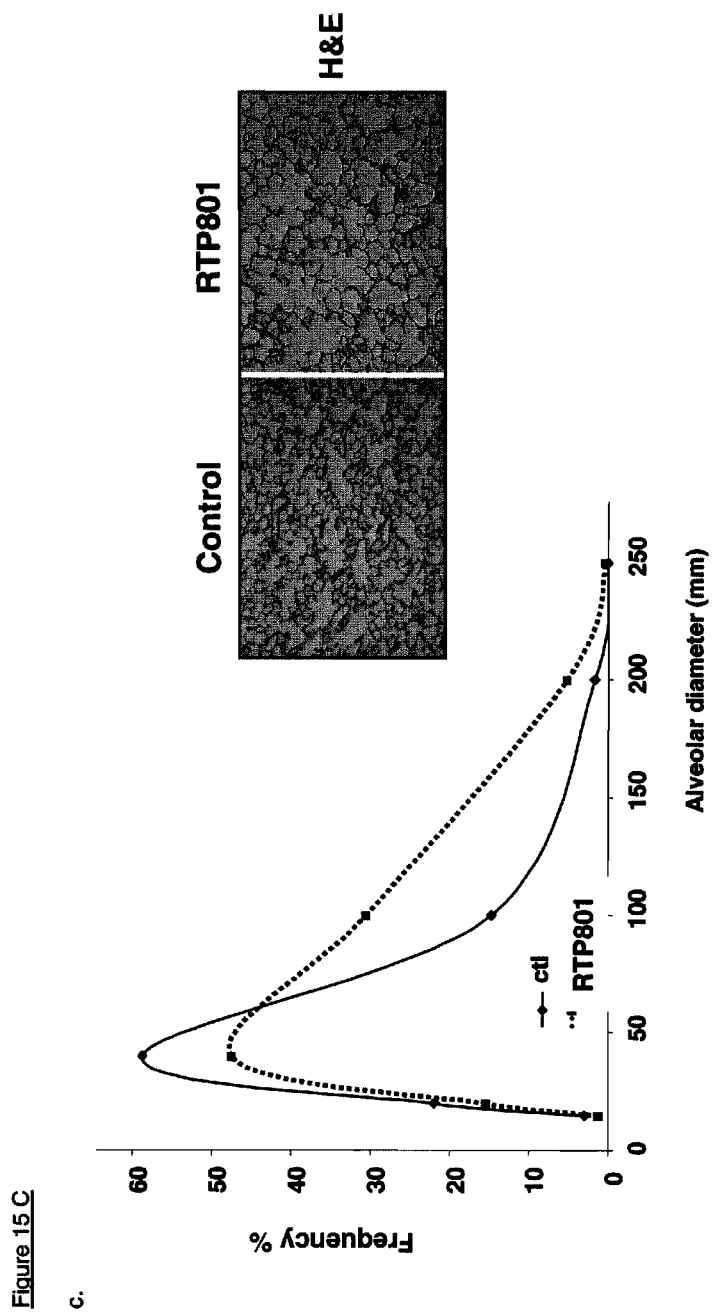
Figure 16A:
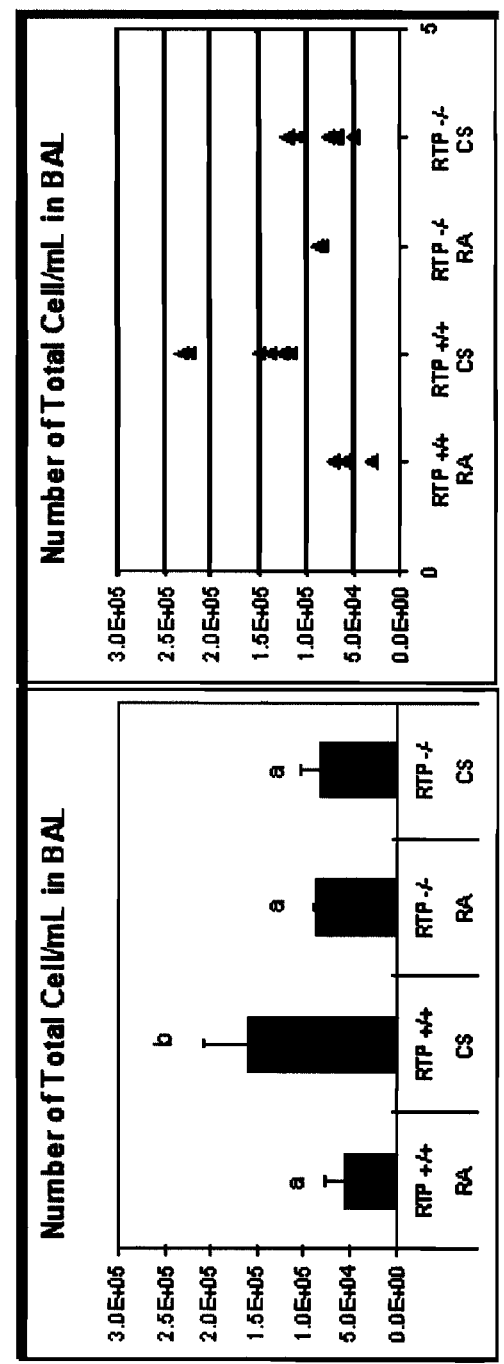
FIG. 16 A-C shows the results of a short-t (7 days) cigarette smoking model in RTP801 KO and WT mice.
Figure 16:
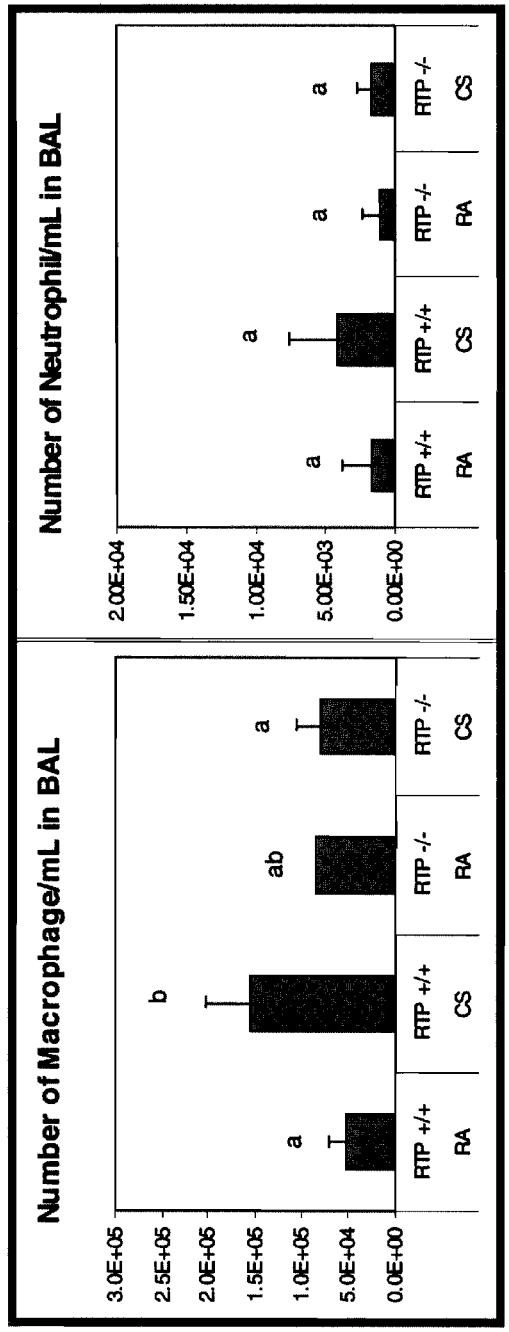
Figure 16:
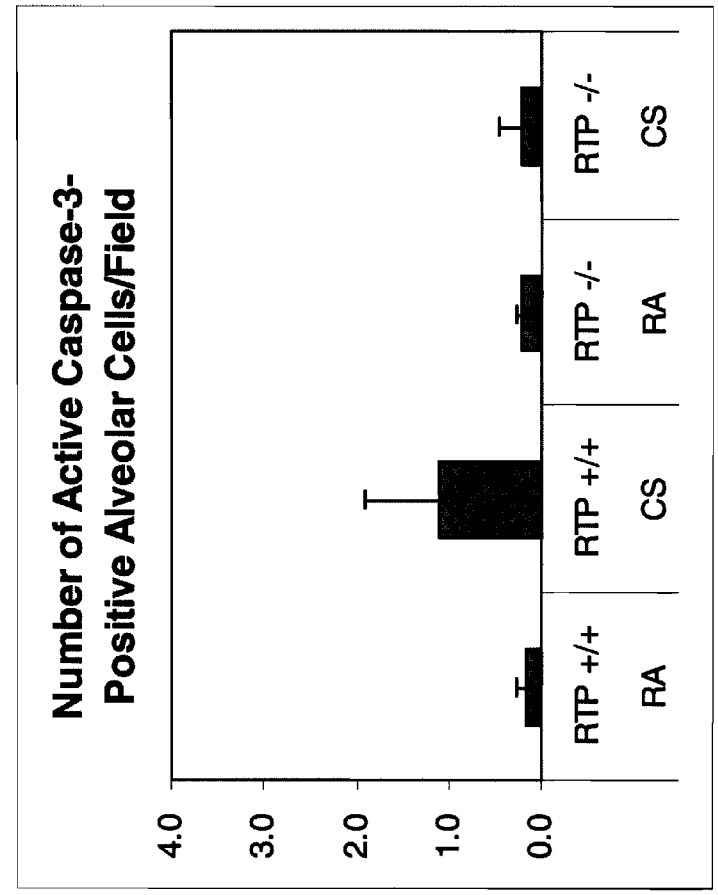
Figure 17A:
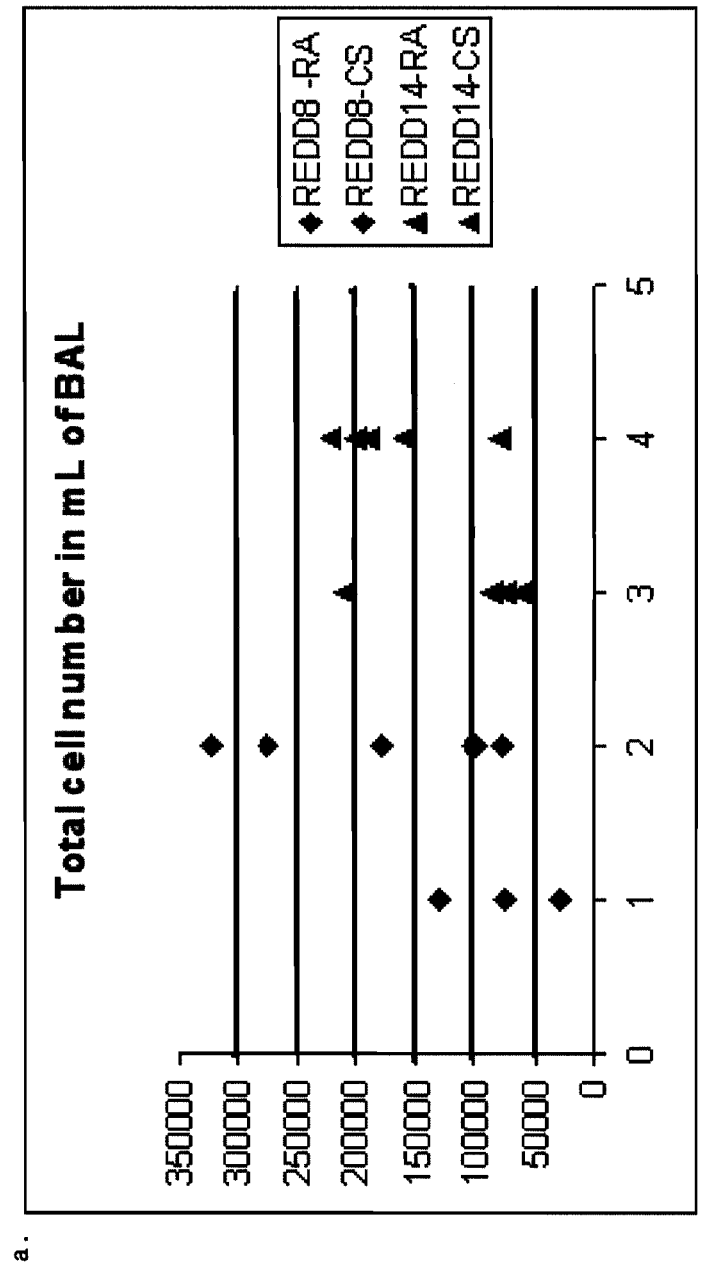
FIG. 17 A-C shows the results of a short-term cigarette smoking model in WT mice instilled with active anti-RTP801 (REDD14) and control (REDD8) siRNA.
Figure 17:
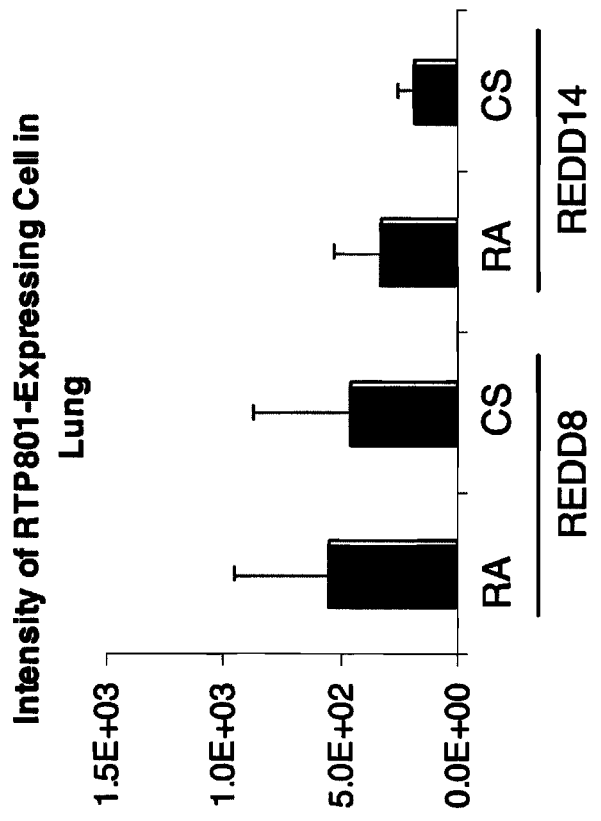
Figure 17:
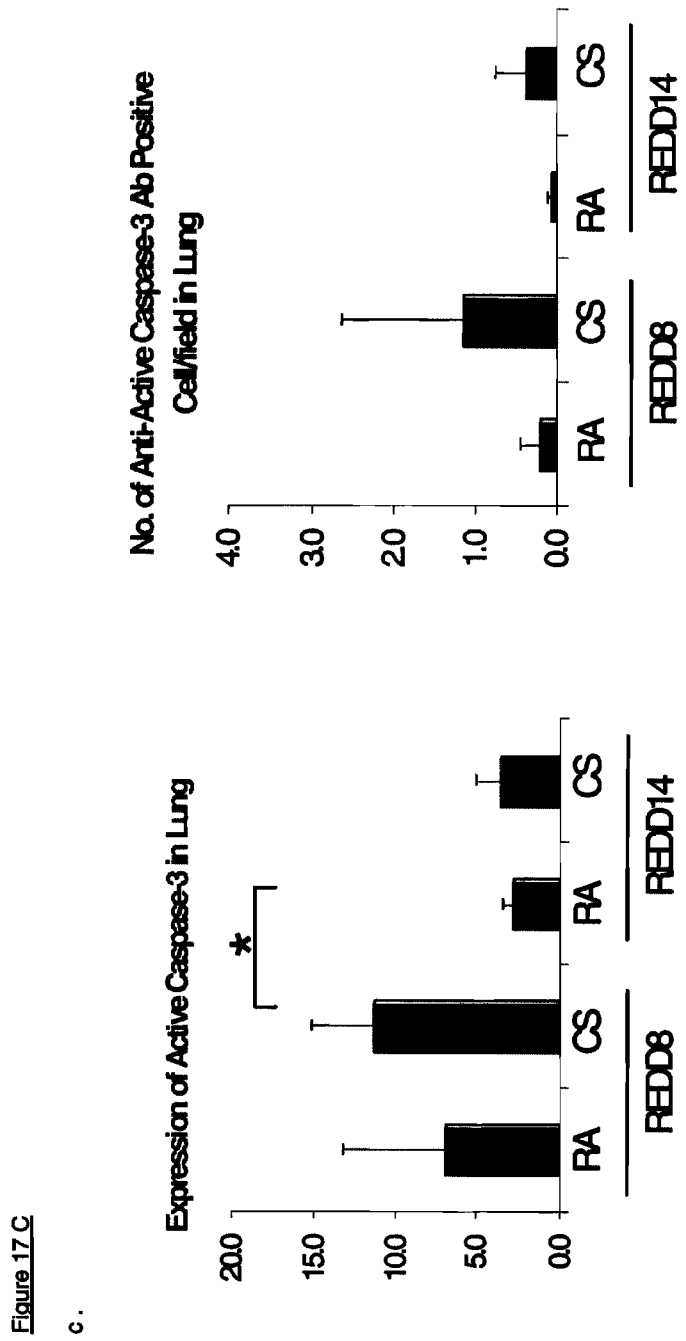
Figure 18:
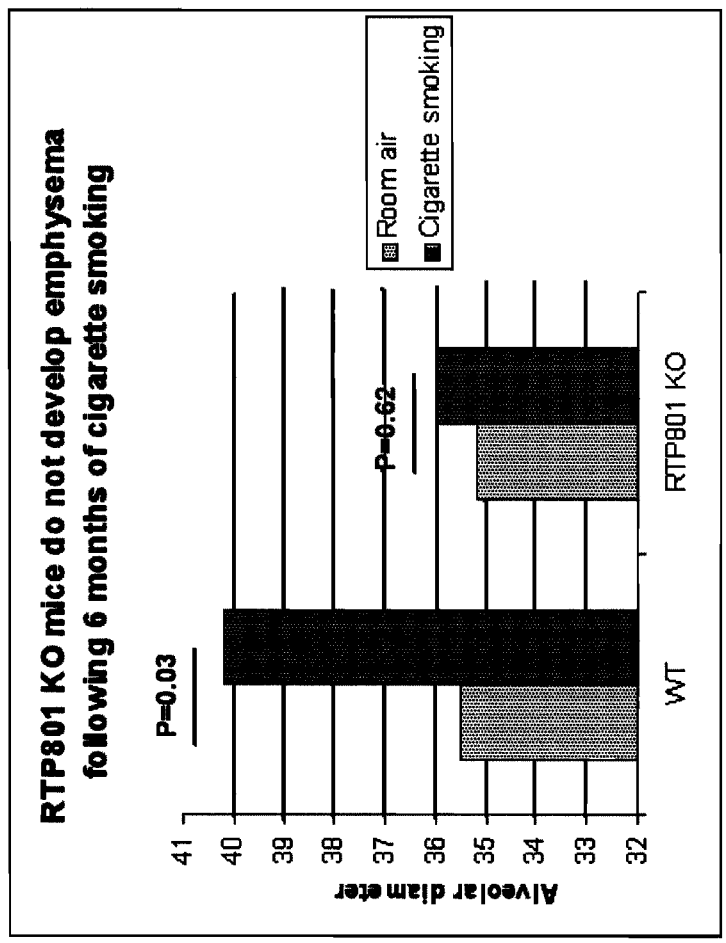
FIG. 18 shows the results of experiments with RTP801 KO mice in a long-term CS model.

1. Instillation of an RTP801 expressing plasmid results in an emphysema-like phenotype in mouse lungs which is evident by (1) increase in bronchoalveolar lavage cell counts (FIG. 15*a*); (2) apoptosis of lung septal cells (FIG. 15*b*) and increase in the alveolar diameter (FIG. 15*c*).
2. Instillation of RTP801 siRNA (REDD14) results in reduction of RTP801 expression in the lungs (FIG. 17*b*).
3. RTP801 KO mice are protected from emphysema development following 6 months of cigarette smoking as evident by the lack of enlargement of alveolar diameter. (FIG. 18).
4. RTP801 KO mice are protected from cigarette smoking induced inflammation as evident by reduced number of inflammatory bronchoalveolage cells following 1 week of cigarette smoking (FIG. 16, a-b).
5. RTP801 KO mice are protected from cigarette smoking induced apoptosis of lung septal cells as evidenced by lung section staining for activated caspase (FIG. 16*c*).
6. REDD14-instilled mice are partially protected from cigarette smoking induced inflammation as evident by reduced number of inflammatory bronchoalveolage cells following 1 week of cigarette smoking (FIG. 17*a*).
7. REDD14-instilled mice are partially protected from cigarette smoking induced apoptosis of lung septal cells as evidenced by lung section staining for activated caspase and by immunoblotting of lung extracts with anti-activated caspase 3 antibodies ((FIG. 17*c*)

Example 8

Models and Results Relating to Microvascular Disorders

The compounds of the present invention were tested in animal models of a range of microvascular disorders as described below.

1. Diabetic Retinopathy

RTP801 promotes neuronal cell apoptosis and generation of reactive oxygen species in vitro. The inventor of the current invention also found that in RTP801 knockout (KO) mice subjected to the model of retinopathy of prematurity (ROP), pathologic neovascularization NV was reduced under hypoxic conditions, despite elevations in VEGF, whereas the lack of this gene did not influence physiologic neonatal retinal NV. Moreover, in this model, lack of RTP801 was also protective against hypoxic neuronal apoptosis and hyperoxic vaso-obliteration.

Experiment 1

Diabetes was induced in 8 wk old RTP801 KO and C57/129sv wildtype (WT) littermate mice by intraperitoneal injection of STZ. After 4 weeks, ERG (single white flash, $1.4 \times 10^4$ ftc, 5 ms) was obtained from the left eye after 1 hour of dark adaptation. RVP was assessed from both eyes using the Evans-blue albumin permeation technique.

Results

Blood glucose was not different between diabetic (DM) WT and DM KO (495±109 vs 513±76 mg/dl), nor nondiabetic (NDM) WT and KO (130-110 vs 135±31 mg/di, respectively). RVP in the DM WT group was increased 138% (51.2±37.9 µL/g/hr, n=8) compared to NDM WT (21.5±18.8 µL/g/hr, n=9, p=0.055). In contrast, RVP was reduced by 80% in DM KO (9.5±8.5 µL/g/hr, n=6, p=0.023) as compared to the DM WT mice, resulting in a 140% decrease of diabetes-induced RVP. In DM WT mice, there was a prolongation (p<0.05) of the oscillatory potential implicit times for OP2 (11%), OP3 (12%), & OP4 (14%) and for the B-wave (23%) as compared to NDM WT. A-wave was not significantly changed. These changes were normalized ~100% in DM KO mice for OP3 & OP4 and 65% for B-wave as compared to NDM KO. Conclusion: Knock out of RTP801 ameliorates diabetes-induced RVP and ERG abnormalities in mice, suggesting that this hypoxia inducible gene may serve an important role in the pathogenesis of early diabetic retinal disease.

Experiment 2

Diabetes was induced in RTP801 knockout and in control wild type mice with the matched genetic background. In addition, it was induced in C57B16 mice, which were subsequently used for intravitreal injection of anti-RTP801 and control siRNAs. For diabetes induction, the mice were injected with streptozotocin (STZ 90 mg/kg/d for 2 days after overnight fast). Animal physiology was monitored throughout the study for changes in blood glucose, body weight, and hematocrit. Vehicle-injected mice served as controls. The appropriate animals were treated by intravitreal injections of 1 µg of REDD14 anti-RTP801 siRNA or 1 µg of anti-GFP control siRNA. siRNA was injected twice in the course of the study—on day 0, when the first STZ injection was performed, and on day 14 after the STZ injection.

Retinal vascular leakage was measured using the Evans-blue (EB) dye technique on the animals after 4 weeks duration of diabetes. Mice had a catheter implanted into the right jugular vein 24 hours prior to Evans Blue (EB) measurements. Retinal permeability measurements in both eyes of each animal followed a standard Evans-blue protocol.

Results

Figure 20:
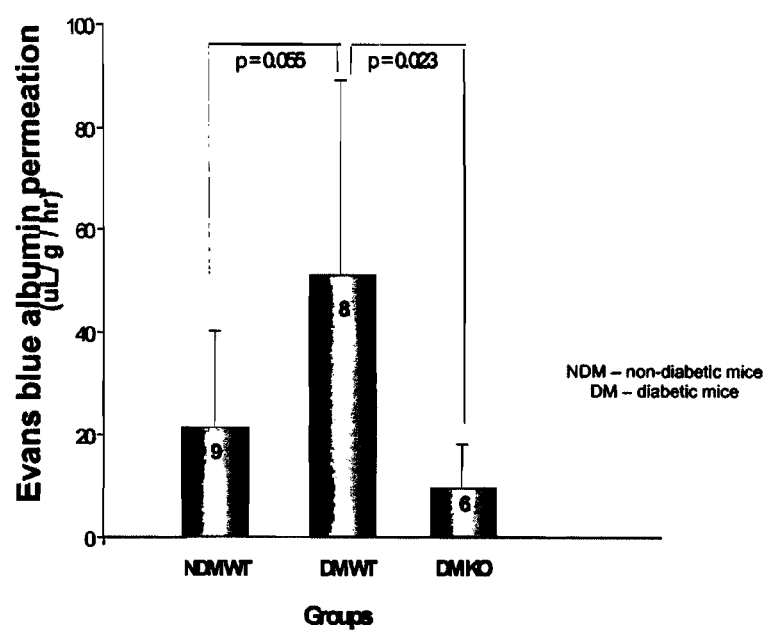
FIG. 20 shows the results of experiments in a mouse Diabetic Retinopathy model system.
Figure 21:
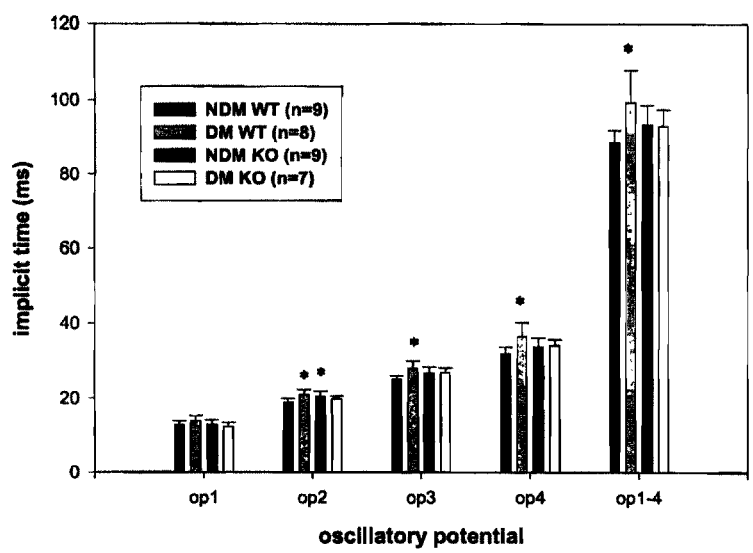
FIG. 21 shows the results of additional experiments in a mouse Diabetic Retinopathy model system.
Figure 22:
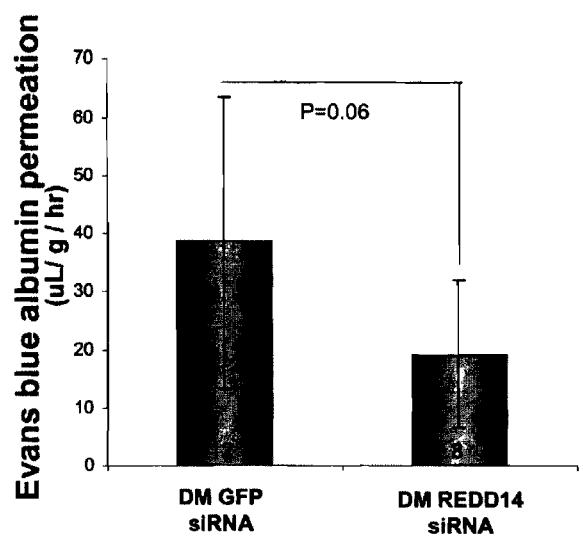
FIG. 22 shows the results of further additional experiments in a mouse Diabetic Retinopathy model system.

1. Retinal blood vessel leakage was reduced by 70% in RTP801 KO diabetic mice compared with wild type diabetic mice (see FIG. 20).
2. The Knock out of RTP801 normalizes ERG abnormalities in mice: In DM WT mice, there was a prolongation (p<0.05) of the oscillatory potential implicit times for OP2 (11%), OP3 (12%), & OP4 (14%) and for the B-wave (23%) as compared to NDM WT. A-wave was not significantly changed. These changes were normalized ~100% in DM RTP801 KO mice for OP3 & OP4 and 65% for B-wave as compared to NDM RTP801 KO (see FIG. 21).
3. Similarly to the results in KO mice, retinal blood vessel leakage was reduced by 50% in diabetic mice injected intravitreally with REDD14 siRNA against RTP801 compared to diabetic mice intraviterally injected with control siRNA against GFP (see FIG. 22).

2. Retinopathy of Prematurity

Retinopathy of prematurity was induced by exposing the test animals to hypoxic and hyperoxic conditions, and subsequently testing the effects on the retina. Results showed that RTP801 KO mice were protected from retinopathy of prematurity, thereby validating the protective effect of RTP801 inhibition.

3. Myocardial Infarction

Myocardial infarction was induced by Left Anterior Descending artery ligation in mice, both short term and long term. Results: reduction of TnT and CPK-MB fraction levels at 24 hrs postinfarct in the blood and better echocardiogram (ejection fraction volume) at 28 days postinfarct in RTP801 KO mice.

4. Microvascular Ischemic Conditions

Animal models for assessing ischemic conditions include:
1. Closed Head Injury (CHI)—Experimental TBI produces a series of events contributing to neurological and neurometabolic cascades, which are related to the degree and extent of behavioral deficits. CHI is induced under anesthesia, while a weight is allowed to free-fall from a prefixed height (Chen et al, J. Neurotrauma 13, 557, 1996) over the exposed skull covering the left hemisphere in the midcoronal plane.
2. Transient middle cerebral artery occlusion (MCAO)—a 90 to 120 minutes transient focal ischemia is performed in adult, male Sprague Dawley rats, 300-370 gr. The method employed is the intraluminal suture MCAO (Longa et al., Stroke, 30, 84, 1989, and Dogan et al., J. Neurochem. 72, 765, 1999). Briefly, under halothane anesthesia, a 3-0-nylon suture material coated with Poly-L-Lysine is inserted into the right internal carotid artery (ICA) through a hole in the external carotid artery. The nylon thread is pushed into the ICA to the right MCA origin (20-23 mm). 90-120 minutes later the thread is pulled off, the animal is closed and allowed to recover.
3. Permanent middle cerebral artery occlusion (MCAO)—occlusion is permanent, unilateral-induced by electrocoagulation of MCA. Both methods lead to focal brain ischemia of the ipsilateral side of the brain cortex leaving the contralateral side intact (control). The left MCA is exposed via a temporal craniectomy, as described for rats by Tamura A. et al., *J Cereb Blood Flow Metab.* 1981; 1:53-60. The MCA and its lenticulostriatal branch are occluded proximally to the medial border of the olfactory tract with microbipolar coagulation. The wound is sutured, and animals returned to their home cage in a room warmed at 26° C. to 28° C. The temperature of the animals is maintained all the time with an automatic thermostat.

5. Acute Renal Failure (ARF)

Testing active siRNA for treating ARF may be done using sepsis-induced ARF or ischemia-reperfusion-induced ARF.

1. Sepsis Induced Arf

Two predictive animal models of sepsis-induced ARF are described by Miyaji T, Hu X, Yuen P S, Muramatsu Y, Iyer S, Hewitt S M, Star R A, 2003, Ethyl pyruvate decreases sepsis-induced acute renal failure and multiple organ damage in aged mice. Kidney Int. November; 64(5):1620-31. These two models are lipopolysaccharide administration and cecal ligation puncture in mice, preferably in aged mice.

2. Ischemia-Reperfusion-Induced ARF

This predictive animal model is described by Kelly K J, Plotkin Z, Vulgamott S L, Dagher P C, 2003 January. *P53 mediates the apoptotic response to GTP depletion after renal ischemia-reperfusion: protective role of a p53 inhibitor*, J Am Soc Nephrol.; 14(1):128-38.

Ischemia-reperfusion injury was induced in rats following 45 minutes bilateral kidney arterial clamp and subsequent release of the clamp to allow 24 hours of reperfusion. 250 µg of REDD14 or GFP siRNA (negative control) were injected into the jugular vein 2 hrs prior to and 30 minutes following the clamp. Additional 250 µg of siRNA were given via the tail vein at 4 and 8 hrs after the clamp. siRNA against GFP served as a negative control. ARF progression was monitored by measurement of serum creatinine levels before and 24 hrs post surgery. At the end of the experiment, the rats were perfused via an indwelling femoral line with warm PBS followed by 4% paraformaldehyde. The left kidneys were removed and stored in 4% paraformaldehyde for subsequent histological analysis. Acute renal failure is frequently defined as an acute increase of the serum creatinine level from baseline. An increase of at least 0.5 mg per dL or 44.2 µmol per L of serum creatinine is considered as an indication for acute renal failure. Serum creatinine was measured at time zero before the surgery and at 24 hours post ARF surgery.

To study the distribution of siRNA in the rat kidney, Cy3-labeled 19-mer blunt-ended siRNA molecules (2 mg/kg) having alternating O-methyl modification in the sugar residues were administered iv for 3-5 min, after which in vivo imaging was conducted using two-photon confocal microscopy. The confocal microscopy analysis revealed that the majority of siRNA in the kidneys is concentrated in the endosomal compartment of proximal tubular cells. Both endosomal and cytoplasmic siRNA fluorescence were relatively stable during the first 2 hrs post delivery and disappeared at 24 hrs.

Figure 19:
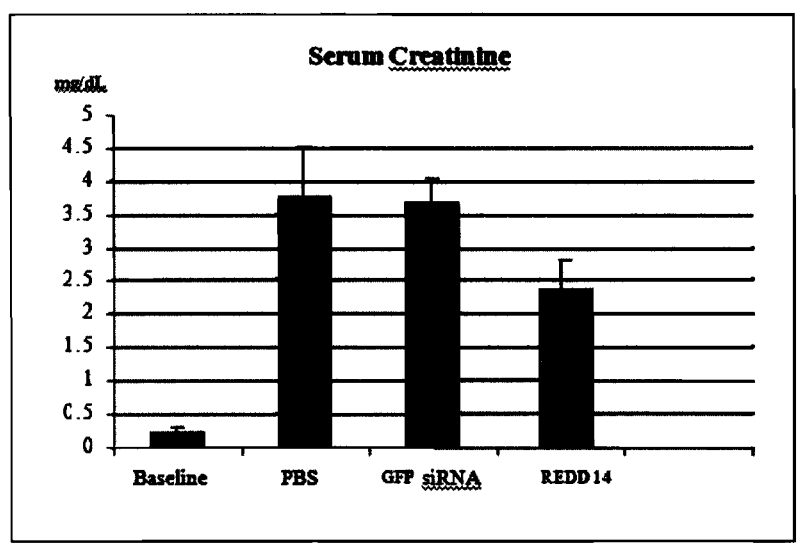
FIG. 19 shows the results of experiments in a mouse ARF model system.

As evident from FIG. 19, there was a ten-fold increase in the level of serum creatinine following a 45-min of kidney bilateral arterial clamp treatment (PBS treatment). Four injections of 801 siRNA (REDD14, SEQ In No.s 16 and 66) (2 hrs prior to the clamp and 30 min, 4 h and 8 h after the clamp) significantly reduced the creatinine level in serum by 40% (P<0.02). These results suggest that 801 siRNA can protect renal tissue from the effects of ischemia-reperfusion injury and thus reduce the severity of ARF.

Example 9

Preparation of siRNAs

Using proprietary algorithms and the known sequence of gene RTP801 (SEQ ID NO:1), the sequences of many potential siRNAs were generated. siRNA molecules according to the above specifications were prepared essentially as described herein.

The siRNAs of the present invention can be synthesized by any of the methods which are well-known in the art for synthesis of ribonucleic (or deoxyribonucleic) oligonucleotides. For example, a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the siRNAs or siRNA fragments of the present invention, two or more such sequences can be synthesized and linked together for use in the present invention.

The siRNA molecules of the invention may be synthesized by procedures known in the art e.g. the procedures as described in Usman et al., 1987, *J. Am. Chem. Soc.*, 109, 7845; Scaringe et al., 1990. *Nucleic Acids Res.*, 18, 5433; Wincott et al., 1995, *Nucleic Acids Res.* 23, 2677-2684; and Wincott et al., 1997, *Methods Mol. Bio.*, 74, 59, and may make use of common nucleic acid protecting and coupling groups, such as dimethoxytrityl at the 5'-end, and phosphoramidites at the 3'-end. The modified (e.g. 2c-O-methylated) nucleotides and unmodified nucleotides are incorporated as desired.

Alternatively, the nucleic acid molecules of the present invention can be synthesized separately and joined together post-synthetically, for example, by ligation (Moore et al., 1992, *Science* 256, 9923; Draper et al., International PCT publication No. WO93/23569; Shabarova et al., 1991, *Nucleic Acids Research* 19, 4247; Bellon et al., 1997, *Nucleosides & Nucleotides*, 16, 951; Bellon et al., 1997, *Bioconjugate Chem.* 8, 204), or by hybridization following synthesis and/or deprotection. The siRNA molecules of the invention can also be synthesized via a tandem synthesis methodology, as described in US patent application publication No. US2004/0019001 (McSwiggen) wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker can be a polynucleotide linker or a non-nucleotide linker.

For further information, see PCT publication No. WO 2004/015107 (ATUGEN).

As described above, the siRNAs of Table A (below) were constructed such that alternate sugars have 2'-O-methyl modification i.e. alternate nucleotides were thus modified. In these preferred embodiments, in one strand of the siRNA the modified nucleotides were numbers 1, 3, 5, 7, 9, 11, 13, 15, 17 and 19 and in the opposite strand the modified nucleotides were numbers 2, 4, 6, 8, 10, 12, 14, 16 and 18. Thus these siRNAs are blunt-ended 19-mer RNA molecules with alternate 2-0'-methyl modifications as described above. The siRNAs of Tables 2 and 3 (below) are also constructed in this manner, the siRNAs of Table B and D are blunt-ended 19-mer RNA molecules with alternate 2-0'-methyl modifications; the siRNAs of Table C are blunt-ended 21-mer RNA molecules with alternate 2-0'-methyl modifications.

Table A details various novel siRNA molecules which were generated and subsequently synthesized for gene RTP801. The two final columns indicate the results of two experiments performed to examine the activity of the novel molecules. Briefly, HeLa or HaCat cells were transfected with a specific novel siRNA to be tested. Expression of the RTP801 polypeptide was then determined by western blotting using an antibody against the RTP801 polypeptide. Referring to the two right-hand columns of Table A, "−" signifies an inactive or low-activity molecule (which does not substantially inhibit the expression of the RTP801 gene); "+" signifies an siRNA molecule with some inhibitory activity (of RTP801 gene expression), "++" signifies a molecule with higher inhibitory activity, and so on. Any one of the siRNA molecules disclosed herein, and in particular the active molecules detailed in Table A are novel and also considered a part of the present invention.

TABLE A

| ID No | Name | ORG | Location | POS | AS (5'->3') | SS (5'->3') | HeLaB, 20 nM | HaCat, 20 nM |
|---|---|---|---|---|---|---|---|---|
| 1 | REDD1 | h | 5'UTR | 128 | UAGAAGCCGCAGCUAGCGC | GCGCUAGCUGCGGCUUCUA | + | + |
| 2 | REDD2 | hmr | CDS | 337 | UCCGAGCUCUCCAGGCUCG | CGAGCCUGGAGAGCUCGGA | − | − |
| 3 | REDD3 | hmr | CDS | 360 | UGCUGCUGUCCAGGGACUC | GAGUCCCUGGACAGCAGCA | − | − |
| 4 | REDD4 | hmr | CDS | 478 | AGCAGCUGCAUCAGGUUGG | CCAACCUGAUGCAGCUGCU | − | − |
| 5 | REDD5 | h | CDS | 728 | UGAGUCCAGGCGCAGCACG | CGUGCUGCGCCUGGACUCA | − | − |
| 6 | Redd6 | hmr | 5'UTR | 119 | CAGCUAGCGCGGUCAGCGA | UCGCUGACCGCGCUAGCUG | − | − |
| 7 | Redd7 | hmr | 5'UTR | 122 | CCGCAGCUAGCGCGGUCAG | CUGACCGCGCUAGCUGCGG | − | − |
| 8 | Redd8 | hmr | 5'UTR | 125 | AAGCCGCAGCUAGCGCGGU | ACCGCGCUAGCUGCGGCUU | − | − |
| 9 | Redd9 | hmr | CDS | 339 | AGUCCGAGCUCUCCAGGCU | AGCCUGGAGAGCUCGGACU | − | − |
| 10 | Redd10 | hmr | CDS | 341 | GCAGUCCGAGCUCUCCAGG | CCUGGAGAGCUCGGACUGC | − | − |
| 11 | Redd11 | hmr | CDS | 363 | UGUUGCUGCUGUCCAGGGA | UCCCUGGACAGCAGCAACA | − | − |
| 12 | Redd12 | hmr | CDS | 369 | AGCCACUGUUGCUGCUGUC | GACAGCAGCAACAGUGGCU | − | − |
| 13 | Redd13 | hmr | CDS | 370 | AAGCCACUGUUGCUGCUGU | ACAGCAGCAACAGUGGCUU | − | − |
| 14 | Redd14 | hmr | CDS | 475 | AGCUGCAUCAGGUUGGCAC | GUGCCAACCUGAUGCAGCU | +++ | +++ |
| 15 | Redd15 | hmr | CDS | 481 | UGCAGCAGCUGCAUCAGGU | ACCUGAUGCAGCUGCUGCA | + | + |
| 16 | Redd16 | hmr | CDS | 486 | UCUCCUGCAGCAGCUGCAU | AUGCAGCUGCUGCAGGAGA | − | − |
| 17 | Redd17 | hmr | CDS | 610 | CCCCGCAGGCCGCACGGCU | AGCCGUGCGGCCUGCGGGG | − | − |
| 18 | Redd18 | hmr | CDS | 750 | CCUGGAUCUUGGGCCAGAG | CUCUGGCCCAAGAUCCAGG | − | − |
| 19 | Redd19 | hmr | CDS | 809 | CAGCGUCAGGGACUGGCUG | CAGCCAGUCCCUGACGCUG | − | − |
| 20 | Redd20 | hmr | 3'UTR | 1097 | AUGCUACAGUACUGAGGGG | CCCCUCAGUACUGUAGCAU | + | + |
| 21 | Redd21 | hmr | 3'UTR | 1419 | GUCUGUAAGAUAGCUGCCU | AGGCAGCUAUCUUACAGAC | + | + |
| 22 | Redd22 | hmr | 3'UTR | 1617 | UUCUAGAUGGAAGACCCAG | CUGGGUCUUCCAUCUAGAA | ++ | ++ |
| 23 | Redd23 | hmr | 3'UTR | 1670 | UUGAACAUCAAGUGUAUUC | GAAUACACUUGAUGUUCAA | ++ | ++ |
| 24 | Redd24 | hmr | 3'UTR | 1693 | AAAUAUUGCAUAGGUCUUA | UAAGACCUAUGGAAUAUUU | + | + |
| 25 | Redd25 | hmr | 3'UTR | 1695 | AAAAAUAUUGCAUAGGUCU | AGACCUAUGCAAUAUUUUU | ++ | ++ |
| 26 | Redd26 | hmr | CDS | 349 | AGGGACUCGCAGUCCGAGC | GCUCGGACUGCGAGUCCCU | − | − |
| 27 | Redd27 | hmr | 3'UTR | 1673 | UACUUGAACAUCAAGUGUA | UACACUUGAUGUUCAAGUA | ++ | ++ |
| 28 | Redd28 | hmr | 3'UTR | 1717 | AAACAUGUUUAUUAGAAAA | UUUUCUAAUAAACAUGUUU | − | − |
| 29 | Redd29 | h | 5'UTR | 99 | AACUGCUAAGACAAGUGCG | CGCACUUGUCUUAGCAGUU | − | − |
| 30 | Redd30 | h | CDS | 213 | ACGACGACGAGAAGCGGUC | GACCGCUUCUCGUCGUCGU | − | − |
| 31 | Redd31 | h | CDS | 393 | AAGCCGUGUCUUCCUCCGG | CCGGAGGAAGACACGGCUU | − | − |
| 32 | Redd32 | h | CDS | 453 | AGUGUUCAUCCUCAGGGUC | GACCCUGAGGAUGAACACU | − | − |
| 33 | Redd33 | h | CDS | 521 | AGGGCGUCGAGAGCCCAGC | GCUGGGCUCUCGACGCCCU | − | − |
| 34 | Redd34 | hr | CDS | 535 | AUCAGCAGGCGCGCAGGGC | GCCCUGCGCGCCUGCUGAU | − | − |
| 35 | Redd35 | h | CDS | 571 | AGUUCUUUGCCCACCUGGC | GCCAGGUGGGCAAAGAACU | − | − |
| 36 | Redd36 | h | CDS | 597 | ACGGCUCGCUGUAGGCCAG | CUGGCCUACAGCGAGCCGU | − | − |
| 37 | Redd37 | h | CDS | 625 | ACGUCCAGCAGCGCCCCCC | GGGGGGCGCUGCUGGACGU | − | − |
| 38 | Redd38 | h | CDS | 829 | AUGACUCGGAAGCCAGUGC | GCACUGGCUUCCGAGUCAU | − | − |
| 39 | Redd39 | h | 3'UTR | 1046 | AACUCAAUGAGCUUCCUGG | CCAGGAAGCUCAUUGAGUU | ++ | ++ |

TABLE A-continued

| ID No | Name | ORG | Location | POS | AS (5'->3') | SS (5'->3') | HeLaB, 20 nM | HaCat, 20 nM |
|---|---|---|---|---|---|---|---|---|
| 40 | REDD40 | h | 3'UTR | 1539 | CUCAACUCUGCAGUACACG | CGUGUACUGCAGAGUUGAG | + | + |
| 41 | Redd41 | h | 3'UTR | 1317 | AGAUACACAAACCACCUCC | GGAGGUGGUUUGUGUAUCU | + | + |
| 42 | Redd42 | h | 3'UTR | 1350 | ACAACAAACACACUUGGUC | GACCAAGUGUGUUUGUUGU | ++ | ++ |
| 43 | Redd43 | hmr | CDS | 473 | CUGCAUCAGGUUGGCACAC | GUGUGCCAACCUGAUGCAG | + | + |
| 44 | REDD44 | h | 3'UTR | 955 | UCCUGCCUCUAGUCUCCAC | GUGGAGACUAGAGGCAGGA | + | + |
| 45 | Redd45 | hmr | CDS | 476 | CAGCUGCAUCAGGUUGGCA | UGCCAACCUGAUGCAGCUG | – | – |
| 46 | Redd46 | hmr | CDS | 479 | CAGCAGCUGCAUCAGGUUG | CAACCUGAUGCAGCUGCUG | – | – |
| 47 | Redd47 | hmr | CDS | 483 | CCUGCAGCAGCUGCAUCAG | CUGAUGCAGCUGCUGCAGG | – | – |
| 48 | Redd48 | hmr | CDS | 485 | CUCCUGCAGCAGCUGCAUC | GAUGCAGCUGCUGCAGGAG | – | – |
| 49 | REDD40.1 | h | 3'UTR | 1536 | AACUCUGCAGUACACGAUG | CAUCGUGUACUGCAGAGUU | ++ | ++ |
| 50 | REDD44.1 | h | 3'UTR | 954 | CCUGCCUCUAGUCUCCACC | GGUGGAGACUAGAGGCAGG | ++ | ++ |

Note that in the above Table A, the sense strands of siRNAs 1-50 have SEQ ID NOS: 3-52 respectively, and the antisense strands of siRNAs 1-50 have SEQ ID NOS: 53-102 respectively. The molecule designated REDD 14 has SEQ ID Nos 16 (Sense strand) and 66 (antisense strand).

TABLE B

| No | Source | Oligo Length | Sense Sirna | AntiSense Sirna | gi9506686 ref NM_019058.1 (Homo sapiens) | gi21312867 ref NM_029083.1 (Mouse) | gi18376838 ref NM_080906.1 (Rat) | Overlap with pet-1 (anti-sense)* |
|---|---|---|---|---|---|---|---|---|
| 51 | Human | 19 | CUAGCCAGUUGGUAAGCCA | UGGCUUACCAACUGGCUAG | [556-574] | – | – | – |
| 52 | Human | 19 | UGAUUCCAGUGGUUGGAAA | UUUCCAACCACUGGAAUCA | [984-1002] | – | – | – |
| 53 | Human | 19 | CCAGUGGUUGGAAAACUGA | UCAGUUUUCCAACCACUGG | [989-1007] | – | – | – |
| 54 | Human | 19 | GCUUCCGAGUCAUCAAGAA | UUCUUGAUGACUCGGAAGC | [835-853] | [763-781] | – | – |
| 55 | Human | 19 | GGAAGCUCAUUGAGUUGUG | CACAACUCAAUGAGCUUCC | [1049-1067] | | – | – |
| 56 | Human, cynomolgus | 19 | CCAUCUGGGUCUUCCAUCU | AGAUGGAAGACCCAGAUGG | [1613-1631] | [1569-1583] | [1610-1624] | + |
| 57 | Human, cynomolgus | 19 | GGAUGUGUGUGUAGCAUGU | ACAUGCUACACACACAUCC | [1152-1170] | – | – | – |
| 58 | Human, cynomolgus | 19 | ACACAUACCCCUCAGUACU | AGUACUGAGGGGUAUGUGU | [1090-1108] | | [1081-1098] | – |
| 59 | Human, cynomolgus | 19 | ACAUACCCCUCAGUACUGU | ACAGUACUGAGGGGUAUGU | [1092-1110] | | [1082-1100] | – |
| 60 | Human, cynomolgus | 19 | CACUGUUCAUGAAUACACU | AGUGUAUUCAUGAACAGUG | [1660-1678] | [1612-1626] | [1652-1666] | + |
| 61 | Human, cynomolgus | 19 | CCAGCUGGAUGUGUGUGUA | UACACACACAUCCAGCUGG | [1146-1164] | [1099-1114] | [1139-1154] | – |
| 62 | Human, cynomolgus | 19 | CGGAACAGCUGCUCAUUGA | UCAAUGAGCAGCUGUUCCG | [868-886] | [801-814] | [854-867] | – |
| 63 | Human, cynomolgus | 19 | GAAGCUCAUUGAGUUGUGU | ACACAACUCAAUGAGCUUC | [1050-1068] | – | – | – |
| 64 | Human, cynomolgus | 19 | GGACACAUACCCCUCAGUA | UACUGAGGGGUAUGUGUCC | [1088-1106] | | | – |
| 65 | Human, cynomolgus | 19 | GGAUCUUUGACACUUGAAA | UUUCAAGUGUCAAAGAUCC | [1463-1501] | [1424-1442] | – | – |

TABLE B-continued

| No | Source | Oligo Length | Sense Sirna | AntiSense Sirna | gi9506686 ref NM_019058.1 (*Homo sapiens*) | gi21312867 ref NM_029083.1 (Mouse) | gi18376838 ref NM_080906.1 (Rat) | Overlap with pet-1 (antisense)* |
|---|---|---|---|---|---|---|---|---|
| 66 | Human, cynomolgus | 19 | GUAGCAUGUACCUUAUUAU | AUAAUAAGGUACAUGCUAC | [1162-1180] | [1112-1128] | — | — |
| 67 | Human, cynomolgus | 19 | UCAGUACUGUAGCAUGGAA | UUCCAUGCUACAGUACUGA | [1101-1119] | | [1091-1106] | — |
| 68 | Human, cynomolgus | 19 | UGUGUAGCAUGUACCUUAU | AUAAGGUACAUGCUACACA | [1159-1177] | [1111-1127] | [1151-1167] | — |
| 69 | Human, cynomolgus | 19 | CUGGAUGUGUGUAGCAU | AUGCUACACACAUCCAG | [1150-1168] | — | — | — |
| 70 | Human, cynomolgus, mouse | 19 | ACACUUGAUGUUCAAGUAU | AUACUUGAACAUCAAGUGU | [1674-1692] | [1622-1640] | | + |
| 71 | Human, cynomolgus, mouse | 19 | GCAUGAAUGUAAGAGUAGG | CCUACUCUUACAUUCAUGC | [1438-1456] | [1379-1397] | | — |
| 72 | Human, cynomolgus, mouse | 19 | AGCAGCAACAGUGGCUUCG | CGAAGCCACUGUUGCUGCU | [372-390] | [300-318] | | — |
| 73 | Human, cynomolgus, mouse | 19 | AUGAAUGUAAGAGUAGGAA | UUCCUACUCUUACAUUCAU | [1440-1458] | [1381-1399] | | — |
| 74 | Human, cynomolgus, mouse | 19 | CAGCAGCAACAGUGGCUUC | GAAGCCACUGUUGCUGCUG | [371-389] | [299-317] | | — |
| 75 | Human, cynomolgus, mouse | 19 | CAUGAAUGUAAGAGUAGGA | UCCUACUCUUACAUUCAUG | [1439-1457] | [1380-1398] | | — |
| 76 | Human, cynomolgus, mouse | 19 | GAUGUUCAAGUAUUAAGAC | GUCUUAAUACUUGAACAUC | [1680-1698] | [1628-1646] | | + |
| 77 | Human, cynomolgus, mouse, rat | 19 | UGAUGCAGCUGCUGCAGGA | UCCUGCAGCAGCUGCAUCA | [494-502] | [412-430] | [465-483] | — |
| 78 | Human, cynomolgus, mouse, rat | 19 | GAAUACACUUGAUGUUCAA | UUGAACAUCAAGUGUAUUC | [1670-1688] | [1618-1636] | | + |
| 79 | Human, cynomolgus, mouse, rat | 19 | UGAAUACACUUGAUGUUCA | UGAACAUCAAGUGUAUUCA | [1669-1687] | [1617-1635] | [1657-1675] | + |
| 80 | Human, cynomolgus, mouse, rat | 19 | AUACACUUGAUGUUCAAGU | ACUUGAACAUCAAGUGUAU | [1672-1690] | [1620-1638] | [1660-1678] | + |
| 81 | Human, cynomolgus, mouse, rat | 19 | CAUGAAUACACUUGAUGUU | AACAUCAAGUGUAUUCAUG | [1667-1685] | [1615-1633] | [1655-1673] | + |
| 82 | Human, cynomolgus, mouse, rat | 19 | CUGGACAGCAGCAACAGUG | CACUGUUGCUGCUGUCCAG | [366-384] | [294-312] | [347-365] | — |
| 83 | Human, cynomolgus, mouse, rat | 19 | GUUCAUGAAUACACUUGAU | AUCAAGUGUAUUCAUGAAC | [1664-1682] | [1612-1630] | [1652-1670] | + |
| 84 | Human, cynomolgus, mouse, rat | 19 | UCAUGAAUACACUUGAUGU | ACAUCAAGUGUAUUCAUGA | [1666-1684] | [1614-1632] | [1654-1672] | + |

TABLE B-continued

| No | Source | Oligo Length | Sense Sirna | AntiSense Sirna | gi9506686 ref NM_019058.1 (*Homo sapiens*) | gi21312867 ref NM_029083.1 (Mouse) | gi18376838 ref NM_080906.1 (Rat) | Overlap with pet-1 (antisense)* |
|---|---|---|---|---|---|---|---|---|
| 85 | Human, cynomolgus, mouse, rat | 19 | UGGACAGCAGCAACAGUGG | CCACUGUUGLUGCUGUCCA | [367-385] | [295-313] | [348-366] | − |
| 86 | Human, cynomolgus, mouse, rat | 19 | UGUGUGCCAACCUGAUGCA | UGCAUCAGGUUGGCACACA | [472-490] | [400-418] | [453-471] | − |
| 87 | Human, cynomolgus, mouse, rat | 19 | UUCAUGAAUACACUUGAUG | CAUCAAGUGUAUUCAUGAA | [1665-1683] | [1613-1631] | [1653-1671] | + |
| 88 | Human, cynomolgus, mouse, rat | 19 | AACCUGAUGCAGCUGCUGC | GCAGCAGCUGCAUCAGGUU | [480-498] | [408-426] | [461-479] | − |
| 89 | Human, cynomolgus, mouse, rat | 19 | AGUCCCUGGACAGCAGCAA | UUGCUGCUGUCCAGGGACU | [361-379] | [289-307] | [342-360] | − |
| 90 | Human, cynomolgus, mouse, rat | 19 | CCCUCAGUACUGUAGCAUG | CAUGCUACALUACUGAGGG | [1098-1116] | [1048-1066] | [1088-1106] | − |
| 91 | Human, cynomolgus, mouse, rat | 19 | CCUGGACAGCAGCAACAGU | ACUGUUCCUGCUGUCCAGG | [365-383] | [293-311] | [346-364] | − |
| 92 | Human, cynomolgus, mouse, rat | 19 | UGUGCCAACCUGAUGGAGC | GCUGCAUCAGGUUGGCACA | [474-492] | [402-420] | [455-473] | − |
| 93 | Human, cynomolgus, mouse, rat | 19 | AAUACACUUGAUGUUCAAG | CUUGAACAUCAAGUGUAUU | [1671-1689] | [1619-1637] | [1659-1677] | + |
| 94 | Human, cynomolgus, mouse, rat | 19 | AUGAAUACACUUGAUGUUC | GAACAUCAAGUGUAUUCAU | [1668-1686] | [1616-1634] | [1656-1674] | − |
| 95 | Human, cynomolgus, rat | 19 | UGAUGGAGCUGCUGCAGGA | UCCUGCAGGAGCUGCAUCA | [484-502] | | [465-483] | + |
| 96 | Human, cynomolgus, rat | 19 | AGAACUGUUUACAUGAAGA | UCUUCAUGUAAACAGUUCU | [1632-1650] | | [1625-1643] | + |
| 97 | Human, cynomolgus, rat | 19 | AUCUAGAACUGUUUACAUG | CAUGUAAACAGUUCUAGAU | [1628-1646] | | [1621-1639] | + |
| 98 | Human, cynomolgus, rat | 19 | CCAUGCCUAGCCUUUGGGA | UCCCAAAGGCUAGGCAUGG | [196-214] | | [186-204] | − |
| 99 | Human, cynomolgus, rat | 19 | CUAGAACUGUUUACAUGAA | UUCAUGUAAACAGUUCUAG | [1630-1648] | | [1623-1641] | + |
| 100 | Human, cynomolgus, rat | 19 | GAACUGUUUACAUGAAGAU | AUCUUCAUGUAAACAGUUC | [1633-1651] | | [1626-1644] | + |
| 101 | Human, cynomolgus, rat | 19 | GGUCUUCCAUCUAGAACUG | CAGUUCUAGAUGGAAGACC | [1620-1638] | | [1613-1631] | + |
| 102 | Human, cynomolgus, rat | 19 | CCAUCUAGAACUGUUUACA | UGUAAACAGUUCUAGAUGG | [1626-1644] | | [1619-1637] | + |

TABLE B-continued

| No | Source | Oligo Length | Sense Sirna | AntiSense Sirna | gi9506686 ref NM_019058.1 (Homo sapiens) | gi21312867 ref NM_029083.1 (Mouse) | gi18376838 ref NM_080906.1 (Rat) | Overlap with pet-1 (antisense)* |
|---|---|---|---|---|---|---|---|---|
| 103 | Human, cynomolgus, rat | 19 | CUUCCAUCUAGAACUGUUU | AAACAGUUCUAGAUGGAAG | [1623-1641] | | [1616-1634] | + |
| 104 | Human, cynomolgus, rat | 19 | UAGAACUGUUUACAUGAAG | CUUCAUGUAAACAGUUCUA | [1631-1649] | | [1624-1642] | + |
| 105 | Human, cynomolgus, rat | 19 | UCUUCCAUCUAGAACUGUU | AACAGUUCUAGAUGGAAGA | [1622-1640] | | [1615-1633] | + |
| 106 | Human, cynomolgus, rat | 19 | CAUCUAGAACUGUUUACAU | AUGUAAACAGUUCUAGAUG | [1627-1645] | | [1620-1638] | + |
| 107 | Human, cynomolgus, rat | 19 | GGGUCUUCCAUCUAGAACU | AGUUCUAGAUGGAAGACCC | [1619-1637] | | [1612-1630] | + |
| 108 | Human, cynomolgus, rat | 19 | UCCAUCUAGAACUGUUUAC | GUAAACAGUUCUAGAUGGA | [1625-1643] | | [1618-1636] | + |
| 109 | Human, cynomolgus, rat | 19 | UCUAGAACUGUUUACAUGA | UCAUGUAAACAGUUCUAGA | [1629-1647] | | [1622-1640] | + |
| 110 | Human, cynomolgus, rat | 19 | UUCCAUCUAGAACUGUUUA | UAAACAGUUCUAGAUGGAA | [1624-1642] | | [1617-1635] | + |
| 111 | Human, cynomolgus, rat | 19 | GUCUUCCAUCUAGAACUGU | ACAGUUCUAGAUGGAAGAC | [1621-1639] | | [1614-1632] | + |
| 112 | Human, mouse | 19 | CAAGUAUUAAGACCUAUGC | GCAUAGGUCUUAAUACUUG | [1686-1704] | [1634-1652] | | + |
| 113 | Human, mouse | 19 | GUAUUAAGACCUAUGCAAU | AUUGCAUAGGUCUUAAUAC | [1689-1707] | [1637-1655] | | + |
| 114 | Human, mouse | 19 | AGUAUUAAGACCUAUGCAA | UUGCAUAGGUCUUAAUACU | [1688-1706] | [1636-1654] | | + |
| 115 | Human, mouse | 19 | AUGUUCAAGUAUUAAGACC | GGUCUUAAUACUUGAACAU | [1681-1699] | [1629-1647] | | + |
| 116 | Human, mouse | 19 | CACUUGAUGUUCAAGUAUU | AAUACUUGAACAUCAAGUG | [1675-1693] | [1623-1641] | | + |
| 117 | Human, mouse | 19 | CCAAGAUCCAGGGGCUGUU | AACAGCCCCUGGAUCUUGG | [757-775] | [685-703] | | − |
| 118 | Human, mouse | 19 | GUUCAAGUAUUAAGACCUA | UAGGUCUUAAUACUUGAAC | [1683-1701] | [1631-1649] | | + |
| 119 | Human, mouse | 19 | UCAAGUAUUAAGACCUAUG | CAUAGGUCUUAAUACUUGA | [1685-1703] | [1633-1651] | | + |
| 120 | Human, mouse | 19 | AAGUAUUAAGACCUAUGCA | UGCAUAGGUCUUAAUACUU | [1687-1705] | [1635-1653] | | + |
| 121 | Human, mouse | 19 | UGUUCAAGUAUUAAGACCU | AGGUCUUAAUACUUGAACA | [1682-1700] | [1630-1648] | | + |
| 122 | Human, mouse, rat | 19 | UGGGUCUUCCAUCUAGAAC | GUUCUAGAUGGAAGACCCA | [1618-1636] | [1570-1588] | [1611-1629] | + |

Note that in the above Table B, the sense strands of siRNAs 51-122 have SEQ ID NOS: 103-174 respectively, and the antisense strands of siRNAs 51-122 have SEQ ID NOS: 175-246 respectively.

TABLE C

| No | Source | Oligo Length | Sense Sirna | AntiSense Sirna | gi9506686 ref NM_019058.1 (Homo sapiens) | gi21312867 ref NM_029083.1 (Mus musculus) | gi18376838 ref NM_080906.1 (Rattus norvegicus) | Overlap with pet-1 (anti-sense) |
|---|---|---|---|---|---|---|---|---|
| 123 | Human | 21 | CCAGGAAGCUCAUUGAGUUGU | ACAACUCAAUGAGCuUCCUGG | [1046-1066] | – | – | – |
| 124 | Human | 21 | CCAUCUGGGUCUUCCAUCUAG | CUAGAUGGAAGACCCAGAUGG | [1613-1633] | [1569-1585] | [1610-1626] | + |
| 125 | Human | 21 | GGAUGUGUGUAGCAUGUAC | GUACAUGCUACACACAUCC | [1152-1172] | [1102-1122] | [1142-1161] | – |
| 126 | Human | 21 | CAAGUGUGUUUGUUGUUUGUU | AACAAACAACAAACACACUUG | [1353-1373] | – | – | – |
| 127 | Human | 21 | CCUCAGUACUGUAGCAUGGAA | UUCCAUGCUACAGUACUGAGG | [1099-1119] | [1049-1066] | [1089-1106] | – |
| 128 | Human | 21 | GACCAAGUGUGUUUGUUGUUU | AAACAACAAACACACUUGGUC | [1350-1370] | – | – | – |
| 129 | Human | 21 | GCUUCCGAGUCAUCAAGAAGA | UCUUCUUGAUGACUCGGAAGC | [835-855] | [763-783] | – | – |
| 130 | Human | 21 | GGAGGUGGGGAAUAGUGUUU | AAACACUAUUCCCCACCUCC | [1024-1044] | [976-986] | – | – |
| 131 | Human | 21 | CAGUACUGUAGCAUGGAACAA | UUGUUCCAUGCUACAGUACUG | [1102-1122] | [1052-1072] | | – |
| 132 | Human, cyno-molgus | 21 | GAAUACACUUGAUGUUCAAGU | ACUUGAACAUCAAGUGUAUUC | [1670-1690] | [1618-1638] | [1658-1678] | + |
| 133 | Human, cyno-molgus | 21 | CAAGUAUUAAGACCUAUGCAA | UUGCAUAGGUCUUAAUACUUG | [1686-1706] | [1634-1654] | [1674-1694] | + |
| 134 | Human, cyno-molgus | 21 | GAACUUUUGGGGUGGAGACUA | UAGUCUCCACCCCAAAAGUUC | [944-964] | – | – | – |
| 135 | Human, cyno-molgus | 21 | GGACACAUACCCCUCAGUACU | AGUACUGAGGGGUAUGUGUCC | [1088-1108] | [1047-1058] | [1081-1098] | – |
| 136 | Human, cyno-molgus | 21 | GGAGGUGGUUUGUGUAUCUUA | UAAGAUACACAAACCACCUCC | [1317-1337] | [1256-1268] | – | – |
| 137 | Human, cyno-molgus | 21 | GGAUCUUUGACACUUGAAAAA | UUUUUCAAGUGUCAAAGAUCC | [1483-1503] | [1424-1442] | – | – |
| 138 | Human, cyno-molgus | 21 | GGUCUUCCAUCUAGAACUGUU | AACAGUUCUAGAUGGAAGACC | [1620-1640] | [1572-1588] | [1613-1633] | + |
| 139 | Human, cyno-molgus | 21 | UGUGUAGCAUGUACCUUAUUA | UAAUAAGGUACAUGCUACACA | [1159-1179] | [1111-1128] | [1151-1169] | – |
| 140 | Human, cyno-molgus | 21 | CAACAAGGCUUCCAGCUGGAU | AUCCAGCUGGAAGCCUUGUUG | [1135-1155] | – | – | – |
| 141 | Human, cyno-molgus | 21 | CACUUGGGAUCUUUGACACUU | AAGUGUCAAAGAUCCCAAGUG | [1477-1497] | – | – | – |
| 142 | Human, cyno-molgus | 21 | CAUCACUACUGACCUGUUGUA | UACAACAGGUCAGUAGUGAUG | [1399-1419] | [1341-1356] | [1383-1398] | – |
| 143 | Human, cyno-molgus | 21 | GUGUGUAGCAUGUACCUUA | UAAGGUACAUGCUACACACAC | [1156-1176] | [1106-1126] | [1146-1166] | – |
| 144 | Human, cyno-molgus, mouse | 21 | GCAUGAAUGUAAGAGUAGGAA | UUCCUACUCUUACAUUCAUGC | [1438-1458] | [1379-1399] | | – |

TABLE C-continued

| No | Source | Oligo Length | Sense Sirna | AntiSense Sirna | gi9506686 ref NM_019058.1 (*Homo sapiens*) | gi21312867 ref NM_029083.1 (*Mus musculus*) | gi18376838 ref NM_080906.1 (*Rattus norvegicus*) | Overlap with pet-1 (antisense) |
|---|---|---|---|---|---|---|---|---|
| 145 | Human, cynomolgus, mouse | 21 | GACAGCAGCAACAGUGGCUUC | GAAGCCACUGUUGCUGCUGUC | [369-389] | [297-317] | | - |
| 146 | Human, cynomolgus, mouse, rat | 21 | UGAUGCAGCUGCUGCAGGAGA | UCUCCUGCAGCAGCUGCAUCA | [484-504] | [412-432] | [465-485] | - |
| 147 | Human, cynomolgus, mouse, rat | 21 | UGAAUACACUUGAUGUUCAAG | CUUGAACAUCAAGUGUAUUCA | [1669-1689] | [1617-1637] | [1657-1677] | + |
| 148 | Human, cynomolgus, mouse, rat | 21 | CAUGAAUACACUUGAUGUUCA | UGAACAUCAAGUGUAUUCAUG | [1667-1687] | [1615-1635] | [1655-1675] | + |
| 149 | Human, cynomolgus, mouse, rat | 21 | GGACAGCAGCAACAGUGGCUU | AAGCCACUGUUGCUGCUGUCC | [368-388] | [296-316] | [349-369] | - |
| 150 | Human, cynomolgus, mouse, rat | 21 | GUUCAUGAAUACACUUGAUGU | ACAUCAAGUGUAUUCAUGAAC | [1664-1684] | [1612-1632] | [1652-1672] | + |
| 151 | Human, cynomolgus, mouse, rat | 21 | UCAUGAAUACACUUGAUGUUC | GAACAUCAAGUGUAUUCAUGA | [1666-1686] | [1614-1634] | [1654-1674] | + |
| 152 | Human, cynomolgus, mouse, rat | 21 | UCCCUGGACAGCAGCAACAGU | ACUGUUGCUGCUGUCCAGGGA | [363-383] | [291-311] | [344-364] | - |
| 153 | Human, cynomolgus, mouse, rat | 21 | AGUCCCUGGACAGCAGCAACA | UGUUCCUGCUGUCCAGGGACU | [361-381] | [289-309] | [342-362] | - |
| 154 | Human, cynomolgus, rat | 21 | GAAUACACUUGAUGUUCAAGU | ACUUGAACAUCAAGUGUAUUC | [1670-1690] | | [1658-1678] | + |
| 155 | Human, cynomolgus, rat | 21 | CUAGAACUGUOUACAUGAAGA | UCUUCAUGUAAACAGUUCUAG | [1630-1650] | | [1623-1643] | + |
| 156 | Human, cynomolgus, rat | 21 | CCAUCUAGAACUGUUUACAUG | CAUGUAAACAGUUCUAGAUGG | [1626-1646] | | [1619-1639] | + |
| 157 | Human, cynomolgus, rat | 21 | CUUCCAUCUAGAACUGUUUAC | GUAAACAGUUCUAGAuGGAAG | [1623-1643] | | [1616-1636] | + |

TABLE C-continued

| No | Source | Oligo Length | Sense Sirna | AntiSense Sirna | gi9506686 ref NM_019058.1 (Homo sapiens) | gi21312867 ref NM_029083.1 (Mus musculus) | gi18376838 ref NM_080906.1 (Rattus norvegicus) | Overlap with pet-1 (antisense) |
|---|---|---|---|---|---|---|---|---|
| 158 | Human, cynomolgus, rat | 21 | UCUUCCAUCUAGAACUGUUUA | UAAACAGUUCUAGAUGGAAGA | [1622-1642] | | [1615-1635] | + |
| 159 | Human, cynomolgus, rat | 21 | CAUCUAGAACUGUUUACAUGA | UCAUGUAAACAGUUCUAGAUG | [1627-1647] | | [1620-1640] | + |
| 160 | Human, cynomolgus, rat | 21 | GGGUCUUCCAUCUAGAACUGU | ACAGUUCUAGAUGGAAGACCC | [1619-1639] | | [1612-1632] | + |
| 161 | Human, cynomolgus, rat | 21 | UCCAUCUAGAACUGUUUACAU | AUGUAAACAGUUCUAGAUGGA | [1625-1645] | | [1618-1638] | + |
| 162 | Human, cynomolgus, rat | 21 | UCUAGAACUGUUUACAUGAAG | CUUCAUGUAAACAGUUCUAGA | [1629-1649] | | [1622-1642] | + |
| 163 | Human, cynomolgus, rat | 21 | UUCCAUCUAGAACUGUUUACA | UGUAAACAGUUCUAGAUGGAA | [1624-1644] | | [1617-1637] | + |
| 164 | Human, cynomolgus, rat | 21 | GUCUUCCAUCUAGAACUGUUU | AAACAGUUCUAGAUGGAAGAC | [1621-1641] | | [1614-1634] | + |
| 165 | Human, mouse | 21 | UGAUGUUCAAGUAUUAAGACC | GGUCUUAAUACUUGAACAUCA | [1679-1699] | [1627-1647] | | + |
| 166 | Human, mouse | 21 | GUUCAAGUAUUAAGACCUAUG | CAUAGGUCUUAAUACUUGAAC | [1683-1703] | [1631-1651] | | + |
| 167 | Human, mouse | 21 | UCAAGUAUUAAGACCUAUGCA | UGCAUAGGUCUUAAUACUUGA | [1685-1705] | [1633-1653] | | + |
| 168 | Human, mouse | 21 | GAUGUUCAAGUAUUAAGACCU | AGGUCUUAAUACUUGAACAUC | [1680-1700] | [1628-1648] | | + |
| 169 | Human, mouse | 21 | UUCAAGUAUUAAGACCUAUGC | GCAUAGGUCUUAAUACUUGAA | [1684-1704] | [1632-1652] | | + |
| 170 | Human, rat | 21 | CUGGGUCUUCCAUCUAGAACU | AGUUCUAGAUGGAAGACCCAG | [1617-1637] | | [1610-1630] | + |
| 171 | Human, rat | 21 | UGGGUCUUCCAUCUAGAACUG | CAGUUCUAGAUGGAAGACCCA | [1618-1638] | | [1611-1631] | + |

Note that in the above Table C, the sense strands of siRNAs 123-171 have SEQ ID NOS: 247-295 respectively, and the antisense strands of siRNAs 123-171 have SEQ ID NOS: 296-344 respectively

TABLE D

| ID No. | Source | Sense siRNA | AntiSense siRNA | Human 801 Gi-56676369 | Mouse 801 Gi-21312867 | Rat 801 Gi-18376838 | Chimpanzee 801 Gi-55633976 | Cynomolgus 801 |
|---|---|---|---|---|---|---|---|---|
| 172 | Human | UGAAAAUUACACCUGGCA | UGCCAGGUGUAAUUUUCA | [1502-1520] (19/19) | [1444-1457] (14/14) | — | — | — |
| 173 | Human | GACACUUGAAAAAUUACAC | GUGUAAUUUUUCAAGUGUC | [1496-1514] (19/19) | [1432-1442] (11/11) | — | — | [1329-1347] (18/19) |

TABLE D-continued

| ID No. | Source | Sense siRNA | AntiSense siRNA | Human 801 Gi-56676369 | Mouse 801 Gi-21312867 | Rat 801 Gi-18376838 | Chimpanzee 801 Gi-55633976 | Cyno-molgus 801 |
|---|---|---|---|---|---|---|---|---|
| 174 | Human | CACUUGAAAAAUUACACCU | AGGUGUAAUUUUUCAAGUG | [1498-1516] (19/19) | [1444-1455] (12/12) | — | — | [1331-1349] (18/19) |
| 175 | Human | UUAGGGGCCAACAAGGCUU | AAGCCUUGUUGGCCCCUAA | [1132-1150] (19/19) | — | — | — | [974-992] (18/19) |
| 176 | Human | ACACUUGAAAAAUUACACC | GGUGUAAUUUUUCAAGUGU | [1497-1515] (19/19) | [1444-1454] (11/11) | — | — | [1330-1348] (18/19) |
| 177 | Human | ACCCUGAGGAUGAACACUU | AAGUGUUCAUCCUCAGGGU | [459-477] (19/19) | — | — | [404-420] (17/17) | [301-317] (17/17) |
| 178 | Human | GUACUGCAGAGUUGAGCUG | CAGCUCAACUCUGCAGUAC | [1547-1565] (19/19) | — | — | — | [1388-1398] (11/11) |
| 179 | Human | GUGUACUGCAGAGUUGAGC | GCUCAACUCUGCAGUACAC | [1545-1563] (19/19) | — | — | — | — |
| 180 | Human | GUGUGUUUGUUGUUUGUUU | AAACAAACAACAAACACAC | [1361-1379] (19/19) | — | — | — | [1195-1206] (12/12) |
| 181 | Human | UUGUGUGCCAACCUGAUGC | GCAUCAGGINGGCACACAA | [476-494] (19/19) | [400-417] (18/18) | [453-470] (18/18) | [422-439] (18/18) | [319-336] (18/18) |
| 182 | Human | AUCGUGUACUGCAGAGUUG | CAACUCUGCAGUACACGAU | [1542-(19/19) | — | — | — | — |
| 183 | Human | CCAUCGUGUACUGCAGAGU | ACUCUGCAGUACACGAUGG | [1540-1558] (19/19) | — | — | — | — |
| 184 | Human | ACUUGAAAAAUUACACCUG | CAGGUGUAAUUUUUCAAGU | [1499-1517] (19/19) | [1444-1456] (13/13) | — | — | — |
| 185 | Human | UGAGGAUGAACACUUGUGU | ACACAAGUGUUCAUCCUCA | [463-481] (19/19) | — | — | [408-426] (18/19) | [305-323] (18/19) |
| 186 | Human | ACCUGGCACCUGCGUUUAA | UUAAACGCAGCUGCCAGGU | [1513-1531] (19/19) | — | — | — | — |
| 187 | Human | CAGAGACGACUGAACUUUU | AAAAGUUCAGUCGUCUCUG | [938-956] (19/19) | — | — | — | — |
| 188 | Human | AAGACAGAGACGACUGAAC | GUUCAGUCGUCUCUGUCUU | [934-952] (19/19) | — | — | — | — |
| 189 | Human | GCAGCUGCGUUUAAGCCUU | AAGGCUUAAACGCAGCUGC | [1518-1536] (19/19) | — | — | — | — |
| 190 | Human | AGGAAGCUCAUUGAGUUGU | ACAACUCAAUGAGCUUCCU | [1053-1071] (19/19) | — | — | — | [895-913] (18/19) |
| 191 | Human | GUGUUUCCAGGAAGCUCA | UGAGCUUCCUGGGAAACAC | [1044-1062] (19/19) | — | — | — | [886-900] (15/15) |
| 192 | Human | GACGACUGAACUUUUGGGG | CCCCAAAAGUUCAGUCGUC | [942-960] (19/19) | — | — | — | [789-802] (14/14) |

TABLE D-continued

| ID No. | Source | Sense siRNA | AntiSense siRNA | Human 801 Gi-56676369 | Mouse 801 Gi-21312867 | Rat 801 Gi-18376838 | Chimpanzee 801 Gi-55633976 | Cynomolgus 801 |
|---|---|---|---|---|---|---|---|---|
| 193 | Human | ACAGAGACGACUGAACUUU | AAAGUUCAGUCGUCUCUGU | [937-955] (19/19) | — | — | — | — |
| 194 | Human | AGGAUGAACACUUGUGUGC | GCACACAAGUGUUCAUCCU | [465-483] (19/19) | — | — | [410-428] (18/19) | [307-325] (18/19) |
| 195 | Human | CUGAGGAUGAACACUUGUG | CACAAGUGUUCAUCCUCAG | [462-480] (19/19) | — | — | [407-425] (18/19) | [304-322] (18/19) |
| 196 | Human | UCUGGGUCUUCCAUCUAGA | UCUAGAUGGAAGACCCAGA | [1621-1639] (19/19) | [1569-1586] (18/18) | [1610-1627] (18/18) | — | [1456-1471] (16/16) |
| 197 | Human | AUCUGGGUCUUCCAUCUAG | CUAGAUGGAAGACCCAGAU | [1620-1638] (19/19) | [1569-1585] (17/17) | [1610-1626] (17/17) | — | [1456-1470] (15/15) |
| 198 | Human | GAAGGGACCAAGUGUGUUU | AAACACACUUGGUCCCUUC | [1350-1368] (19/19) | — | — | — | [1181-1198] (18/18) |
| 199 | Human | AAGGCUUAGGGGCCAACAA | UUGUUGGCCCCUAAGCCUU | [1127-1145] (19/19) | — | — | — | [969-984] (16/16) |
| 200 | Human | UUCCCAGGAAGCUCAUUGA | UCAAUGAGCUUCCUGGGAA | [1048-1066] (19/19) | — | — | — | [890-908] (18/19) |
| 201 | Human, Chimpanzee | UGGGCAAAGAACUACUGCG | CGCAGUAGUUCUUUGCCCA | [582-600] (19/19) | — | — | [527-545] (19/19) | [424-439] (16/16) |
| 202 | Human, Chimpanzee | GGUGGGCAAAGAACUACUG | CAGUAGUUCUUUGCCCACC | [580-598] (19/19) | — | — | [525-543] (19/19) | [422-439] (18/18) |
| 203 | Human, Chimpanzee | GUGGGCAAAGAACUACUGC | GCAGUAGUUCUUUGCCCAC | [581-599] (19/19) | — | — | [526-544] (19/19) | [423-439] (17/17) |
| 204 | Human, Chimpanzee | UGCCUAGCCAGUUGGUAAG | CUUACCAACUGGCUAGGCA | [558-576] (19/19) | — | — | [503-521] (19/19) | — |
| 205 | Human, Chimpanzee | AAGCCAGGUGGGCAAAGAA | UUCUUUGCCCACCUGGCUU | [574-592] (19/19) | [498-511] (14/14) | [551-564] (14/14) | [519-537] (19/19) | [417-434] (18/18) |
| 206 | Human, Chimpanzee | AUGCCUAGCCAGUUGGUAA | UUACCAACUGGCUAGGCAU | [557-575] (19/19) | — | — | [502-520] (19/19) | — |
| 207 | Human, Chimpanzee | UUCCGAGUCAUCAAGAAGA | UCUUCUUGAUGACUCGGAA | [842-860] (19/19) | [769-783] (15/15) | — | [787-805] (19/19) | [687-702] (16/16) |
| 208 | Human, Cynomolgus | GACGCAUGAAUGUAAGAGU | ACUCUUACAUUCAUGCGUC | [1440-1458] (19/19) | [1379-1394] (16/16) | [1421-1434] (14/14) | — | [1273-1291] (19/19) |
| 209 | Human, Cynomolgus | UACAGACGCAUGAAUGUAA | UUACAUUCAUGCGUCUGUA | [1436-1454] (19/19) | [1379-1390] (12/12) | [1421-1432] (12/12) | — | [1269-1287] (19/19) |
| 210 | Human, Cynomolgus | GUGUGUAGCAUGUACCUUA | UAAGGUACAUGCUACACAC | [1163-1181] (19/19) | [1111-1126] (16/16) | [1151-1166] (15/16) | — | [1005-1023] (19/19) |
| 211 | Human, Cynomolgus | ACGCAUGAAUGUAAGAGUA | UACUCUUACAUUCAUGCGU | [1441-1459] (19/19) | [1379-1395] (17/17) | [1421-1434] (14/14) | — | [1274-1292] (19/19) |

TABLE D-continued

| ID No. | Source | Sense siRNA | AntiSense siRNA | Human 801 Gi-56676369 | Mouse 801 Gi-21312867 | Rat 801 Gi-18376838 | Chimpanzee 801 Gi-55633976 | Cyno-molgus 801 |
|---|---|---|---|---|---|---|---|---|
| 212 | Human, Cyno-molgus | AUCUUACAGACGCAUGAAU | AUUCAUGCGUCUGUAAGAU | [1432-1450] (19/19) | [1367-1386] (19/20) | [1409-1428] (19/20) | — | [1265-1283] (19/19) |
| 213 | Human, Cyno-molgus | AGACGCAUGAAUGUAAGAG | CUCUUACAUUCAUGCGUCU | [1439-1457] (19/19) | [1379-1393] (15/15) | [1421-1434] (14/14) | — | [1272-1290] (19/19) |
| 214 | Human, Cyno-molgus | CUAUCUUACAGACGCAUGA | UCAUGCGCUGUAAGAUAG | [1430-1448] (19/19) | [1365-1377] (13/13) | [1407-1419] (13/13) | — | [1263-1281] (19/19) |
| 215 | Human, Cyno-molgus | GCAUCACUACUGACCUGUU | AACAGGUCAGUAGUGAUGC | [1403-1421] (19/19) | [1341-1356] (16/16) | [1383-1398] (16/16) | — | [1236-1254] (19/19) |
| 216 | Human, Cyno-molgus | GGAGCAUCACUACUGACCU | AGGUCAGUAGUGAUGCUCC | [1400-1418] (19/19) | [1341-1353] (13/13) | [1377-1395] (18/19) | — | [1233-1251] (19/19) |
| 217 | Human, Cyno-molgus | AUGAAACAAAGGCUUAGGG | CCCUAAGCCUUUGUUUCAU | [1119-1137] (19/19) | [1064-1081] (18/18) | [1104-1118] (15/15) | — | [961-979] (19/19) |
| 218 | Human, Cyno-molgus | AGCUAUCUUACAGACGCAU | AUGCGUCUGUAAGAUAGCU | [1428-1446] (19/19) | [1363-1377] (15/15) | [1405-1419] (15/15) | — | [1261-1279] (19/19) |
| 219 | Human, Cyno-molgus | UAGGCAGCUAUCUUACAGA | UCUGUAAGAUAGCUGCCUA | [1423-1441] (19/19) | [1359-1376] (18/18) | [1401-1418] (18/18) | — | [1256-1274] (19/19) |
| 220 | Human, Cyno-molgus | ACCUGUUGUAGGCAGCUAU | AUAGCUGCCUACAACAGGU | [1415-1433] (19/19) | — | — | — | [1248-1266] (19/19) |
| 221 | Human, Cyno-molgus | AGCAUCACUACUGACCUGU | ACAGGUCAGUAGUGAUGCU | [1402-1420] (19/19) | [1341-1355] (15/15) | [1383-1397] (15/15) | — | [1235-1253] (19/19) |
| 222 | Human, Cyno-molgus | UCUGAUCGGAGCAUCACUA | UAGUGAUGCUCCGAUCAGA | [1393-1411] (19/19) | — | — | — | [1226-1244] (19/1) |
| 223 | Human, Cyno-molgus | UGACAGUUAACAGUGGUGU | ACACCACUGUUAACUGUCA | [1195-1213] (19/9) | — | — | — | [1037-1055] (19/19) |
| 224 | Human, Cyno-molgus | CUGACAGUUAACAGUGGUG | CACCACUGUUAACUGUCAG | [1194-1212] (19/19) | — | — | — | [1036-1054] (19/19) |
| 225 | Human, Cyno-molgus | GUUACUGACAGUUAACAGU | ACUGUUAACUGUCAGUAAC | [1190-1208] (19/19) | — | — | — | [1032-1050] (19/19) |
| 226 | Human, Cyno-molgus | UUGUUACUGACAGUUAACA | UGUUAACUGUCAGUAACAA | [1188-1206] (19/19) | — | — | — | [1030-1048] (19/19) |
| 227 | Human, Cyno-molgus | UACUCACUGUUCAUGAAUA | UAUUCAUGAACAGUGAGUA | [1661-1679] (19/19) | [1612-1622] (11/11) | [1644-1662] (18/19) | — | [1493-1511] (19/19) |
| 228 | Human, Cyno-molgus | UCACUUGGGAUCUUUGACA | UGUCAAAGAUCCCAAGUGA | [1481-1499] (19/19) | — | — | — | [1314-1332] (19/19) |
| 229 | Human, Cyno-molgus | ACAGACGCAUGAAUGUAAG | CUUACAUUCAUGCGUCUGU | [1437-1455] (19/19) | [1379-1391] (13/13) | [1421-1433] (13/13) | — | [1270-1288] (19/19) |
| 230 | Human, Cyno-molgus | CAGCUAUCUUACAGACGCA | UGCGUCUGUAAGAUAGCUG | [1427-1445] (19/19) | [1362-1377] (16/16) | [1404-1419] (16/16) | — | [1260-1278] (19/19) |

TABLE D-continued

| ID No. | Source | Sense siRNA | AntiSense siRNA | Human 801 Gi-56676369 | Mouse 801 Gi-21312867 | Rat 801 Gi-18376838 | Chimpanzee 801 Gi-55633976 | Cyno-molgus 801 |
|---|---|---|---|---|---|---|---|---|
| 231 | Human, Cyno-molgus | UCACUACUGACCUGUUGUA | UACAACAGGUCAGUAGUGA | [1406-1424] (19/19) | [1341-1356] (16/16) | [1383-1398] (16/16) | — | [1239-1257] (19/19) |
| 232 | Human, Cyno-molgus | GAGCAUCACUACUGACCUG | CAGGUCAGUAGUGAUGCUC | [1401-1419] (19/19) | [1341-1354] (14/14) | [1378-1396] (18/19) | — | [1234-1252] (19/19) |
| 234 | Human, Cyno-molgus | GUGUAUCUUACUGGUCUGA | UCAGACCAGUAAGAUACAC | [1333-1351] (19/19) | — | — | — | [1164-1182] (19/19) |
| 235 | Human, Cyno-molgus | GUGGUUUGUGUAUCUUACU | AGUAAGAUACACAAACCAC | [1326-1344] (19/19) | [1256-1268] (13/13) | — | — | [1157-1175] (19/19) |
| 236 | Human, Cyno-molgus | ACAGUUAACAGUGGUGUGA | UCACACCACUGUUAACUGU | [1197-1215] (19/19) | — | — | — | [1039-1057] (19/19) |
| 237 | Human, Cyno-molgus | AACUGAGGCAGCCACCUAA | UUAGGUGGCUGCCUCAGUU | [1007-1025] (19/19) | — | — | — | [849-867] (19/19) |
| 238 | Human, Cyno-molgus | UGUUCAUGAAUACACUUGA | UCAAGUGUAUUCAUGAACA | [1668-1686] (19/19) | [1612-1629] (18/18) | [1652-1669] (18/18) | — | [1500-1518] (19/19) |
| 239 | Human, Cyno-molgus | CUGUUCAUGAAUACACUUG | CAAGUGUAUUCAUGAACAG | [1667-1685] (19/19) | [1612-1628] (17/17) | [1652-1668] (17/17) | — | [1499-1517] (19/19) |
| 240 | Human, Cyno-molgus | AGAUACUCACUGUUCAUGA | UCAUGAACAGUGAGUAUCU | [1658-1676] (19/19) | — | — | — | [1490-1508] (19/19) |
| 241 | Human, Cyno-molgus | CAGACGCAUGAAUGUAAGA | UCUUACAUUCAUGCGUCUG | [1438-1456] (19/19) | [1379-1392] (14/14) | [1421-1434] (14/14) | — | [1271-1289] (19/19) |
| 242 | Human, Cyno-molgus | GCAGCUAUCUUACAGACGC | GCGUCUGUAAGAUAGCUGC | [1426-1444] (19/19) | [1361-1377] (17/17) | [1403-1419] (17/17) | — | [1259-1277] (19/19) |
| 243 | Human, Cyno-molgus | GGCAGCUAUCUUACAGACG | CGUCUGUAAGAUAGCUGCC | [1425-1443] (19/19) | [1360-1377] (18/18) | [1402-1419] (18/18) | — | [1258-1276] (19/19) |
| 244 | Human, Cyno-molgus | GGUUUGUGUAUCUUACUGG | CCAGUAAGAUACACAAACC | [1328-1346] (19/19) | [1256-1268] (13/13) | — | — | [1159-1177] (19/19) |
| 245 | Human, Cyno-molgus | GAGGUGGUUUGUGUAUCUU | AAGAUACACAAACCACCUC | [1323-1341] (19/19) | [1256-1268] (13/13) | — | — | [1154-1172] (19/19) |
| 246 | Human, Cyno-molgus | GUGGAGGUGGUUUGUGUAU | AUACACAAACCACCUCCAC | [1320-1338] (19/19) | — | — | — | [1151-1169] (19/19) |
| 247 | Human, Cyno-molgus | UACUGACAGUUAACAGUGG | CCACUGUUAACUGUCAGUA | [1192-1210] (19/19) | — | — | — | [1034-1052] (19/19) |
| 248 | Human, Cyno-molgus | GUGUAGCAUGUACCUUAUU | AAUAAGGUACAUGCUACAC | [1165-1183] (19/19) | [1111-1128] (18/18) | [1151-1168] (17/18) | — | [1007-1025] (19/19) |
| 249 | Human, Cyno-molgus, Chimp-anzee | AGGUGGGCAAAGAACUACU | AGUAGUUCUUUGCCCACCU | [579-597] (19/19) | — | — | [524-542] (19/19) | [421-439] (19/19) |

TABLE D-continued

| ID No. | Source | Sense siRNA | AntiSense siRNA | Human 801 Gi-56676369 | Mouse 801 Gi-21312867 | Rat 801 Gi-18376838 | Chimpanzee 801 Gi-55633976 | Cynomolgus 801 |
|---|---|---|---|---|---|---|---|---|
| 250 | Human, Cynomolgus, Chimpanzee | GUGACCCUGAGGAUGAACA | UGUUCAUCCUCAGGGUCAC | [456-474] (19/19) | — | — | [401-419] (19/19) | [298-316] (19/19) |
| 251 | Human, Cynomolgus, Chimpanzee | CAGGUGGGCAAAGAACUAC | GUAGUUCUUUGCCCACCUG | [578-596] (19/19) | [501-517] (16/17) | [554-570] (16/17) | [523-541] (19/19) | [420-438] (19/19) |
| 252 | Human, Cynomolgus, Chimpanzee | CCAGGUGGGCAAAGAACUA | UAGUUCUUUGCCCACCUGG | [577-595] (19/19) | [500-517] (17/18) | [553-570] (17/18) | [522-540] (19/19) | [419-437] (19/19) |
| 253 | Human, Cynomolgus, Chimpanzee | AUCCAGGGGCUGUUUAGCU | AGCUAAACAGCCCCUGGAU | [767-785] (19/19) | [690-703] (14/14) | — | [712-730] (19/19) | [609-627] (19/19) |
| 254 | Human, Cynomolgus, Chimpanzee | AAGAUCCAGGGGCUGUUUA | UAAACAGCCCCUGGAUCUU | [764-782] (19/19) | [687-703] (17/17) | [740-756] (16/17) | [709-727] (19/19) | [606-624] (19/19) |
| 255 | Human, Cynomolgus, Mouse | GCAUGAAACAAAGGCUUAG | CUAAGCCUUUGUUUCAUGC | [1117-1135] (19/19) | [1062-1080] (19/19) | [1102-1118] (17/17) | — | [959-977] (19/19) |
| 256 | Human, Cynomolgus, Mouse | AGCAUGAAACAAAGGCUUA | UAAGCCUUUGUUUCAUGCU | [1116-1134] (19/19) | [1061-1079] (19/19) | [1101-1118] (18/18) | — | [958-976] (19/19) |
| 257 aka 801_1 | Human, Cynomolgus, Mouse, Rat | UACUGUAGCAUGAAACAAA | UUUGUUUCAUGCUACAGUA | [1110-1128] (19/19) | [1055-1073] (19/19) | [1095-1113] (19/19) | — | [952-970] (19/19) |
| 258 | Human, Cynomolgus, Mouse, Rat | UAGCAUGAAACAAAGGCUU | AAGCCUUUGUUUCAUGCUA | [1115-1133] (19/19) | [1060-1078] (19/19) | [1100-1118] (19/19) | — | [957-975] (19/19) |
| 259 | Human, Cynomolgus, Mouse, Rat | GUAGCAUGAAACAAAGGCU | AGCCUUUGUUUCAUGCUAC | [1114-1132] (19/19) | [1059-1077] (19/19) | [1099-1117] (19/19) | — | [956-974] (19/19) |
| 260 aka 801_4 | Human, Cynomolgus, Mouse, Rat | CAGUACUGUAGCAUGAAAC | GUUUCAUGCUACAGUACUG | [110-1125] (19/19) | [1052-1070] (19/19) | [1092-1110] (19/19) | — | [949-967] (19/19) |
| 261 | Human, Cynomolgus, Mouse, Rat | GUACUGUACCAUGAAACAA | UUGUUUCAUGCUACAGUAC | [1109-1127] (19/19) | [1054-1072] (19/19) | [1094-1112] (19/19) | — | [951-969] (19/19) |
| 262 | Human, Cynomolgus, Mouse, Rat | UCAGUACUGUAGCAUGAAA | UUUCAUGUACAGUACUGA | [1106-1124] (19/19) | [1051-1069] (19/19) | [1091-1109] (19/19) | — | [948-966] (19/19) |

TABLE D-continued

| ID No. | Source | Sense siRNA | AntiSense siRNA | Human 801 Gi-56676369 | Mouse 801 Gi-21312867 | Rat 801 Gi-18376838 | Chimpanzee 801 Gi-55633976 | Cyno-molgus 801 |
|---|---|---|---|---|---|---|---|---|
| 263 | Human, Cyno-molgus, Mouse, Rat | UGUAGCAUGAAACAAAGGC | GCCUUUGUUUCAUGCUACA | [1113-1131] (19/19) | [1058-1076] (19/19) | [1098-1116] (19/19) | — | [955-973] (19/19) |
| 264 | Human, Cyno-molgus, Mouse, Rat | ACUGUAGCAUGAAACAAAG | CUUUGUUUCAUGCUACAGU | [1111-1129] (19/19) | [1056-1074] (19/19) | [1096-1114] (19/19) | — | [953-971] (19/19) |
| 265 | Human, Cyno-molgus, Mouse, Rat | CUGUAGCAUGAAACAAAGG | CCUUUGUUUCAUGCUACAG | [1112-1130] (19/19) | [1057-1075] (19/19) | [1097-1115] (19/19) | — | [954-972] (19/19) |
| 266 | Human, Cyno-molgus, Mouse, Rat | AGUACUGUAGCAUGAAACA | UGUUUCAUGCUACAGUACU | [1108-1126] (19/19) | [1053-1071] (19/19) | [1093-1111] (19/19) | — | [950-968] (19/19) |
| 267 | Human, Cyno-molgus, Mouse, Rat | CCUCAGUACUGUACCAUGA | UCAUGUACAGUACUGAGG | [1104-1122] (19/19) | [1049-1067] (19/19) | [1089-1107] (19/19) | — | [946-964] (19/19) |
| 268 | Human, Cyno-molgus, Mouse, Rat | CUCAGUACUGUAGCAUGAA | UUCAUGCUACAGUACUGAG | [1105-1123] (19/19) | [1050-1068] (19/19) | [1090-1108] (19/19) | — | [947-965] (19/19) |

Note that in the above Table D, the sense strands of siRNAs 172-232 and 234-268 have SEQ ID NOS: 345-440 respectively, and the antisense strands of siRNAs 172-232 and 234-268 have SEQ ID NOS: 441-536 respectively

Example 10

Pharmacology and Drug Delivery

The nucleotide sequences of the present invention can be delivered either directly or with viral or non-viral vectors. When delivered directly the sequences are generally rendered nuclease resistant. Alternatively the sequences can be incorporated into expression cassettes or constructs such that the sequence is expressed in the cell as discussed herein below. Generally the construct contains the proper regulatory sequence or promoter to allow the sequence to be expressed in the targeted cell.

The compounds or pharmaceutical compositions of the present invention are administered and dosed in accordance with good medical practice, taking into account the clinical condition of the individual patient, the disease to be treated, the site and method of administration, scheduling of administration, patient age, sex, body weight and other factors known to medical practitioners.

The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

The treatment generally has a length proportional to the length of the disease process and drug effectiveness and the patient species being treated. It is noted that humans are treated generally longer than the mice or other experimental animals exemplified herein.

The compounds of the present invention can be administered by any of the conventional routes of administration. It should be noted that the compound can be administered as the compound or as pharmaceutically acceptable salt and can be administered alone or as an active ingredient in combination with pharmaceutically acceptable carriers, solvents, diluents, excipients, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. Liquid forms may be prepared for injection, the term including subcutaneous, transdermal, intravenous, intramuscular, intrathecal, and other parental routes of administration. The liquid compositions include aqueous solutions, with and without organic cosolvents, aqueous or oil suspensions, emulsions with edible oils, as well as similar pharmaceutical vehicles. In addition, under certain circumstances the compositions for use in the novel treatments of the present invention may be formed as aerosols, for intranasal and like administration. The patient being treated is a warm-blooded animal and, in particular, mammals including man. The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention.

When administering the compound of the present invention parenterally, it is generally formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, can also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it is desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the compound utilized in the present invention can be administered orally to the patient. Conventional methods such as administering the compound in tablets, suspensions, solutions, emulsions, capsules, powders, syrups and the like are usable. Known techniques which deliver it orally or intravenously and retain the biological activity are preferred. In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used.

In general, the active dose of compound for humans is in the range of from 1 ng/kg to about 20-100 mg/kg body weight per day, preferably about 0.01 mg to about 2-10 mg/kg body weight per day, in a regimen of one dose per day or twice or three or more times per day for a period of 1-2 weeks or longer, preferably for 24- to 48 hrs or by continuous infusion during a period of 1-2 weeks or longer.

Administration of Compounds of the Present Invention to the Eye

The compounds of the present invention can be administered to the eye topically or in the form of an injection, such as an intravitreal injection, a sub-retinal injection or a bilateral injection. Further information on administration of the compounds of the present invention can be found in Tolentino et al., *Retina* 24 (2004) 132-138; Reich et al., *Molecular vision* 9 (2003) 210-216.

Pulmonary Administration of Compounds of the Present Invention

The therapeutic compositions of the present invention are preferably administered into the lung by inhalation of an aerosol containing these compositions/compounds, or by intranasal or intratracheal instillation of said compositions. Formulating the compositions in liposomes may benefit absorption. Additionally, the compositions may include a PFC liquid such as perflubron, and the compositions may be formulated as a complex of the compounds of the invention with polyethylemeimine (PEI).

For further information on pulmonary delivery of pharmaceutical compositions see Weiss et al., *Human gene therapy* 10:2287-2293 (1999); Densmore at al., *Molecular therapy* 1:180-188 (1999); Gautam et al., *Molecular therapy* 3:551-556 (2001); and Shahiwala & Misra, *AAPS Pharm Sci Tech* 5 (2004). Additionally, respiratory formulations for siRNA are described in U.S. patent application No. 2004/0063654 of Davis et el.

Further, The compounds of the present invention may be administered topically where appropriate (such as in the case of diabetic foot ulcers for example), optionally in a lipid/liposome formulation.

Administration of Compounds of the Present Invention to the Ear

A preferred administration mode is topical delivery of the RTP801 inhibitors onto the round window membrane of the cochlea as disclosed for example in Tanaka et al. (Hear Res. 2003 March; 177(1-2):21-31). An additional mode of administration to the ear is by trans-tympanic injection.

In the treatment of pressure sores or other wounds, the administration of the pharmaceutical composition is preferably by topical application to the damaged area, but the compositions may also be administered systemically.

Additional formulations for improved delivery of the compounds of the present invention can include non-formulated compounds, compounds covalently bound to cholesterol, and compounds bound to targeting antibodies (Song et al., Antibody mediated in vivo delivery of small interfering RNAs via cell-surface receptors, Nat. Biotechnol. 2005 June; 23(6): 709-17).

All of the siRNAs disclosed herein may be administered in a non-formulated format as naked siRNAs, for the treatment of any of the diseases or conditions disclosed herein. The term "naked siRNA" refers to siRNA molecules that are free from any delivery vehicle that acts to assist, promote or facilitate entry into the cell, including viral sequences, viral particles, liposome formulations, lipofectin or precipitating agents and the like. For example, siRNA in PBS is "naked siRNA".

Further, administration of any naked siRNA, oligonucleotide, combination of naked siRNAs or combination of naked siRNA and additional molecule in order to treat any of the diseases and conditions disclosed herein is within the scope of the present invention.

However, as disclosed herein, the siRNA molecules of the invention can also be delivered in liposome formulations and lipofectin formulations and the like and can be prepared by methods well known to those skilled in the art. Such methods are described, for example, in U.S. Pat. Nos. 5,593,972, 5,589,466, and 5,580,859, which are herein incorporated by reference.

Example 11

Ex Vivo Model for Cisplatin-Induced Ototoxicity and the Protective Effect of RTP801 siRNA Cisplatin-induced ototoxicity is induced in cochlear and vestibular organotypic cultures. Postnatal day 3-4 rat pups are used to prepare the cochlear and vestibular organotypic cultures as detailed in Zhang et al., Neuroscience 120 (2003) 191-205. Cochleae are carefully dissected out and the cochlear tissue containing the spiral ganglion, organ of Corti and the middle turn are removed to prepare the organotypic cultures as described in Zhang et al. The cultures are placed in a $CO_2$ incubator for 24 h for conditioning before treatment. After conditioning, the cultures are treated with cisplatin alone at 1, 5 or 10 μg/ml for 48 h. To study the protective effect of RTP801 siRNA, the cochlear explants (5 cochleas per group) are treated for 48 h with 10 μg/ml cisplatin and varying concentrations of RTP801 siRNA with or without Lipofectamine. Untreated control cultures and cultures treated with RTP801 siRNA for 48 h are run in parallel. At the end of the experiments, the cultures are fixed with 10% formalin and stained with FITC-conjugated phalloidin. The numbers of inner hair cells and outer hair cells per 0.25 mm length of the cochlean are counted and the mean number of hair cells are determined for each treatment.

Example 12

In Vivo Model for Gentamicin-Induced Ototoxicity and the Protective Effect of RTP801 siRNA Chinchillas are either treated with gentamicin sulfate alone for 5 days (125-300 mg/kg, intramuscular) or in combination with RTP801 siRNA. The siRNA molecules are administered topically onto the round window membrane of the cochlea two days prior to and during the 5 days exposure to gentamicin. At the end of the treatment, the animals are killed by exposure to carbon dioxide and decapitation. The cochleas are removed and prepared for staining with FITC-conjugated phalloidin to determine the numbers of inner hair cells and outer hair cells in the cochlean tissue (as described in Ding et al., Hearing Research 164 (2002) 115-126 and in Wang et al., The Journal of Neuroscience 23(24):8596-8607).

Example 13

In Vivo Model for Acoustic Trauma and the Protective Effect of RTP801 siRNA

Pigmented guinea pigs are used in the acoustic trauma study (described in Wang et al., The Journal of Neuroscience 23(24):8596-8607). RTP801 siRNA molecules are administered topically onto the round window membrane of the cochlea over a period of 7 days. Untreated left cochleae served as controls for the effectiveness of the acoustic trauma on causing auditory hair cell loss and loss of hearing function. Animals are exposed to acoustic trauma [6 kHz, 120 dB sound pressure level (SPL), 30 min], and audiograms of both ears are derived from the compound action potentials (CAPS) recorded from the auditory nerves via chronic round window membrane electrodes. The CAP audiograms from both ears are measured daily in awake animals. 30 d after sound exposure, animals are sacrificed, and their cochleae are prepared for a quantitative evaluation of hair cell losses using scanning electron microscopy in order to count all hair cells for the entire length of the cochlear duct.

Example 14

Experimental Results Relating to 801_1 (Id No. 257 in Table D. SEQ ID No:527 [Antisense Strand]) and 801_4 (ID No. 260 in Table D. SEQ ID NO:530 [Antisense Strand])

In Vitro Efficacy in HEK293 Cells

Figure 28:
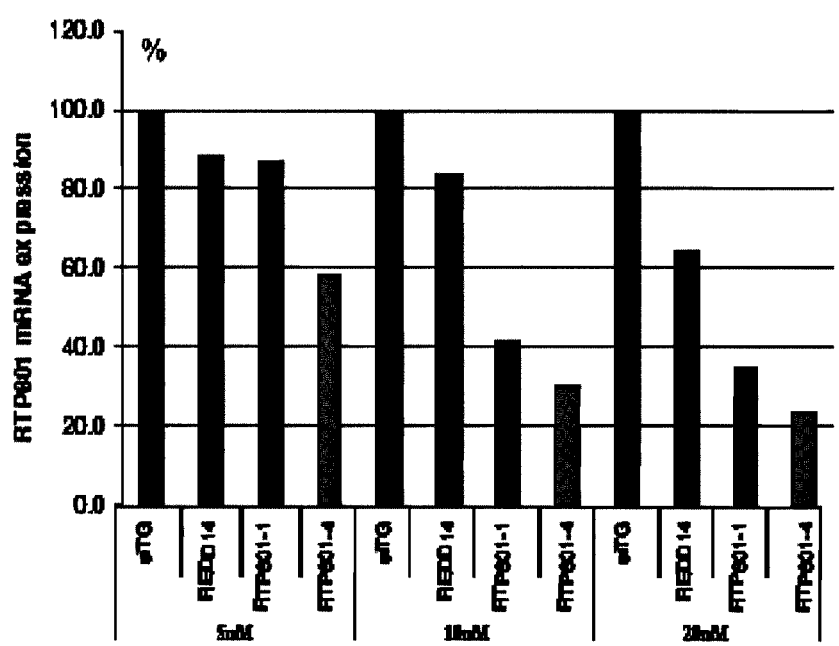
FIG. 28 shows efficacy results relating to 801_1 (SEQ ID Nos 430 and 527) and 801_4 (SEQ ID Nos 433 and 530)

Three different concentrations of siRNAs, 5, 10 and 20 nm were transfected into HEK293 cells. Identical concentrations of an irrelevant siRNA (siTG) were used as a negative control, whereas identical concentrations of REDD14 were used as a positive control. 72 hours following transfection, the cells were harvested; RNA was purified and used as a template in a qPCR reaction for the quantitative determination of the levels of endogenous RTP801 transcript. Human Cyclophilin A was used as an internal reference for qPCR. Reference-normalized data was further subjected to biological normalization: For each siRNA concentration, the detected RTP801 levels were expressed as percent of RTP801 in the corresponding negative control sample. The results are shown in FIG. 28.

In Vitro Efficacy in BE2C Cells

Figure 29:
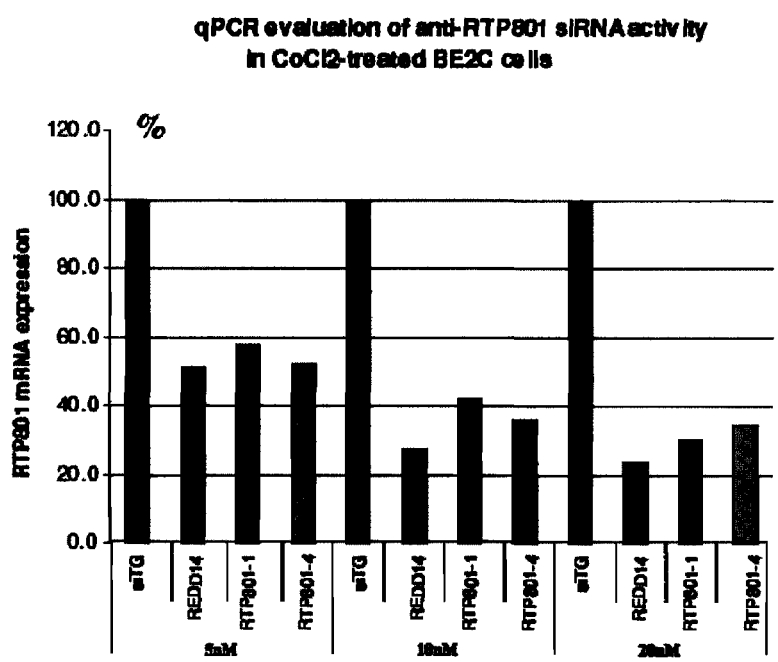
FIG. 29 shows further efficacy results relating to 801_1 (SEQ ID Nos 430 and 527) and 801_4 (SEQ ID Nos 433 and 530)

Whereas basal RTP801 expression levels were analyzed in the HEK293 cells, for assessment of the siRNA ability to decrease induced RTP801 expression levels, BE2C cells treated with $CoCl_2$ as an inducer of RTP801 were used. The design and data evaluation were essentially as described above. 24 hrs after siRNA transfection, the BE2C cells were treated with 10 uM $CoCl_2$ for an additional 24 his and then processed for RNA extraction. The results are shown in FIG. 29.

The results indicate that 801_1 and 801_4 are at least as effective as REDD14 against RTP801 in in vitro assays.

In Vivo Efficacy in the Mouse CNV Model

The experiments were performed as described in Example 6, with the following experimental groups:

TABLE 4

| Group | Mean CNV volume (μm³) | SEM | Number of laser spots |
|---|---|---|---|
| PBS | 471698.3 | 26163.96 | 22 |
| REDD14 (0.05 μg) | 237326.9 | 24136.19 | 29 |
| REDD14 (0.1 μg) | 182997.0 | 29213.92 | 25 |
| REDD14 (0.5 μg) | 207235.7 | 20420.18 | 29 |
| RTP801#1 siRNA (0.05 μg) | 334196.8 | 32429.66 | 30 |
| RTP801#1 siRNA (0.1 μg) | 176091.1 | 37343.13 | 24 |
| RTP801#1 siRNA (0.5 μg) | 226063.0 | 17906.91 | 33 |
| RTP801#2 siRNA (0.05 μg) | 304325.6 | 30584.33 | 30 |
| RTP801#2 siRNA (0.1 μg) | 265668.3 | 20287.93 | 28 |
| RTP801#2 siRNA (0.5 μg) | 269164.4 | 24776.41 | 31 |

Figure 30:
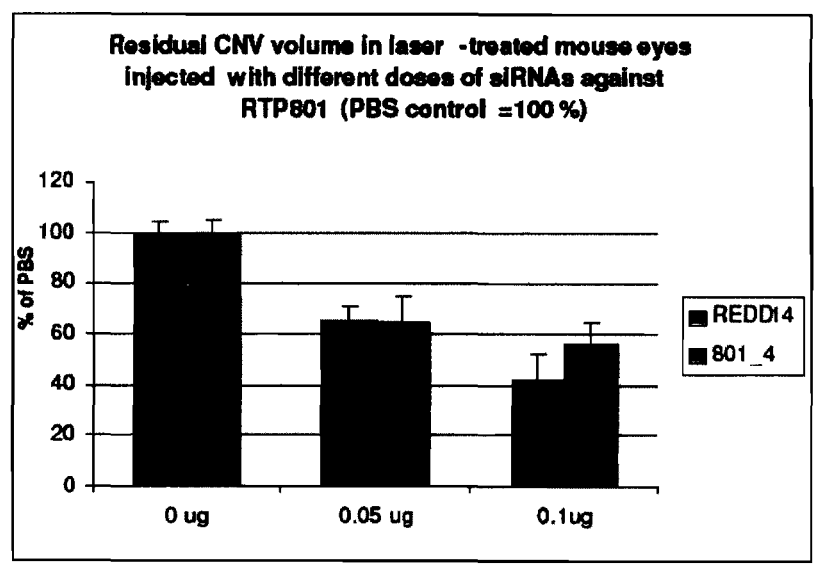
FIG. 30 shows further efficacy results relating to 801_1 (SEQ ID Nos 430 and 527) and 801_4 (SEQ ID Nos 433 and 530).

The results are presented in FIG. 30, and show that 801_4 is at least as effective as REDD14 in the in vivo model of mouse CNV.

Example 15

Models and Results Relating to Deafness

The Effect of an Exemplary (p53) siRNA Treatment on Acoustic-Induced Hair Cell Death in the Cochlea of Chinchilla The activity of an exemplary siRNA (QM5- and p53) in an acoustic trauma model was studied in chinchilla. A group of seven animals underwent acoustic trauma. Animals were exposed to an octave band of noise centered at 4 kHz for 3 h at 105 dB. The left ear of the noise-exposed chinchillas was treated with 30 µg of siRNA in ~20 µL; the right ear was treated with vehicle. The mean threshold of the compound action potential recorded from the round window was determined 2.5 weeks after the acoustic trauma in order to determine if the thresholds in the siRNA-treated ear were lower (better) than the untreated (vehicle) ear. The mean thresholds were lower in the siRNA-treated ears versus the untreated ears. The difference at 4 kHz was statistically significant ($p<0.033$). These results indicate that the exemplary p53 siRNA administered to the round window of the cochlea is capable of reducing the damage caused by acoustic trauma.

The Effect of p53 or 801 siRNA Treatment on Cisplatin-Induced Hair Cell Death in the Cochlea of Rats Male Wistar Rats were tested for basal auditory brainstem response thresholds for signals of clicks, 8, 16 and 32 kHz prior to cisplatin treatment. Following the basal auditory brainstem response testing, cisplatin was administered as an intraperitoneal infusion of 13 mg/kg over 30 minutes. Treated ears received either 15 ug/4 microliters of the exemplary p53 siRNA (as above) or RTP801 siRNA REDD14 (sequence No. 14 in Table A, SEQ ID No.s 16 (sense) and 66 (antisense)) applied directly to the round window membrane. Control ears were treated with either non-related GFP siRNA or PBS. The siRNA molecules were administered between 3-5 days prior to cisplatin administration in order to examine protective effect on the cochlea.

The auditory brainstem response testing was repeated 3 days after cisplatin administration. The auditory brainstem response thresholds were compared between pretreatment and posttreatment and the shift in thresholds is indicated in Table 5. Higher shift in thresholds following cisplatin treatment is indicative for more severe hair cells loss in the cochlea. After the repeat of auditory brainstem response testing, animals were sacrificed and cochleae were removed and processed for scanning electron microscopy (SEM) to quantify outer hair cell (OHC) loss in the hook region (high frequency region). The percentage of outer hair cell loss was calculated by dividing the number of missing or severely damaged cells by the total number of outer hair cells in the field of the photograph.

Table 5 demonstrates the results obtained from four animals underwent the cisplatin-induced damage and analysed for outer hair cell loss in the Hook region. As revealed from the results, animals that received the siRNA directed against p53 or 801 exhibited lower outer hair cell loss and smaller shifts in the threshold for signals of 32 kHz. Both parameters indicate that siRNA directed against p53 or 801 is protective against cisplatin-induced damage in the cochlea.

TABLE 5

Hair cell loss versus threshold shift in cisplatin-treated cochlea of rats

| Treatment | Outer hair cell (OHC) loss | Auditory brainstem response (Threshold shift at 32 KHz) |
|---|---|---|
| QC/L P53 siRNA (QM5) | 50% | 10 dB |
| QC/R PBS | 100% | 30 dB |
| QF/L P53 siRNA (QM5) | 20% | 10 dB |
| QF/R GFP | 56% | 27.5 dB |
| QJ/R 801 siRNA (REDD14) | 20% | 17.5 dB |
| QJ/L GFP | 100% | 27.5 dB |
| QN/L 801 siRNA (REDD14) | 0% | 10 dB |
| QN/R PBS | 100% | 17.5 dB |

---

The invention claimed is:

1. A method of treating a patient suffering from a hearing disorder which comprises administering to the patient a pharmaceutical composition comprising an RTP801 inhibitor in an amount effective to treat the patient.

2. The method according to claim 1, wherein the hearing disorder is acoustic trauma.

3. The method according to claim 1, wherein the RTP801 inhibitor comprises a polynucleotide which specifically hybridizes to mRNA transcribed from the RTP801 gene as set forth in SEQ ID NO:1 and down regulates expression of the RTP801 gene in the patient.

4. The method according to claim 1, wherein the RTP801 inhibitor comprises an antibody which specifically binds to an epitope present within an RTP801 polypeptide the sequence of which is set forth in SEQ ID No:2 and inhibits the activity of the RTP801 polypeptide in the patient.

5. The method according to claim 3, wherein the polynucleotide is an siRNA.

6. The method according to claim 5, wherein the siRNA comprises consecutive nucleotides having a sequence identical to any sequence set forth in any one of the sequences listed in Tables A-D (SEQ ID NOs:3-536).

7. The method of claim 6, wherein the siRNA comprises a double-stranded compound having the structure:

5'(N)x-Z3'                    (antisense strand)

3'Z'—(N')y5'                  (sense strand)

wherein each N and N' is a ribonucleotide which may be modified or unmodified in its sugar residue and each of (N)x and (N')y is an oligomer in which each consecutive N or N' is joined to the next N or N' by a covalent bond; wherein each of x and y is an integer between 19 and 40; wherein each of Z and Z' may be present or absent, but if present is dTdT and is covalently attached at the 3' terminus of the strand in which it is present;

and wherein the sequence of (N)x comprises a sequence set forth in SEQ ID NOS: 66, 74, 75, 79, 525 or 528.

8. The method according to claim 7, wherein in the double-stranded compound the covalent bond is a phosphodiester bond, wherein x=y=19, wherein Z and Z' are both absent, wherein at least one ribonucleotide is modified in its sugar residue at the 2' position with a methoxy(2'-O-methyl), wherein alternating ribonucleotides are 2'-O-methyl sugar modified in both the antisense strand and the sense strand and wherein the ribonucleotide at the 5' terminus and at the 3' terminus of the antisense strand is modified in its sugar residue, and the ribonucleotide at the 5' terminus and at the 3' terminus of the sense strand is unmodified in its sugar residue.

9. The method according to claim 7 wherein in the double-stranded compound the sequence of (N)x comprises SEQ ID NO:525 or SEQ ID NO:528.

10. The method according to claim 7, wherein the double-stranded compound lacks a terminal phosphate.

11. The method according to claim 7, wherein the double-stranded compound is phosphorylated or non-phosphorylated.

12. The method according to claim 7, wherein in the double-stranded compound the dinucleotide dTdT is covalently attached to the 3' terminus of at least one strand.

13. The method according to claim 7, wherein in the double-stranded compound at least one nucleotide a sugar residue is modified.

14. The method according to claim 13, wherein
the 2' OH group of the sugar residue is replaced by a group or moiety selected from the group consisting of —H, —OCH$_3$, —OCH$_2$CH$_3$, —OCH$_2$CH$_2$, CH$_3$, —NH$_2$ and F.

15. The method according to claim 13, wherein in the double-stranded compound the modification is a —OCH$_3$ modification.

16. The method according to claim 15, wherein the double-stranded compound comprises unmodified and 2'-O-methyl sugar modified ribonucleotides wherein 2'-O-methyl sugar modified ribonucleotides are present in the first, third, fifth, seventh, ninth, eleventh, thirteenth, fifteenth, seventeenth and nineteenth positions of the antisense strand and in the second, fourth, sixth, eighth, tenth, twelfth, fourteenth, sixteenth and eighteenth positions of the sense strand.

17. The method according to claim 1, wherein the hearing disorder is an ototoxin-induced hearing impairment.

18. The method according to claim 17, wherein administering the RTP801 inhibitor minimizes damage to auditory hair cells.

19. The method according to claim 7, wherein in the double-stranded molecule the sequence of (N)x comprises SEQ ID NO:66.

* * * * *